(12) United States Patent
Ratcliffe et al.

(10) Patent No.: US 8,927,811 B2
(45) Date of Patent: Jan. 6, 2015

(54) PLANTS WITH ENHANCED SIZE AND GROWTH RATE

(75) Inventors: Oliver J. Ratcliffe, Oakland, CA (US);
Peter P. Repetti, Emeryville, CA (US);
Neal I. Gutterson, Oakland, CA (US);
Robert A. Creelman, Castro Valley, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 984 days.

(21) Appl. No.: 12/376,569

(22) PCT Filed: Aug. 3, 2007

(86) PCT No.: PCT/US2007/017321
§ 371 (c)(1),
(2), (4) Date: Feb. 5, 2009

(87) PCT Pub. No.: WO2008/021021
PCT Pub. Date: Feb. 21, 2008

(65) Prior Publication Data
US 2010/0223689 A1    Sep. 2, 2010

Related U.S. Application Data

(60) Provisional application No. 60/836,243, filed on Aug. 7, 2006.

(51) Int. Cl.
*A01H 5/00* (2006.01)
*A01H 5/10* (2006.01)
*A01H 1/00* (2006.01)
*C12N 15/82* (2006.01)
*C07K 14/415* (2006.01)

(52) U.S. Cl.
CPC .......... *C12N 15/8261* (2013.01); *C07K 14/415* (2013.01)
USPC ........... 800/298; 800/278; 800/290; 800/287; 435/320.1; 435/419

(58) Field of Classification Search
None
See application file for complete search history.

(56) References Cited

U.S. PATENT DOCUMENTS

| 2003/0126638 | A1 | 7/2003 | Allen et al. | |
|---|---|---|---|---|
| 2003/0204870 | A1* | 10/2003 | Allen et al. | 800/281 |
| 2004/0019927 | A1* | 1/2004 | Sherman et al. | 800/278 |
| 2005/0086718 | A1 | 4/2005 | Heard et al. | |

FOREIGN PATENT DOCUMENTS

| WO | WO0028058 A2 | 5/2000 |
|---|---|---|
| WO | WO2004076638 A2 | 9/2004 |
| WO | WO2005033319 A2 | 4/2005 |

OTHER PUBLICATIONS

European Patent Office Examination Report dated Sep. 24, 2010 for European Patent Application No. EP 07 836 472.6.
European Patent Office Examination Report dated Feb. 16, 2010 for European Patent Application No. EP 07 83 6472.6.

* cited by examiner

*Primary Examiner* — Stuart F Baum
(74) *Attorney, Agent, or Firm* — Dentons US LLP

(57) ABSTRACT

Polynucleotides and polypeptides incorporated into expression vectors have been introduced into plants and were ectopically expressed. The polypeptides of the invention regulate transcription in these plants and have been shown to confer at least one regulatory activity that results in increased size, biomass, growth rate, and/or yield as compared to a control plan.

20 Claims, 18 Drawing Sheets

Figure 1:
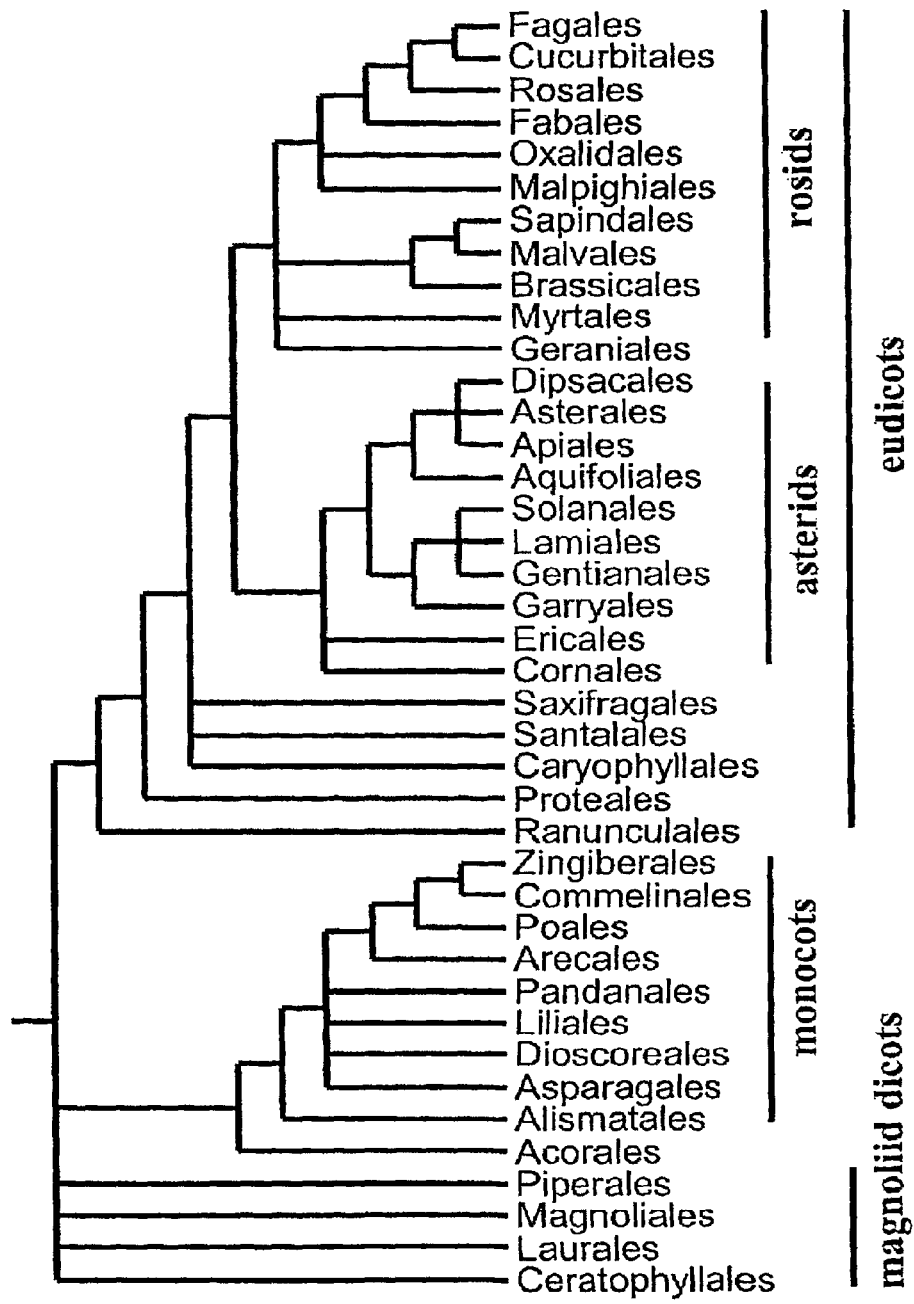

```
G2632  (28)  ----------------------------------MGIEDMHSKSDSGGNKVDSEVHGTVSSSIN-SLNPWHR----AAAACNA
G926   (32)  ---------------------------------------MQSKPGRE-NEEEVNNHHAVQQPMM-YAEPWWKNNSFGVVPQA
G3924  (16)  ---------------------------------------MESRPGGTNLVEPRG-QGALPSGIP-IQQPWWTT--SAGVGAV
G3920   (8)  ---------------------------------------MPGKPDTDDWRVERGEQIQFQSSIYSHHQPWWR------GVGEN
G3921  (22)  ------------------------------------------------------------MEDHSVHPMSKSNHGSLSGNGYEMKH
G4264  (26)  ------------------------------------------------------MPVILREMEDHSVHPMSKSNHGSLSGNGYEMKH
G3922  (24)  ------------------------------------------------------MPVILREMEDHSVHPMSKSNHGSLSGNGYEMKH
G3926  (18)  ----------------------------------------MIMLLQEMENHPVQCMAKTNYDFLARNNYPMKQ
G3925  (20)  ----------------------------------------------------------MLPP----HLTENGTVMIQ
G928   (10)  MMHQMLNKKDSATHSTLPYLNTSISWGVVPTDSVANRRGPAESLSLK-VDSRPG-HIQTT
G931    (6)  -MDKKVSFTSSVAHSTPPYLSTSISWG-LPTKS----NGVTESLSLKVVDARPE-RLINT
G1363  (14)  -MQEFHSSKDSLPCPATSWDNS---------VFT-NSNVQGSS--SLTDNNTLSLT--MEMKQ
G1782  (12)  -MQVFQRKED-------SSWGNS---------------MPTTNSNIQGSESFSLTKDMIMSTTQLPAMKH
G2344   (4)  -------------------------------------------------------------MTS
G929    (2)  -------------------------------------------------------------MTS
G1334  (30)  ----------------------------------------MQT--EELLSPPQTPWWNAFGSQPLTTE
G927   (34)  ----------------------------------------MAMQTVREGLFSAPQTSWWTAFGSQPLAPE
```

FIG. 4A

| | | |
|---|---|---|
| G2632 | (28) | NSSVEAGDKSSKSIALALESNGSKSPS-----NRDN-TVNKESQVTTSPQSAGDYSDKNQ |
| G926 | (32) | RPSGIPSNSSSLDCPNGSESNDVHSASEDGALNGENDGTWKDSQAATSSRSDNHGMEGND |
| G3924 | (16) | SPAVVAPGSGAGISLSGRDGGGD--------DAAEESSDDSRRSGETKDGSTDQEKHH |
| G3920 | (8) | ----ASKSSSDDQLNGSIVNG--------------ITRSETNDKSGGGVAKEY---QNIKH |
| G3921 | (22) | PGHEVCDRDSS-SESDR-SHQEASAAAESSPD-EHTSTQ------SD-NDEDHGKDNQDTL |
| G4264 | (26) | SGHKVCDRDSS-SESDR-SHQEASAAAESSPN-EHTSTQ------SD-NDEDHGKDNQDTM |
| G3922 | (24) | SGHKVCDRDSS-SESDR-SHQEASAAAESSPN-EHTSTQ------SD-NDEDHGKDNQDTM |
| G3926 | (18) | LVQRNSDGDSSPTKSGE-SHQEASAVSDSSLNGQHTSPQSVFVPSDINNNDSCGERDHGT |
| G3925 | (20) | FGHKMPDYESSATQSTSGSPREVSGMSEGSLNEQNDQSG-------NLDGYTKSDEGKM |
| G928 | (10) | KQISFQDQDSSSTQSTGQSYTEVASSGDDNPSRQISFSAKS----GSEITQRKGFASNPK |
| G931 | (6) | KNISFQDQDSSSTLSSAQSSNDVTSSGDDNPSRQISFLAHSDVCKGFEETQRKRFAIKS- |
| G1363 | (14) | TGFQMQHYDSSSTQSTGGES-YSEVASLSEPTNRYGHNIVVTHLSGYKENPENPIG--SH |
| G1782 | (12) | SGLQLQNQDSTSSQSTEEESGGGEVASFGEYK-RYGCSIVNNNLSGYIENLGKPIENYTK |
| G2344 | (4) | SIHELSDNIGSHEKQEQRDSHFQPPIPSARNYESIVTSLVYSDPGTTNS---------- |
| G929 | (2) | SVHELSDNNESHAKKERPDSQTRPQVPSGRSSESIDTNSVYSEP-------------- |
| G1334 | (30) | SLSGEASDSFTGVKAVTTEAEQGVVDKQT-STTLFTFSPGGEKSSRDVPKPH-VAFAMQS |
| G927 | (34) | SLAGD-SDSFAGVKVGSVGETRQRVDKQSNSATHLAFSLGDVKSPRLVPKPHGATFSMQS |

FIG. 4B

| | | | |
|---|---|---|---|
| G2632 | (28) | ESLHHG--ITQPPPHP-QLVGHTVGWASSNPYQDPYYAGVMGAYGHHPLGFVP------- | |
| G926 | (32) | PALSIRNMHDQPLVQPPELVGHYIACVP-NPYQDPYYGGLMGAYGHQQLGFRP------- | |
| G3924 | (16) | ATSQMTALASDYLTPFSQELNQPIASAAYQYPDSYYMGMVGPYGPQAMSAQTH------- | |
| G3920 | (8) | AMLSTPFTMEKHLAPNPQMELVGHSVVLTSPYSDAQYGQILTTYGQQVMINP-------- | |
| G3921 | (22) | KPVLSLGKEGSATGAPKLHYSPSFACI--PYTADAYYGAVGVLTGYPPHAIV-------- | |
| G4264 | (26) | KPVLSLGKEGSAFLAPKLHYSPSFACI--PYTSDAYYSAVGVLTGYPPHAIV-------- | |
| G3922 | (24) | KPVLSLGKEGSAFLAPKLHYSPSFACI--PYTADAYYSGVGVSTGYAPHAIVCSLLIFQF | |
| G3926 | (18) | KSVLSLGNTEAAFPPSKFDYNQPFACVSYPYGTDPYYG--GVSTGYTSHAFV-------- | |
| G3925 | (20) | MSALSLGKSETVYAHSEPDRSQPFGIS--YPYADSFYG--GAVATYGTHAIM-------- | |
| G928 | (10) | QGSMTGFPNIHFAPA----QANFSFH----YADP-HYGGLLAATYLPQAPTC-------- | |
| G931 | (6) | GSSTAGIADIHSSPS----KANFSFH----YADP-HFGGLMPAAYLPQATIW-------- | |
| G1363 | (14) | SISK---VSQDSVVLPIEA--ASWPLH---GNVTPHFNGFLSFPYASQHTVQ-------- | |
| G1782 | (12) | SITTSSMVSQDSVFPAPTSGQISWSLQ---CAETSHFNGFLAPEYASTPTALP------- | |
| G2344 | (4) | ----MAPGQYP----YPDPYYRSIFAPP---PQPYTGV------- | |
| G929 | (2) | ----MAHGLYP----YPDPYYRSVFAQQAYLPHPYPGV------- | |
| G1334 | (30) | ACFEFG--------FAQPMMYTKHPHVEQ-YYGVVSAYGSQRSSGRVMI------- | |
| G927 | (34) | PCLELG--------FSQPPIYTKYPYGEQQYYGVVSAYGSQ---SRVML------- | |

FIG. 4C

```
                                                                      conserved domain
G2632 (28) -------------YGGMPH-SRMPLPPEMAQ-EPVFVNAKQYQAILRRQARAKAEL----E
G926  (32) -------------YLGMPR-ERTALPLDMAQ-EPVYVNAKQYEGILRRRKARAKAEL----E
G3924 (16) -------------FQLPGLTH-SRMPLPLEISE-EPVYVNAKQYHGILRRRQSRAKAEL----E
G3920  (8) -------------QLYGMHH-ARMPLPLEMEE-EPVYVNAKQYHGILRRRQSRAKAEI----E
G3921 (22) -------------HPQQNDTTN-TPGMLPVEP-AEEPIYVNAKQYHAILRRRQTRAKLEA----Q
G4264 (26) -------------HPQQNDTTN-TPGMLPVEP-AEEPIYVNAKQYHAILRRRQTRAKLEA----Q
G3922 (24) LSSWPHSVHPQQNDTTN-TPGMLPVEP-AEEPIYVNAKQYHAILRRRQTRAKLEA----Q
G3926 (18) -------------HPQITGAAN-SRMPLAVDPSVEEPIFVNAKQYNAILRRRQTRAKLEA----Q
G3925 (20) -------------HPQIVGVMSSSRVPLPIEPATEEPIYVNAKQYHAILRRRQLRAKLEA----E
G928  (10) -------------NPQMVSMIP-GRVPLPAELTETDPVFVNAKQYHAIMRRRQQRAKLEA----Q
G931   (6) -------------NPQMT-----RVPLPFDLIENEPVFVNAKQFHAIMRRRQQRAKLEA----Q
G1363 (14) -------------HPQIRGLVP-SRMPLPHNIPENEPIFVNAKQYQAILRRERRAKLEA----Q
G1782 (12) -------------HLEMMGLVS-SRVPLPHHIQENEPIFVNAKQYHAILRRRKHRAKLEA----Q
G2344  (4) -------------HLQLMGVQQ-QGVPLPSDAVE-EPVFVNAKQYHGILRRRQSRARLES----Q
G929   (2) -------------QLQLMGMQQ-PGVPLQCDAVE-EPVFVNAKQYHGILRRRQSRAKLEA----R
G1334 (30) -------------PLKMETEEDGTIYVNSKQYHGIIRRRQSRAKA--------E
G927  (34) -------------PLNMET-EDSTIYVNSKQYHGIIRRRQSRAKAAAVLDQK
```

FIG. 4D

```
                     conserved domain
G2632 (28)  KKLIKSRKPYLHESRHQHAMRRPRGTGGRFAKKTNTEASKRKAE---------------------
G926  (32)  RKVIRDRKPYLHESRHKHAMRRARASGGRFA--KKSEVEAG----------------------
G3924 (16)  KKVVKSRKPYLHESRHQHAMRRARGTGGRFLNTKKNEDGAPSEK-------------------
G3920  (8)  KKVIKNRKPYLHESRHLHAMRRARGNGGRFLNTKKLENNNSNST-------------------
G3921 (22)  NKMVKGRKPYLHESRHRHAMKRARGSGGRFLNTKQLQDQNQQFQE------------------
G4264 (26)  NKMVKNRKPYLHESRHRHAMKRARGSGGRFLNTKQLQEQNQQYQ-------------------
G3922 (24)  NKMVKNRKPYLHESRHRHAMKRARGSGGRFLNTKQLQEQNQQYQ-------------------
G3926 (18)  NKAVKGRKPYLHESRHHHAMKRARGSGGRFLTKKELLEQQQQQQQQ-----------------
G3925 (20)  NKLVKNRKPYLHESRHQHAMKRARGTGGRFLNTKQQPE-------------------------
G928  (10)  NKLIRARKPYLHESRHVHALKRPRGSGGRFLNTKLLQESEQAAAREQEQDKLGQQVNRK----
G931   (6)  NKLIKARKPYLHESRHVHALKRPRGSGGRFLNTKKLQESTD--------PKQDMPIQQQHAT-
G1363 (14)  NKLIKVRKPYLHESRHLHALKRVRGSGGRFLNTKKHQESNSS-------LSPPFLIPPHVFK-
G1782 (12)  NKLIKCRKPYLHESRHLHALKRARGSGGRFLNTKKLQESSNS-------LCSSQMANGQNFS-
G2344  (4)  NKVIKSRKPYLHESRHLHAIRRPRGCGGRFLNAKKED-EHHED--------------------
G929   (2)  NRAIKAKKPYMHESRHLHAIRRPRGCGGRFLNAKKENGDHKEEE-------------------
G1334 (30)  KLS-RCRKPYMHHSRHLHAMRRPRGSGGRFLNTKT------ADAAK-----------------
G927  (34)  KLSSRCRKPYMHHSRHLHALRRPRGSGGRFLNTKSQNLENSGTNAKKG---------------
```

FIG. 4E

| | | | |
|---|---|---|---|
| G2632 | (28) | ————————————————————————————————— | —————————EKSNGHVTQSPSPSSSNS————————— | —————————DQGEAWNGD |
| G926 | (32) | ————————————————————————————————— | —————————EDAGGRDRERGSATNS————————— | —————————SGSEQVETD |
| G3924 | (16) | ————————————————————————————————— | —————————AEPNKGEQNSGYRRIP————————— | —————————PDLQLLQKE |
| G3920 | (8) | ————————————————————————————————— | SDKGNNTRANASTNSPNTQLLFTNNLNLGSSNVSQATVQHMTE |
| G3921 | (22) | ————————————————————————————————— | —————————ASSGSMCSKIIGN————————— | —————————SIISQSGPTCTPSS |
| G4264 | (26) | ————————————————————————————————— | —————————ASSGSLCSKIIAN————————— | —————————SIISQSGPTCTPSS |
| G3922 | (24) | ————————————————————————————————— | —————————ASSGSLCSKIIAN————————— | —————————SIISQSGPTCTPSS |
| G3926 | (18) | ————————————————————————————————— | —————————KPPPASAQSPTGRARTSG————————— | —————————GAVVLGKNLCPENS |
| G3925 | (20) | ————————————————————————————————— | —————————ASDGGTPRLVSAN————————— | —————————GVVFSKHEHSLSS |
| G928 | (10) | TNMSRFEAHMLQNNKDR-SSTTSGSDITSVSD————————— | —————————GADIFGHTEFQFSG |
| G931 | (6) | GNMSRFVLYQLQNSNDCDCSTTSRSDITSASD————————— | —————————SVNLFGHSEFLISD |
| G1363 | (14) | NSPGKFRQMDISRGGVVSSVSTTSCSDITGNN————————— | —————————NDMFQQNPQFRFSG |
| G1782 | (12) | MSP——————HGGGSGIGSSSISPSSNSNCIN————————— | —————————MFQ—NPQFRFSG |
| G2344 | (4) | ————————————————————————————————— | —————————————SSHEE————————— | —————————KSNLSAGKSAMAAS |
| G929 | (2) | ————————————————————————————————— | —————————EATSDENTSEA————————— | —————————SSSLRSEKLAMATS |
| G1334 | (30) | ————————————————————————————————— | —————————QSKP———SNSQS————————— | —————————SEVFHPENETINSS |
| G927 | (34) | ————————————————————————————————— | DGSMQIQSQPKPQQSNSQN————————— | —————————SEVVHPENGTMNLS |

FIG. 4F

| | | |
|---|---|---|
| G2632 | (28) | YRTPQGDEMQSSAYKRREEGECSGQQWNSLSSNHPSQARLAIK---------- |
| G926  | (32) | ----------------------SNETLN--SSGAP------------------ |
| G3924 | (16) | T---------------------------------------------------- |
| G3920 | (8)  | QSFTIGYHNGNGLTALYRSQANGKKEGNCFGKERDPNGDFK------------- |
| G3921 | (22) | GTAGASTAS-QDRSCLPSVGFRPTTNFSDQGRGGLKLAVIGMQQRVSTIR---- |
| G4264 | (26) | GTAGASTAG-QDRSCLPSVGFRPTTNFSDQGRGGLKLAVIGMQQRVSTIR---- |
| G3922 | (24) | DTAGLQQPA-RTAAACPRWASAPQP---------TSVSKVEAARSWS------ |
| G3926 | (18) | TSCSPSTPTGSEISSISFGGGMLAHQEHISFASADRHPTMNQNHRVPVMR---- |
| G3925 | (20) | ----------SDLHHRAKEGA-------------------------------- |
| G928  | (10) | FPTPINRAMLVHGQSNDMHGGGDMHHFSVHI---------------------- |
| G931  | (6)  | CPSQTNPTMYVHGQSNDMHGGRNTHHFSVHI---------------------- |
| G1363 | (14) | YPSNHHVSVLM------------------------------------------ |
| G1782 | (12) | YPSTHHASALMSGT--------------------------------------- |
| G2344 | (4)  | --SGTS----------------------------------------------- |
| G929  | (2)  | GPNGRS----------------------------------------------- |
| G1334 | (30) | REANESNLSDSAVTSMDYFLSSSAYSPGGMVMPIKWN--AAAMDIGCCKLNI   |
| G927  | (34) | ---NGLNVSGSEVTSMNYFLSSPVHSLGGMVMPSKWIAAAAMDNGCCNFKT    |

FIG. 4G

```
G3547   (46)   MDHQGHS----QNPSMGVVGSGAQLAYGSNPYQPGQITG--PPGSVVTSVGTIQSTGQPAG
G3894  (174)   MDQHGNG----QPPGIGVVTSSA--PIYGAPYQANQMAGPSPPAVSAGAIQSPQAAGLAAS
G3892  (175)   MDHHGNG----QPP-----------------------------VSAGAIQSPQAAGLSAS
G489    (52)   MDQQDHG----QSGAMN--------------------------YGTNPYQTNPMSTTAATVA
G714    (48)   MDQQ--G----QSSAMN--------------------------YGSNPYQTNAMTTTPT--
G3542   (50)   MEPSSQPQPVMGVATGGSQAYPP--PAAAYPPQAMVPGAPAVVPPGSQPSAPFPTNPAQL
G3544   (54)   MEPSSQPQPAIGVVAGGSQVYP-----AYRPAATVPTAPAVIPAGSQPAPSFPANPDQL
G3551  (178)   MEPSPQP----MGVAAGGSQVYP----ASAYPPAATVAPA-SVVSAGLQSGQPFPANPGHM
G3552   (42)   MEPSPQP----MGVAAGGSQVYP----ASAYPPAATVAPA-SVVSAGLQSGQPFPANPGHM
G3548   (58)   -----------MGVATG-ASQMAYSSHYPTAPMVASGTPAVAVPSPTQAPAAFS
G3549  (182)   MDKSEQT----QQQQQQQHVMGVAAG-ASQMAYSSHYPTASMVASGTPAVTAPSPTQAPAAFS
G3550   (56)   MDKSEQTQQQQQQQQQHVMGVAAG-ASQMAYSSHYPTASMVASGTPAVTAPSPTQAPAAFS
G483    (44)   MEQSEEG----QQQQQQGVMDYVP---PHAYQ--------------SGP-----------V
G3899  (179)   MDESEEP----QQQEAVIDSAS--QMTYGVPHYHAVGLGVATGTPVVPVSAPTQHPTG-T
G1646   (66)   MDNNNNNNQQPP-----------------------------------PTSVYPPGSAVTTVIPPPP
G715    (60)   MDTNN----QQPP----------------------------------PSAAG--------IPPPP
G3883  (186)   MDSNQQTQS------------------------------------TPYPP---QPPTSA
G3886   (62)   METNNQQQQQQGA--------------------------------QAQSGP---YPVAGA
G3884  (187)   MENN-QQS-------------------------------------AANAA-----A
G3543   (68)   MDNQQLPY-AGQP--------------------------------AAAGAG----APV
G3889   (64)   MDNQPLPYSTGQP--------------------------------PAPG-G----APV
G3909   (40)   MEP-KSTTPPPPP-----------------------------VMGAPIAYPPPPGAAYPAGPY
G3546   (38)   MEP-KSTTPPPPPP----------------------------VLGAPVPYPPAGAYPPPVGPY
G3911   (36)   MDPNKSSTPPPPP-----------------------------VMGAPVAYPPP-AYPPGVAAG
G1818   (76)   MENNNNNH---------------------------------------
G1836   (72)   MENNNGNN---------------------------------------
G1819   (74)   MEENNGNNNHYLP------------------------------QPSSS
G1820   (70)   MAENNNNNGDNMN------------------------------NDNHQ
G490    (78)   MRRPKSSHVRMEP------------------------------VAPRSHN
G1249   (82)   ---------------KIALAVPVLVSKSLELFLQDLCDRTYE
G3074   (80)   MRKKLDTRFPAARIKKIMQADEDVG------
G3075   (84)   MVSSKKPKEKKARSDVVVNKASG--------RSKRSSGSRTKKTSNKVNIVKKPEIYE
```

FIG. 5A

```
                                                                              conserved domain
G3547  (46)  -AQLGQHQLAYQHIHQQQQHQ----------------------LQQQLQQFWSSQYQEIEKVT--DFKNHSLP
G3894 (174)  SAQMAQHQLAYQHIHQQQQQQ----------------------LQQQLQTFWANQYQEIEHVT--DFKNHSLP
G3892 (175)  SAQMAQHQLAYQHIHQQQQQQ----------------------LQQQLQTFWANQYQEIEHVT--DFKNHSLP
G489   (52)  GGAAQPGQLAFHQIHQQQQQQ----------------------LAQQLQAFWENQFKEIEKTT--DFKKHSLP
G714   (48)  -GSDHP---AYHQIHQQQQQQ----------------------LTQQLQSFWETQFKEIEKTT--DFKNHSLP
G3542  (50)  SAQHQLVYQQAQQFHQQL-QQQ---------------------QQQQLREFWANQMEEIEQTT--DFKNHSLP
G3544  (54)  SAQHQLVYQQAQQFHQQL-QQQ---------------------QQRQLQQFWAERLVDIEQTT--DFKNHSLP
G3551 (178)  SAQHQIVYQQAQQFHQQL-QQQ---------------------QQQQLQQFWVERMTEIEATT--DFKNHNLP
G3552  (42)  SAQHQIVYQQAQQFHQQL-QQQ---------------------QQQQLQQFWVERMTEIEATT--DFKNHNLP
G3548  (58)  SSAHQLAYQQAQHFHHQQ-QQH---------------------QQQQLQMFWSNQMQEIEQTI--DFKNHSLP
G3549 (182)  SSAHQLAYQQAQHFHHQQ-QQH---------------------QQQQLQMFWSNQMQEIEQTI--DFKNHQLP
G3550  (56)  SSAHQLAYQQAQHFHHQQ-QQH---------------------QQQQLQMFWSNQMQEIEQTI--DFKNHQLP
G483   (44)  NAASHMAFQQAHHFHHHH-QQQ---------------------QQQQLQMFWANQMQEIEHTT--DFKNHTLP
G3899 (179)  TSQQQPEYYEAQHVYQQQ-QLQ---------------------LRTQLQAFWANQIQEIGQTP--DFKNHSLP
G1646  (66)  SGSASIVTGGGATYHHLLQQQQ---------------------QQLQMFWTYQRQEIEQVN--DFKNHQLP
G715   (60)  PGTTISAAGGGASYHHLLQQQQ---------------------QQLQLFWTYQRQEIEQVN--DFKNHQLP
G3883 (186)  ITPPSSATATAPPFHHLLQQQQ---------------------QQLQMFWSYQRQEIEQVN--DFKNHQLP
G3886  (62)  GGSAGAGAGAPPPFQHLLQQQQ---------------------QQLQMFWSYQRQEIEHVN--DFKNHQLP
G3884 (187)  AAAAAAAYPAQPPYHHLLQQQQ---------------------QQLQMFWTYQRQEIEQVN--DFKNHQLP
G3543  (68)  PGVPGAGGPPAVPHHHLLQQQ----------------------AQLQAFWAYQRQEAERASAS DFKNHQLP
G3889  (64)  AGMPGAAGLPPVPHHHLLQQQ----------------------AQLQAFWAYQRQEAERASAS DFKNHQLP
G3909  (40)  VHAPAAALYPPPPLPPAPPSSQQGAA------------------AAHQQQLFWAEQYREIEATT--DFKNHNLP
G3546  (38)  AHAPP---LYAPPPPAAAAASAAATAASQQAAAAQLQNFWAEQYREIHTT--DFKNHNLP
G3911  (36)  AGAYPPQLYAPP---AAAAAQQAAAA-----------------QQQQIFWAEQYREIEATT--DFKNHNLP
G1818  (76)  ------QQPPKDNE--------------------------------QLKSFWSKG---MEGDL--NVKNHEFP
G1836  (72)  ------QLPPKGNE--------------------------------QLKSFWSKE---MEGNL--DFKNHDLP
G1819  (74)  QLPPPPLYYQSMPLPSYSLPLP-----------------------YSPQMRNYWIAQ---MGNAT--DVKHHAFP
G1820  (70)  Q----PPSYSQLPPMASS----------------------------NPQLRNYWIEQ---METVS--DFKNRQLP
G490   (78)  TMPMLDQFRSNHPETSKIEGVSS-----------------------LDTALKVFWNNQREQLGNFAG----QTHLP
G1249  (82)  --------------------------------------------------------MEEEE--GSIRPEFP
G3074  (80)  ITLERGAKTVSSLHLKHCVERYNVFDFLREVVSKVPDYGHSQGQHGDVTMDDRSISKRR
G3075  (84)  ISESSSSDSVEEAIRGDEAKKSNGVVSKRGNGKSVGIPTKTSKNREEDDGGAEDAKIKFP
```

```
                    conserved domain
G3547   (46)   -------------NDIAAAITRID-IFDFLVDIVPR----EDLKDEVLAS-------IPRGTMPVAG
G3894  (174)   -------------NDIAAAITRID-IFDFLVDIVPR----EDLKDEVLAT-------IPRGTLPVGG
G3892  (175)   -------------NDIAAAITRID-IFDFLVDIVPR----EDLKDEVLAT-------IPRGTLPVGG
G489    (52)   -------------NDIAAAVTRID-IFDFLVDIVPR----EDLKDEVLAT-------IPRGTVPEAA
G714    (48)   -------------NDIAAAVTRID-IFDFLVDIVPR----EDLRDEVLGS-------VG---AEAAT
G3542   (50)   -------------NDIAAAITRID-IFDFLVDIVPR----EDLRDEVLGG-------LPRVGLPPNV
G3544   (54)   -------------NDIAAAITRID-IYDFLVDIVPR----DEMKEEGLG-------LPRAGLPP-L
G3551  (178)   -------------NDIAAAITRID-MYDFLVDIVPR----DDLKEEGVG-------LPRAGLPP-M
G3552   (42)   -------------NDIAAAITRID-IYDFLVDIVPR----DEMKEDGIG-------LPRAGLPP-M
G3548   (58)   -------------NDIAAAISRND-VFDFLVDIIPR----DEMKEDGIG-------LPRAGLPP-M
G3549  (182)   -------------NDIAAAISRND-VFDFLVDIIPR----DELKEEGLG-------ITKATIP-LV
G3550   (56)   -------------NDIAAAISRND-VFDFLVDIIPR----DELKEEGLG-------ITKATIP-LV
G483    (44)   -------------NDIAAAISRTD-VFDFLVDIIPR----DELKEEGLG-------ITKATIP-LV
G3899  (179)   -------------NDIAAAISRTD-IFDFLVDIIPR----DELKEEGLG-------VTKGTIPSVV
G1646   (66)   -------------NDIAAAITRID-IFDFLVDIVPR----EEIKEEED-------ITKATIPLLG
G715    (60)   -------------NDIAAAITRID-IFDFLVDIVPR----DEIK----D-------AASALGGGMV
G3883  (186)   -------------NDIAAAITRID-IFDFLVDIVPR----DEIKDETG-------EAAVLGGGMVV
G3886   (62)   -------------NDIAAAITRID-IFDFLVDIVPR----DEIKDD-------LAPMVG-------
G3884  (187)   -------------KDVAAAIARTD-VFDFLVDIVPR----DEIKEGG-------AALVG-------
G3543   (68)   -------------NDVAAAIARTD-VFDFLVDIVPR----EEAKEEPGSALGFAAGGPAGP-VGLGPAGIV
G3889   (64)   -------------SDIAAAVARTE-VFDFLVDIVPR----EEAKEEPGSALGFAAPG-TGVVGAGAPG
G3909   (40)   -------------SDIAAAIARTE-VFDFLVDIVPR----DEAKDADS-------A
G3546   (38)   -------------SDIAAAIARTE-VFDFLVDIVPR----DEAKDAEA-------A
G3911   (36)   -------------SDVDAVVSQTV-IFDFLRDDVPKDEGEPVVAAADPVD------AA
G1818   (76)   -------------SNVDAAVAQTV-IFDFLLDDDIEVKRESVAAAADP-------DVADHVAVP
G1836   (72)   SDTLTRSDISAATTRSF-KFTFLGDVVPR----DPSVVTDDP-------VAMP
G1819   (74)   -------------SDISNAVASSF-TYDFLLDVVPK----DESIATADPG-------VL
G1820   (70)   -------------CDIFQAVKNSG-TYDFLIDRVPFG-PHCVTHQGVQP-------FVAMP
G490    (78)   -------------CDIFQAVKNSG-TYDFLIDRVPFG-PHCVTHQGVQP-------PAEM
G1249   (82)   -------------DHLRIAVKRHQPTSDFLLDSLPLP-AQPVKHTKSVS-------
G3074   (80)   -------------EMEVEAANSGQPPPEDNVKMHASESSPQEDEKKGIDG-------TAASNEDTKQHL
G3075   (84)   -------------KHLSSVVSNDQ-RYEFLADSVPEKLKAEAALEEWER-------
```

FIG. 5E

| Sequence | Position | Residues |
|---|---|---|
| G3547 | (46) | Q-----------MWPQPPDQRQSSPEH-------- |
| G3894 | (174) | P-----------IWPQQQQPPSDS----------- |
| G3892 | (175) | P-----------IWPQQQQPPSDS----------- |
| G489 | (52) | P-----------MWQQQAPDQPDQEN--------- |
| G714 | (48) | P-----------MWQQPGPEQQDPDN--------- |
| G3542 | (50) | E-----------EAPEEQHSLPESS---------- |
| G3544 | (54) | E-----------EPPAEQQSD-------------- |
| G3551 | (178) | E-----------QAPEEQQSA-------------- |
| G3552 | (42) | E-----------QAPEEQQSA-------------- |
| G3548 | (58) | Q-----------QPPQHQQTDS------------- |
| G3549 | (182) | Q-----------QPPQHQQTDS------------- |
| G3550 | (56) | Q-----------QPPQHQQTDS------------- |
| G483 | (44) | Q-----------HPDES------------------ |
| G3899 | (179) | H-----------KDQE--ENGD------------- |
| G1646 | (66) | SVWQNSAGGGDDVSYGSGGSSGHGNLDSQG----- |
| G715 | (60) | SVWQTSTGTGDDVSYGSGGSSGQGNLDGQG----- |
| G3883 | (186) | SVWQTAG---TDDGSYGSGVTGGQGNLDGQG---- |
| G3886 | (62) | SVWQSA----AEDASYGTGPAGAQRSLDGQS---- |
| G3884 | (187) | SVWQTA----EDNSYASGGSSGQGNLDGQS----- |
| G3543 | (68) | GSFSEEGQQGFAGHGGAAASFPPAPPSSESIWFHACIAEVLASYYSCSNQMLNVSVINCG |
| G3889 | (64) | GSFSEEGQ-GFGAGHGGAASFPPAPPTSE------ |
| G3909 | (40) | ---------------------------------- |
| G3546 | (38) | ---------------------------------- |
| G3911 | (36) | ---------------------------------- |
| G1818 | (76) | DAT---------GANGGN--GGN------------ |
| G1836 | (72) | EAR---------GKKGGD-DGN------------- |
| G1819 | (74) | EAA---------GEIGGSSGGN------------- |
| G1820 | (70) | DDA---------EDNGGNGGGN------------- |
| G490 | (78) | ---------------------------------- |
| G1249 | (82) | ---------------------------------- |
| G3074 | (80) | MDPAQLASLGKRIDEDEEDYDEEG----------- |
| G3075 | (84) | ---------------------------------- |

FIG. 5F

| | |
|---|---|
| G3547 | (46) |
| G3894 | (174) |
| G3892 | (175) |
| G489 | (52) |
| G714 | (48) |
| G3542 | (50) |
| G3544 | (54) |
| G3551 | (178) |
| G3552 | (42) |
| G3548 | (58) |
| G3549 | (182) |
| G3550 | (56) |
| G483 | (44) |
| G3899 | (179) |
| G1646 | (66) |
| G715 | (60) |
| G3883 | (186) |
| G3886 | (62) |
| G3884 | (187) TYLNRCTWTLKLIKGCTIY |
| G3543 | (68) |
| G3889 | (64) |
| G3909 | (40) |
| G3546 | (38) |
| G3911 | (36) |
| G1818 | (76) |
| G1836 | (72) |
| G1819 | (74) |
| G1820 | (70) |
| G490 | (78) |
| G1249 | (82) |
| G3074 | (80) |
| G3075 | (84) |

FIG. 5G

SEQUENCE LISTING

<160> NUMBER OF SEQ ID NOS: 216

<210> SEQ ID NO 1
<211> LENGTH: 953
<212> TYPE: DNA
<213> ORGANISM: Arabidopsis thaliana

<220> FEATURE:
<223> OTHER INFORMATION: G929

<400> SEQUENCE: 1

```
ggagagacct ttaacaattt tctgagggta agatccagag attgattgaa tcagcttact    60
attttatata attcagtttg ttgttcctca gacttgtaac taggacagtc ttctcatgaa   120
tcatgacttc ttcagtacat gagctctctg ataacaatga aagtcatgcg aagaaagaac   180
gtccagattc ccaaacccga ccacaggttc cttcaggacg aagttcggaa tctattgata   240
caaactctgt ctactcagag cccatggcac atggattata cccgtatcca gatccttact   300
acagaagcgt ctttgcacag caagcgtatc ttccacatcc ctatcctggg gtccaattgc   360
agttaatggg aatgcagcag ccaggagttc cattgcaatg tgatgcagtc gaggaacctg   420
tttttgttaa cgcaaagcaa taccatggta tactcaggcg caggcaatcc cgggcaaaac   480
ttgaggcacg aaatagagcc atcaaagcaa aaagccata catgcatgaa tctcggcatt   540
tacatgcgat aagacggcca agaggatgtg gtggccggtt tctcaatgcc aagaaggaaa   600
atggagacca aaggaggag gaggaggcaa cctctgatga aacacttca gaagcaagtt   660
ccagcctcag gtccgagaaa ttagctatgg ctacttctgg tcctaatggt agatcttgag   720
gaaggtttct gcacaaccac aagtttagtt tctattttgg gtggatgttc tcagggcatc   780
atcgtcttta tgttttttgg atacgctgtg tacaggttat ttgctagggt aaactttgtt   840
ttagcgatta gaaataaaac taagcaaaga atgaaaagt gtgattggaa gtattgttgt   900
accaaattga tattctttgc caatgaactc atgttttgga aagtaaaaaa aaa           953
```

<210> SEQ ID NO 2
<211> LENGTH: 198
<212> TYPE: PRT
<213> ORGANISM: Arabidopsis thaliana
<220> FEATURE:
<223> OTHER INFORMATION: G929 polypeptide (domain in aa coordinates: 98-157)

<400> SEQUENCE: 2

```
Met Thr Ser Ser Val His Glu Leu Ser Asp Asn Asn Glu Ser His Ala
1               5                   10                  15

Lys Lys Glu Arg Pro Asp Ser Gln Thr Arg Pro Gln Val Pro Ser Gly
            20                  25                  30

Arg Ser Ser Glu Ser Ile Asp Thr Asn Ser Val Tyr Ser Glu Pro Met
        35                  40                  45

Ala His Gly Leu Tyr Pro Tyr Pro Asp Pro Tyr Tyr Arg Ser Val Phe
    50                  55                  60

Ala Gln Gln Ala Tyr Leu Pro His Pro Tyr Pro Gly Val Gln Leu Gln
65                  70                  75                  80

Leu Met Gly Met Gln Gln Pro Gly Val Pro Leu Gln Cys Asp Ala Val
                85                  90                  95

Glu Glu Pro Val Phe Val Asn Ala Lys Gln Tyr His Gly Ile Leu Arg
            100                 105                 110

Arg Arg Gln Ser Arg Ala Lys Leu Glu Ala Arg Asn Arg Ala Ile Lys
        115                 120                 125

Ala Lys Lys Pro Tyr Met His Glu Ser Arg His Leu His Ala Ile Arg
    130                 135                 140

Arg Pro Arg Gly Cys Gly Gly Arg Phe Leu Asn Ala Lys Lys Glu Asn
145                 150                 155                 160
```

```
Gly Asp His Lys Glu Glu Glu Ala Thr Ser Asp Glu Asn Thr Ser
                165                 170                 175

Glu Ala Ser Ser Ser Leu Arg Ser Glu Lys Leu Ala Met Ala Thr Ser
            180                 185                 190

Gly Pro Asn Gly Arg Ser
        195

<210> SEQ ID NO 3
<211> LENGTH: 573
<212> TYPE: DNA
<213> ORGANISM: Arabidopsis thaliana
<220> FEATURE:
<223> OTHER INFORMATION: G2344

<400> SEQUENCE: 3
atgacttctt caatccatga gctttctgat aacattggaa gtcatgagaa gcaagaacag      60
agagattctc atttccaacc accaatccct tctgcaagaa attatgaatc aattgttaca     120
agtttagtct actcagaccc ggggactaca aattccatgg cacctggaca atatccatat     180
ccagatcctt actacagaag catatttgca ccgcctccac aaccgtatac cggggtacat     240
ctacagttga tgggagtgca gcaacaaggc gttcctttac catctgatgc agtcgaggaa     300 cctgttttg ttaacgcaaa gcaataccac ggtatactaa ggcgcagaca atcaagagca      360
agacttgagt ctcagaataa agtcatcaag tcacgtaagc cgtatttgca tgaatctcgg     420
catttgcatg cgataagacg accaagagga tgtggcgggc ggtttctaaa tgccaagaag     480
gaggatgagc atcacgaaga cagtagtcat gaagaaaaat ccaaccttag cgctggtaaa     540
tccgccatgg ctgcttctag tggtacatct tga                                 573

<210> SEQ ID NO 4
<211> LENGTH: 190
<212> TYPE: PRT
<213> ORGANISM: Arabidopsis thaliana
<220> FEATURE:
<223> OTHER INFORMATION: G2344 polypeptide (domain in aa coordinates:
      100-159)

<400> SEQUENCE: 4

Met Thr Ser Ser Ile His Glu Leu Ser Asp Asn Ile Gly Ser His Glu
1               5                   10                  15

Lys Gln Glu Gln Arg Asp Ser His Phe Gln Pro Pro Ile Pro Ser Ala
            20                  25                  30

Arg Asn Tyr Glu Ser Ile Val Thr Ser Leu Val Tyr Ser Asp Pro Gly
        35                  40                  45

Thr Thr Asn Ser Met Ala Pro Gly Gln Tyr Pro Tyr Pro Asp Pro Tyr
    50                  55                  60

Tyr Arg Ser Ile Phe Ala Pro Pro Gln Pro Tyr Thr Gly Val His
65                  70                  75                  80

Leu Gln Leu Met Gly Val Gln Gln Gln Gly Val Pro Leu Pro Ser Asp
                85                  90                  95

Ala Val Glu Glu Pro Val Phe Val Asn Ala Lys Gln Tyr His Gly Ile
            100                 105                 110

Leu Arg Arg Arg Gln Ser Arg Ala Arg Leu Glu Ser Gln Asn Lys Val
        115                 120                 125

Ile Lys Ser Arg Lys Pro Tyr Leu His Glu Ser Arg His Leu His Ala
    130                 135                 140

Ile Arg Arg Pro Arg Gly Cys Gly Gly Arg Phe Leu Asn Ala Lys Lys
145                 150                 155                 160
```

Glu Asp Glu His His Glu Asp Ser Ser His Glu Glu Lys Ser Asn Leu
                165                 170                 175

Ser Ala Gly Lys Ser Ala Met Ala Ala Ser Ser Gly Thr Ser
            180                 185                 190

<210> SEQ ID NO 5
<211> LENGTH: 1180
<212> TYPE: DNA
<213> ORGANISM: Arabidopsis thaliana
<220> FEATURE:
<223> OTHER INFORMATION: G931

<400> SEQUENCE: 5

```
ggaggttctt tgacagacac atgtatcatc aatcttctct gttgaagcag agagagagag      60
agctaattgt tgcctctgag tcacatggat aagaaagttt catttactag ctctgtggca     120
cattcaactc caccatacct tagtacttcc atctcatggg gacttccaac caaatccaat     180
ggtgtgactg aatcactgag tttgaaggtg gtagatgcaa gaccagaacg tcttataaac     240
acaaagaata tcagtttcca ggaccaggat tcatcttcaa ctctgtcctc tgctcaatct     300
tctaacgatg ttacaagtag tggagatgat aaccccctcaa gacaaatctc attttagca     360
cattcagatg tttgtaaagg atttgaagaa actcaaagga agcgatttgc aattaaatca     420
ggctcctcca cggcaggaat cgctgatatt cactcttctc cttccaaggc taacttctca     480
tttcactatg ccgatccaca ttttggtggt ttaatgcctg cggcttacct accacaggca     540
acaatatgga atccccaaat gactcgagtt ccgctaccat tcgatctcat agagaatgag     600
cctgtctttg tcaatgcaaa gcaattccat gcaattatga ggaggaggca acagcgtgct     660
aagctagagg cgcaaaacaa actaatcaaa gcccgtaagc cgtatcttca tgaatctcga     720
catgttcacg ctcttaaacg acctagagga tctggtggaa gattcctaaa caccaaaaag     780
cttcaagaat ctacagatcc aaaacaagac atgccaatcc aacagcaaca cgcaacggga     840
aacatgtcaa gatttgtgct ttatcagttg cagaacagca atgactgtga ttgttcaacc     900
acttctcgct ctgacatcac atctgcttct gacagcgtta atctctttgg acactctgaa     960
tttctgatat cagattgccc atctcagaca aacccaacaa tgtatgttca tggtcaatca    1020
aatgacatgc atggaggtag gaacacacac catttctctg tccatatctg agccggtgga    1080
atctggtaat gtgtacgttc ctacaaaaaa agggaagtca tccttggctg ctacttcgct    1140
tattagctag ttcttatttc acacgctttg tccagatatc                          1180
```

<210> SEQ ID NO 6
<211> LENGTH: 328
<212> TYPE: PRT
<213> ORGANISM: Arabidopsis thaliana
<220> FEATURE:
<223> OTHER INFORMATION: G931 polypeptide (domain in aa coordinates:
      172-231)

<400> SEQUENCE: 6

Met Asp Lys Lys Val Ser Phe Thr Ser Ser Val Ala His Ser Thr Pro
1               5                   10                  15

Pro Tyr Leu Ser Thr Ser Ile Ser Trp Gly Leu Pro Thr Lys Ser Asn
            20                  25                  30

Gly Val Thr Glu Ser Leu Ser Leu Lys Val Val Asp Ala Arg Pro Glu
        35                  40                  45

Arg Leu Ile Asn Thr Lys Asn Ile Ser Phe Gln Asp Gln Asp Ser Ser
    50                  55                  60

Ser Thr Leu Ser Ser Ala Gln Ser Ser Asn Asp Val Thr Ser Gly
65                  70                  75                  80

Asp Asp Asn Pro Ser Arg Gln Ile Ser Phe Leu Ala His Ser Asp Val
                85                  90                  95

Cys Lys Gly Phe Glu Glu Thr Gln Arg Lys Arg Phe Ala Ile Lys Ser
            100                 105                 110

Gly Ser Ser Thr Ala Gly Ile Ala Asp Ile His Ser Ser Pro Ser Lys
        115                 120                 125

Ala Asn Phe Ser Phe His Tyr Ala Asp Pro His Phe Gly Gly Leu Met
130                 135                 140

Pro Ala Ala Tyr Leu Pro Gln Ala Thr Ile Trp Asn Pro Gln Met Thr
145                 150                 155                 160

Arg Val Pro Leu Pro Phe Asp Leu Ile Glu Asn Glu Pro Val Phe Val
                165                 170                 175

Asn Ala Lys Gln Phe His Ala Ile Met Arg Arg Gln Gln Arg Ala
            180                 185                 190

Lys Leu Glu Ala Gln Asn Lys Leu Ile Lys Ala Arg Lys Pro Tyr Leu
        195                 200                 205

His Glu Ser Arg His Val His Ala Leu Lys Arg Pro Arg Gly Ser Gly
210                 215                 220

Gly Arg Phe Leu Asn Thr Lys Lys Leu Gln Glu Ser Thr Asp Pro Lys
225                 230                 235                 240

Gln Asp Met Pro Ile Gln Gln His Ala Thr Gly Asn Met Ser Arg
            245                 250                 255

Phe Val Leu Tyr Gln Leu Gln Asn Ser Asn Asp Cys Asp Cys Ser Thr
        260                 265                 270

Thr Ser Arg Ser Asp Ile Thr Ser Ala Ser Asp Ser Val Asn Leu Phe
        275                 280                 285

Gly His Ser Glu Phe Leu Ile Ser Asp Cys Pro Ser Gln Thr Asn Pro
    290                 295                 300

Thr Met Tyr Val His Gly Gln Ser Asn Asp Met His Gly Gly Arg Asn
305                 310                 315                 320

Thr His His Phe Ser Val His Ile
                325

<210> SEQ ID NO 7
<211> LENGTH: 956
<212> TYPE: DNA
<213> ORGANISM: Glycine max
<220> FEATURE:
<223> OTHER INFORMATION: G3920

<400> SEQUENCE: 7
agttggtgct aagatgccag ggaaacctga cactgatgat tggcgtgtag agcgtgggga      60
gcagattcag tttcagtctt ccatttactc tcatcatcag ccttggtggc gcggagtggg     120
ggaaaatgcc tccaaatcat cttcagatga tcagttaaat ggttcaatcg tgaatggtat     180
cacgcggtct gagaccaatg ataagtcagg cggaggtgtt gccaaagaat accaaaacat     240
caaacatgcc atgttgtcaa ccccatttac catggagaaa catcttgctc caaatcccca     300
gatggaactt gttggtcatt cagttgtttt aacatctcct tattcagatg cacagtatgg     360
tcaaatcttg actacttacg ggcaacaagt tatgataaat cctcagttgt atggaatgca     420
tcatgctaga atgcctttgc cacttgaaat ggaagaggag cctgtttatg tcaatgcgaa     480
gcagtatcat ggtatttttga ggcgaagaca gtcacgtgct aaggctgaga ttgaaaagaa     540

```
agtaatcaaa acaggaagc catacctcca tgaatcccgt caccttcatg caatgagaag    600
ggcaagaggc aacggtggtc gctttctcaa cacaaagaag cttgaaaata caattctaa    660 ttccacttca gacaaaggca acaatactcg tgcaaacgcc tcaacaaact cgcctaacac    720
tcaacttttg ttcaccaaca atttgaatct aggctcatca aatgtttcac aagccacagt    780
tcagcacatg cacacagagc agagtttcac tataggttac cataatggaa atggtcttac    840
agcactatac cgttcacaag caaatgggaa aaggaggga aactgctttg gtaaagagag    900
ggaccctaat ggggatttca ataacactt ccctcagcca tacagcaaga gttagg        956
```

<210> SEQ ID NO 8
<211> LENGTH: 303
<212> TYPE: PRT
<213> ORGANISM: Glycine max
<220> FEATURE:
<223> OTHER INFORMATION: G3920 polypeptide (domain in aa coordinates: 149-208)

<400> SEQUENCE: 8

```
Met Pro Gly Lys Pro Asp Thr Asp Asp Trp Arg Val Glu Arg Gly Glu
1               5                   10                  15

Gln Ile Gln Phe Gln Ser Ser Ile Tyr Ser His His Gln Pro Trp Trp
            20                  25                  30

Arg Gly Val Gly Glu Asn Ala Ser Lys Ser Ser Asp Asp Gln Leu
        35                  40                  45

Asn Gly Ser Ile Val Asn Gly Ile Thr Arg Ser Glu Thr Asn Asp Lys
    50                  55                  60

Ser Gly Gly Gly Val Ala Lys Glu Tyr Gln Asn Ile Lys His Ala Met
65                  70                  75                  80

Leu Ser Thr Pro Phe Thr Met Glu Lys His Leu Ala Pro Asn Pro Gln
                85                  90                  95

Met Glu Leu Val Gly His Ser Val Val Leu Thr Ser Pro Tyr Ser Asp
            100                 105                 110

Ala Gln Tyr Gly Gln Ile Leu Thr Thr Tyr Gly Gln Gln Val Met Ile
        115                 120                 125

Asn Pro Gln Leu Tyr Gly Met His His Ala Arg Met Pro Leu Pro Leu
    130                 135                 140

Glu Met Glu Glu Pro Val Tyr Val Asn Ala Lys Gln Tyr His Gly
145                 150                 155                 160

Ile Leu Arg Arg Arg Gln Ser Arg Ala Lys Ala Glu Ile Glu Lys Lys
                165                 170                 175

Val Ile Lys Asn Arg Lys Pro Tyr Leu His Glu Ser Arg His Leu His
            180                 185                 190

Ala Met Arg Arg Ala Arg Gly Asn Gly Gly Arg Phe Leu Asn Thr Lys
        195                 200                 205

Lys Leu Glu Asn Asn Asn Ser Asn Ser Thr Ser Asp Lys Gly Asn Asn
    210                 215                 220

Thr Arg Ala Asn Ala Ser Thr Asn Ser Pro Asn Thr Gln Leu Leu Phe
225                 230                 235                 240

Thr Asn Asn Leu Asn Leu Gly Ser Ser Asn Val Ser Gln Ala Thr Val
                245                 250                 255

Gln His Met His Thr Glu Gln Ser Phe Thr Ile Gly Tyr His Asn Gly
            260                 265                 270

Asn Gly Leu Thr Ala Leu Tyr Arg Ser Gln Ala Asn Gly Lys Lys Glu
        275                 280                 285
```

```
Gly Asn Cys Phe Gly Lys Glu Arg Asp Pro Asn Gly Asp Phe Lys
        290                 295                 300
```

```
<210> SEQ ID NO 9
<211> LENGTH: 1516
<212> TYPE: DNA
<213> ORGANISM: Arabidopsis thaliana
<220> FEATURE:
<223> OTHER INFORMATION: G928

<400> SEQUENCE: 9
ctcatggcga tgttggtttc ccaggaaagg taaaagagac ggagacgaac caaaacaagg      60
aagaaagaag aagatcttac atacgaagat cactctctga ttcactctga gagacaaact     120
ggtttacttt ggttctgttt gacaaaagga gacatgcaaa aataaatctc tatcccttgt     180
ttttcttctt cgcttcatcg attactcaaa gaggttgttg ttgtgagaa taattagctt      240 gttaaggaag acgttatgat gcatcagatg ttgaataaga aagattcagc tactcattcc     300
actttgccat accttaatac tagcatctct tggggagtgg ttccaactga ttccgttgct     360
aatcgtcgcg gtcctgctga atcactaagc ttgaaggttg attcaagacc tgggcatata     420
caaactacaa agcaaatcag ttttcaggac caagattcat cttcaacaca gtccactggt     480
caatcttata ctgaagttgc tagtagtggt gatgataatc cttccagaca aatctccttt     540
tcggctaaat caggatctga ataactcaa cggaaggggt ttgcaagtaa tcctaaacaa      600
ggctcgatga ctggatttcc gaatattcac tttgctcctg cacaggctaa tttctcattt     660
cactatgctg atccacatta tggtggttta ttagctgcaa cttacctacc acaggcacca     720
acatgcaatc tcaaatggt gagtatgatt cctggtcgtg ttcctttacc agcagagctc      780
acagaaactg atccagtctt tgtcaatgcg aagcaatacc acgcaattat gaggaggaga     840
cagcaacgtg ctaagcttga ggctcaaaac aaactaatca gagcccgtaa gccctatctt     900
catgagtctc gacatgttca tgctcttaaa aggccaagag gatctggtgg aagattccta     960
aacaccaaaa aacttcttca gaatccgaa caggctgctg ctagagaaca agaacaggac    1020
aagttaggcc aacaggtaaa cagaaagacc aacatgtcta gattcgaagc tcatatgctg    1080
cagaacaaca aagaccgcag ctcaaccact tctggctcag acatcacctc tgtttccgac    1140
ggtgctgata tctttggaca cactgaattc cagttttcag gtttcccaac tccgataaac    1200
cgagccatgc ttgttcatgg tcagtctaat gacatgcatg gaggtggaga catgcaccat    1260
ttctctgtcc atatctgaga cagtggatct tggtgctgtg ttcatgttcc caccaagaag    1320
gggaagtcat ccttggctac tactagttct ttcgcttgtt gtaacttcag tgtttttatt    1380
tcatattatg tctgtgttag acatcacaag aacgaccaag atcttcactt tgaaacactc    1440
tattaccttt tcatcttctg ttaccatgga tctcttgtct aaactagtga tatgattctt    1500
ctgataaaaa aaaaaa                                                    1516
```

```
<210> SEQ ID NO 10
<211> LENGTH: 340
<212> TYPE: PRT
<213> ORGANISM: Arabidopsis thaliana
<220> FEATURE:
<223> OTHER INFORMATION: G928 polypeptide (domain in aa coordinates:
      179-238)

<400> SEQUENCE: 10

Met Met His Gln Met Leu Asn Lys Lys Asp Ser Ala Thr His Ser Thr
1               5                   10                  15
```

```
Leu Pro Tyr Leu Asn Thr Ser Ile Ser Trp Gly Val Val Pro Thr Asp
         20                  25                  30

Ser Val Ala Asn Arg Arg Gly Pro Ala Glu Ser Leu Ser Leu Lys Val
         35                  40                  45

Asp Ser Arg Pro Gly His Ile Gln Thr Thr Lys Gln Ile Ser Phe Gln
 50                  55                  60

Asp Gln Asp Ser Ser Ser Thr Gln Ser Thr Gly Gln Ser Tyr Thr Glu
 65                  70                  75                  80

Val Ala Ser Ser Gly Asp Asp Asn Pro Ser Arg Gln Ile Ser Phe Ser
                 85                  90                  95

Ala Lys Ser Gly Ser Glu Ile Thr Gln Arg Lys Gly Phe Ala Ser Asn
             100                 105                 110

Pro Lys Gln Gly Ser Met Thr Gly Phe Pro Asn Ile His Phe Ala Pro
         115                 120                 125

Ala Gln Ala Asn Phe Ser Phe His Tyr Ala Asp Pro His Tyr Gly Gly
130                 135                 140

Leu Leu Ala Ala Thr Tyr Leu Pro Gln Ala Pro Thr Cys Asn Pro Gln
145                 150                 155                 160

Met Val Ser Met Ile Pro Gly Arg Val Pro Leu Pro Ala Glu Leu Thr
                165                 170                 175

Glu Thr Asp Pro Val Phe Val Asn Ala Lys Gln Tyr His Ala Ile Met
             180                 185                 190

Arg Arg Arg Gln Gln Arg Ala Lys Leu Glu Ala Gln Asn Lys Leu Ile
         195                 200                 205

Arg Ala Arg Lys Pro Tyr Leu His Glu Ser Arg His Val His Ala Leu
     210                 215                 220

Lys Arg Pro Arg Gly Ser Gly Gly Arg Phe Leu Asn Thr Lys Lys Leu
225                 230                 235                 240

Leu Gln Glu Ser Glu Gln Ala Ala Ala Arg Glu Gln Glu Gln Asp Lys
                245                 250                 255

Leu Gly Gln Gln Val Asn Arg Lys Thr Asn Met Ser Arg Phe Glu Ala
             260                 265                 270

His Met Leu Gln Asn Asn Lys Asp Arg Ser Ser Thr Thr Ser Gly Ser
         275                 280                 285

Asp Ile Thr Ser Val Ser Asp Gly Ala Asp Ile Phe Gly His Thr Glu
     290                 295                 300

Phe Gln Phe Ser Gly Phe Pro Thr Pro Ile Asn Arg Ala Met Leu Val
305                 310                 315                 320

His Gly Gln Ser Asn Asp Met His Gly Gly Gly Asp Met His His Phe
                325                 330                 335

Ser Val His Ile
         340

<210> SEQ ID NO 11
<211> LENGTH: 927
<212> TYPE: DNA
<213> ORGANISM: Arabidopsis thaliana
<220> FEATURE:
<223> OTHER INFORMATION: G1782

<400> SEQUENCE: 11
atgcaagtgt ttcaaaggaa agaagattca tcttggggaa actcaatgcc tacaacaaat      60
tcaaatattc aaggatctga atctttcagc ttgactaagg atatgataat gtctacaaca     120
caattacccg cgatgaaaca ttcgggtttg cagctgcaaa atcaagattc aacctcatca     180
```

```
caatctactg aagaagaatc aggcggcggt gaagttgcaa gctttggaga atataagcgt      240
tatggatgca gcattgttaa taacaatctc tcaggttaca tcgaaaactt gggaaagcct      300
attgaaaatt atactaagtc aattactacc tcgtcgatgg tgtctcaaga ctctgtgttt      360
cctgctccta cttctggtca aatatcttgg tctcttcaat gtgctgaaac gtcacatttc      420
aatggtttct ggctcctga atatgcatca acaccaacgg cgctgccaca tttagagatg       480
atgggtttgg tttcttcaag agtgccattg cctcatcaca ttcaagaaa tgaaccaata       540 tttgtcaatg cgaaacagta tcatgcgatt ctccgtcgca ggaagcaccg tgctaaactc      600
gaagctcaga acaaactcat caaatgccgt aaaccgtacc ttcatgagtc tcgccatctt      660
catgctttaa agagagctag aggctccggt ggacgtttcc tcaatacaaa gaagcttcaa      720
gaatcatcaa actcactgtg ttcttctcaa atggcaaatg acaaaattt ctctatgagc       780 cctcacggtg gtggaagcgg aatcgggtct agttcgatct caccgagctc caattcaaac      840
tgtatcaaca tgttccaaaa cccgcagttc agattctcag gttatccgtc aacacaccat      900
gcctcagctc tcatgtcagg gacttga                                           927
```

<210> SEQ ID NO 12
<211> LENGTH: 308
<212> TYPE: PRT
<213> ORGANISM: Arabidopsis thaliana
<220> FEATURE:
<223> OTHER INFORMATION: G1782 polypeptide (domain in aa coordinates:
      178-237)

<400> SEQUENCE: 12

```
Met Gln Val Phe Gln Arg Lys Glu Asp Ser Ser Trp Gly Asn Ser Met
1               5                   10                  15

Pro Thr Thr Asn Ser Asn Ile Gln Gly Ser Glu Ser Phe Ser Leu Thr
            20                  25                  30

Lys Asp Met Ile Met Ser Thr Thr Gln Leu Pro Ala Met Lys His Ser
        35                  40                  45

Gly Leu Gln Leu Gln Asn Gln Asp Ser Thr Ser Ser Gln Ser Thr Glu
    50                  55                  60

Glu Glu Ser Gly Gly Gly Glu Val Ala Ser Phe Gly Glu Tyr Lys Arg
65                  70                  75                  80

Tyr Gly Cys Ser Ile Val Asn Asn Asn Leu Ser Gly Tyr Ile Glu Asn
                85                  90                  95

Leu Gly Lys Pro Ile Glu Asn Tyr Thr Lys Ser Ile Thr Thr Ser Ser
            100                 105                 110

Met Val Ser Gln Asp Ser Val Phe Pro Ala Pro Thr Ser Gly Gln Ile
        115                 120                 125

Ser Trp Ser Leu Gln Cys Ala Glu Thr Ser His Phe Asn Gly Phe Leu
    130                 135                 140

Ala Pro Glu Tyr Ala Ser Thr Pro Thr Ala Leu Pro His Leu Glu Met
145                 150                 155                 160

Met Gly Leu Val Ser Ser Arg Val Pro Leu Pro His His Ile Gln Glu
                165                 170                 175

Asn Glu Pro Ile Phe Val Asn Ala Lys Gln Tyr His Ala Ile Leu Arg
            180                 185                 190

Arg Arg Lys His Arg Ala Lys Leu Glu Ala Gln Asn Lys Leu Ile Lys
        195                 200                 205

Cys Arg Lys Pro Tyr Leu His Glu Ser Arg His Leu His Ala Leu Lys
    210                 215                 220
```

```
Arg Ala Arg Gly Ser Gly Gly Arg Phe Leu Asn Thr Lys Lys Leu Gln
225                 230                 235                 240

Glu Ser Ser Asn Ser Leu Cys Ser Ser Gln Met Ala Asn Gly Gln Asn
                245                 250                 255

Phe Ser Met Ser Pro His Gly Gly Gly Ser Gly Ile Gly Ser Ser Ser
            260                 265                 270

Ile Ser Pro Ser Ser Asn Ser Asn Cys Ile Asn Met Phe Gln Asn Pro
        275                 280                 285

Gln Phe Arg Phe Ser Gly Tyr Pro Ser Thr His His Ala Ser Ala Leu
    290                 295                 300

Met Ser Gly Thr
305

<210> SEQ ID NO 13
<211> LENGTH: 1011
<212> TYPE: DNA
<213> ORGANISM: Arabidopsis thaliana
<220> FEATURE:
<223> OTHER INFORMATION: G1363

<400> SEQUENCE: 13
cgtctaccta ctatggtctg gagattagtt cgtttattga actaatgttt tagacaatgc     60
aagagttcca tagtagcaaa gattcattgc cttgtcctgc aacttcttgg gataactctg    120
tcttcaccaa ctcaaatgtc caaggatcat catccttgac cgataacaac actttaagct    180
tgacaatgga gatgaaacaa actggttttc aaatgcagca ctatgattcc tcctctactc    240
aatccactgg aggagaatca tatagtgaag ttgctagctt aagtgaacct actaatcgtt    300
atggccacaa cattgttgtc actcatctct caggttacaa agaaaacccg gaaaatccta    360
ttggaagtca ttcgatatca aaggtgtctc aagattcagt ggttcttcct attgaggcgg    420
cttcttggcc tttacacggc aatgtaacgc cacatttcaa tggtttcttg tcttttcctt    480
atgcatcaca acacacggtg cagcatcctc aaatcagagg gttggttccg tctagaatgc    540 cttttgcctca caacattcca gagaacgaac caattttcgt caatgcaaaa cagtaccaag    600
ccattctccg ccgcagagag cgccgtgcaa agcttgaagc tcagaacaag ctcatcaaag    660
tccgcaaacc atatcttcac gagtcgcggc acctccatgc actaaagaga gttagaggct    720
ctggtggacg tttcctcaac acaaagaagc atcaagaatc aaattcctca ctatctcctc    780
cattcttgat tccacctcat gtcttcaaga actctccagg aaagttccgg caaatggaca    840
tttcaagggg tggggttgtg tctagtgtct cgacaacatc ttgctcggac ataaccggga    900
acaacaacga catgttccag caaaacccac aattcaggtt ctcaggttat ccatcaaacc    960
accatgtctc agtcctcatg tgagagagct cccgcaagtg gtggatgagg c           1011

<210> SEQ ID NO 14
<211> LENGTH: 308
<212> TYPE: PRT
<213> ORGANISM: Arabidopsis thaliana
<220> FEATURE:
<223> OTHER INFORMATION: G1363 polypeptide (domain in aa coordinates:
      171-230)

<400> SEQUENCE: 14

Met Gln Glu Phe His Ser Ser Lys Asp Ser Leu Pro Cys Pro Ala Thr
1               5                   10                  15

Ser Trp Asp Asn Ser Val Phe Asn Ser Asn Val Gln Gly Ser Ser
            20                  25                  30
```

Ser Leu Thr Asp Asn Asn Thr Leu Ser Leu Thr Met Glu Met Lys Gln
            35                  40                  45

Thr Gly Phe Gln Met Gln His Tyr Asp Ser Ser Thr Gln Ser Thr
    50                  55                  60

Gly Gly Glu Ser Tyr Ser Glu Val Ala Ser Leu Ser Glu Pro Thr Asn
65                  70                  75                  80

Arg Tyr Gly His Asn Ile Val Val Thr His Leu Ser Gly Tyr Lys Glu
                85                  90                  95

Asn Pro Glu Asn Pro Ile Gly Ser His Ser Ile Ser Lys Val Ser Gln
            100                 105                 110

Asp Ser Val Val Leu Pro Ile Glu Ala Ala Ser Trp Pro Leu His Gly
            115                 120                 125

Asn Val Thr Pro His Phe Asn Gly Phe Leu Ser Phe Pro Tyr Ala Ser
            130                 135                 140

Gln His Thr Val Gln His Pro Gln Ile Arg Gly Leu Val Pro Ser Arg
145                 150                 155                 160

Met Pro Leu Pro His Asn Ile Pro Glu Asn Glu Pro Ile Phe Val Asn
                165                 170                 175

Ala Lys Gln Tyr Gln Ala Ile Leu Arg Arg Arg Glu Arg Ala Lys
            180                 185                 190

Leu Glu Ala Gln Asn Lys Leu Ile Lys Val Arg Lys Pro Tyr Leu His
            195                 200                 205

Glu Ser Arg His Leu His Ala Leu Lys Arg Val Arg Gly Ser Gly Gly
        210                 215                 220

Arg Phe Leu Asn Thr Lys Lys His Gln Glu Ser Asn Ser Ser Leu Ser
225                 230                 235                 240

Pro Pro Phe Leu Ile Pro Pro His Val Phe Lys Asn Ser Pro Gly Lys
                245                 250                 255

Phe Arg Gln Met Asp Ile Ser Arg Gly Gly Val Val Ser Ser Val Ser
            260                 265                 270

Thr Thr Ser Cys Ser Asp Ile Thr Gly Asn Asn Asp Met Phe Gln
            275                 280                 285

Gln Asn Pro Gln Phe Arg Phe Ser Gly Tyr Pro Ser Asn His His Val
        290                 295                 300

Ser Val Leu Met
305

<210> SEQ ID NO 15
<211> LENGTH: 1959
<212> TYPE: DNA
<213> ORGANISM: Oryza sativa
<220> FEATURE:
<223> OTHER INFORMATION: G3924

<400> SEQUENCE: 15
gactggatcc tgattggcgt tgcggccaat caggatcctg ctggatcctg attggatcct      60
gattggcgtt gcggccgtgt ctctactgtt gttgttgttg tgttttttt ttcttttta      120 ccttttttg ccgccttggt tttgatgcgg agtctggatg tttctacttt tggatggggt      180
ttttttacct tacccgaccg aattcgtggg tggattggat gcggttcatg gaagggaacg      240
ggatcttggt cggctactcg gatgggggt ttgccggccg gttgggattt cgggaaccgg      300
atcgaggaag aggcggagga gaattgatcc gcggcggcgg cggcggagga ggaggagaga      360
atatgtggtg attttcatct gagcccggtt gcagaagtcc aactgtatcg agaatcttta      420

```
ctcggttcgt actacagtcc cccacgctgg tattcaagga atcttctctg gatggaccag    480
ttcttggttg gtcccggttc tttcatgtcc agttccccat ggtggttcag ttggcagttg    540
tgccctagtt gttgtaggag taattgtcgg tggcttaaaa tggttcatgc tcgtcagttc    600
ttccgagcat tccgaggtga gcgagcatgg agtcgaggcc gggggaacc aacctcgtgg     660
agccgagggg gcagggcgcg ctgccgtccg gcataccgat ccagcagccg tggtggacga    720
cctccgccgg ggtcggggcg gtgtcgcccg ccgtcgtggc gccggggagc ggtgcgggga    780
tcagcctgtc gggcagggat ggcggcggcg acgacgcggc agaggagagc agcgatgact    840
cacgaagatc aggggagacc aaagatggaa gcactgatca agaaaagcat catgcaacat    900
cgcagatgac tgctttggca tcagactatt taacaccatt ttcacagctg aactaaaacc    960
aaccaattgc ttcggcagca taccagtacc ctgactctta ctatatgggc atggttggtc    1020
cctatggacc tcaagctatg tccgcacaga ctcatttcca gctacctgga ttaactcact    1080
ctcgtatgcc gttgcctctt gaaatatctg aggagcctgt ttatgtaaat gctaagcaat    1140
atcatggaat tttaagacgg aggcagtcac gtgcgaaggc tgaacttgag aaaaaagttg    1200
ttaaatcaag aaagccctat cttcatgagt ctcgtcatca acatgctatg cgaagggcaa    1260
gaggaacggg tggacgcttc ctgaacacaa agaaaaatga gatggtgct cccagtgaga     1320
aagccgaacc aaacaaagga gagcagaact ccgggtatcg ccggatcct cctgacttac      1380
agctcctaca gaaggaaaca tgaagtagcg gctcgaaacc tagaacagtg gcttctgtcc    1440
accggcattc actcttgagg gtggattctt gctccagaat tgtgctgcca tctttcaaat    1500
gatcttcatc gtgcaaagta attatatgta cattcctctg aatgatctat gcaccaattg    1560
ttgatcctgg cagggtaata atctggatgt attgagtcca tcacagtgcg aatgtcacgg    1620
gtagatctgc tgttttcagg caattcattc ttggctttct atcccacccg ttgttgttgc    1680
aagttaagct agcagtactt gtctcagtgt ccgtgagacg tttgtgtaag attaggttaa    1740
actagaagtt gtaatgctgt attaagtgtt tgtatttcta atatgaaccg taacaaggcc    1800
agagcagaac tcgttataca tacaaaaatt gatggccagg tcagtgttac cgtattatta    1860
tgcaatggca aagcttgca taaggcgtgg tgccactcgt tgctttgctg tatgtttttg     1920
agtttcattc gatttatttt cactgttgag tttgtgggt                            1959
```

<210> SEQ ID NO 16
<211> LENGTH: 258
<212> TYPE: PRT
<213> ORGANISM: Oryza sativa
<220> FEATURE:
<223> OTHER INFORMATION: G3924 polypeptide (domain in aa coordinates:
      163-222)

<400> SEQUENCE: 16

Met Glu Ser Arg Pro Gly Gly Thr Asn Leu Val Glu Pro Arg Gly Gln
1               5                   10                  15

Gly Ala Leu Pro Ser Gly Ile Pro Ile Gln Gln Pro Trp Trp Thr Thr
            20                  25                  30

Ser Ala Gly Val Gly Ala Val Ser Pro Ala Val Val Ala Pro Gly Ser
        35                  40                  45

Gly Ala Gly Ile Ser Leu Ser Gly Arg Asp Gly Gly Asp Asp Ala
    50                  55                  60

Ala Glu Glu Ser Ser Asp Asp Ser Arg Arg Ser Gly Glu Thr Lys Asp
65                  70                  75                  80

Gly Ser Thr Asp Gln Glu Lys His His Ala Thr Ser Gln Met Thr Ala

```
                     85                  90                  95
Leu Ala Ser Asp Tyr Leu Thr Pro Phe Ser Gln Leu Glu Leu Asn Gln
            100                 105                 110

Pro Ile Ala Ser Ala Ala Tyr Gln Tyr Pro Asp Ser Tyr Tyr Met Gly
            115                 120                 125

Met Val Gly Pro Tyr Gly Pro Gln Ala Met Ser Ala Gln Thr His Phe
            130                 135                 140

Gln Leu Pro Gly Leu Thr His Ser Arg Met Pro Leu Pro Leu Glu Ile
145                 150                 155                 160

Ser Glu Glu Pro Val Tyr Val Asn Ala Lys Gln Tyr His Gly Ile Leu
                165                 170                 175

Arg Arg Arg Gln Ser Arg Ala Lys Ala Glu Leu Glu Lys Lys Val Val
            180                 185                 190

Lys Ser Arg Lys Pro Tyr Leu His Glu Ser Arg His Gln His Ala Met
            195                 200                 205

Arg Arg Ala Arg Gly Thr Gly Gly Arg Phe Leu Asn Thr Lys Lys Asn
            210                 215                 220

Glu Asp Gly Ala Pro Ser Glu Lys Ala Glu Pro Asn Lys Gly Glu Gln
225                 230                 235                 240

Asn Ser Gly Tyr Arg Arg Ile Pro Pro Asp Leu Gln Leu Leu Gln Lys
                245                 250                 255

Glu Thr

<210> SEQ ID NO 17
<211> LENGTH: 1631
<212> TYPE: DNA
<213> ORGANISM: Oryza sativa
<220> FEATURE:
<223> OTHER INFORMATION: G3926

<400> SEQUENCE: 17
gagtacaaag gagagagaga gagagactct agtgcatatt tggcaggaag agccgaagag     60
gggaggtgag gatcagagga ggcagcctca tcgtcatgct tcagcactag tagtagtagt    120
gccaccattt ctttgccctc gatctttccc cagagagaga gagagagaga gagagagtct    180
tgattggggg aggagagagg gagagagaga aagagagagg acagaaaatg tttgtggatc    240
ttgagtaatg ccttctaata atgataatgc tgttgcaaga aatggagaat catcctgtcc    300
aatgcatggc caagaccaac tatgattttc ttgccaggaa taactatcca atgaaacagt    360
tagttcagag gaactctgat ggtgactcgt caccaacaaa gtctggggag tctcaccaag    420
aagcatctgc agtaagtgac agcagtctca acggacaaca cacctcacca caatcagtgt    480
ttgtcccctc agatattaac aacaatgata gttgtgggga gcgggaccat ggcactaagt    540
cggtattgtc tttggggaac acagaagctg cctttcctcc ttcaaagttc gattacaacc    600
agccttttgc atgtgtttct tatccatatg gtactgatcc atattatggt ggagtatcaa    660
caggatacac ttcacatgca tttgttcatc ctcaaattac tggtgctgca aactctagga    720
tgccattggc tgttgatcct tctgtagaag agcccatatt tgtcaatgca aagcaataca    780
atgcgatcct tagaagaagg caaacgcgtg caaaattgga ggcccaaaat aaggcggtga    840
aaggtcggaa gccttacctc catgaatctc gacatcatca tgctatgaag cgagcccgtg    900
gatcaggtgg tcggttcctt accaaaaagg agctgctgga acagcagcag cagcagcagc    960
agcagaagcc accaccggca tcagctcagt ctccaacagg tagagccaga acgagcggcg   1020
gtgccgttgt ccttggcaag aacctgtgcc cagagaacag cacatcctgc tcgccatcga   1080
```

```
caccgacagg ctccgagatc tccagcatct catttggggg cggcatgctg gctcaccaag    1140
agcacatcag cttcgcatcc gctgatcgcc accccacaat gaaccagaac caccgtgtcc    1200
ccgtcatgag gtgaaaacct cgggatcgcg ggacacgggc ggttctggtt taccctcact    1260
ggcgcactcc ggtgtgcccg tggcaattca tccttggctt atgaagtatc tacctgataa    1320
tagtctgctg tcagtttata tgcaatgcaa cctctgtcag ataaactctt atagtttgtt    1380
ttattgtaag ctatgactga acgaactgtc gagcagatgg ctaatttgta tgttgtgggt    1440
acagaaatcc tgaagctttt gatgtaccta attgcctttt gcttatactc ttggtgtata    1500
cccattacca agttgcctta aaaccctcc aattatgtaa tcagtcatgg ttttatagaa    1560
ccttgccaca tgtaatcaat cacctgtttt tgtaaattga tctataaacg ctataggctg    1620
ctgtgttatc t                                                         1631
```

<210> SEQ ID NO 18
<211> LENGTH: 317
<212> TYPE: PRT
<213> ORGANISM: Oryza sativa
<220> FEATURE:
<223> OTHER INFORMATION: G3926 polypeptide (domain in aa coordinates: 164-222)

<400> SEQUENCE: 18

```
Met Ile Met Leu Leu Gln Glu Met Glu Asn His Pro Val Gln Cys Met
1               5                   10                  15

Ala Lys Thr Asn Tyr Asp Phe Leu Ala Arg Asn Asn Tyr Pro Met Lys
            20                  25                  30

Gln Leu Val Gln Arg Asn Ser Asp Gly Asp Ser Ser Pro Thr Lys Ser
        35                  40                  45

Gly Glu Ser His Gln Glu Ala Ser Ala Val Ser Asp Ser Ser Leu Asn
    50                  55                  60

Gly Gln His Thr Ser Pro Gln Ser Val Phe Val Pro Ser Asp Ile Asn
65                  70                  75                  80

Asn Asn Asp Ser Cys Gly Glu Arg Asp His Gly Thr Lys Ser Val Leu
                85                  90                  95

Ser Leu Gly Asn Thr Glu Ala Ala Phe Pro Pro Ser Lys Phe Asp Tyr
            100                 105                 110

Asn Gln Pro Phe Ala Cys Val Ser Tyr Pro Tyr Gly Thr Asp Pro Tyr
        115                 120                 125

Tyr Gly Gly Val Ser Thr Gly Tyr Thr Ser His Ala Phe Val His Pro
    130                 135                 140

Gln Ile Thr Gly Ala Ala Asn Ser Arg Met Pro Leu Ala Val Asp Pro
145                 150                 155                 160

Ser Val Glu Glu Pro Ile Phe Val Asn Ala Lys Gln Tyr Asn Ala Ile
                165                 170                 175

Leu Arg Arg Arg Gln Thr Arg Ala Lys Leu Glu Ala Gln Asn Lys Ala
            180                 185                 190

Val Lys Gly Arg Lys Pro Tyr Leu His Glu Ser Arg His His His Ala
        195                 200                 205

Met Lys Arg Ala Arg Gly Ser Gly Gly Arg Phe Leu Thr Lys Lys Glu
    210                 215                 220

Leu Leu Glu Gln Gln Gln Gln Gln Gln Gln Lys Pro Pro Pro Ala
225                 230                 235                 240

Ser Ala Gln Ser Pro Thr Gly Arg Ala Arg Thr Ser Gly Gly Ala Val
                245                 250                 255
```

Val Leu Gly Lys Asn Leu Cys Pro Glu Asn Ser Thr Ser Cys Ser Pro
            260                 265                 270

Ser Thr Pro Thr Gly Ser Glu Ile Ser Ser Ile Ser Phe Gly Gly Gly
        275                 280                 285

Met Leu Ala His Gln Glu His Ile Ser Phe Ala Ser Ala Asp Arg His
    290                 295                 300

Pro Thr Met Asn Gln Asn His Arg Val Pro Val Met Arg
305                 310                 315

<210> SEQ ID NO 19
<211> LENGTH: 1020
<212> TYPE: DNA
<213> ORGANISM: Oryza sativa
<220> FEATURE:
<223> OTHER INFORMATION: G3925

<400> SEQUENCE: 19

```
ccacgcgtcc ggcaaggtga gaagtgagga ggcagcaagg gaggaggttt gccggagagg    60
ggacatgctc cctcctcatc tcacagaaaa tggcacagta atgattcagt ttggtcataa   120
aatgcctgac tacgagtcat cagctaccca atcaactagt ggatctcctc gtgaagtgtc   180
tggaatgagc gaaggaagcc tcaatgagca gaatgatcaa tctggtaatc ttgatggtta   240
cacgaagagt gatgaaggta agatgatgtc agctttatct ctgggcaaat cagaaactgt   300
gtatgcacat tcggaacctg accgtagcca acccttggc atatcatatc catatgctga   360
ttcgttctat ggtggtgctg tagcgactta tggcacacat gctattatgc atccccagat   420
tgtgggcgtg atgtcatcct cccgagtccc gctaccaata gaaccagcca ccgaagagcc   480
tatttatgta aatgcaaagc aataccatgc gattctccga aggagacagc tccgtgcaaa   540
gttagaggct gaaacaagc tggtgaaaaa ccgcaagccg tacctccatg aatcccggca   600
tcaacacgcg atgaaaagag ctcggggaac agggggggaga ttcctcaaca caaagcagca   660
gcctgaagct tcagatggtg cacccccaag gctcgtctct gcaaacggcg ttgtgttctc   720
aaagcacgag cacagcttgt cgtccagtga tctccatcat cgtgcgaaag agggcgcttg   780
agatcctcgc cgtttctgtc atggcaaatc atccttggct tatgtgtggt gcccagcaaa   840
aaaaaatctg actgaacctg tgtgtaaact gatgggtatg ggtgggtttt gtgcaactgt   900
tacttgggtg cttgaaatct gtttctgtgt ttcctctgcc tccttagttt ggagacggtg   960
cagctgcagc tggtaccagt aatctgatca tgctagactt gtgacaaaaa aaaaaaaaaa  1020
```

<210> SEQ ID NO 20
<211> LENGTH: 238
<212> TYPE: PRT
<213> ORGANISM: Oryza sativa
<220> FEATURE:
<223> OTHER INFORMATION: G3925 polypeptide (domain in aa coordinates: 138-197)

<400> SEQUENCE: 20

Met Leu Pro Pro His Leu Thr Glu Asn Gly Thr Val Met Ile Gln Phe
1               5                   10                  15

Gly His Lys Met Pro Asp Tyr Glu Ser Ser Ala Thr Gln Ser Thr Ser
            20                  25                  30

Gly Ser Pro Arg Glu Val Ser Gly Met Ser Glu Gly Ser Leu Asn Glu
        35                  40                  45

Gln Asn Asp Gln Ser Gly Asn Leu Asp Gly Tyr Thr Lys Ser Asp Glu
    50                  55                  60

```
Gly Lys Met Met Ser Ala Leu Ser Leu Gly Lys Ser Glu Thr Val Tyr
 65                  70                  75                  80

Ala His Ser Glu Pro Asp Arg Ser Gln Pro Phe Gly Ile Ser Tyr Pro
                 85                  90                  95

Tyr Ala Asp Ser Phe Tyr Gly Gly Ala Val Ala Thr Tyr Gly Thr His
            100                 105                 110

Ala Ile Met His Pro Gln Ile Val Gly Val Met Ser Ser Ser Arg Val
        115                 120                 125

Pro Leu Pro Ile Glu Pro Ala Thr Glu Glu Pro Ile Tyr Val Asn Ala
130                 135                 140

Lys Gln Tyr His Ala Ile Leu Arg Arg Arg Gln Leu Arg Ala Lys Leu
145                 150                 155                 160

Glu Ala Glu Asn Lys Leu Val Lys Asn Arg Lys Pro Tyr Leu His Glu
                165                 170                 175

Ser Arg His Gln His Ala Met Lys Arg Ala Arg Gly Thr Gly Gly Arg
            180                 185                 190

Phe Leu Asn Thr Lys Gln Gln Pro Glu Ala Ser Asp Gly Gly Thr Pro
        195                 200                 205

Arg Leu Val Ser Ala Asn Gly Val Val Phe Ser Lys His Glu His Ser
210                 215                 220

Leu Ser Ser Ser Asp Leu His His Arg Ala Lys Glu Gly Ala
225                 230                 235
```

<210> SEQ ID NO 21
<211> LENGTH: 885
<212> TYPE: DNA
<213> ORGANISM: Zea mays
<220> FEATURE:
<223> OTHER INFORMATION: G3921

<400> SEQUENCE: 21

| | | | | |
|---|---|---|---|---|
| atggaggatc attctgtcca tcccatgtct aagtctaacc atggctcctt gtcaggaaat | 60 |
| ggttatgaga tgaaacatcc aggccatgaa gtttgcgata gggattcatc atcggagtct | 120 |
| gatcggtctc accaagaagc atcagcagcg agtgaaagca gtccagatga acacacatca | 180 |
| actcaatcag acaatgatga agatcatggg aaggataatc aggacacatt gaagccagta | 240 |
| tgtccttgg ggaaggaagg ctctgccact ggggcccaa aattacatta gcccatct | 300 |
| tttgcttgta ttccttatac tgctgacgct tactatggtg ccgttggggt cttgacagga | 360 |
| tatcctccac atgccattgt ccatcccag caaatgata caacgaacac tccgggtatg | 420 |
| ttacctgtgg aacctgcaga agaaccaata tatgttaatg caaaacaata ccatgcaatc | 480 |
| cttaggagga ggcaaacacg tgctaaattg gaggcccaga acaagatggt gaaaggtcgg | 540 |
| aagccatacc ttcatgagtc ccgacatcgt catgccatga acgggcccg tggctcagga | 600 |
| gggcggttcc tcaacacaaa gcagctccag gaccaaaacc agcagtttca ggaagcgtcg | 660 |
| agtggttcaa tgtgctcaaa gatcattggc aacagcataa tctcccaaag tggccccacc | 720 |
| tgcacgccct cttctggcac tgcaggtgct tcaacagcca gccaggaccg cagctgcttg | 780 |
| ccctcagttg gcttccgccc cacaaccaac ttcagtgacc aaggtcgagg aggcttgaag | 840 |
| ctggccgtga tcggcatgca gcagcgtgtt tccaccataa ggtga | 885 |

<210> SEQ ID NO 22
<211> LENGTH: 294
<212> TYPE: PRT
<213> ORGANISM: Zea mays

```
<220> FEATURE:
<223> OTHER INFORMATION: G3921 polypeptide (domain in aa coordinates:
      148-207)

<400> SEQUENCE: 22

Met Glu Asp His Ser Val His Pro Met Ser Lys Ser Asn His Gly Ser
1               5                   10                  15

Leu Ser Gly Asn Gly Tyr Glu Met Lys His Pro Gly His Glu Val Cys
                20                  25                  30

Asp Arg Asp Ser Ser Glu Ser Asp Arg Ser His Gln Glu Ala Ser
            35                  40                  45

Ala Ala Ser Glu Ser Ser Pro Asp Glu His Thr Ser Thr Gln Ser Asp
        50                  55                  60

Asn Asp Glu Asp His Gly Lys Asp Asn Gln Asp Thr Leu Lys Pro Val
65                  70                  75                  80

Leu Ser Leu Gly Lys Glu Gly Ser Ala Thr Gly Ala Pro Lys Leu His
                85                  90                  95

Tyr Ser Pro Ser Phe Ala Cys Ile Pro Tyr Thr Ala Asp Ala Tyr Tyr
                100                 105                 110

Gly Ala Val Gly Val Leu Thr Gly Tyr Pro Pro His Ala Ile Val His
            115                 120                 125

Pro Gln Gln Asn Asp Thr Thr Asn Thr Pro Gly Met Leu Pro Val Glu
        130                 135                 140

Pro Ala Glu Glu Pro Ile Tyr Val Asn Ala Lys Gln Tyr His Ala Ile
145                 150                 155                 160

Leu Arg Arg Arg Gln Thr Arg Ala Lys Leu Glu Ala Gln Asn Lys Met
                165                 170                 175

Val Lys Gly Arg Lys Pro Tyr Leu His Glu Ser Arg His Arg His Ala
            180                 185                 190

Met Lys Arg Ala Arg Gly Ser Gly Gly Arg Phe Leu Asn Thr Lys Gln
        195                 200                 205

Leu Gln Asp Gln Asn Gln Gln Phe Gln Glu Ala Ser Ser Gly Ser Met
        210                 215                 220

Cys Ser Lys Ile Ile Gly Asn Ser Ile Ile Ser Gln Ser Gly Pro Thr
225                 230                 235                 240

Cys Thr Pro Ser Ser Gly Thr Ala Gly Ala Ser Thr Ala Ser Gln Asp
                245                 250                 255

Arg Ser Cys Leu Pro Ser Val Gly Phe Arg Pro Thr Thr Asn Phe Ser
            260                 265                 270

Asp Gln Gly Arg Gly Gly Leu Lys Leu Ala Val Ile Gly Met Gln Gln
        275                 280                 285

Arg Val Ser Thr Ile Arg
    290

<210> SEQ ID NO 23
<211> LENGTH: 1405
<212> TYPE: DNA
<213> ORGANISM: Zea mays
<220> FEATURE:
<223> OTHER INFORMATION: G3922

<400> SEQUENCE: 23
tgggaccctc gaggccggcc gggatacgat tccgaagaag gtagcgaccc acgcgcgcgg    60
gccagaggcc ggaagaggga gatacaggtt aattttagg taccagatca tctgatttct    120
cagaagcaaa atgttgtttg gagctcagtg acaccatctt gtaatgcctg tgattttacg    180
```

```
ggaaatggag gatcattctg tccatcccat gtctaagtct aaccatggct ccttgtcagg    240
aaatggttat gagatgaaac attcaggcca taaagtttgc gatagggatt catcatcgga    300
gtctgatcgg tctcaccaag aagcatcagc agcaagtgaa agcagtccaa atgaacacac    360
atcaactcaa tcagacaatg atgaagatca tgggaaagat aatcaggaca caatgaagcc    420
agtattgtcc ttggggaagg aaggctctgc ctttttggcc ccaaaattac attacagccc    480
atcttttgct tgtattcctt atactgctga tgcttattat agtggggttg ggtctcgac     540 aggatatgct ccacatgcca ttgtatgttc actcttaatc tttcagtttc tgtcttcctg    600
gccacattct gtccatcccc agcaaaatga taacgaac actccgggta tgttacctgt     660
ggaacctgca gaagaaccaa tatatgttaa tgcaaaacaa taccatgcaa tccttaggag    720
gaggcaaaca cgtgctaaat ggaggccca gaacaagatg gtgaaaaatc ggaagccata    780
tcttcatgag tcccgacatc gtcatgccat gaaacgggct cgtggatcag gaggacggtt    840
cctcaacaca aagcagctcc aggagcagaa ccagcagtat caggcatcga gtggttcatt    900
gtgctcaaag atcattgcca acagcataat ctcccaaagt ggccccacct gcacgccctc    960
ttctgacact gcaggtcttc agcagccagc caggaccgcg gctgcttgcc ctcggtgggc    1020
ttccgcccca cagccaactt cagtgagcaa ggtggaggcg gctcgaagct ggtcgtgaac    1080
ggcatgcagc agcgtgtttc caccataagg tgaagagaag tgggcacgac accattccca    1140
ggcgcgcact gcctgtggca actcatcctt ggcttttgaa actatggata tgcaatggac    1200
atgtagcttc gagttcctca gaataaccaa acgtgaagaa tatgcaaagt cctttgaga    1260 tttgctgtag ctgaaagaac tgtggttagg ttgagttct tcctggagac tgatccatac    1320
atgacatgct acctcgtgct gagtttctga ggtgaagcca tcgaaacatg accgtgtggt    1380
tcagtaaaaa aaaaaaaaaa aaaaa                                         1405
```

<210> SEQ ID NO 24
<211> LENGTH: 304
<212> TYPE: PRT
<213> ORGANISM: Zea mays
<220> FEATURE:
<223> OTHER INFORMATION: G3922 polypeptide (domain in aa coordinates: 171-230)

<400> SEQUENCE: 24

```
Met Pro Val Ile Leu Arg Glu Met Glu Asp His Ser Val His Pro Met
1               5                   10                  15

Ser Lys Ser Asn His Gly Ser Leu Ser Gly Asn Gly Tyr Glu Met Lys
            20                  25                  30

His Ser Gly His Lys Val Cys Asp Arg Asp Ser Ser Ser Glu Ser Asp
        35                  40                  45

Arg Ser His Gln Glu Ala Ser Ala Ala Ser Glu Ser Pro Asn Glu
    50                  55                  60

His Thr Ser Thr Gln Ser Asp Asn Asp Glu Asp His Gly Lys Asp Asn
65                  70                  75                  80

Gln Asp Thr Met Lys Pro Val Leu Ser Leu Gly Lys Glu Gly Ser Ala
                85                  90                  95

Phe Leu Ala Pro Lys Leu His Tyr Ser Pro Ser Phe Ala Cys Ile Pro
            100                 105                 110

Tyr Thr Ala Asp Ala Tyr Tyr Ser Gly Val Gly Val Ser Thr Gly Tyr
        115                 120                 125

Ala Pro His Ala Ile Val Cys Ser Leu Leu Ile Phe Gln Phe Leu Ser
    130                 135                 140
```

```
Ser Trp Pro His Ser Val His Pro Gln Gln Asn Asp Thr Thr Asn Thr
145                 150                 155                 160

Pro Gly Met Leu Pro Val Glu Pro Ala Glu Glu Pro Ile Tyr Val Asn
            165                 170                 175

Ala Lys Gln Tyr His Ala Ile Leu Arg Arg Arg Gln Thr Arg Ala Lys
        180                 185                 190

Leu Glu Ala Gln Asn Lys Met Val Lys Asn Arg Lys Pro Tyr Leu His
    195                 200                 205

Glu Ser Arg His Arg His Ala Met Lys Arg Ala Arg Gly Ser Gly Gly
210                 215                 220

Arg Phe Leu Asn Thr Lys Gln Leu Gln Glu Gln Asn Gln Gln Tyr Gln
225                 230                 235                 240

Ala Ser Ser Gly Ser Leu Cys Ser Lys Ile Ile Ala Asn Ser Ile Ile
            245                 250                 255

Ser Gln Ser Gly Pro Thr Cys Thr Pro Ser Ser Asp Thr Ala Gly Leu
            260                 265                 270

Gln Gln Pro Ala Arg Thr Ala Ala Ala Cys Pro Arg Trp Ala Ser Ala
        275                 280                 285

Pro Gln Pro Thr Ser Val Ser Lys Val Glu Ala Ala Arg Ser Trp Ser
    290                 295                 300

<210> SEQ ID NO 25
<211> LENGTH: 1155
<212> TYPE: DNA
<213> ORGANISM: Zea mays
<220> FEATURE:
<223> OTHER INFORMATION: G4264

<400> SEQUENCE: 25
tggtttcggc aatttgggtt aattttagg taccagatca tctgatttct cagaagcaaa      60
atgttgtttg gagctcagtg acaccatctt gtaatgcctg tgattttacg ggaaatggag    120
gatcattctg tccatcccat gtctaagtct aaccatggct ccttgtcagg aaatggttat    180
gagatgaaac attcaggcca taaagtttgc gataggatt catcatcgga gtctgatcgg     240
tctcaccaag aagcatcagc agcaagtgaa agcagtccaa atgaacacac atcaactcaa    300
tcagacaatg atgaagatca tgggaaagat aatcaggaca caatgaagcc agtattgtcc    360
ttggggaagg aaggctctgc ctttttggcc ccaaaattac attacagccc atcttttgct    420
tgtattcctt atacttctga tgcttattat agtgcggttg gggtcttgac aggatatcct    480
ccacatgcca ttgtccatcc ccagcaaaat gatacaacga acactccggg tatgttacct    540
gtggaacctg cagaagaacc aatatatgtt aatgcaaaac aataccatgc aatccttagg    600
aggaggcaaa cacgtgctaa attggaggcc cagaacaaga tggtgaaaaa tcggaagcca    660
tatcttcatg agtcccgaca tcgtcatgcc atgaaacggg ctcgtggatc aggaggacgg    720
ttcctcaaca caaagcagct ccaggagcag aaccagcagt atcaggcatc gagtggttca    780
ttgtgctcaa agatcattgc caacagcata atctcccaaa gtggccccac ctgcacgccc    840
tcttctggca ctgcaggtgc ttcaacagcc ggccaggacc gcagctgctt gccctcagtt    900
ggcttccgcc ccacgacaaa cttcagtgac caaggtcgag gaggcttgaa gttggccgtg    960
atcggcatgc agcagcgtgt tccaccata aggtgaagag aagtgggcac aacaccattc      1020
ccaggcacac tgcctgtggc aactcatcct tggctcttgg aactttgaat atgcaatcga    1080
catgtagctt gagatcctca gaataaacca aaccttcagt tatatgcaag cctttttga    1140
```
ggttgctgtt gctgt                                              1155

<210> SEQ ID NO 26
<211> LENGTH: 300
<212> TYPE: PRT
<213> ORGANISM: Zea mays
<220> FEATURE:
<223> OTHER INFORMATION: G4264 polypeptide (domain in aa coordinates: 155-214)

<400> SEQUENCE: 26

Met Pro Val Ile Leu Arg Glu Met Glu Asp His Ser Val His Pro Met
1               5                   10                  15

Ser Lys Ser Asn His Gly Ser Leu Ser Gly Asn Gly Tyr Glu Met Lys
            20                  25                  30

His Ser Gly His Lys Val Cys Asp Arg Asp Ser Ser Ser Glu Ser Asp
        35                  40                  45

Arg Ser His Gln Glu Ala Ser Ala Ser Glu Ser Ser Pro Asn Glu
    50                  55                  60

His Thr Ser Thr Gln Ser Asp Asn Asp Glu Asp His Gly Lys Asp Asn
65                  70                  75                  80

Gln Asp Thr Met Lys Pro Val Leu Ser Leu Gly Lys Glu Gly Ser Ala
                85                  90                  95

Phe Leu Ala Pro Lys Leu His Tyr Ser Pro Ser Phe Ala Cys Ile Pro
            100                 105                 110

Tyr Thr Ser Asp Ala Tyr Tyr Ser Ala Val Gly Val Leu Thr Gly Tyr
        115                 120                 125

Pro Pro His Ala Ile Val His Pro Gln Gln Asn Asp Thr Thr Asn Thr
    130                 135                 140

Pro Gly Met Leu Pro Val Glu Pro Ala Glu Glu Pro Ile Tyr Val Asn
145                 150                 155                 160

Ala Lys Gln Tyr His Ala Ile Leu Arg Arg Arg Gln Thr Arg Ala Lys
                165                 170                 175

Leu Glu Ala Gln Asn Lys Met Val Lys Asn Arg Lys Pro Tyr Leu His
            180                 185                 190

Glu Ser Arg His Arg His Ala Met Lys Arg Ala Arg Gly Ser Gly Gly
        195                 200                 205

Arg Phe Leu Asn Thr Lys Gln Leu Gln Glu Gln Asn Gln Gln Tyr Gln
    210                 215                 220

Ala Ser Ser Gly Ser Leu Cys Ser Lys Ile Ile Ala Asn Ser Ile Ile
225                 230                 235                 240

Ser Gln Ser Gly Pro Thr Cys Thr Pro Ser Ser Gly Thr Ala Gly Ala
                245                 250                 255

Ser Thr Ala Gly Gln Asp Arg Ser Cys Leu Pro Ser Val Gly Phe Arg
            260                 265                 270

Pro Thr Thr Asn Phe Ser Asp Gln Gly Arg Gly Gly Leu Lys Leu Ala
        275                 280                 285

Val Ile Gly Met Gln Gln Arg Val Ser Thr Ile Arg
    290                 295                 300

<210> SEQ ID NO 27
<211> LENGTH: 912
<212> TYPE: DNA
<213> ORGANISM: Arabidopsis thaliana
<220> FEATURE:
<223> OTHER INFORMATION: G2632

<400> SEQUENCE: 27

```
atgggaattg aagacatgca ttcaaaatct gacagtggtg ggaacaaggt tgattcagag      60
gttcatggta cagtatcgtc gtcgataaat agtttaaacc cttggcatcg tgctgctgct     120
gcttgcaatg caaattctag tgtggaagct ggagataaat cttctaagtc aatagcatta     180
gcattggaat caaacggttc caaatcacca tccaatagag ataatactgt taacaaggaa     240
tcacaagtca aacgtctcc acaatcagct ggagattata gtgataaaaa ccaagaatct     300
ctgcatcatg gcatcacaca acctcctcct caccctcaac ttgttggcca cagttgga     360
tgggcatcct caaatccata ccaggatcca tattatgcag gagtgatggg agcctatgga     420
catcatcccc tggggtttgt tccatatggt gggatgcctc attcaagaat gccactgccg     480
cctgagatgg cacaagaacc agttttcgtg aatgctaaac agtaccaggc gattctgagg     540
cgaaggcagg cacgcgccaa ggcagagcta gagaagaagc taataaaatc agaaagcct      600
tatctacatg aatctcggca tcaacatgct atgaggaggc aagggtac tggaggacgg       660
tttgcaaaga aaccaacac cgaagcttca aagcgtaaag ctgaagaaaa gagcaatggt      720
catgttactc agtccccgtc atcatctaat tctgatcaag gtgaagcttg gaatggtgac     780
tatagaacac ctcagggaga tgagatgcag agctcagctt ataagagaag ggaagaagga    840
gagtgttcag ggcagcaatg gaacagcctt tcctcaaacc atccttctca gctcgtcta     900
gccattaaat ga                                                         912

<210> SEQ ID NO 28
<211> LENGTH: 303
<212> TYPE: PRT
<213> ORGANISM: Arabidopsis thaliana
<220> FEATURE:
<223> OTHER INFORMATION: G2632 polypeptide (domain in aa coordinates:
      166-223)

<400> SEQUENCE: 28

Met Gly Ile Glu Asp Met His Ser Lys Ser Asp Ser Gly Gly Asn Lys
1               5                   10                  15

Val Asp Ser Glu Val His Gly Thr Val Ser Ser Ser Ile Asn Ser Leu
            20                  25                  30

Asn Pro Trp His Arg Ala Ala Ala Ala Cys Asn Ala Asn Ser Ser Val
        35                  40                  45

Glu Ala Gly Asp Lys Ser Ser Lys Ser Ile Ala Leu Ala Leu Glu Ser
    50                  55                  60

Asn Gly Ser Lys Ser Pro Ser Asn Arg Asp Asn Thr Val Asn Lys Glu
65                  70                  75                  80

Ser Gln Val Thr Thr Ser Pro Gln Ser Ala Gly Asp Tyr Ser Asp Lys
                85                  90                  95

Asn Gln Glu Ser Leu His His Gly Ile Thr Gln Pro Pro His Pro
            100                 105                 110

Gln Leu Val Gly His Thr Val Gly Trp Ala Ser Ser Asn Pro Tyr Gln
        115                 120                 125

Asp Pro Tyr Tyr Ala Gly Val Met Gly Ala Tyr Gly His His Pro Leu
    130                 135                 140

Gly Phe Val Pro Tyr Gly Gly Met Pro His Ser Arg Met Pro Leu Pro
145                 150                 155                 160

Pro Glu Met Ala Gln Glu Pro Val Phe Val Asn Ala Lys Gln Tyr Gln
                165                 170                 175

Ala Ile Leu Arg Arg Arg Gln Ala Arg Ala Lys Ala Glu Leu Glu Lys
            180                 185                 190
```

```
Lys Ile Lys Ser Arg Lys Pro Tyr Leu His Glu Ser Arg His Gln
    195                 200                 205

His Ala Met Arg Arg Pro Arg Gly Thr Gly Gly Arg Phe Ala Lys Lys
    210                 215                 220

Thr Asn Thr Glu Ala Ser Lys Arg Lys Ala Glu Glu Lys Ser Asn Gly
225                 230                 235                 240

His Val Thr Gln Ser Pro Ser Ser Asn Ser Asp Gln Gly Glu Ala
                245                 250                 255

Trp Asn Gly Asp Tyr Arg Thr Pro Gln Gly Asp Glu Met Gln Ser Ser
                260                 265                 270

Ala Tyr Lys Arg Arg Glu Glu Gly Glu Cys Ser Gly Gln Gln Trp Asn
            275                 280                 285

Ser Leu Ser Ser Asn His Pro Ser Gln Ala Arg Leu Ala Ile Lys
        290                 295                 300
```

<210> SEQ ID NO 29
<211> LENGTH: 1274
<212> TYPE: DNA
<213> ORGANISM: Arabidopsis thaliana
<220> FEATURE:
<223> OTHER INFORMATION: G1334

<400> SEQUENCE: 29

| | | | | | |
|---|---|---|---|---|---|
| atagctccca | actaatagga | atctcaagct | tctcactctc | tcttgttttt | ccattggact | 60 |
| tttggaacat | aagctatgca | aactgaggag | cttttgtcgc | caccacagac | tccttggtgg | 120 |
| aatgcttttg | gatctcagcc | gttgactaca | gagagccttt | ccggcgaagc | ttctgattca | 180 |
| ttcaccggag | ttaaggcagt | tactacggag | gcagaacaag | gtgtggtgga | taaacaaact | 240 |
| tctacaactc | tcttcacttt | ctcacctggt | ggtgaaaaga | gttcaagaga | tgtgccaaag | 300 |
| cctcatgttg | ctttcgcgat | gcaatcagct | tgcttcgagt | ttggatttgc | tcagccaatg | 360 |
| atgtacacaa | agcatcctca | tgttgaacaa | tactatggag | ttgtttcagc | atacggatct | 420 |
| cagaggtctt | cgggccgagt | aatgattcca | ctgaagatgg | agacagaaga | agatggtacc | 480 |
| atctatgtga | actcaaagca | gtaccatgga | attatcaggc | gacgccagtc | ccgagcaaag | 540 |
| gctgaaaaac | tgagtagatg | ccgtaagcca | tatatgcatc | actcacgcca | tctccatgct | 600 |
| atgcgccgtc | ctagaggatc | tggcgggcgt | tccttgaaca | ccaagacagc | tgatgcggct | 660 |
| aagcagtcta | agccgagtaa | ttctcagagt | tctgaagtct | tcatccggaa | aaatgagacc | 720 |
| ataaactcat | cgagggaagc | aaatgagtca | aatctctcgg | attctgcagt | tacaagtatg | 780 |
| gattactttc | taagttcgtc | ggcttattct | cctggtggca | tggtcatgcc | tatcaagtgg | 840 |
| aatgcagcag | caatggatat | tggctgctgc | aaacttaata | tatgatcagc | agataggga | 900 |
| caagacatga | ttggtcacca | gtccttttgt | cttgtccctt | atctttcagc | caaacggaaa | 960 |
| gagaacttgt | gtcttggaaa | aaagacattg | agtttccttg | gtttataaga | ttggtccttt | 1020 |
| taccatccgt | ttggctgtaa | acaggcaaat | catctttggc | tcatgcttca | tcaagttctt | 1080 |
| atcttcgtct | gttttcttct | acgcatcttc | ataagatctc | tgaactagtg | aataacattt | 1140 |
| cctagcatca | tgtttcaact | agtgtgtgtt | gtaagaaact | ctgccttatt | tccagatgat | 1200 |
| gtattgtgtg | taacgtgttt | atgaaacaaa | cgtaagactt | tcaagttaaa | aaaaaaaaa | 1260 |
| aaaaaaaaa | aaaa | | | | | 1274 |

<210> SEQ ID NO 30
<211> LENGTH: 269

-continued

<210> TYPE: PRT
<213> ORGANISM: Arabidopsis thaliana
<220> FEATURE:
<223> OTHER INFORMATION: G1334 polypeptide (domain in aa coordinates: 133-190)

<400> SEQUENCE: 30

Met Gln Thr Glu Glu Leu Leu Ser Pro Pro Gln Thr Pro Trp Trp Asn
1               5                   10                  15

Ala Phe Gly Ser Gln Pro Leu Thr Thr Glu Ser Leu Ser Gly Glu Ala
            20                  25                  30

Ser Asp Ser Phe Thr Gly Val Lys Ala Val Thr Thr Glu Ala Glu Gln
        35                  40                  45

Gly Val Val Asp Lys Gln Thr Ser Thr Thr Leu Phe Thr Phe Ser Pro
    50                  55                  60

Gly Gly Glu Lys Ser Ser Arg Asp Val Pro Lys Pro His Val Ala Phe
65                  70                  75                  80

Ala Met Gln Ser Ala Cys Phe Glu Phe Gly Phe Ala Gln Pro Met Met
                85                  90                  95

Tyr Thr Lys His Pro His Val Glu Gln Tyr Tyr Gly Val Val Ser Ala
            100                 105                 110

Tyr Gly Ser Gln Arg Ser Ser Gly Arg Val Met Ile Pro Leu Lys Met
        115                 120                 125

Glu Thr Glu Glu Asp Gly Thr Ile Tyr Val Asn Ser Lys Gln Tyr His
    130                 135                 140

Gly Ile Ile Arg Arg Arg Gln Ser Arg Ala Lys Ala Glu Lys Leu Ser
145                 150                 155                 160

Arg Cys Arg Lys Pro Tyr Met His Ser Arg His Leu His Ala Met
                165                 170                 175

Arg Arg Pro Arg Gly Ser Gly Arg Phe Leu Asn Thr Lys Thr Ala
            180                 185                 190

Asp Ala Ala Lys Gln Ser Lys Pro Ser Asn Ser Gln Ser Ser Glu Val
        195                 200                 205

Phe His Pro Glu Asn Glu Thr Ile Asn Ser Ser Arg Glu Ala Asn Glu
    210                 215                 220

Ser Asn Leu Ser Asp Ser Ala Val Thr Ser Met Asp Tyr Phe Leu Ser
225                 230                 235                 240

Ser Ser Ala Tyr Ser Pro Gly Gly Met Val Met Pro Ile Lys Trp Asn
                245                 250                 255

Ala Ala Ala Met Asp Ile Gly Cys Cys Lys Leu Asn Ile
            260                 265

<210> SEQ ID NO 31
<211> LENGTH: 1388
<212> TYPE: DNA
<213> ORGANISM: Arabidopsis thaliana
<220> FEATURE:
<223> OTHER INFORMATION: G926

<400> SEQUENCE: 31
ccaaaatcta gggttttctt ctcgcccaat ttcactttc ttctacgaaa ttctccattc      60
ctgccggctg tcgggttttc tgaatcgatt ctccttcacc aacttcttct ctggttctgt    120
tcgattctga ttttttttca aggtcaattt tttcttctct ttaaactctg caaaatcgtg    180
atcgattaaa ttcacctcag ggttttttga tttctgaaag aagttaatct tcttcgaagg    240
cgattgcaaa agagtgctct gctgtgaatt tccactgaga tgcaatcaaa accgggaaga    300

-continued

```
gaaaacgaag aggaagtcaa taatcaccat gctgttcagc agccgatgat gtatgcagag    360
ccctggtgga aaacaactc ctttggtgtt gtacctcaag cgagaccttc tggaattcca    420
tcaaattcct cttctttgga ttgccccaat ggttccgagt caaacgatgt tcattcagca    480
tctgaagacg gtgcgttgaa tggtgaaaac gatggcactt ggaaggattc acaagctgca    540
acttcctctc gttcagataa tcacggaatg gaaggaaatg acccagcgct ctctatccgt    600
aacatgcatg atcagccact tgtacaacca ccagagcttg ttggacacta tatcgcttgt    660
gtcccaaacc catatcagga tccatattat ggggggattga tgggagcata tggtcatcag    720
caattgggtt ttcgtccata tcttggaatg cctcgtgaaa aacagctct gccacttgac     780
atggcacaag agcccgttta tgtgaatgca aagcagtacg agggaattct aaggcgaaga    840
aaagcacgtg ccaaggcaga gctagagagg aaagtcatcc gggacagaaa gccatatctt    900
cacgagtcaa gacacaagca tgcaatgaga agggcacgag cgagtggagg ccggtttgcg    960
aagaaaagtg aggtagaagc gggagaggat gcaggaggga gagacagaga aaggggttca   1020
gcaaccaact catcaggctc tgaacaagtt gagacagact ctaatgagac cctgaattct   1080
tctggtgcac cataataaaa aaagccaaag ctctgagagg agagagagac acacactttg   1140
gctaatataa tccattgcct caaaccggca atcattctt ggcttttcg ttttttgtgtt     1200
tgctagttgt tcttgtcaga gtctcatatt gtgtgggttt aacagttatg atgaatgtac   1260
aaagagcgag ttatgttagg tgttagattt tggagacaag agacaaagga atagcaagta   1320
ggtcttgttt ttattctttg acctttttt tctcttttgc aaaattgaaa aatacgtttg    1380
cttaaaaa                                                             1388
```

<210> SEQ ID NO 32
<211> LENGTH: 271
<212> TYPE: PRT
<213> ORGANISM: Arabidopsis thaliana
<220> FEATURE:
<223> OTHER INFORMATION: G926 polypeptide (domain in aa coordinates: 171-228)

<400> SEQUENCE: 32

```
Met Gln Ser Lys Pro Gly Arg Glu Asn Glu Glu Glu Val Asn Asn His
1               5                   10                  15

His Ala Val Gln Gln Pro Met Met Tyr Ala Glu Pro Trp Trp Lys Asn
                20                  25                  30

Asn Ser Phe Gly Val Val Pro Gln Ala Arg Pro Ser Gly Ile Pro Ser
            35                  40                  45

Asn Ser Ser Leu Asp Cys Pro Asn Gly Ser Glu Ser Asn Asp Val
        50                  55                  60

His Ser Ala Ser Glu Asp Gly Ala Leu Asn Gly Glu Asn Asp Gly Thr
65                  70                  75                  80

Trp Lys Asp Ser Gln Ala Ala Thr Ser Ser Arg Ser Asp Asn His Gly
                85                  90                  95

Met Glu Gly Asn Asp Pro Ala Leu Ser Ile Arg Asn Met His Asp Gln
                100                 105                 110

Pro Leu Val Gln Pro Glu Leu Val Gly His Tyr Ile Ala Cys Val
            115                 120                 125

Pro Asn Pro Tyr Gln Asp Pro Tyr Tyr Gly Gly Leu Met Gly Ala Tyr
        130                 135                 140

Gly His Gln Gln Leu Gly Phe Arg Pro Tyr Leu Gly Met Pro Arg Glu
145                 150                 155                 160
```

```
Arg Thr Ala Leu Pro Leu Asp Met Ala Gln Glu Pro Val Tyr Val Asn
            165                 170                 175

Ala Lys Gln Tyr Glu Gly Ile Leu Arg Arg Lys Ala Arg Ala Lys
        180                 185                 190

Ala Glu Leu Glu Arg Lys Val Ile Arg Asp Lys Pro Tyr Leu His
        195                 200                 205

Glu Ser Arg His Lys His Ala Met Arg Arg Ala Arg Ala Ser Gly Gly
            210                 215                 220

Arg Phe Ala Lys Lys Ser Glu Val Glu Ala Gly Glu Asp Ala Gly Gly
225                 230                 235                 240

Arg Asp Arg Glu Arg Gly Ser Ala Thr Asn Ser Ser Gly Ser Glu Gln
                245                 250                 255

Val Glu Thr Asp Ser Asn Glu Thr Leu Asn Ser Ser Gly Ala Pro
            260                 265                 270

<210> SEQ ID NO 33
<211> LENGTH: 1385
<212> TYPE: DNA
<213> ORGANISM: Arabidopsis thaliana
<220> FEATURE:
<223> OTHER INFORMATION: G927

<400> SEQUENCE: 33
ggaatctgaa gctcttctct actctctact ctatcactcc atctgtgaac atatctttct      60
tattcttcta ggcactatct attttcact ttttgtaatt ggaatttgga gatggctatg     120
caaactgtga gagaaggtct cttctctgct ccacagactt cttggtggac tgcttttgga     180
tctcagccgt tggctccgga gagtctcgcc ggcgattctg actcattcgc cggagttaag     240
gtcggatctg tcggagagac aagacaacgt gtggataaac agagcaactc tgcaacgcac     300
ttagcttcct cacttggtga tgtaaagagt ccaagacttg tgccaaagcc tcatggagct     360
actttctcaa tgcaatcacc ttgcttggaa cttggatttt ctcagccacc gatctataca     420
aagtatccct atggagaaca acaatactat ggagttgttt cagcctatgg atctcagagc     480
agggtaatgc ttcctctaaa catggaaacg gaagatagta ccatctatgt gaactcaaag     540
caataccatg gaatcataag gagacgccaa tcccgcgcaa aggctgctgc tgttcttgat     600
cagaagaaat tgagtagtag atgccgcaag ccatatatgc atcattcgcg ccatctccat     660
gcattgcggc gtcctagagg atccggtggg agattcttga cactaaaag tcagaacttg     720 gaaaatagcg gaaccaatgc aaagaaaggt gatggaagta tgcagattca gtctcagcct     780
aagcctcagc aaagtaactc tcagaattct gaagttgttc atccggaaaa cgggaccatg     840
aacttatcga acggattaaa tgtgtcggga tcagaagtta ctagcatgaa ctacttccta     900
agttctcccg ttcattctct tggtggcatg gtaatgccta gcaagtggat agcagcagca     960
gcagcaatgg ataatggctg ctgcaatttc aaaacctgat cctttaccgt tcacagtca    1020 aacggagaga gataaagaac tcttgccttg gtataaagga ttttcctttt tgccaatccg   1080
ctttggctgt gaacaggcaa atcatctttg gctcattctc tattaaggta acttcgccgt   1140
gaggtgaaaa aagctttgat atatttatct tcagtgtaaa agtagttaaa actggtgaag   1200
aacaatgatg tgtttggtca ctaaacccac ttgttccaac tagtagtgtg tgttttaaga   1260
aaactctgtt atctgatttt gtagctctct ctggctttgt gtgttctca aacaactgta   1320 acaacttta agttatgtgg tttatgtaac atatttaaga cctgtgtttt tgtataaaaa   1380
aaaaa                                                              1385
```

```
<210> SEQ ID NO 34
<211> LENGTH: 295
<212> TYPE: PRT
<213> ORGANISM: Arabidopsis thaliana
<220> FEATURE:
<223> OTHER INFORMATION: G927 polypeptide (domain in aa coordinates:
      136-199)

<400> SEQUENCE: 34

Met Ala Met Gln Thr Val Arg Glu Gly Leu Phe Ser Ala Pro Gln Thr
1               5                   10                  15

Ser Trp Trp Thr Ala Phe Gly Ser Gln Pro Leu Ala Pro Glu Ser Leu
            20                  25                  30

Ala Gly Asp Ser Asp Ser Phe Ala Gly Val Lys Val Gly Ser Val Gly
        35                  40                  45

Glu Thr Arg Gln Arg Val Asp Lys Gln Ser Asn Ser Ala Thr His Leu
    50                  55                  60

Ala Phe Ser Leu Gly Asp Val Lys Ser Pro Arg Leu Val Pro Lys Pro
65                  70                  75                  80

His Gly Ala Thr Phe Ser Met Gln Ser Pro Cys Leu Glu Leu Gly Phe
                85                  90                  95

Ser Gln Pro Pro Ile Tyr Thr Lys Tyr Pro Tyr Gly Glu Gln Gln Tyr
            100                 105                 110

Tyr Gly Val Val Ser Ala Tyr Gly Ser Gln Ser Arg Val Met Leu Pro
        115                 120                 125

Leu Asn Met Glu Thr Glu Asp Ser Thr Ile Tyr Val Asn Ser Lys Gln
130                 135                 140

Tyr His Gly Ile Ile Arg Arg Arg Gln Ser Arg Ala Lys Ala Ala Ala
145                 150                 155                 160

Val Leu Asp Gln Lys Lys Leu Ser Ser Arg Cys Arg Lys Pro Tyr Met
                165                 170                 175

His His Ser Arg His Leu His Ala Leu Arg Arg Pro Arg Gly Ser Gly
            180                 185                 190

Gly Arg Phe Leu Asn Thr Lys Ser Gln Asn Leu Glu Asn Ser Gly Thr
        195                 200                 205

Asn Ala Lys Lys Gly Asp Gly Ser Met Gln Ile Gln Ser Gln Pro Lys
210                 215                 220

Pro Gln Gln Ser Asn Ser Gln Asn Ser Glu Val Val His Pro Glu Asn
225                 230                 235                 240

Gly Thr Met Asn Leu Ser Asn Gly Leu Asn Val Ser Gly Ser Glu Val
                245                 250                 255

Thr Ser Met Asn Tyr Phe Leu Ser Ser Pro Val His Ser Leu Gly Gly
            260                 265                 270

Met Val Met Pro Ser Lys Trp Ile Ala Ala Ala Ala Met Asp Asn
        275                 280                 285

Gly Cys Cys Asn Phe Lys Thr
        290                 295

<210> SEQ ID NO 35
<211> LENGTH: 1446
<212> TYPE: DNA
<213> ORGANISM: Zea mays
<220> FEATURE:
<223> OTHER INFORMATION: G3911

<400> SEQUENCE: 35
accacacgtc cgcccacgcg tccgcctacg cgtcggcgga ctcgcgtgcc cccacgcggg      60
```

```
cgggcttggc ttgggactgg gccgcccggc cgcgaggaat aaactcactc ctgccttcat    120
acgtatccat agccgcggca gtacgtgtat gtggttagct atacgcgacc tcagctcggg    180
cgcaagctac aacgccgacc aggcgagaag aagcatcgat agtgtgacga gctaacccac    240
cagcagcaac gtaatccaaa tccatggaca accagccgct gccctactcc acaggccagc    300
cccctgcccc cggaggagcc ccggtggcgg gcatgcctgg gcggccggc ctcccacccg     360
tgccgcacca cctacccgtt ccatctcaag tgaaagagat gacaactgtc ctaacaaaca    420
aactagggct caaaactaac ttcaaaaaaa tcacccacta aaagcacctt cctcttcctc    480
ttcctccgcc cccaatcccc ctcgtctcac aaccctagct gccccgaat ccatggatcc     540
taacaaatcc agcaccccgc cgccgcctcc agtcatgggt gccccgttg cctaccctcc     600
gcctgcgtac cctcccggtg tggccgccgg cgccggcgcc tacccgccgc agctctacgc    660
accgccggct gctgccgcgg cccagcaggc ggcggccgcg cagcagcagc agctgcagat    720
attctgggcg gagcagtacc gcgagatcga ggccactacc gacttcaaga atcacaacct    780
cccgctcgcc cgcatcaaga agatcatgaa agccgacgag gacgtccgca tgatcgccgc    840
cgaggctccc gtggtgttcg cccggggcctg cgagatgttc atcctcgagc tcacccatcg    900
cggctgggcg cacgccgaag agaacaagcg ccgcacgctc cagaaatccg acattgccgc    960
tgccatcgcc cgcaccgagg tattcgactt ccttgtggac atcgttccgc gcgacgacgg   1020
taaagacgct gatgcggcgg ccgccgcagc tgccgcggct gccgggatcc cgcgccccgc   1080
cgccggagta ccagccaccg accctctcgc ctactactac gtgcctcagc agtaatgtat   1140
catcatcacg ttattgttcc gtctatgtgc ctgagcaata atgtatcatc attgccttat   1200
tgttccgggg cagttgtgtt atttgtgtct gtttagttgc tgctgctgtt accgcgtaat   1260
agcatatgtg ttatctgtgt ctgtttagtt gctgctgctg ttgccgcgta ataaaacttg   1320
gtcatttacg gggctccctc aagattaaga attgagttgt ttgatggtag aatcctggta   1380
aggttgttgt aactggggggg cgcctttgtt tgggctggta gtgtatgcct aggcctcact   1440
tatctg                                                              1446
```

<210> SEQ ID NO 36
<211> LENGTH: 200
<212> TYPE: PRT
<213> ORGANISM: Zea mays
<220> FEATURE:
<223> OTHER INFORMATION: G3911 polypeptide (domain in aa coordinates: 83-148)

<400> SEQUENCE: 36

```
Met Asp Pro Asn Lys Ser Ser Thr Pro Pro Pro Pro Val Met Gly
1               5                   10                  15

Ala Pro Val Ala Tyr Pro Pro Ala Tyr Pro Pro Gly Val Ala Ala
                20                  25                  30

Gly Ala Gly Ala Tyr Pro Pro Gln Leu Tyr Ala Pro Ala Ala Ala
            35                  40                  45

Ala Ala Gln Gln Ala Ala Ala Ala Gln Gln Gln Gln Leu Gln Ile Phe
        50                  55                  60

Trp Ala Glu Gln Tyr Arg Glu Ile Glu Ala Thr Thr Asp Phe Lys Asn
65                  70                  75                  80

His Asn Leu Pro Leu Ala Arg Ile Lys Lys Ile Met Lys Ala Asp Glu
                85                  90                  95

Asp Val Arg Met Ile Ala Ala Glu Ala Pro Val Val Phe Ala Arg Ala
```

```
            100                 105                 110
Cys Glu Met Phe Ile Leu Glu Leu Thr His Arg Gly Trp Ala His Ala
            115                 120                 125

Glu Glu Asn Lys Arg Arg Thr Leu Gln Lys Ser Asp Ile Ala Ala Ala
            130                 135                 140

Ile Ala Arg Thr Glu Val Phe Asp Phe Leu Val Asp Ile Val Pro Arg
145                 150                 155                 160

Asp Asp Gly Lys Asp Ala Asp Ala Ala Ala Ala Ala Ala Ala Ala Ala
                165                 170                 175

Ala Gly Ile Pro Arg Pro Ala Ala Gly Val Pro Ala Thr Asp Pro Leu
            180                 185                 190

Ala Tyr Tyr Tyr Val Pro Gln Gln
            195                 200
```

<210> SEQ ID NO 37
<211> LENGTH: 618
<212> TYPE: DNA
<213> ORGANISM: Oryza sativa
<220> FEATURE:
<223> OTHER INFORMATION: G3546

<400> SEQUENCE: 37

```
atggagccca atccaccac ccctcctccg cctcctccgc ccccgtgct gggcgccccc      60
gtcccttacc cgccggcggg agcctacccc ccacccgtcg ggccctacgc ccacgcgccg     120
ccgctctacg ccccgcctcc ccccgccgcc gccgccgcct ccgccgccgc caccgccgcc     180
tcgcagcagg ccgccgccgc gcagctccag aacttctggg cggagcagta ccgcgagatc     240
gagcacacca ccgacttcaa gaaccacaac ctcccctcg cccgcatcaa gaagatcatg     300
aaggccgacg aggacgtccg catgatcgcc gccgaggccc ccgtcgtgtt cgccagggcg     360
tgcgagatgt tcatcctcga gctcacccac cgcggctggg cgcacgccga ggagaacaag     420
cgccgcacgc tccagaagtc cgacatcgcc gccgccatcg cccgcaccga ggtcttcgac     480
ttcctcgtcg acatcgtgcc ccgcgacgag gccaaggacg ccgaggccgc cgccgccgtt     540
gccgccggga tccccacc cgccgccggt ttgcccgcca ccgaccccat ggcctactac     600
tatgtccagc cgcagtaa                                                    618
```

<210> SEQ ID NO 38
<211> LENGTH: 205
<212> TYPE: PRT
<213> ORGANISM: Oryza sativa
<220> FEATURE:
<223> OTHER INFORMATION: G3546 polypeptide (domain in aa coordinates: 91-156)

<400> SEQUENCE: 38

```
Met Glu Pro Lys Ser Thr Thr Pro Pro Pro Pro Pro Pro Pro Pro Val
1               5                   10                  15

Leu Gly Ala Pro Val Pro Tyr Pro Pro Ala Gly Ala Tyr Pro Pro Pro
            20                  25                  30

Val Gly Pro Tyr Ala His Ala Pro Pro Leu Tyr Ala Pro Pro Pro
        35                  40                  45

Ala Ala Ala Ala Ala Ser Ala Ala Thr Ala Ser Gln Gln Ala
        50                  55                  60

Ala Ala Ala Gln Leu Gln Asn Phe Trp Ala Glu Gln Tyr Arg Glu Ile
65                  70                  75                  80

Glu His Thr Thr Asp Phe Lys Asn His Asn Leu Pro Leu Ala Arg Ile
```

```
                85                  90                  95

Lys Lys Ile Met Lys Ala Asp Glu Asp Val Arg Met Ile Ala Ala Glu
            100                 105                 110

Ala Pro Val Val Phe Ala Arg Ala Cys Glu Met Phe Ile Leu Glu Leu
        115                 120                 125

Thr His Arg Gly Trp Ala His Ala Glu Glu Asn Lys Arg Arg Thr Leu
    130                 135                 140

Gln Lys Ser Asp Ile Ala Ala Ile Ala Arg Thr Glu Val Phe Asp
145                 150                 155                 160

Phe Leu Val Asp Ile Val Pro Arg Asp Glu Ala Lys Asp Ala Glu Ala
                165                 170                 175

Ala Ala Ala Val Ala Ala Gly Ile Pro His Pro Ala Ala Gly Leu Pro
            180                 185                 190

Ala Thr Asp Pro Met Ala Tyr Tyr Tyr Val Gln Pro Gln
        195                 200                 205

<210> SEQ ID NO 39
<211> LENGTH: 865
<212> TYPE: DNA
<213> ORGANISM: Zea mays
<220> FEATURE:
<223> OTHER INFORMATION: G3909

<400> SEQUENCE: 39
ccctgaccgc cgtaacaccc taggcaatgg agcccaaatc caccacccct ccccgcccc      60
ccgtgatggg cgcgcccatc gcgtatcctc ccccgcccgg cgccgcgtac cccgccgggc    120
cgtacgtgca cgcgccggcg gccgcgctct accctcctcc tccccctgccg ccggcgcccc   180
cctcctcgca gcagggcgcc gcggcggcgc accagcagca gctattctgg gcggagcaat    240
accgcgagat cgaggccacc accgacttca agaaccacaa cctgccgctc gcccgcatca    300
agaagatcat gaaggccgac gaggacgtgc gcatgatcgc cgccgaggcg cccgtcgtct    360
tctcccgcgc ctgcgagatg ttcatcctcg agctcaccca ccgcggctgg gcacacgccg    420
aggagaacaa gcgccgcacg ctgcagaagt ccgacatcgc cgccgccgtc gcgcgcaccg    480
aggtcttcga cttcctcgtc gacatcgtgc cgcgggacga ggccaaggac gccgactccg    540
ccgccatggg agcagccggg atcccgcacc ccgccgccgg cctgcccgcc gccgatccca    600
tgggctacta ctacgtccag ccgccgcagt aacgaatttg cttccttatc atggcttcgc    660
ttccatgcag cctttgcggg ttttagtaaa ctattattat tactgagagt gccctgttgt    720
tacccatgct ctgttgttgc cacccaataa ctcgatgacc tgatgatcat ctgatgtgcc    780
ccccgttccg taacaagtga ttccatttct gatttcagag aaaaaaaaaa aaaaaaaaa    840
aaaaaaaaaa aaaaaaaaaa aaaaa                                          865

<210> SEQ ID NO 40
<211> LENGTH: 201
<212> TYPE: PRT
<213> ORGANISM: Zea mays
<220> FEATURE:
<223> OTHER INFORMATION: G3909 polypeptide (domain in aa coordinates:
      86-151)

<400> SEQUENCE: 40

Met Glu Pro Lys Ser Thr Thr Pro Pro Pro Pro Val Met Gly Ala
1               5                   10                  15

Pro Ile Ala Tyr Pro Pro Pro Gly Ala Ala Tyr Pro Ala Gly Pro
            20                  25                  30
```

```
Tyr Val His Ala Pro Ala Ala Ala Leu Tyr Pro Pro Pro Leu Pro
         35                  40                  45

Pro Ala Pro Pro Ser Ser Gln Gln Gly Ala Ala Ala His Gln Gln
 50                  55                  60

Gln Leu Phe Trp Ala Glu Gln Tyr Arg Glu Ile Glu Ala Thr Thr Asp
 65                  70                  75                  80

Phe Lys Asn His Asn Leu Pro Leu Ala Arg Ile Lys Lys Ile Met Lys
                 85                  90                  95

Ala Asp Glu Asp Val Arg Met Ile Ala Ala Glu Ala Pro Val Val Phe
            100                 105                 110

Ser Arg Ala Cys Glu Met Phe Ile Leu Glu Leu Thr His Arg Gly Trp
        115                 120                 125

Ala His Ala Glu Glu Asn Lys Arg Arg Thr Leu Gln Lys Ser Asp Ile
    130                 135                 140

Ala Ala Ala Val Ala Arg Thr Glu Val Phe Asp Phe Leu Val Asp Ile
145                 150                 155                 160

Val Pro Arg Asp Glu Ala Lys Asp Ala Asp Ser Ala Ala Met Gly Ala
                165                 170                 175

Ala Gly Ile Pro His Pro Ala Ala Gly Leu Pro Ala Ala Asp Pro Met
            180                 185                 190

Gly Tyr Tyr Tyr Val Gln Pro Pro Gln
        195                 200
```

<210> SEQ ID NO 41
<211> LENGTH: 1256
<212> TYPE: DNA
<213> ORGANISM: Zea mays
<220> FEATURE:
<223> OTHER INFORMATION: G3552

<400> SEQUENCE: 41

```
ttaagaacct agtaggcaga cccggccggc gtagagaggg ggggaggtcg acgagacaga      60
gagagaaggc caagaggctt cctctcccca ttcctccctt ccgtgcccta gccgagccag     120
ccgcgaggaa ggaggcatcc cgccgtctcg cctggcgccc gcccgtcggc cgaccttctg     180
ccgcagcttc caattctaaa aagatcatag atttttgtgc aagagcgagt ggatatggaa     240
ccatcccctc agcctatggg tgtcgctgcc ggtgggtcac aagtgtatcc tgcctctgcc     300
tatccgcctg cagcaacagt agctcctgct tctgttgtat ctgctggttt acagtcaggg     360
cagccattcc cagccaaccc tggtcatatg agtgctcagc accagattgt ctaccaacaa     420
gctcaacaat tccaccaaca gctccagcag cagcaacagc agcagcttca gcagttctgg     480
gtcgaacgca tgactgaaat tgaggcgacg actgatttca agaaccacaa cttgccactt     540
gcgaggataa agaagatcat gaaggccgat gaagatgttc gcatgatctc agccgaagct     600
cctgtggtct tcgcaaaagc ttgtgagata ttcatactgg agctgacact taggtcgtgg     660
atgcacactg aggagaacaa gcgccgcacc ttgcaaaaga tgacattgc agcagcgatc     720
actaggactg acatttatga cttcttggtc gacattgttc caggatga gatgaaggag     780
gacggaattg gcttcctag ggctggtctg ccaccatgg gagccccagc tgatgcatat      840
ccatactact acatgccaca gcagcaggtg cctggttctg aatggttta tggtgcccag      900
caagggcacc cagtgactta tttgtggcag gagcctcagc aacagcagga gcaagctcct     960
gaagagcagc aatctgcatg aaagtggctg agaatattgc tcagaagcta tcacctgatt    1020
cagagttctc atttaggtt gtccaaactg caggttttct tagtaatatc gttggttatc    1080
```

```
aaactgaaac aggcgattct aagtagggtg tagcatcatg gtagtttcat ttctgcttgt    1140
gatgttagtt gaaaggataa tgattagtgg ctagtggatt aaagttacca taccatttcc    1200
ttctattccg aaagtttgcc tccatgaggc ctctgatatg acgaaaaaat aaaaaa        1256
```

<210> SEQ ID NO 42
<211> LENGTH: 248
<212> TYPE: PRT
<213> ORGANISM: Zea mays
<220> FEATURE:
<223> OTHER INFORMATION: G3552 polypeptide (domain in aa coordinates: 100-165)

<400> SEQUENCE: 42

```
Met Glu Pro Ser Pro Gln Pro Met Gly Val Ala Ala Gly Gly Ser Gln
1               5                   10                  15

Val Tyr Pro Ala Ser Ala Tyr Pro Pro Ala Ala Thr Val Ala Pro Ala
            20                  25                  30

Ser Val Val Ser Ala Gly Leu Gln Ser Gly Gln Pro Phe Pro Ala Asn
        35                  40                  45

Pro Gly His Met Ser Ala Gln His Gln Ile Val Tyr Gln Gln Ala Gln
    50                  55                  60

Gln Phe His Gln Gln Leu Gln Gln Gln Gln Gln Gln Gln Leu Gln Gln
65                  70                  75                  80

Phe Trp Val Glu Arg Met Thr Glu Ile Glu Ala Thr Thr Asp Phe Lys
                85                  90                  95

Asn His Asn Leu Pro Leu Ala Arg Ile Lys Lys Ile Met Lys Ala Asp
            100                 105                 110

Glu Asp Val Arg Met Ile Ser Ala Glu Ala Pro Val Val Phe Ala Lys
        115                 120                 125

Ala Cys Glu Ile Phe Ile Leu Glu Leu Thr Leu Arg Ser Trp Met His
    130                 135                 140

Thr Glu Glu Asn Lys Arg Arg Thr Leu Gln Lys Asn Asp Ile Ala Ala
145                 150                 155                 160

Ala Ile Thr Arg Thr Asp Ile Tyr Asp Phe Leu Val Asp Ile Val Pro
                165                 170                 175

Arg Asp Glu Met Lys Glu Asp Gly Ile Gly Leu Pro Arg Ala Gly Leu
            180                 185                 190

Pro Pro Met Gly Ala Pro Ala Asp Ala Tyr Pro Tyr Tyr Met Pro
        195                 200                 205

Gln Gln Gln Val Pro Gly Ser Gly Met Val Tyr Gly Ala Gln Gln Gly
    210                 215                 220

His Pro Val Thr Tyr Leu Trp Gln Glu Pro Gln Gln Gln Glu Gln
225                 230                 235                 240

Ala Pro Glu Glu Gln Gln Ser Ala
                245
```

<210> SEQ ID NO 43
<211> LENGTH: 748
<212> TYPE: DNA
<213> ORGANISM: Arabidopsis thaliana
<220> FEATURE:
<223> OTHER INFORMATION: G483

<400> SEQUENCE: 43

```
gagatagctt agcaatggag cagtcagaag agggtcaaca gcaacagcaa cagggagtga     60
tggattatgt acctcctcat gcttatcaga gtgggccagt aaatgcagct tcccatatgg    120
```

```
cattccaaca agctcaccac ttccaccacc accatcagca gcaacaacag cagcagcttc      180
agatgttctg ggctaaccaa atgcaagaga tcgagcatac cactgatttc aagaaccaca      240
cccttcccct agcccgcatc aagaagatca tgaaagctga tgaagatgtg aggatgatct      300
ctgcggaggc tcctgtgatt tttgccaagg cctgtgagat gttcattttg agctcactc      360 tacgtgcttg gatccacacc gaggagaaca agaggaggac cttgcagaag aacgacatcg      420
ccgctgccat ttccaggacc gacgtgtttg atttccttgt ggacataatc ccgagggacg      480
agctgaaaga agaaggttta ggcgtgacca aagggaccat accatcggtg gtgggttccc      540
cgccatacta ttacttgcaa caacagggga tgatgcaaca ctggcccag gagcaacacc       600 ctgatgagtc ttaaaacttt tcccctttcg tttgtttggt tgtatcgtag taaggtagct      660
ctgctctgct gggaaccatt tctattgtgt tctgtaatga catgttagta tatccccagt      720
ctatatctat ggcaatgcag tttctgtt                                         748
```

<210> SEQ ID NO 44
<211> LENGTH: 199
<212> TYPE: PRT
<213> ORGANISM: Arabidopsis thaliana
<220> FEATURE:
<223> OTHER INFORMATION: G483 polypeptide (domain in aa coordinates: 77-142)

<400> SEQUENCE: 44

```
Met Glu Gln Ser Glu Glu Gly Gln Gln Gln Gln Gln Gly Val Met
1               5                   10                  15

Asp Tyr Val Pro Pro His Ala Tyr Gln Ser Gly Pro Val Asn Ala Ala
            20                  25                  30

Ser His Met Ala Phe Gln Gln Ala His His Phe His His His Gln
        35                  40                  45

Gln Gln Gln Gln Gln Gln Leu Gln Met Phe Trp Ala Asn Gln Met Gln
    50                  55                  60

Glu Ile Glu His Thr Thr Asp Phe Lys Asn His Thr Leu Pro Leu Ala
65                  70                  75                  80

Arg Ile Lys Lys Ile Met Lys Ala Asp Glu Asp Val Arg Met Ile Ser
                85                  90                  95

Ala Glu Ala Pro Val Ile Phe Ala Lys Ala Cys Glu Met Phe Ile Leu
            100                 105                 110

Glu Leu Thr Leu Arg Ala Trp Ile His Thr Glu Glu Asn Lys Arg Arg
        115                 120                 125

Thr Leu Gln Lys Asn Asp Ile Ala Ala Ala Ile Ser Arg Thr Asp Val
    130                 135                 140

Phe Asp Phe Leu Val Asp Ile Ile Pro Arg Asp Glu Leu Lys Glu Glu
145                 150                 155                 160

Gly Leu Gly Val Thr Lys Gly Thr Ile Pro Ser Val Val Gly Ser Pro
                165                 170                 175

Pro Tyr Tyr Tyr Leu Gln Gln Gln Gly Met Met Gln His Trp Pro Gln
            180                 185                 190

Glu Gln His Pro Asp Glu Ser
        195
```

<210> SEQ ID NO 45
<211> LENGTH: 1123
<212> TYPE: DNA
<213> ORGANISM: Glycine max
<220> FEATURE:

<223> OTHER INFORMATION: G3547

<400> SEQUENCE: 45

```
acagcttttg ttctagcact tcgctgtctg aggttctgga ttctcagtgt ttgcggagcg      60
cagcatcatc ttttagggaa gaatggatca tcaagggcat agccagaacc catctatggg     120
ggttgttggt agtggagctc aattagcata tggttctaac ccatatcagc caggccaaat     180
aactgggcca ccggggtctg ttgtgacatc agttgggacc attcaatcca ccggtcaacc     240
tgctggagct cagcttggac agcatcaact tgcttatcag catattcatc agcaacaaca     300
gcaccagctt cagcaacagc tccaacaatt tggtcaagc cagtaccaag aaattgagaa      360
ggttactgat tttaagaacc acagtcttcc cctggcaagg atcaagaaga ttatgaaggc     420
tgacgaggat gttaggatga tatcagctga agcaccagtc attttgcaa gggcatgtga      480
aatgttcata ttagagttaa ccctgcgctc ttggaatcac actgaagaga acaaaaggcg     540
aacacttcag aaaaatgata ttgctgctgc tatcacaagg actgacatct ttgatttctt     600
ggttgacatt gtgcctcgtg aggacttgaa agatgaagtg cttgcatcaa tcccaagagg     660
aacaatgcct gttgcagggc ctgctgatgc ccttccatac tgctacatgc cgcctcagca     720
tccgtcccaa gttggagctg ctggtgtcat aatgggtaag cctgtgatgg acccaaacat     780
gtatgctcag cagtctcacc cttacatggc accacaaatg tggccacagc caccagacca     840
acgacagtcg tctccagaac attagctgat gtgtcgtgga aattaagata accaggcact     900
ggaatcagtt gtgaatgtca aactgaatgg ttgggaaggt cgatactaca tagcgagcag     960
aagctgtagc tgatagttta catgcaatgc agactataaa catatgtaga taatgtgcta    1020
gggaaaactt aaccttatct ttgatttagc tggaaaaaat ggtatttttc attttaattc    1080
acaggtcatc agatgataat atttatttac tggtgcatag cag                      1123
```

<210> SEQ ID NO 46
<211> LENGTH: 260
<212> TYPE: PRT
<213> ORGANISM: Glycine max
<220> FEATURE:
<223> OTHER INFORMATION: G3547 polypeptide (domain in aa coordinates: 102-167)

<400> SEQUENCE: 46

```
Met Asp His Gln Gly His Ser Gln Asn Pro Ser Met Gly Val Val Gly
1               5                   10                  15

Ser Gly Ala Gln Leu Ala Tyr Gly Ser Asn Pro Tyr Gln Pro Gly Gln
            20                  25                  30

Ile Thr Gly Pro Pro Gly Ser Val Val Thr Ser Val Gly Thr Ile Gln
        35                  40                  45

Ser Thr Gly Gln Pro Ala Gly Ala Gln Leu Gly Gln His Gln Leu Ala
    50                  55                  60

Tyr Gln His Ile His Gln Gln Gln His Gln Leu Gln Gln Gln Leu
65                  70                  75                  80

Gln Gln Phe Trp Ser Ser Gln Tyr Gln Glu Ile Glu Lys Val Thr Asp
                85                  90                  95

Phe Lys Asn His Ser Leu Pro Leu Ala Arg Ile Lys Lys Ile Met Lys
            100                 105                 110

Ala Asp Glu Asp Val Arg Met Ile Ser Ala Glu Ala Pro Val Ile Phe
        115                 120                 125

Ala Arg Ala Cys Glu Met Phe Ile Leu Glu Leu Thr Leu Arg Ser Trp
    130                 135                 140
```

Asn His Thr Glu Glu Asn Lys Arg Arg Thr Leu Gln Lys Asn Asp Ile
145                 150                 155                 160

Ala Ala Ala Ile Thr Arg Thr Asp Ile Phe Asp Phe Leu Val Asp Ile
            165                 170                 175

Val Pro Arg Glu Asp Leu Lys Asp Glu Val Leu Ala Ser Ile Pro Arg
        180                 185                 190

Gly Thr Met Pro Val Ala Gly Pro Ala Asp Ala Leu Pro Tyr Cys Tyr
    195                 200                 205

Met Pro Pro Gln His Pro Ser Gln Val Gly Ala Ala Gly Val Ile Met
210                 215                 220

Gly Lys Pro Val Met Asp Pro Asn Met Tyr Ala Gln Gln Ser His Pro
225                 230                 235                 240

Tyr Met Ala Pro Gln Met Trp Pro Gln Pro Pro Asp Gln Arg Gln Ser
                245                 250                 255

Ser Pro Glu His
        260

<210> SEQ ID NO 47
<211> LENGTH: 925
<212> TYPE: DNA
<213> ORGANISM: Arabidopsis thaliana
<220> FEATURE:
<223> OTHER INFORMATION: G714

<400> SEQUENCE: 47

| | | | | |
|---|---|---|---|---|
| ccacgcgtcc | gcgtcaatct | ttgagtttgg | tagagaaatg | gatcaacaag gacaatcatc | 60 |
| agctatgaac | tatggttcaa | acccatatca | aaccaacgcc | atgaccacta caccaaccgg | 120 |
| ttcagaccat | ccagcttacc | atcagatcca | ccagcaacaa | caacaacagc tcactcaaca | 180 |
| gcttcaatct | ttctgggaga | ctcaattcaa | agagattgag | aaaaccactg atttcaagaa | 240 |
| ccatagcctt | ccattggcaa | gaatcaagaa | aatcatgaaa | gctgatgaag atgtgcgtat | 300 |
| gatctcggcc | gaggcgcctg | ttgtgttcgc | cagggcctgc | gagatgttta ttctggagct | 360 |
| tacgttaagg | tcttggaacc | atactgagga | gaacaagaga | aggacgttgc agaagaatga | 420 |
| tatcgcggct | gcggtgacta | gaactgatat | ttttgatttt | cttgtggata ttgttcctcg | 480 |
| ggaggatctt | cgtgatgaag | tctttgggtgg | tgttggtgct | gaagctgcta cagctgcggg | 540 |
| ttatccgtat | ggatacttgc | ctcctggaac | agctccaatt | gggaacccgg aatggttat | 600 |
| gggtaacccg | ggcgcgtatc | cgccgaaggc | gtatatgggt | cagccaatgt ggcaacaacc | 660 |
| aggacctgag | cagcaggatc | ctgacaatta | gcttggccta | ataaactagc cgtctaattc | 720 |
| gaagctctcc | ccggtggatc | tactcaagaa | gaagaatgtt | aatagaaaac tattgcgaca | 780 |
| taaaaagttt | ggtgtagtag | aataatttct | gttttatgat | ccatggattt atcaattgtt | 840 |
| attcagtttg | gtttatcttg | tcatcaaact | gttttcggtc | aatgtaacaa attcataaat | 900 |
| tgagaattga | acttacaaaa | ggcta | | | 925 |

<210> SEQ ID NO 48
<211> LENGTH: 217
<212> TYPE: PRT
<213> ORGANISM: Arabidopsis thaliana
<220> FEATURE:
<223> OTHER INFORMATION: G714 polypeptide (domain in aa coordinates:
    71-136)

<400> SEQUENCE: 48

Met Asp Gln Gln Gly Gln Ser Ser Ala Met Asn Tyr Gly Ser Asn Pro

```
              1               5                  10                 15
Tyr Gln Thr Asn Ala Met Thr Thr Thr Pro Thr Gly Ser Asp His Pro
                 20                  25                 30
Ala Tyr His Gln Ile His Gln Gln Gln Gln Gln Leu Thr Gln Gln
         35                  40                 45
Leu Gln Ser Phe Trp Glu Thr Gln Phe Lys Glu Ile Glu Lys Thr Thr
 50                  55                 60
Asp Phe Lys Asn His Ser Leu Pro Leu Ala Arg Ile Lys Lys Ile Met
 65                  70                 75                 80
Lys Ala Asp Glu Asp Val Arg Met Ile Ser Ala Glu Ala Pro Val Val
                 85                  90                 95
Phe Ala Arg Ala Cys Glu Met Phe Ile Leu Glu Leu Thr Leu Arg Ser
                 100                 105                110
Trp Asn His Thr Glu Glu Asn Lys Arg Arg Thr Leu Gln Lys Asn Asp
             115                 120                 125
Ile Ala Ala Ala Val Thr Arg Thr Asp Ile Phe Asp Phe Leu Val Asp
 130                 135                 140
Ile Val Pro Arg Glu Asp Leu Arg Asp Glu Val Leu Gly Gly Val Gly
145                 150                 155                 160
Ala Glu Ala Ala Thr Ala Ala Gly Tyr Pro Tyr Gly Tyr Leu Pro Pro
             165                 170                 175
Gly Thr Ala Pro Ile Gly Asn Pro Gly Met Val Met Gly Asn Pro Gly
             180                 185                 190
Ala Tyr Pro Pro Lys Ala Tyr Met Gly Gln Pro Met Trp Gln Gln Pro
             195                 200                 205
Gly Pro Glu Gln Gln Asp Pro Asp Asn
             210                 215

<210> SEQ ID NO 49
<211> LENGTH: 780
<212> TYPE: DNA
<213> ORGANISM: Oryza sativa
<220> FEATURE:
<223> OTHER INFORMATION: G3542

<400> SEQUENCE: 49
atggaaccat cctcacagcc tcagcctgtg atgggtgttg ccactggtgg gtcacaagca      60
tatcctcctc ctgctgctgc atatccacct caagccatgg ttcctggagc tcctgctgtt     120
gttcctcctg ctcacagcc  atcagcacca ttccccacta atccagctca actcagtgct     180
cagcaccagc tagtctacca caagcccag  caatttcatc agcagctgca gcaacagcaa     240
cagcagcaac tccgtgagtt ctgggctaac caaatggaag agattgagca acaaccgac      300
ttcaagaacc acagcttgcc actcgcaagg ataaagaaga taatgaaggc tgatgaggat     360
gtccggatga tctcggcaga agccccgtt  gtcttcgcaa aggcatgcga ggtattcata     420
ttagagttaa cattgaggtc gtggatgcac acggaggaga caagcgccg  gaccttgcag     480
aagaatgaca ttgcagctgc catcaccagg actgatatct atgacttctt ggtggacata     540
gttcccaggg atgaaatgaa agaagaaggg cttgggcttc cgagggttgg cctaccgcct     600
aatgtggggg gcgcagcaga cacatatcca tattactacg tgccagcgca gcaggggcct     660
ggatcaggaa tgatgtacgg tggacagcaa ggtcacccgg tgacgtatgt gtggcagcag     720
cctcaagagc aacaggaaga ggcccctgaa gagcagcact ctctgccaga aagtagctaa     780

<210> SEQ ID NO 50
```

<211> LENGTH: 259
<212> TYPE: PRT
<213> ORGANISM: Oryza sativa
<220> FEATURE:
<223> OTHER INFORMATION: G3542 polypeptide (domain in aa coordinates: 106-171)

<400> SEQUENCE: 50

Met Glu Pro Ser Ser Gln Pro Gln Pro Val Met Gly Val Ala Thr Gly
1               5                   10                  15

Gly Ser Gln Ala Tyr Pro Pro Pro Ala Ala Tyr Pro Pro Gln Ala
            20                  25                  30

Met Val Pro Gly Ala Pro Ala Val Val Pro Pro Gly Ser Gln Pro Ser
        35                  40                  45

Ala Pro Phe Pro Thr Asn Pro Ala Gln Leu Ser Ala Gln His Gln Leu
    50                  55                  60

Val Tyr Gln Gln Ala Gln Gln Phe His Gln Gln Leu Gln Gln Gln Gln
65                  70                  75                  80

Gln Gln Gln Leu Arg Glu Phe Trp Ala Asn Gln Met Glu Glu Ile Glu
                85                  90                  95

Gln Thr Thr Asp Phe Lys Asn His Ser Leu Pro Leu Ala Arg Ile Lys
            100                 105                 110

Lys Ile Met Lys Ala Asp Glu Asp Val Arg Met Ile Ser Ala Glu Ala
        115                 120                 125

Pro Val Val Phe Ala Lys Ala Cys Glu Val Phe Ile Leu Glu Leu Thr
    130                 135                 140

Leu Arg Ser Trp Met His Thr Glu Glu Asn Lys Arg Arg Thr Leu Gln
145                 150                 155                 160

Lys Asn Asp Ile Ala Ala Ala Ile Thr Arg Thr Asp Ile Tyr Asp Phe
                165                 170                 175

Leu Val Asp Ile Val Pro Arg Asp Glu Met Lys Glu Glu Gly Leu Gly
            180                 185                 190

Leu Pro Arg Val Gly Leu Pro Pro Asn Val Gly Gly Ala Ala Asp Thr
        195                 200                 205

Tyr Pro Tyr Tyr Tyr Val Pro Ala Gln Gln Gly Pro Gly Ser Gly Met
    210                 215                 220

Met Tyr Gly Gly Gln Gln Gly His Pro Val Thr Tyr Val Trp Gln Gln
225                 230                 235                 240

Pro Gln Glu Gln Gln Glu Ala Pro Glu Gln His Ser Leu Pro
                245                 250                 255

Glu Ser Ser

<210> SEQ ID NO 51
<211> LENGTH: 927
<212> TYPE: DNA
<213> ORGANISM: Arabidopsis thaliana
<220> FEATURE:
<223> OTHER INFORMATION: G489

<400> SEQUENCE: 51
gaattcggca cgagacccac caagaggatc aaccagtctc ttccccttca gattctcctt      60
tccacagtaa tggatcaaca agaccatgga cagtctggag ctatgaacta tggcacaaac     120
ccataccaaa ccaacccgat gagcaccact gctgctactg tagcaggagg tgcggcacaa     180
ccaggccagc tggcgttcca ccagatccat cagcagcagc agcagcaaca gctggcacag     240
cagcttcaag cattttggga gaaccaattc aaagagattg agaagactac cgatttcaag     300

```
aagcacagcc ttccccttgc gagaatcaag aaaatcatga aagcggatga agatgtccgt    360
atgatctcgg ctgaggcgcc tgtcgtgttt gcaagggcct gtgagatgtt catcctggag    420
ctgacactca ggtcgtggaa ccacactgag gagaataaga ggcggacgtt gcagaagaac    480
gatattgctg ctgctgtgac tagaaccgat atttttgatt tccttgtgga tattgttccc    540
cgggaggatc tccgagatga agtcttggga agtattccga ggggcactgt cccggaagct    600
gctgctgctg gttacccgta tggatacttg cctgcaggaa ctgctccaat aggaaatccg    660
ggaatggtta tgggtaatcc cggtggtgcg tatccaccta atccttatat gggtcaacca    720
atgtggcaac aacaggcacc tgaccaacct gaccaggaaa attagcaaga aactgtgagt    780
cttcccgctt cttttaggcc taccttgtag tcttggggtt ttgtttctgt tttcgaataa    840
tggtaacctt tgtataactt atttcagtat cgtctcagtt tggtactatg tcagttttgg    900
taaaaaaaaa aaaaaaaaaa aaaaaaa                                        927
```

<210> SEQ ID NO 52
<211> LENGTH: 231
<212> TYPE: PRT
<213> ORGANISM: Arabidopsis thaliana
<220> FEATURE:
<223> OTHER INFORMATION: G489 polypeptide (domain in aa coordinates: 81-146)

<400> SEQUENCE: 52

```
Met Asp Gln Gln Asp His Gly Gln Ser Gly Ala Met Asn Tyr Gly Thr
1               5                   10                  15

Asn Pro Tyr Gln Thr Asn Pro Met Ser Thr Thr Ala Ala Thr Val Ala
            20                  25                  30

Gly Gly Ala Ala Gln Pro Gly Gln Leu Ala Phe His Gln Ile His Gln
        35                  40                  45

Gln Gln Gln Gln Gln Gln Leu Ala Gln Gln Leu Gln Ala Phe Trp Glu
    50                  55                  60

Asn Gln Phe Lys Glu Ile Glu Lys Thr Thr Asp Phe Lys Lys His Ser
65                  70                  75                  80

Leu Pro Leu Ala Arg Ile Lys Lys Ile Met Lys Ala Asp Glu Asp Val
                85                  90                  95

Arg Met Ile Ser Ala Glu Ala Pro Val Val Phe Ala Arg Ala Cys Glu
            100                 105                 110

Met Phe Ile Leu Glu Leu Thr Leu Arg Ser Trp Asn His Thr Glu Glu
        115                 120                 125

Asn Lys Arg Arg Thr Leu Gln Lys Asn Asp Ile Ala Ala Ala Val Thr
    130                 135                 140

Arg Thr Asp Ile Phe Asp Phe Leu Val Asp Ile Val Pro Arg Glu Asp
145                 150                 155                 160

Leu Arg Asp Glu Val Leu Gly Ser Ile Pro Arg Gly Thr Val Pro Glu
                165                 170                 175

Ala Ala Ala Ala Gly Tyr Pro Tyr Gly Tyr Leu Pro Ala Gly Thr Ala
            180                 185                 190

Pro Ile Gly Asn Pro Gly Met Val Met Gly Asn Pro Gly Gly Ala Tyr
        195                 200                 205

Pro Pro Asn Pro Tyr Met Gly Gln Pro Met Trp Gln Gln Gln Ala Pro
    210                 215                 220

Asp Gln Pro Asp Gln Glu Asn
225                 230
```

<210> SEQ ID NO 53
<211> LENGTH: 753
<212> TYPE: DNA
<213> ORGANISM: Oryza sativa
<220> FEATURE:
<223> OTHER INFORMATION: G3544

<400> SEQUENCE: 53

```
atggagccat catcacaacc tcagccggca attggtgttg ttgctggtgg atcacaagtg      60
taccctgcat accggcctgc agcaacagtg cctacagctc ctgctgtcat tcctgccggt     120
tcacagccag caccgtcgtt ccctgccaac cctgatcaac tgagtgctca gcaccagctc     180
gtctatcagc aagcccagca atttcaccag cagcttcagc agcagcaaca gcgtcaactc     240
cagcagtttt gggctgaacg tctggtcgat attgaacaaa ctactgactt caagaaccac     300
agcttgccac ttgctaggat aaagaagatc atgaaggcag atgaggacgt tcgcatgatc     360
tccgcagagg ctcctgtgat ctttgcgaaa gcatgtgaga tattcatact ggagctgacc     420
ctgagatcat ggatgcacac ggaggagaac aagcgccgta ccttgcagaa gaatgacata     480
gcagctgcca tcaccaggac ggatatgtac gatttcttgg tagatatagt tcccagggat     540
gacttgaagg aggagggagt tgggctccct agggctggat tgccgccctt gggtgtccct     600
gctgactcat atccgtatgg ctactatgtg ccacagcagc aggtcccagg tgcaggaata     660
gcgtatggtg gtcagcaagg tcatccgggg tatctgtggc aggatcctca ggaacagcag     720
gaagagcctc ctgcagagca gcaaagtgat taa                                  753
```

<210> SEQ ID NO 54
<211> LENGTH: 250
<212> TYPE: PRT
<213> ORGANISM: Oryza sativa
<220> FEATURE:
<223> OTHER INFORMATION: G3544 polypeptide (domain in aa coordinates: 102-167)

<400> SEQUENCE: 54

```
Met Glu Pro Ser Ser Gln Pro Gln Pro Ala Ile Gly Val Val Ala Gly
1               5                   10                  15

Gly Ser Gln Val Tyr Pro Ala Tyr Arg Pro Ala Thr Val Pro Thr
            20                  25                  30

Ala Pro Ala Val Ile Pro Ala Gly Ser Gln Pro Ala Ser Phe Pro
        35                  40                  45

Ala Asn Pro Asp Gln Leu Ser Ala Gln His Gln Leu Val Tyr Gln Gln
    50                  55                  60

Ala Gln Gln Phe His Gln Gln Leu Gln Gln Gln Gln Gln Arg Gln Leu
65                  70                  75                  80

Gln Gln Phe Trp Ala Glu Arg Leu Val Asp Ile Glu Gln Thr Thr Asp
                85                  90                  95

Phe Lys Asn His Ser Leu Pro Leu Ala Arg Ile Lys Lys Ile Met Lys
            100                 105                 110

Ala Asp Glu Asp Val Arg Met Ile Ser Ala Glu Ala Pro Val Ile Phe
        115                 120                 125

Ala Lys Ala Cys Glu Ile Phe Ile Leu Glu Leu Thr Leu Arg Ser Trp
    130                 135                 140

Met His Thr Glu Glu Asn Lys Arg Arg Thr Leu Gln Lys Asn Asp Ile
145                 150                 155                 160

Ala Ala Ala Ile Thr Arg Thr Asp Met Tyr Asp Phe Leu Val Asp Ile
                165                 170                 175
```

-continued

```
Val Pro Arg Asp Asp Leu Lys Glu Glu Gly Val Gly Leu Pro Arg Ala
            180                 185                 190

Gly Leu Pro Pro Leu Gly Val Pro Ala Asp Ser Tyr Pro Tyr Gly Tyr
        195                 200                 205

Tyr Val Pro Gln Gln Gln Val Pro Gly Ala Gly Ile Ala Tyr Gly Gly
    210                 215                 220

Gln Gln Gly His Pro Gly Tyr Leu Trp Gln Asp Pro Gln Glu Gln Gln
225                 230                 235                 240

Glu Glu Pro Pro Ala Glu Gln Gln Ser Asp
                245                 250
```

<210> SEQ ID NO 55
<211> LENGTH: 1126
<212> TYPE: DNA
<213> ORGANISM: Glycine max
<220> FEATURE:
<223> OTHER INFORMATION: G3550

<400> SEQUENCE: 55

```
cttgcgccca atttccatgg aactgtaaag agaggatagt tagaagatta atcttaaag      60
cagtaagtca tcatggataa atcagagcag actcaacagc agcagcagca acaacagcat    120
gtgatgggag ttgccgcagg ggctagccaa atggcctatt cttctcacta cccgactgct    180
tccatggtgg cttctggcac gcccgctgta actgctcctt ccccaactca ggctccagct    240
gccttctcta gttctgctca ccagcttgca taccagcaag cacagcattt ccaccaccaa    300
cagcagcaac accaacaaca gcagcttcaa atgttctggt caaaccaaat gcaagaaatt    360
gagcaaacaa ttgactttaa aaaccatagc cttcctcttg ctcggataaa aaagataatg    420
aaagctgatg aagatgtccg gatgatttca gcagaagctc cggtcatatt tgcaaaagct    480
tgtgaaatgt tcatattaga gttgacgttg cgatcttgga tccacacaga agagaacaag    540
aggagaactc tacaaaagaa tgatatagca gctgctattt cgagaaacga tgttttttgat    600
ttcttggttg atattattcc aagagatgag ttgaaagagg aaggacttgg aataaccaag    660
gctactattc cgttagtggg ttctccagct gatatgccat attactatgt ccctccacag    720
catcctgttg taggaccacc tgggatgatc atgggcaagc ccattggcgc tgagcaagca    780
acactatatt ctacacagca gcctcgacct cctgtggcgt tcatgccatg gcctcataca    840
caaccctgc aacagcagcc accccaacat caacaaacag actcatgatg actatgcaat    900
tcaattaggt tggaaagtag cctgcacctt ttgattatta caaatttact taatgccttt    960
cagccagctg tagtttagtg ttgtgcattg aaaaaaagca aaagattgtt ttgaggtttc   1020
ttgcactcat ttatgattgt atgagctctt gtgatgagtt acttttggtt gtgtttacta   1080
ttggtgtagt ggttaaatta tttggcagct gtccataacc agagag                  1126
```

<210> SEQ ID NO 56
<211> LENGTH: 271
<212> TYPE: PRT
<213> ORGANISM: Glycine max
<220> FEATURE:
<223> OTHER INFORMATION: G3550 polypeptide (domain in aa coordinates:
      107-172)

<400> SEQUENCE: 56

```
Met Asp Lys Ser Glu Gln Thr Gln Gln Gln Gln Gln Gln Gln Gln His
1               5                   10                  15

Val Met Gly Val Ala Ala Gly Ala Ser Gln Met Ala Tyr Ser Ser His
            20                  25                  30
```

```
Tyr Pro Thr Ala Ser Met Val Ala Ser Gly Thr Pro Ala Val Thr Ala
         35                  40                  45

Pro Ser Pro Thr Gln Ala Pro Ala Ala Phe Ser Ser Ser Ala His Gln
     50                  55                  60

Leu Ala Tyr Gln Gln Ala Gln His Phe His His Gln Gln Gln Gln His
 65                  70                  75                  80

Gln Gln Gln Gln Leu Gln Met Phe Trp Ser Asn Gln Met Gln Glu Ile
                 85                  90                  95

Glu Gln Thr Ile Asp Phe Lys Asn His Ser Leu Pro Leu Ala Arg Ile
            100                 105                 110

Lys Lys Ile Met Lys Ala Asp Glu Asp Val Arg Met Ile Ser Ala Glu
            115                 120                 125

Ala Pro Val Ile Phe Ala Lys Ala Cys Glu Met Phe Ile Leu Glu Leu
        130                 135                 140

Thr Leu Arg Ser Trp Ile His Thr Glu Glu Asn Lys Arg Arg Thr Leu
145                 150                 155                 160

Gln Lys Asn Asp Ile Ala Ala Ala Ile Ser Arg Asn Asp Val Phe Asp
                165                 170                 175

Phe Leu Val Asp Ile Ile Pro Arg Asp Glu Leu Lys Glu Gly Leu
                180                 185                 190

Gly Ile Thr Lys Ala Thr Ile Pro Leu Val Gly Ser Pro Ala Asp Met
            195                 200                 205

Pro Tyr Tyr Tyr Val Pro Pro Gln His Pro Val Val Gly Pro Pro Gly
        210                 215                 220

Met Ile Met Gly Lys Pro Ile Gly Ala Glu Gln Ala Thr Leu Tyr Ser
225                 230                 235                 240

Thr Gln Gln Pro Arg Pro Pro Val Ala Phe Met Pro Trp Pro His Thr
                245                 250                 255

Gln Pro Leu Gln Gln Gln Pro Pro Gln His Gln Gln Thr Asp Ser
            260                 265                 270

<210> SEQ ID NO 57
<211> LENGTH: 1223
<212> TYPE: DNA
<213> ORGANISM: Glycine max
<220> FEATURE:
<223> OTHER INFORMATION: G3548

<400> SEQUENCE: 57
caaaccaaac ctctctttct cagtttctct ctcttagggt tttctcctcc cccattgacc      60
caccgtccat cgcaaaggaa gtcgcgccca atttccatgg actcagcagc aacatcagca     120
tgggatgggc gttgccacag gtgctagcca aatggcctat tcttctcact acccgactgc     180
tcccatggtg gcttctggca cgcctgctgt agctgttcct tccccaactc aggctccagc     240
tgccttctct agttctgctc accagcttgc ataccagcaa gcacagcatt ccaccacca     300 acagcagcaa caccaacaac agcagcttca atgttctggt caaaccaaa tgcaagaaat     360 tgagcaaaca attgacttta aaaccacag tcttcctctt gctcggataa aaagataat      420 gaaagctgat gaagatgtcc ggatgatttc tgcagaagct ccagtcatat ttgcaaagc      480 atgtgaaatg ttcatattag agttgacgtt gagatcttgg atccacacag aagagaacaa     540
gaggagaact ctacaaaaga atgatatagc agctgctatt tcgagaaacg atgttttga      600 tttcttggtt gatattatcc caagagatga gttgaaagag gaaggacttg gaataaccaa     660
ggctactatt ccattggtga attctccagc tgatatgcca tattactatg tccctccaca     720
```

```
gcatcctgtt gtaggacctc ctgggatgat catgggcaag cccgttggtg ctgagcaagc    780
aacgctgtat tctacacagc agcctcgacc tcccatggcg ttcatgccat ggccccatac    840
acaaccccag caacagcagc caccccaaca tcaacaaaca gactcatgat gaccatgcaa    900
ttcaattagg tcggaaagta gcatgcacct tatgattatt acaaatttac ttaatgcctt    960
taagtcagct gtagtttagt gttttgcatt gaaaaatgcc aaagattgtt tgaggtttct   1020
tgcactcatt tatgattgta tgagctctta tgctgagtta cttttggttg tgtttatttg   1080
aggtactggt gtggtagtta aattagtttg tagctgtcca taagtaaaca gcgtagctgc   1140
ttaattagga ggtctgaaat gatgaaatag tttgtattgt tattgcagaa ggtaggtttt   1200
attcagtatt tcattctact gca                                           1223
```

<210> SEQ ID NO 58
<211> LENGTH: 254
<212> TYPE: PRT
<213> ORGANISM: Glycine max
<220> FEATURE:
<223> OTHER INFORMATION: G3548 polypeptide (domain in aa coordinates: 90-155)

<400> SEQUENCE: 58

```
Met Gly Val Ala Thr Gly Ala Ser Gln Met Ala Tyr Ser Ser His Tyr
1               5                   10                  15

Pro Thr Ala Pro Met Val Ala Ser Gly Thr Pro Ala Val Ala Val Pro
            20                  25                  30

Ser Pro Thr Gln Ala Pro Ala Ala Phe Ser Ser Ser Ala His Gln Leu
        35                  40                  45

Ala Tyr Gln Gln Ala Gln His Phe His His Gln Gln Gln His Gln
    50                  55                  60

Gln Gln Gln Leu Gln Met Phe Trp Ser Asn Gln Met Gln Glu Ile Glu
65                  70                  75                  80

Gln Thr Ile Asp Phe Lys Asn His Ser Leu Pro Leu Ala Arg Ile Lys
                85                  90                  95

Lys Ile Met Lys Ala Asp Glu Asp Val Arg Met Ile Ser Ala Glu Ala
            100                 105                 110

Pro Val Ile Phe Ala Lys Ala Cys Glu Met Phe Ile Leu Glu Leu Thr
        115                 120                 125

Leu Arg Ser Trp Ile His Thr Glu Glu Asn Lys Arg Arg Thr Leu Gln
    130                 135                 140

Lys Asn Asp Ile Ala Ala Ala Ile Ser Arg Asn Asp Val Phe Asp Phe
145                 150                 155                 160

Leu Val Asp Ile Ile Pro Arg Asp Glu Leu Lys Glu Glu Gly Leu Gly
                165                 170                 175

Ile Thr Lys Ala Thr Ile Pro Leu Val Asn Ser Pro Ala Asp Met Pro
            180                 185                 190

Tyr Tyr Tyr Val Pro Pro Gln His Pro Val Val Gly Pro Pro Gly Met
        195                 200                 205

Ile Met Gly Lys Pro Val Gly Ala Glu Gln Ala Thr Leu Tyr Ser Thr
    210                 215                 220

Gln Gln Pro Arg Pro Pro Met Ala Phe Met Pro Trp Pro His Thr Gln
225                 230                 235                 240

Pro Gln Gln Gln Gln Pro Pro Gln His Gln Gln Thr Asp Ser
                245                 250
```

```
<210> SEQ ID NO 59
<211> LENGTH: 705
<212> TYPE: DNA
<213> ORGANISM: Arabidopsis thaliana
<220> FEATURE:
<223> OTHER INFORMATION: G715

<400> SEQUENCE: 59
atggatacca acaaccagca accacctccc tccgccgccg gaatccctcc tccaccacct    60
ggaaccacca tctccgccgc aggaggagga gcttcttacc accaccttct ccaacaacaa   120
caacaacagc tccaactatt ctggacctac caacgccaag agatcgaaca agttaacgat   180
ttcaaaaacc atcagcttcc actagctagg ataaaaaaga tcatgaaagc cgatgaagat   240
gttcgtatga tctccgcaga agcaccgatt ctcttcgcga aagcttgtga gcttttcatt   300
ctcgagctca cgatcagatc ttggcttcac gctgaggaga taaacgtcg tacgcttcag    360
aaaaacgata tcgctgctgc gattactagg actgatatct tcgatttcct tgttgatatt   420
gttcctagag atgagattaa ggacgaagcc gcagtcctcg gtggtggaat ggtggtggct   480
cctaccgcga gcggcgtgcc ttactattat ccgccgatgg gacaaccagc tggtcctgga   540
gggatgatga ttgggagacc agctatggat ccgaatggtg tttatgtcca gcctccgtct   600
caggcgtggc agagtgtttg gcagacttcg acggggacgg gagatgatgt ctcttatggt   660
agtggtggaa gttccggtca agggaatctc gacggccaag gttaa               705

<210> SEQ ID NO 60
<211> LENGTH: 234
<212> TYPE: PRT
<213> ORGANISM: Arabidopsis thaliana
<220> FEATURE:
<223> OTHER INFORMATION: G715 polypeptide (domain in aa coordinates:
      66-131)

<400> SEQUENCE: 60

Met Asp Thr Asn Asn Gln Gln Pro Pro Ser Ala Ala Gly Ile Pro
1               5                   10                  15

Pro Pro Pro Gly Thr Thr Ile Ser Ala Ala Gly Gly Gly Ala Ser
                20                  25                  30

Tyr His His Leu Leu Gln Gln Gln Gln Gln Leu Gln Leu Phe Trp
                35                  40                  45

Thr Tyr Gln Arg Gln Glu Ile Glu Gln Val Asn Asp Phe Lys Asn His
    50                  55                  60

Gln Leu Pro Leu Ala Arg Ile Lys Lys Ile Met Lys Ala Asp Glu Asp
65                  70                  75                  80

Val Arg Met Ile Ser Ala Glu Ala Pro Ile Leu Phe Ala Lys Ala Cys
                85                  90                  95

Glu Leu Phe Ile Leu Glu Leu Thr Ile Arg Ser Trp Leu His Ala Glu
                100                 105                 110

Glu Asn Lys Arg Arg Thr Leu Gln Lys Asn Asp Ile Ala Ala Ala Ile
                115                 120                 125

Thr Arg Thr Asp Ile Phe Asp Phe Leu Val Asp Ile Val Pro Arg Asp
            130                 135                 140

Glu Ile Lys Asp Glu Ala Ala Val Leu Gly Gly Gly Met Val Val Ala
145                 150                 155                 160

Pro Thr Ala Ser Gly Val Pro Tyr Tyr Tyr Pro Pro Met Gly Gln Pro
                165                 170                 175

Ala Gly Pro Gly Gly Met Met Ile Gly Arg Pro Ala Met Asp Pro Asn
                180                 185                 190
```

Gly Val Tyr Val Gln Pro Pro Ser Gln Ala Trp Gln Ser Val Trp Gln
            195                 200                 205

Thr Ser Thr Gly Thr Gly Asp Val Ser Tyr Gly Ser Gly Ser
            210                 215                 220

Ser Gly Gln Gly Asn Leu Asp Gly Gln Gly
225                 230

<210> SEQ ID NO 61
<211> LENGTH: 711
<212> TYPE: DNA
<213> ORGANISM: Glycine max
<220> FEATURE:
<223> OTHER INFORMATION: G3886

<400> SEQUENCE: 61

```
atggagacca acaaccagca acaacaacaa caaggagctc aagcccaatc gggaccctac      60
cccgtcgccg cgccggcgg cagtgcaggt gcaggtgcag gcgctcctcc cctttccag      120
caccttctcc agcagcagca gcagcagctc agatgttct ggtcttacca gcgtcaagaa      180
atcgagcacg tgaacgactt taagaatcac cagctccctc ttgcccgcat caagaagatc      240
atgaaggcca acgaggatgt ccgcatgatc tccgccgagg cccccatcct cttcgccaag      300
gcctgcgagc tcttcatcct cgagctcacc atccgctcct ggctccacgc cgaggagaac      360
aagcgccgca ccctccagaa gaacgacatc gccgccgcca tcacccgcac cgacattttc      420
gacttcctcg ttgatattgt cccccgcgac gagatcaagg acgacgctgc tcttgtgggg      480
gccaccgcca gtggggtgcc ttactactac ccgcccattg acagcctgc cgggatgatg      540
attggccgcc cgccgtcga tcccgccacc ggggtttatg tccagccgcc ctcccaggca      600
tggcagtccg tctggcagtc cgctgccgag gacgcttcct atggcaccgg ccccgccggt      660
gcccagcgga gccttgatgg ccagagctag ctcgagcctg caggaagggc g              711
```

<210> SEQ ID NO 62
<211> LENGTH: 229
<212> TYPE: PRT
<213> ORGANISM: Glycine max
<220> FEATURE:
<223> OTHER INFORMATION: G3886 polypeptide (domain in aa coordinates:
      72-137)

<400> SEQUENCE: 62

Met Glu Thr Asn Asn Gln Gln Gln Gln Gln Gly Ala Gln Ala Gln
1               5                   10                  15

Ser Gly Pro Tyr Pro Val Ala Gly Ala Gly Ser Ala Gly Ala Gly
            20                  25                  30

Ala Gly Ala Pro Pro Pro Phe Gln His Leu Leu Gln Gln Gln Gln
            35                  40                  45

Gln Leu Gln Met Phe Trp Ser Tyr Gln Arg Gln Glu Ile Glu His Val
            50                  55                  60

Asn Asp Phe Lys Asn His Gln Leu Pro Leu Ala Arg Ile Lys Lys Ile
65                  70                  75                  80

Met Lys Ala Asp Glu Asp Val Arg Met Ile Ser Ala Glu Ala Pro Ile
                    85                  90                  95

Leu Phe Ala Lys Ala Cys Glu Leu Phe Ile Leu Glu Leu Thr Ile Arg
                    100                 105                 110

Ser Trp Leu His Ala Glu Glu Asn Lys Arg Arg Thr Leu Gln Lys Asn
            115                 120                 125

```
Asp Ile Ala Ala Ala Ile Thr Arg Thr Asp Ile Phe Asp Phe Leu Val
        130                 135                 140

Asp Ile Val Pro Arg Asp Glu Ile Lys Asp Asp Ala Ala Leu Val Gly
145                 150                 155                 160

Ala Thr Ala Ser Gly Val Pro Tyr Tyr Pro Pro Ile Gly Gln Pro
            165                 170                 175

Ala Gly Met Met Ile Gly Arg Pro Ala Val Asp Pro Ala Thr Gly Val
        180                 185                 190

Tyr Val Gln Pro Pro Ser Gln Ala Trp Gln Ser Val Trp Gln Ser Ala
            195                 200                 205

Ala Glu Asp Ala Ser Tyr Gly Thr Gly Pro Ala Gly Ala Gln Arg Ser
210                 215                 220

Leu Asp Gly Gln Ser
225
```

<210> SEQ ID NO 63
<211> LENGTH: 760
<212> TYPE: DNA
<213> ORGANISM: Zea mays
<220> FEATURE:
<223> OTHER INFORMATION: G3889

<400> SEQUENCE: 63

```
cccagcagca acgtaatcca aatccatgga caaccagccg ctgccctact ccacaggcca      60
gccccctgcc cccggaggag ccccggtggc gggcatgcct ggcgcggccg gcctcccacc     120
cgtgccgcac caccacctgc tccagcagca ggcccagctg caggcgttct gggcgtacca     180
gcgccaggag gcggagcgcg cgtccgcgtc ggacttcaag aaccaccagc tgcctctggc     240
ccggatcaag aagatcatga aggccgacga ggacgtgcgc atgatctccg ccgaggcgcc     300
cgtgctgttc gccaaggcct gcgagctctt catcctcgag ctcactatcc gctcctggct     360
ccacgccgag gagaacaagc gccgcaccct gcagcgcaac gacgtcgccg cggccatcgc     420
gcgcaccgac gtcttcgatt tcctcgtcga catcgtgccc cgcgaggagg ccaaggagga     480
gcccggcagc gccctcggct cgcggcgcc tgggaccggc gtcgtcgggg ctggcgcccc     540
gggcggggcg ccagccgccg ggatgcccta ctactatccg ccgatggggc agccggcgcc     600
gatgatgccg gcctggcatg ttccggcctg gacccggcc tggcagcaag ggcagcgga      660
tgtcgatcag agcggcagct tcagcgagga aggacaaggg tttggagcag gccatggcgg     720
cgccgctagc ttccctcctg cgcctccgac ctccgagtga                           760
```

<210> SEQ ID NO 64
<211> LENGTH: 244
<212> TYPE: PRT
<213> ORGANISM: Zea mays
<220> FEATURE:
<223> OTHER INFORMATION: G3889 polypeptide (domain in aa coordinates: 69-134)

<400> SEQUENCE: 64

```
Met Asp Asn Gln Pro Leu Pro Tyr Ser Thr Gly Gln Pro Pro Ala Pro
1               5                   10                  15

Gly Gly Ala Pro Val Ala Gly Met Pro Gly Ala Ala Gly Leu Pro Pro
            20                  25                  30

Val Pro His His His Leu Leu Gln Gln Gln Ala Gln Leu Gln Ala Phe
        35                  40                  45

Trp Ala Tyr Gln Arg Gln Glu Ala Glu Arg Ala Ser Ala Ser Asp Phe
    50                  55                  60
```

```
Lys Asn His Gln Leu Pro Leu Ala Arg Ile Lys Lys Ile Met Lys Ala
 65                  70                  75                  80

Asp Glu Asp Val Arg Met Ile Ser Ala Glu Ala Pro Val Leu Phe Ala
                 85                  90                  95

Lys Ala Cys Glu Leu Phe Ile Leu Glu Leu Thr Ile Arg Ser Trp Leu
            100                 105                 110

His Ala Glu Glu Asn Lys Arg Arg Thr Leu Gln Arg Asn Asp Val Ala
        115                 120                 125

Ala Ala Ile Ala Arg Thr Asp Val Phe Asp Phe Leu Val Asp Ile Val
130                 135                 140

Pro Arg Glu Glu Ala Lys Glu Glu Pro Gly Ser Ala Leu Gly Phe Ala
145                 150                 155                 160

Ala Pro Gly Thr Gly Val Val Gly Ala Gly Pro Gly Gly Ala Pro
                165                 170                 175

Ala Ala Gly Met Pro Tyr Tyr Tyr Pro Pro Met Gly Gln Pro Ala Pro
            180                 185                 190

Met Met Pro Ala Trp His Val Pro Ala Trp Asp Pro Ala Trp Gln Gln
        195                 200                 205

Gly Ala Ala Asp Val Asp Gln Ser Gly Ser Phe Ser Glu Glu Gly Gln
210                 215                 220

Gly Phe Gly Ala Gly His Gly Gly Ala Ala Ser Phe Pro Pro Ala Pro
225                 230                 235                 240

Pro Thr Ser Glu

<210> SEQ ID NO 65
<211> LENGTH: 800
<212> TYPE: DNA
<213> ORGANISM: Arabidopsis thaliana
<220> FEATURE:
<223> OTHER INFORMATION: G1646

<400> SEQUENCE: 65
gatcttttga tccaatcaca aggcaaagat ccaatggaca taacaacaa caacaacaac      60
cagcaaccac caccaacctc cgtctatcca cctggctccg ccgtcacaac cgtaatccct     120
cctccaccat ctggatctgc atcaatagtc accggaggag gagcgacata ccaccacctc    180
ctccagcaac aacagcaaca gcttcaaatg ttctggacat accagagaca agagatcgaa    240
caggtaaacg atttcaaaaa ccatcagctc cctctagctc gtatcaaaaa aatcatgaaa    300
gctgatgaag atgtgcgtat gatctccgcc gaagcaccga ttctcttcgc gaaagcttgt    360
gagcttttca ttctcgaact tacgattaga tcttggcttc acgctgaaga gaacaaacgt    420
cgtacgcttc agaaaaacga tatcgctgct gcgattacta gaaccgatat cttcgatttc    480
cttgttgata ttgttcctag ggaagagatc aaggaagagg aagatgcagc atcggctctt    540
ggtggaggag gtatggttgc tcccgccgcg agcggtgttc cttattatta tccaccgatg    600
ggacaaccgg cggttcctgg agggatgatg attggaagac cggcgatgga tcctagcggt    660
gtttatgctc agcctccttc tcaggcatgg caaagcgttt ggcagaattc agctggtggt    720
ggtgatgatg tgtcttatgg aagtggagga agtagcggcc atggtaatct cgatagccaa    780
gggtaagtga attctagtag                                                800

<210> SEQ ID NO 66
<211> LENGTH: 250
<212> TYPE: PRT
<213> ORGANISM: Arabidopsis thaliana
```

<220> FEATURE:
<223> OTHER INFORMATION: G1646 polypeptide (domain in aa coordinates: 79-144)

<400> SEQUENCE: 66

```
Met Asp Asn Asn Asn Asn Asn Asn Gln Gln Pro Pro Pro Thr Ser
1               5                   10                  15

Val Tyr Pro Pro Gly Ser Ala Val Thr Thr Val Ile Pro Pro Pro
            20                  25                  30

Ser Gly Ser Ala Ser Ile Val Thr Gly Gly Gly Ala Thr Tyr His His
        35                  40                  45

Leu Leu Gln Gln Gln Gln Gln Gln Leu Gln Met Phe Trp Thr Tyr Gln
    50                  55                  60

Arg Gln Glu Ile Glu Gln Val Asn Asp Phe Lys Asn His Gln Leu Pro
65                  70                  75                  80

Leu Ala Arg Ile Lys Lys Ile Met Lys Ala Asp Glu Asp Val Arg Met
                85                  90                  95

Ile Ser Ala Glu Ala Pro Ile Leu Phe Ala Lys Ala Cys Glu Leu Phe
            100                 105                 110

Ile Leu Glu Leu Thr Ile Arg Ser Trp Leu His Ala Glu Glu Asn Lys
        115                 120                 125

Arg Arg Thr Leu Gln Lys Asn Asp Ile Ala Ala Ile Thr Arg Thr
    130                 135                 140

Asp Ile Phe Asp Phe Leu Val Asp Ile Val Pro Arg Glu Glu Ile Lys
145                 150                 155                 160

Glu Glu Glu Asp Ala Ala Ser Ala Leu Gly Gly Gly Gly Met Val Ala
                165                 170                 175

Pro Ala Ala Ser Gly Val Pro Tyr Tyr Tyr Pro Pro Met Gly Gln Pro
            180                 185                 190

Ala Val Pro Gly Gly Met Met Ile Gly Arg Pro Ala Met Asp Pro Ser
        195                 200                 205

Gly Val Tyr Ala Gln Pro Pro Ser Gln Ala Trp Gln Ser Val Trp Gln
    210                 215                 220

Asn Ser Ala Gly Gly Gly Asp Asp Val Ser Tyr Gly Ser Gly Gly Ser
225                 230                 235                 240

Ser Gly His Gly Asn Leu Asp Ser Gln Gly
                245                 250
```

<210> SEQ ID NO 67
<211> LENGTH: 915
<212> TYPE: DNA
<213> ORGANISM: Oryza sativa
<220> FEATURE:
<223> OTHER INFORMATION: G3543

<400> SEQUENCE: 67

```
atggacaacc agcagctacc ctacgccggt cagccggcgg ccgcaggcgc cggagccccg      60
gtgccgggcg tgcctggcgc gggcgggccg ccggcggtgc cgcaccacca cctgctccag     120
cagcagcagg cgcagctgca ggcgttctgg gcgtaccagc ggcaggaggc ggagcgcgcg     180
tcggcgtcgg acttcaagaa ccaccagctg ccgctggcgg ggatcaagaa gatcatgaag     240
gcggacgagg acgtgcgcat gatctcggcg gaggcgcccg tgctgttcgc caaggcgtgc     300
gagctcttca tcctggagct caccatccgc tcgtggctgc acgccgagga gaacaagcgc     360
cgcaccctgc agcgcaagga cgtcgccgcc gccatcgcgc gcaccgacgt gttcgacttc     420
ctcgtcgaca tcgtgccgcg ggaggaggcc aaggaggagc ccggcagcgc gctcgggttc     480
```

-continued

```
gcggcgggag ggcccgccgg cgccgttgga gcggccggcc ccgccgcggg gctgccgtac      540
tactacccgc cgatggggca gccggcgccg atgatgccgg cgtggcatgt tccggcgtgg      600
gacccggcgt ggcagcaagg agcagcgccg gatgtggacc agggcgccgc cggcagcttc      660
agcgaggaag ggcagcaagg ttttgcaggc catggcggtg cggcagctag cttccctcct      720
gcacctccaa gctccgaata gtgatgatcc atatggttcc atgcatgcat cgctgaggtg      780
ctagctagct actatagctg ctcaaatcaa atgctcaatg tgtcggtaat taattaatgt      840
ggtacgtatt aacttaaccg atgtacgtaa tggacgctca agctaattaa gggatgtaca      900
atttactaaa aaaaa                                                      915
```

<210> SEQ ID NO 68
<211> LENGTH: 246
<212> TYPE: PRT
<213> ORGANISM: Oryza sativa
<220> FEATURE:
<223> OTHER INFORMATION: G3543 polypeptide (domain in aa coordinates: 70-135)

<400> SEQUENCE: 68

```
Met Asp Asn Gln Gln Leu Pro Tyr Ala Gly Gln Pro Ala Ala Ala Gly
1               5                   10                  15

Ala Gly Ala Pro Val Pro Gly Val Pro Gly Ala Gly Gly Pro Pro Ala
            20                  25                  30

Val Pro His His His Leu Leu Gln Gln Gln Gln Ala Gln Leu Gln Ala
        35                  40                  45

Phe Trp Ala Tyr Gln Arg Gln Glu Ala Glu Arg Ala Ser Ala Ser Asp
    50                  55                  60

Phe Lys Asn His Gln Leu Pro Leu Ala Gly Ile Lys Lys Ile Met Lys
65                  70                  75                  80

Ala Asp Glu Asp Val Arg Met Ile Ser Ala Glu Ala Pro Val Leu Phe
                85                  90                  95

Ala Lys Ala Cys Glu Leu Phe Ile Leu Glu Leu Thr Ile Arg Ser Trp
            100                 105                 110

Leu His Ala Glu Glu Asn Lys Arg Arg Thr Leu Gln Arg Lys Asp Val
        115                 120                 125

Ala Ala Ala Ile Ala Arg Thr Asp Val Phe Asp Phe Leu Val Asp Ile
    130                 135                 140

Val Pro Arg Glu Glu Ala Lys Glu Glu Pro Gly Ser Ala Leu Gly Phe
145                 150                 155                 160

Ala Ala Gly Gly Pro Ala Gly Ala Val Gly Ala Ala Gly Pro Ala Ala
                165                 170                 175

Gly Leu Pro Tyr Tyr Tyr Pro Pro Met Gly Gln Pro Ala Pro Met Met
            180                 185                 190

Pro Ala Trp His Val Pro Ala Trp Asp Pro Ala Trp Gln Gln Gly Ala
        195                 200                 205

Ala Pro Asp Val Asp Gln Gly Ala Ala Gly Ser Phe Ser Glu Glu Gly
    210                 215                 220

Gln Gln Gly Phe Ala Gly His Gly Gly Ala Ala Ala Ser Phe Pro Pro
225                 230                 235                 240

Ala Pro Pro Ser Ser Glu
                245
```

<210> SEQ ID NO 69
<211> LENGTH: 732

```
<212> TYPE: DNA
<213> ORGANISM: Arabidopsis thaliana
<220> FEATURE:
<223> OTHER INFORMATION: G1820

<400> SEQUENCE: 69
ctcacttcca acatccaaat ccctagaaat tgtaaatggc tgagaacaac aacaacaacg      60
gcgacaacat gaacaacgac aaccaccagc aaccaccgtc gtactcgcag ctgccgccga     120
tggcatcatc caaccctcag ttacgtaatt actggattga gcagatggaa accgtctcgg     180
atttcaaaaa ccgtcagctt ccattggctc gaattaagaa gatcatgaag gctgatccag     240
atgtgcacat ggtctccgca gaggctccga tcatcttcgc aaaggcttgc gaaatgttca     300
tcgttgatct cacgatgcgg tcgtggctca agccgagga gaacaaacgc cacacgcttc      360
agaaatcgga tatctccaac gcagtggcta gctctttcac ctacgatttc cttcttgatg     420
ttgtccctaa ggacgagtct atcgccaccg ctgatcctgg cttttgtggct atgccacatc    480
ctgacggtgg aggagtaccg caatattatt atccaccggg agtggtgatg ggaactccta     540
tggttggtag tggaatgtac gcgccatcgc aggcgtggcc agcagcggct ggtgacgggg     600
aggatgatgc tgaggataat ggaggaaacg gcggcggaaa ttgaagtgta gatttagggt     660
ttgtaaccgc ctatgtggga aatttgaaat ttggtggtgt ttattagggt tcttcaattc     720
gtcggatttg ct                                                          732

<210> SEQ ID NO 70
<211> LENGTH: 202
<212> TYPE: PRT
<213> ORGANISM: Arabidopsis thaliana
<220> FEATURE:
<223> OTHER INFORMATION: G1820 polypeptide (domain in aa coordinates:
      55-120)

<400> SEQUENCE: 70

Met Ala Glu Asn Asn Asn Asn Gly Asp Asn Met Asn Asn Asp Asn
1               5                   10                  15

His Gln Gln Pro Pro Ser Tyr Ser Gln Leu Pro Pro Met Ala Ser Ser
                20                  25                  30

Asn Pro Gln Leu Arg Asn Tyr Trp Ile Glu Gln Met Glu Thr Val Ser
            35                  40                  45

Asp Phe Lys Asn Arg Gln Leu Pro Leu Ala Arg Ile Lys Lys Ile Met
        50                  55                  60

Lys Ala Asp Pro Asp Val His Met Val Ser Ala Glu Ala Pro Ile Ile
65                  70                  75                  80

Phe Ala Lys Ala Cys Glu Met Phe Ile Val Asp Leu Thr Met Arg Ser
                85                  90                  95

Trp Leu Lys Ala Glu Glu Asn Lys Arg His Thr Leu Gln Lys Ser Asp
            100                 105                 110

Ile Ser Asn Ala Val Ala Ser Ser Phe Thr Tyr Asp Phe Leu Leu Asp
        115                 120                 125

Val Val Pro Lys Asp Glu Ser Ile Ala Thr Ala Asp Pro Gly Phe Val
    130                 135                 140

Ala Met Pro His Pro Asp Gly Gly Val Pro Gln Tyr Tyr Tyr Pro
145                 150                 155                 160

Pro Gly Val Val Met Gly Thr Pro Met Val Gly Ser Gly Met Tyr Ala
                165                 170                 175

Pro Ser Gln Ala Trp Pro Ala Ala Ala Gly Asp Gly Glu Asp Asp Ala
            180                 185                 190
```

```
Glu Asp Asn Gly Gly Asn Gly Gly Gly Asn
        195                 200
```

<210> SEQ ID NO 71
<211> LENGTH: 668
<212> TYPE: DNA
<213> ORGANISM: Arabidopsis thaliana
<220> FEATURE:
<223> OTHER INFORMATION: G1836

<400> SEQUENCE: 71

```
ataacaagcc tagaacacta gaaacttcaa aaaagaaaaa aatcttatgg agaacaacaa      60
cggcaacaac cagctgccac cgaaaggtaa cgagcaactg aagagtttct ggtcaaaaga     120
gatggaaggt aacttagatt tcaaaaatca cgaccttcct ataactcgta tcaagaagat     180
tatgaagtat gatccggatg tgactatgat agctagtgag gctccaatcc tcctctcgaa     240
agcatgtgag atgtttatca tggatctcac gatgcgttcg tggctccatg ctcaggaaag     300
caaacgagtc acgctacaga aatctaatgt cgatgccgca gtggctcaaa ctgttatctt     360
tgatttcttg cttgatgatg acattgaggt aaagagagag tctgttgccg ccgctgctga     420
tcctgtggcc atgccaccta ttgacgatgg agagctgcct ccaggaatgg taattggaac     480
tcctgtttgt tgtagtcttg gaatccacca accacaacca caaatgcagg catggcctgg     540
agcttggacc tcggtgtctg gtgaggagga agaagcgcgt gggaaaaaag gaggtgacga     600
cggaaactaa taagtggaat acgttttagg gtattttcaa gggaatatgt agtaaatagt     660
catggatc                                                             668
```

<210> SEQ ID NO 72
<211> LENGTH: 187
<212> TYPE: PRT
<213> ORGANISM: Arabidopsis thaliana
<220> FEATURE:
<223> OTHER INFORMATION: G1836 polypeptide (domain in aa coordinates: 37-102)

<400> SEQUENCE: 72

```
Met Glu Asn Asn Asn Gly Asn Asn Gln Leu Pro Pro Lys Gly Asn Glu
1               5                   10                  15

Gln Leu Lys Ser Phe Trp Ser Lys Glu Met Glu Gly Asn Leu Asp Phe
            20                  25                  30

Lys Asn His Asp Leu Pro Ile Thr Arg Ile Lys Lys Ile Met Lys Tyr
        35                  40                  45

Asp Pro Asp Val Thr Met Ile Ala Ser Glu Ala Pro Ile Leu Leu Ser
    50                  55                  60

Lys Ala Cys Glu Met Phe Ile Met Asp Leu Thr Met Arg Ser Trp Leu
65                  70                  75                  80

His Ala Gln Glu Ser Lys Arg Val Thr Leu Gln Lys Ser Asn Val Asp
                85                  90                  95

Ala Ala Val Ala Gln Thr Val Ile Phe Asp Phe Leu Leu Asp Asp Asp
            100                 105                 110

Ile Glu Val Lys Arg Glu Ser Val Ala Ala Ala Asp Pro Val Ala
        115                 120                 125

Met Pro Pro Ile Asp Asp Gly Glu Leu Pro Pro Gly Met Val Ile Gly
    130                 135                 140

Thr Pro Val Cys Cys Ser Leu Gly Ile His Gln Pro Gln Pro Gln Met
145                 150                 155                 160
```

```
Gln Ala Trp Pro Gly Ala Trp Thr Ser Val Ser Gly Glu Glu Glu
            165                 170                 175
Ala Arg Gly Lys Lys Gly Gly Asp Asp Gly Asn
        180                 185

<210> SEQ ID NO 73
<211> LENGTH: 639
<212> TYPE: DNA
<213> ORGANISM: Arabidopsis thaliana
<220> FEATURE:
<223> OTHER INFORMATION: G1819

<400> SEQUENCE: 73
atggaagaga acaacggcaa caacaaccac tacctgccgc aaccatcgtc ttcccaactg     60
ccgccgccac cattgtatta tcaatcaatg ccgttgccgt catattcact gccgctgccg    120
tactcaccgc agatgcggaa ttattggatt gcgcagatgg gaaacgcaac tgatgttaag    180
catcatgcgt ttccactaac caggataaag aaaatcatga agtccaaccc ggaagtgaac    240
atggtcactg cagaggctcc ggtccttata tcgaaggcct gtgagatgct cattcttgat    300
ctcacaatgc gatcgtggct tcataccgtg gagggcggtc gccaaactct caagagatcc    360
gatacgctca cgagatccga tatctccgcc gcaacgactc gtagtttcaa atttaccttc    420
cttggcgacg ttgtcccaag agacccttcc gtcgttaccg atgatcccgt gctacatccg    480
gacggtgaag tacttcctcc gggaacggtg ataggatatc cggtgtttga ttgtaatggt    540
gtgtacgcgt caccgccaca gatgcaggag tggccggcgg tgcctggtga cggagaggag    600
gcagctgggg aaattggagg aagcagcggc ggtaattga                           639

<210> SEQ ID NO 74
<211> LENGTH: 212
<212> TYPE: PRT
<213> ORGANISM: Arabidopsis thaliana
<220> FEATURE:
<223> OTHER INFORMATION: G1819 polypeptide (domain in aa coordinates:
      64-135)

<400> SEQUENCE: 74

Met Glu Glu Asn Asn Gly Asn Asn Asn His Tyr Leu Pro Gln Pro Ser
1               5                   10                  15
Ser Ser Gln Leu Pro Pro Pro Leu Tyr Tyr Gln Ser Met Pro Leu
            20                  25                  30
Pro Ser Tyr Ser Leu Pro Leu Pro Tyr Ser Pro Gln Met Arg Asn Tyr
        35                  40                  45
Trp Ile Ala Gln Met Gly Asn Ala Thr Asp Val Lys His His Ala Phe
    50                  55                  60
Pro Leu Thr Arg Ile Lys Lys Ile Met Lys Ser Asn Pro Glu Val Asn
65                  70                  75                  80
Met Val Thr Ala Glu Ala Pro Val Leu Ile Ser Lys Ala Cys Glu Met
                85                  90                  95
Leu Ile Leu Asp Leu Thr Met Arg Ser Trp Leu His Thr Val Glu Gly
            100                 105                 110
Gly Arg Gln Thr Leu Lys Arg Ser Asp Thr Leu Thr Arg Ser Asp Ile
        115                 120                 125
Ser Ala Ala Thr Thr Arg Ser Phe Lys Phe Thr Phe Leu Gly Asp Val
    130                 135                 140
Val Pro Arg Asp Pro Ser Val Val Thr Asp Asp Pro Val Leu His Pro
145                 150                 155                 160
```

```
Asp Gly Glu Val Leu Pro Pro Gly Thr Val Ile Gly Tyr Pro Val Phe
            165                 170                 175

Asp Cys Asn Gly Val Tyr Ala Ser Pro Pro Gln Met Gln Glu Trp Pro
        180                 185                 190

Ala Val Pro Gly Asp Gly Glu Glu Ala Ala Gly Glu Ile Gly Gly Ser
    195                 200                 205

Ser Gly Gly Asn
    210

<210> SEQ ID NO 75
<211> LENGTH: 1740
<212> TYPE: DNA
<213> ORGANISM: Arabidopsis thaliana
<220> FEATURE:
<223> OTHER INFORMATION: G1818

<400> SEQUENCE: 75
```

| | | | | | |
|---|---|---|---|---|---|
| taacaaatca | aataattaga | gaaataacca | aaatttaact | tttagaggga | ctacaggatt | 60 |
| tgtactttgt | acattcatat | attattgtta | tatatcgttt | catacattaa | tttgaaccaa | 120 |
| tgtaaattaa | gtaaaattca | atttaacatc | atgagcaaat | tcttattaaa | attctcttaa | 180 |
| aattttgagc | aaattatgct | ttcacattta | acatttgaaa | acatcatttt | taacaagata | 240 |
| ttcaaaacta | agttttgtac | agcaaaattt | taactttcaa | ttttatagag | aaaaaggtat | 300 |
| tttttttttt | gtttcatttt | tataagacta | ttatttggta | tataatatac | actttaagta | 360 |
| aaaacaaatc | tctttctttt | ttcttcttat | aataccaacc | acaagtctgt | cagtcacaca | 420 |
| catacagtta | ataacattaa | atattcttaa | caaactacta | aataggttga | gattcatata | 480 |
| tgtaaagaga | tcacttctta | atcttatcct | accatatctt | atatacgctt | aattttcctt | 540 |
| tatatatgca | aacctccaca | taaaaatatc | tcaaacccaa | acacttcaaa | caaaaaaaaa | 600 |
| atggagaaca | acaacaacaa | ccaccaacag | ccaccgaaag | ataacgagca | actaaagagt | 660 |
| ttctggtcaa | aggggatgga | aggtgacttg | aatgtcaaga | atcacgagtt | ccccatctct | 720 |
| cgtatcaaga | ggataatgaa | gtttgatccg | gatgtgagta | tgatcgctgc | tgaggctcca | 780 |
| aatctcttat | ctaaggcttg | tgaaatgttt | gtcatggacc | tcacgatgcg | ttcatggctc | 840 |
| catgctcaag | agagcaaccg | actcacgata | cggaaatctg | atgttgatgc | cgtagtgtct | 900 |
| caaaccgtca | tctttgattt | cttgcgtgat | gatgtcccta | aggacgaggg | agagcccgtt | 960 |
| gtcgccgctg | ctgatcctgt | ggacgatgtt | gctgatcatg | tggctgtgcc | agatcttaac | 1020 |
| aatgaagaac | tgccgccggg | aacggtgata | ggaactccgg | tttgttacgg | tttaggaata | 1080 |
| cacgcgccac | acccgcagat | gcctggagct | tggaccgagg | aggatgcgac | tggggcaaat | 1140 |
| ggaggaaacg | gtgggaatta | atatttggat | tgggttttgt | aaccgctgtt | gtgagaactt | 1200 |
| gaatttcttt | ttgagttctg | cttatgtttt | caatgttatg | ttttttagtt | gttgaatgta | 1260 |
| tttctgttgt | tttgtccaaa | aaaaaaaaag | aatgtatttc | tgttgttgtc | tttcaaatga | 1320 |
| atctaatggt | ttatgaatat | tggctttaga | ttaatttatg | catacaaaaa | cacaaggatt | 1380 |
| acggataaaa | aagtcctcag | tttacccatg | gaaacataat | cttctagtga | ttccttatga | 1440 |
| gagtagaaaa | gaatcatata | ttataatcta | tttcataaga | gatagggtac | tgtaaacaag | 1500 |
| gatgtttatt | cggctatttc | tttttttttt | aatcactttt | acttgtcaag | actcttttgt | 1560 |
| gtttgcagct | ttttgttaga | ttacattcta | gaggcaacaa | gatccagaga | tctagcaaaa | 1620 |
| aaaacttatt | ttgaaacctg | aatctatttt | aaaaatttc | caactcattt | ttcgttctta | 1680 |
| ttctttgttt | tccaacggaa | tttggcgcac | aaacgattta | tttgaatttt | gtctttcaag | 1740 |

```
<210> SEQ ID NO 76
<211> LENGTH: 186
<212> TYPE: PRT
<213> ORGANISM: Arabidopsis thaliana
<220> FEATURE:
<223> OTHER INFORMATION: G1818 polypeptide (domain in aa coordinates:
      38-102)

<400> SEQUENCE: 76

Met Glu Asn Asn Asn Asn Asn His Gln Gln Pro Pro Lys Asp Asn Glu
1               5                   10                  15

Gln Leu Lys Ser Phe Trp Ser Lys Gly Met Glu Gly Asp Leu Asn Val
            20                  25                  30

Lys Asn His Glu Phe Pro Ile Ser Arg Ile Lys Arg Ile Met Lys Phe
        35                  40                  45

Asp Pro Asp Val Ser Met Ile Ala Ala Glu Ala Pro Asn Leu Leu Ser
    50                  55                  60

Lys Ala Cys Glu Met Phe Val Met Asp Leu Thr Met Arg Ser Trp Leu
65                  70                  75                  80

His Ala Gln Glu Ser Asn Arg Leu Thr Ile Arg Lys Ser Asp Val Asp
                85                  90                  95

Ala Val Val Ser Gln Thr Val Ile Phe Asp Phe Leu Arg Asp Asp Val
            100                 105                 110

Pro Lys Asp Glu Gly Glu Pro Val Val Ala Ala Ala Asp Pro Val Asp
        115                 120                 125

Asp Val Ala Asp His Val Ala Val Pro Asp Leu Asn Asn Glu Glu Leu
    130                 135                 140

Pro Pro Gly Thr Val Ile Gly Thr Pro Val Cys Tyr Gly Leu Gly Ile
145                 150                 155                 160

His Ala Pro His Pro Gln Met Pro Gly Ala Trp Thr Glu Glu Asp Ala
                165                 170                 175

Thr Gly Ala Asn Gly Gly Asn Gly Gly Asn
            180                 185

<210> SEQ ID NO 77
<211> LENGTH: 588
<212> TYPE: DNA
<213> ORGANISM: Arabidopsis thaliana
<220> FEATURE:
<223> OTHER INFORMATION: G490

<400> SEQUENCE: 77
atgaggaggc caaagtcatc tcacgtcagg atggaacctg ttgcgcctcg ttcacataac     60
acgatgccaa tgcttgatca atttcgatct aatcatcctg aaacaagcaa gatcgagggg    120
gtctcttcgt tggacacagc tctgaaggtg ttttggaata tcaaagggag cagctagga     180 aactttgcag ccaaactca tttgccgcta tctagggtca gaaagatttt gaaatctgat     240
cctgaagtca agaagataag ctgtgatgtt cctgcttttgt tttcgaaagc ctgtgaatac    300
ttcattctag aggtaacatt acgagcttgg atgcatactc aatcatgcac tcgtgagacc    360
atccggcgtt gtgatatctt ccaggccgta aagaactcag gaacttatga tttcctgatt    420
gatcgtgtcc cttttggacc gcactgtgtc acccatcagg gtgtgcaacc tcctgctgaa    480
atgattttgc cggatatgaa tgttccaatc gatatggacc agattgagga ggagaatatg    540
atggaagagc gctctgtcgg gtttgacctc aactgtgatc tccagtga                 588
```

<210> SEQ ID NO 78
<211> LENGTH: 195
<212> TYPE: PRT
<213> ORGANISM: Arabidopsis thaliana
<220> FEATURE:
<223> OTHER INFORMATION: G490 polypeptide (domain in aa coordinates: 68-133)

<400> SEQUENCE: 78

```
Met Arg Arg Pro Lys Ser Ser His Val Arg Met Glu Pro Val Ala Pro
1               5                   10                  15

Arg Ser His Asn Thr Met Pro Met Leu Asp Gln Phe Arg Ser Asn His
            20                  25                  30

Pro Glu Thr Ser Lys Ile Glu Gly Val Ser Ser Leu Asp Thr Ala Leu
        35                  40                  45

Lys Val Phe Trp Asn Asn Gln Arg Glu Gln Leu Gly Asn Phe Ala Gly
50                  55                  60

Gln Thr His Leu Pro Leu Ser Arg Val Arg Lys Ile Leu Lys Ser Asp
65                  70                  75                  80

Pro Glu Val Lys Lys Ile Ser Cys Asp Val Pro Ala Leu Phe Ser Lys
                85                  90                  95

Ala Cys Glu Tyr Phe Ile Leu Glu Val Thr Leu Arg Ala Trp Met His
            100                 105                 110

Thr Gln Ser Cys Thr Arg Glu Thr Ile Arg Arg Cys Asp Ile Phe Gln
        115                 120                 125

Ala Val Lys Asn Ser Gly Thr Tyr Asp Phe Leu Ile Asp Arg Val Pro
    130                 135                 140

Phe Gly Pro His Cys Val Thr His Gln Gly Val Gln Pro Pro Ala Glu
145                 150                 155                 160

Met Ile Leu Pro Asp Met Asn Val Pro Ile Asp Met Asp Gln Ile Glu
                165                 170                 175

Glu Glu Asn Met Met Glu Glu Arg Ser Val Gly Phe Asp Leu Asn Cys
            180                 185                 190

Asp Leu Gln
        195
```

<210> SEQ ID NO 79
<211> LENGTH: 882
<212> TYPE: DNA
<213> ORGANISM: Arabidopsis thaliana
<220> FEATURE:
<223> OTHER INFORMATION: G3074

<400> SEQUENCE: 79

```
atgaggaaga agctcgatac tcggttccca gctgctcgta ttaaaaagat tatgcaagct     60
gatgaggatg ttggcaagat agctttggca gtgcctgtct tagtctcaaa atctttggag    120
ttgttcttgc aagacctttg tgatcgtaca tatgaaatta cccttgaaag aggtgccaag    180
actgtgagct cattgcacct aaaacattgt gtggaaagat ataacgtgtt tgattttctg    240
agggaagttg tgagtaaggt gcctgactat ggccattccc aagggcaagg acatggtgat    300
gttaccatgg atgatcgcag catctccaag agaaggaagc ccatcagcga tgaagtgaat    360
gacagtgacg aggaatataa gaaaagcaaa acgaagagat agggagtgc taagaccagt     420
ggcagggggtg gtagaggaag agggcgagga agaggtcgtg gtggacgagc tgcaaaagca    480
gccgaaagag agggtctcaa ccgcgagatg aagtagaag ccgccaattc tggacagcca     540
ccaccagaag acaatgtcaa gatgcatgcg tcagagtcat caccacaaga ggatgagaag    600
```

```
aaaggcatcg acggcacagc agcatcgaac gaagacacca agcaacacct tcaaagtccc    660
aaagaaggca ttgactttga tctcaacgct gaatccctcg acctaaacga gaccaaactg    720
gcaccagcca caggcacaac cacaaccaca actgcagcaa cagactctga ggagtattcg    780
ggctggccta tgatggacat aagcaaaatg gatccagcac agcttgctag tctgggtaag    840
aggatagacg aggatgagga agattatgac gaagaaggct aa                       882
```

<210> SEQ ID NO 80
<211> LENGTH: 293
<212> TYPE: PRT
<213> ORGANISM: Arabidopsis thaliana
<220> FEATURE:
<223> OTHER INFORMATION: G3074 polypeptide (domain in aa coordinates: 9-73)

<400> SEQUENCE: 80

```
Met Arg Lys Lys Leu Asp Thr Arg Phe Pro Ala Ala Arg Ile Lys Lys
1               5                   10                  15

Ile Met Gln Ala Asp Glu Asp Val Gly Lys Ile Ala Leu Ala Val Pro
            20                  25                  30

Val Leu Val Ser Lys Ser Leu Glu Leu Phe Leu Gln Asp Leu Cys Asp
        35                  40                  45

Arg Thr Tyr Glu Ile Thr Leu Glu Arg Gly Ala Lys Thr Val Ser Ser
    50                  55                  60

Leu His Leu Lys His Cys Val Glu Arg Tyr Asn Val Phe Asp Phe Leu
65                  70                  75                  80

Arg Glu Val Val Ser Lys Val Pro Asp Tyr Gly His Ser Gln Gly Gln
                85                  90                  95

Gly His Gly Asp Val Thr Met Asp Asp Arg Ser Ile Ser Lys Arg Arg
            100                 105                 110

Lys Pro Ile Ser Asp Glu Val Asn Asp Ser Asp Glu Glu Tyr Lys Lys
        115                 120                 125

Ser Lys Thr Gln Glu Ile Gly Ser Ala Lys Thr Ser Gly Arg Gly Gly
    130                 135                 140

Arg Gly Arg Gly Arg Gly Arg Gly Gly Arg Ala Ala Lys Ala
145                 150                 155                 160

Ala Glu Arg Glu Gly Leu Asn Arg Glu Met Glu Val Glu Ala Ala Asn
                165                 170                 175

Ser Gly Gln Pro Pro Glu Asp Asn Val Lys Met His Ala Ser Glu
            180                 185                 190

Ser Ser Pro Gln Glu Asp Glu Lys Lys Gly Ile Asp Gly Thr Ala Ala
        195                 200                 205

Ser Asn Glu Asp Thr Lys Gln His Leu Gln Ser Pro Lys Glu Gly Ile
    210                 215                 220

Asp Phe Asp Leu Asn Ala Glu Ser Leu Asp Leu Asn Glu Thr Lys Leu
225                 230                 235                 240

Ala Pro Ala Thr Gly Thr Thr Thr Thr Thr Ala Ala Thr Asp Ser
                245                 250                 255

Glu Glu Tyr Ser Gly Trp Pro Met Met Asp Ile Ser Lys Met Asp Pro
            260                 265                 270

Ala Gln Leu Ala Ser Leu Gly Lys Arg Ile Asp Glu Asp Glu Glu Asp
        275                 280                 285

Tyr Asp Glu Glu Gly
    290
```

-continued

<210> SEQ ID NO 81
<211> LENGTH: 738
<212> TYPE: DNA
<213> ORGANISM: Arabidopsis thaliana
<220> FEATURE:
<223> OTHER INFORMATION: G1249

<400> SEQUENCE: 81

```
tcgaccgttc ttctcaatct caccaatcgg tttaagctga aaacccgaat tagcaaaatc      60
ttcgttcggg ctgttttggt taatccggtt tacatgtttt ctcattgctc attttcattt     120
tcccgccgtg acagagcgcg taaatctcaa acccctaaaa atgtcgaaca tatacaattc     180
attaccttaa tcagattttc tcaacagaat caaaatcaaa atccatggag gaagaagaag     240
gatcaatccg accagagttt ccaatcggaa gagtaaagaa gataatgaaa ctggacaaag     300
acatcaacaa aatcaactca gaagctcttc acgtcatcac ttactccacc gaactcttcc     360
tccacttcct cgccgagaaa tctgctgttg ttacggcgga gaagaagcgt aagactgtta     420
atctcgatca tttaagaatc gccgtgaaaa gacaccaacc tactagtgat ttcctcttag     480
actcgcttcc gttgccggct cagcctgtca acataccaa atcggtttcc gacaagaaga      540
ttccggcgcc gccaattggg actcgtcgta tcgatgattt cttcagtaaa gggaaagcaa     600
agactgattc agcctaaagt aaaatttctc attttgttca caattgcaaa ttttactctg     660
ttctcaaatc aaaatcttgt tttgctaaaa gtgtagtgag aatgtatgga tcatgaggaa     720
cttttatagg aagcggcc                                                   738
```

<210> SEQ ID NO 82
<211> LENGTH: 130
<212> TYPE: PRT
<213> ORGANISM: Arabidopsis thaliana
<220> FEATURE:
<223> OTHER INFORMATION: G1249 polypeptide (domain in aa coordinates: 12-76)

<400> SEQUENCE: 82

```
Met Glu Glu Glu Gly Ser Ile Arg Pro Glu Phe Pro Ile Gly Arg
 1               5                  10                  15

Val Lys Lys Ile Met Lys Leu Asp Lys Asp Ile Asn Lys Ile Asn Ser
                20                  25                  30

Glu Ala Leu His Val Ile Thr Tyr Ser Thr Glu Leu Phe Leu His Phe
            35                  40                  45

Leu Ala Glu Lys Ser Ala Val Val Thr Ala Glu Lys Lys Arg Lys Thr
        50                  55                  60

Val Asn Leu Asp His Leu Arg Ile Ala Val Lys Arg His Gln Pro Thr
65                  70                  75                  80

Ser Asp Phe Leu Leu Asp Ser Leu Pro Leu Pro Ala Gln Pro Val Lys
                85                  90                  95

His Thr Lys Ser Val Ser Asp Lys Lys Ile Pro Ala Pro Pro Ile Gly
            100                 105                 110

Thr Arg Arg Ile Asp Asp Phe Phe Ser Lys Gly Lys Ala Lys Thr Asp
        115                 120                 125

Ser Ala
    130
```

<210> SEQ ID NO 83
<211> LENGTH: 621
<212> TYPE: DNA
<213> ORGANISM: Arabidopsis thaliana
<220> FEATURE:

<223> OTHER INFORMATION: G3075

<400> SEQUENCE: 83

```
atggtgtcgt caaagaaacc caaggagaag aaggcgagga gcgatgtcgt cgtcaataaa      60
gcgagtggtc ggagtaaacg cagctccggt tccagaacga agaagacgtc gaacaaggtt     120
aacattgtga agaagaagcc ggagatttac gagatctcag aatcatcgag cagtgactct     180
gtggaagaag caataagagg cgatgaggcg aagaaaagta acggcgtcgt gagcaagagg     240
ggtaacggaa agagtgtagg aattccgacg aagacgagta aaaatcgaga gaggacgat      300
ggaggcgcgg aagatgctaa gatcaagttt ccgatgaatc ggattcggcg gatcatgaga     360
agcgataatt ctgctcctca gattatgcag gatgctgtat tcttgtcaa caaagccacg      420
gagatgttca ttgagcggtt ttctgaagaa gcttatgata gttccgtcaa ggacaaaaag     480
aaattcatcc actacaaaca cctctcatcc gtagtgagta acgaccagag atacgagttc     540
cttgcagata gtgttcccga gaaacttaaa gcagaggccg cgttggagga atgggaaaga     600
ggcatgacag atgcaggctg a                                                621
```

<210> SEQ ID NO 84
<211> LENGTH: 206
<212> TYPE: PRT
<213> ORGANISM: Arabidopsis thaliana
<220> FEATURE:
<223> OTHER INFORMATION: G3075 polypeptide (domain in aa coordinates: 110-173)

<400> SEQUENCE: 84

```
Met Val Ser Ser Lys Lys Pro Lys Glu Lys Lys Ala Arg Ser Asp Val
1               5                   10                  15
Val Val Asn Lys Ala Ser Gly Arg Ser Lys Arg Ser Ser Gly Ser Arg
            20                  25                  30
Thr Lys Lys Thr Ser Asn Lys Val Asn Ile Val Lys Lys Pro Glu
        35                  40                  45
Ile Tyr Glu Ile Ser Glu Ser Ser Ser Asp Ser Val Glu Glu Ala
    50                  55                  60
Ile Arg Gly Asp Glu Ala Lys Lys Ser Asn Gly Val Val Ser Lys Arg
65                  70                  75                  80
Gly Asn Gly Lys Ser Val Gly Ile Pro Thr Lys Thr Ser Lys Asn Arg
                85                  90                  95
Glu Glu Asp Asp Gly Gly Ala Glu Asp Ala Lys Ile Lys Phe Pro Met
            100                 105                 110
Asn Arg Ile Arg Arg Ile Met Arg Ser Asp Asn Ser Ala Pro Gln Ile
        115                 120                 125
Met Gln Asp Ala Val Phe Leu Val Asn Lys Ala Thr Glu Met Phe Ile
    130                 135                 140
Glu Arg Phe Ser Glu Glu Ala Tyr Asp Ser Ser Val Lys Asp Lys Lys
145                 150                 155                 160
Lys Phe Ile His Tyr Lys His Leu Ser Ser Val Val Ser Asn Asp Gln
                165                 170                 175
Arg Tyr Glu Phe Leu Ala Asp Ser Val Pro Glu Lys Leu Lys Ala Glu
            180                 185                 190
Ala Ala Leu Glu Glu Trp Glu Arg Gly Met Thr Asp Ala Gly
        195                 200                 205
```

<210> SEQ ID NO 85
<211> LENGTH: 60

```
<212> TYPE: PRT
<213> ORGANISM: Arabidopsis thaliana
<220> FEATURE:
<223> OTHER INFORMATION: G929 conserved domain

<400> SEQUENCE: 85

Glu Pro Val Phe Val Asn Ala Lys Gln Tyr His Gly Ile Leu Arg Arg
1               5                  10                  15

Arg Gln Ser Arg Ala Lys Leu Glu Ala Arg Asn Arg Ala Ile Lys Ala
            20                  25                  30

Lys Lys Pro Tyr Met His Glu Ser Arg His Leu His Ala Ile Arg Arg
        35                  40                  45

Pro Arg Gly Cys Gly Gly Arg Phe Leu Asn Ala Lys
    50                  55                  60

<210> SEQ ID NO 86
<211> LENGTH: 60
<212> TYPE: PRT
<213> ORGANISM: Arabidopsis thaliana
<220> FEATURE:
<223> OTHER INFORMATION: G2344 conserved domain

<400> SEQUENCE: 86

Glu Pro Val Phe Val Asn Ala Lys Gln Tyr His Gly Ile Leu Arg Arg
1               5                  10                  15

Arg Gln Ser Arg Ala Arg Leu Glu Ser Gln Asn Lys Val Ile Lys Ser
            20                  25                  30

Arg Lys Pro Tyr Leu His Glu Ser Arg His Leu His Ala Ile Arg Arg
        35                  40                  45

Pro Arg Gly Cys Gly Gly Arg Phe Leu Asn Ala Lys
    50                  55                  60

<210> SEQ ID NO 87
<211> LENGTH: 60
<212> TYPE: PRT
<213> ORGANISM: Arabidopsis thaliana
<220> FEATURE:
<223> OTHER INFORMATION: G931 conserved domain

<400> SEQUENCE: 87

Glu Pro Val Phe Val Asn Ala Lys Gln Phe His Ala Ile Met Arg Arg
1               5                  10                  15

Arg Gln Gln Arg Ala Lys Leu Glu Ala Gln Asn Lys Leu Ile Lys Ala
            20                  25                  30

Arg Lys Pro Tyr Leu His Glu Ser Arg His Val His Ala Leu Lys Arg
        35                  40                  45

Pro Arg Gly Ser Gly Gly Arg Phe Leu Asn Thr Lys
    50                  55                  60

<210> SEQ ID NO 88
<211> LENGTH: 60
<212> TYPE: PRT
<213> ORGANISM: Glycine max
<220> FEATURE:
<223> OTHER INFORMATION: G3920 conserved domain

<400> SEQUENCE: 88

Glu Pro Val Tyr Val Asn Ala Lys Gln Tyr His Gly Ile Leu Arg Arg
1               5                  10                  15

Arg Gln Ser Arg Ala Lys Ala Glu Ile Glu Lys Lys Val Ile Lys Asn
            20                  25                  30
```

```
Arg Lys Pro Tyr Leu His Glu Ser Arg His Leu His Ala Met Arg Arg
        35                  40                  45

Ala Arg Gly Asn Gly Gly Arg Phe Leu Asn Thr Lys
    50                  55                  60

<210> SEQ ID NO 89
<211> LENGTH: 60
<212> TYPE: PRT
<213> ORGANISM: Arabidopsis thaliana
<220> FEATURE:
<223> OTHER INFORMATION: G928 conserved domain

<400> SEQUENCE: 89

Asp Pro Val Phe Val Asn Ala Lys Gln Tyr His Ala Ile Met Arg Arg
1               5                   10                  15

Arg Gln Gln Arg Ala Lys Leu Glu Ala Gln Asn Lys Leu Ile Arg Ala
            20                  25                  30

Arg Lys Pro Tyr Leu His Glu Ser Arg His Val His Ala Leu Lys Arg
        35                  40                  45

Pro Arg Gly Ser Gly Gly Arg Phe Leu Asn Thr Lys
    50                  55                  60

<210> SEQ ID NO 90
<211> LENGTH: 60
<212> TYPE: PRT
<213> ORGANISM: Arabidopsis thaliana
<220> FEATURE:
<223> OTHER INFORMATION: G1782 conserved domain

<400> SEQUENCE: 90

Glu Pro Ile Phe Val Asn Ala Lys Gln Tyr His Ala Ile Leu Arg Arg
1               5                   10                  15

Arg Lys His Arg Ala Lys Leu Glu Ala Gln Asn Lys Leu Ile Lys Cys
            20                  25                  30

Arg Lys Pro Tyr Leu His Glu Ser Arg His Leu His Ala Leu Lys Arg
        35                  40                  45

Ala Arg Gly Ser Gly Gly Arg Phe Leu Asn Thr Lys
    50                  55                  60

<210> SEQ ID NO 91
<211> LENGTH: 60
<212> TYPE: PRT
<213> ORGANISM: Arabidopsis thaliana
<220> FEATURE:
<223> OTHER INFORMATION: G1363 conserved domain

<400> SEQUENCE: 91

Glu Pro Ile Phe Val Asn Ala Lys Gln Tyr Gln Ala Ile Leu Arg Arg
1               5                   10                  15

Arg Glu Arg Arg Ala Lys Leu Glu Ala Gln Asn Lys Leu Ile Lys Val
            20                  25                  30

Arg Lys Pro Tyr Leu His Glu Ser Arg His Leu His Ala Leu Lys Arg
        35                  40                  45

Val Arg Gly Ser Gly Gly Arg Phe Leu Asn Thr Lys
    50                  55                  60

<210> SEQ ID NO 92
<211> LENGTH: 60
<212> TYPE: PRT
<213> ORGANISM: Oryza sativa
<220> FEATURE:
<223> OTHER INFORMATION: G3924 conserved domain
```

<400> SEQUENCE: 92

Glu Pro Val Tyr Val Asn Ala Lys Gln Tyr His Gly Ile Leu Arg Arg
1               5                   10                  15

Arg Gln Ser Arg Ala Lys Ala Glu Leu Glu Lys Lys Val Val Lys Ser
            20                  25                  30

Arg Lys Pro Tyr Leu His Glu Ser Arg His Gln His Ala Met Arg Arg
        35                  40                  45

Ala Arg Gly Thr Gly Gly Arg Phe Leu Asn Thr Lys
    50                  55                  60

<210> SEQ ID NO 93
<211> LENGTH: 59
<212> TYPE: PRT
<213> ORGANISM: Oryza sativa
<220> FEATURE:
<223> OTHER INFORMATION: G3926 conserved domain

<400> SEQUENCE: 93

Glu Pro Ile Phe Val Asn Ala Lys Gln Tyr Asn Ala Ile Leu Arg Arg
1               5                   10                  15

Arg Gln Thr Arg Ala Lys Leu Glu Ala Gln Asn Lys Ala Val Lys Gly
            20                  25                  30

Arg Lys Pro Tyr Leu His Glu Ser Arg His His His Ala Met Lys Arg
        35                  40                  45

Ala Arg Gly Ser Gly Gly Arg Phe Leu Thr Lys
    50                  55

<210> SEQ ID NO 94
<211> LENGTH: 60
<212> TYPE: PRT
<213> ORGANISM: Oryza sativa
<220> FEATURE:
<223> OTHER INFORMATION: G3925 conserved domain

<400> SEQUENCE: 94

Glu Pro Ile Tyr Val Asn Ala Lys Gln Tyr His Ala Ile Leu Arg Arg
1               5                   10                  15

Arg Gln Leu Arg Ala Lys Leu Glu Ala Glu Asn Lys Leu Val Lys Asn
            20                  25                  30

Arg Lys Pro Tyr Leu His Glu Ser Arg His Gln His Ala Met Lys Arg
        35                  40                  45

Ala Arg Gly Thr Gly Gly Arg Phe Leu Asn Thr Lys
    50                  55                  60

<210> SEQ ID NO 95
<211> LENGTH: 60
<212> TYPE: PRT
<213> ORGANISM: Zea mays
<220> FEATURE:
<223> OTHER INFORMATION: G3921 conserved domain

<400> SEQUENCE: 95

Glu Pro Ile Tyr Val Asn Ala Lys Gln Tyr His Ala Ile Leu Arg Arg
1               5                   10                  15

Arg Gln Thr Arg Ala Lys Leu Glu Ala Gln Asn Lys Met Val Lys Gly
            20                  25                  30

Arg Lys Pro Tyr Leu His Glu Ser Arg His Arg His Ala Met Lys Arg
        35                  40                  45

Ala Arg Gly Ser Gly Gly Arg Phe Leu Asn Thr Lys

-continued

```
<210> SEQ ID NO 96
<211> LENGTH: 60
<212> TYPE: PRT
<213> ORGANISM: Zea mays
<220> FEATURE:
<223> OTHER INFORMATION: G3922 conserved domain

<400> SEQUENCE: 96

Glu Pro Ile Tyr Val Asn Ala Lys Gln Tyr His Ala Ile Leu Arg Arg
1               5                   10                  15

Arg Gln Thr Arg Ala Lys Leu Glu Ala Gln Asn Lys Met Val Lys Asn
            20                  25                  30

Arg Lys Pro Tyr Leu His Glu Ser Arg His Arg His Ala Met Lys Arg
        35                  40                  45

Ala Arg Gly Ser Gly Gly Arg Phe Leu Asn Thr Lys
    50                  55                  60

<210> SEQ ID NO 97
<211> LENGTH: 60
<212> TYPE: PRT
<213> ORGANISM: Zea mays
<220> FEATURE:
<223> OTHER INFORMATION: G4264 conserved domain

<400> SEQUENCE: 97

Glu Pro Ile Tyr Val Asn Ala Lys Gln Tyr His Ala Ile Leu Arg Arg
1               5                   10                  15

Arg Gln Thr Arg Ala Lys Leu Glu Ala Gln Asn Lys Met Val Lys Asn
            20                  25                  30

Arg Lys Pro Tyr Leu His Glu Ser Arg His Arg His Ala Met Lys Arg
        35                  40                  45

Ala Arg Gly Ser Gly Gly Arg Phe Leu Asn Thr Lys
    50                  55                  60

<210> SEQ ID NO 98
<211> LENGTH: 58
<212> TYPE: PRT
<213> ORGANISM: Arabidopsis thaliana
<220> FEATURE:
<223> OTHER INFORMATION: G2632 conserved domain

<400> SEQUENCE: 98

Glu Pro Val Phe Val Asn Ala Lys Gln Tyr Gln Ala Ile Leu Arg Arg
1               5                   10                  15

Arg Gln Ala Arg Ala Lys Ala Glu Leu Glu Lys Lys Leu Ile Lys Ser
            20                  25                  30

Arg Lys Pro Tyr Leu His Glu Ser Arg His Gln His Ala Met Arg Arg
        35                  40                  45

Pro Arg Gly Thr Gly Gly Arg Phe Ala Lys
    50                  55

<210> SEQ ID NO 99
<211> LENGTH: 58
<212> TYPE: PRT
<213> ORGANISM: Arabidopsis thaliana
<220> FEATURE:
<223> OTHER INFORMATION: G1334 conserved domain

<400> SEQUENCE: 99

Asp Gly Thr Ile Tyr Val Asn Ser Lys Gln Tyr His Gly Ile Ile Arg
```

```
                1               5                  10                  15
            Arg Arg Gln Ser Arg Ala Lys Ala Glu Lys Leu Ser Arg Cys Arg Lys
                            20                  25                  30

Pro Tyr Met His His Ser Arg His Leu His Ala Met Arg Arg Pro Arg
                        35                  40                  45

Gly Ser Gly Gly Arg Phe Leu Asn Thr Lys
                    50                  55

<210> SEQ ID NO 100
<211> LENGTH: 58
<212> TYPE: PRT
<213> ORGANISM: Arabidopsis thaliana
<220> FEATURE:
<223> OTHER INFORMATION: G926 conserved domain

<400> SEQUENCE: 100

Glu Pro Val Tyr Val Asn Ala Lys Gln Tyr Glu Gly Ile Leu Arg Arg
1               5                   10                  15

Arg Lys Ala Arg Ala Lys Ala Glu Leu Glu Arg Lys Val Ile Arg Asp
                20                  25                  30

Arg Lys Pro Tyr Leu His Glu Ser Arg His Lys His Ala Met Arg Arg
            35                  40                  45

Ala Arg Ala Ser Gly Gly Arg Phe Ala Lys
        50                  55

<210> SEQ ID NO 101
<211> LENGTH: 64
<212> TYPE: PRT
<213> ORGANISM: Arabidopsis thaliana
<220> FEATURE:
<223> OTHER INFORMATION: G927 conserved domain

<400> SEQUENCE: 101

Ser Thr Ile Tyr Val Asn Ser Lys Gln Tyr His Gly Ile Ile Arg Arg
1               5                   10                  15

Arg Gln Ser Arg Ala Lys Ala Ala Val Leu Asp Gln Lys Lys Leu
                20                  25                  30

Ser Ser Arg Cys Arg Lys Pro Tyr Met His His Ser Arg His Leu His
            35                  40                  45

Ala Leu Arg Arg Pro Arg Gly Ser Gly Gly Arg Phe Leu Asn Thr Lys
        50                  55                  60

<210> SEQ ID NO 102
<211> LENGTH: 66
<212> TYPE: PRT
<213> ORGANISM: Zea mays
<220> FEATURE:
<223> OTHER INFORMATION: G3911 conserved domain

<400> SEQUENCE: 102

Leu Pro Leu Ala Arg Ile Lys Lys Ile Met Lys Ala Asp Glu Asp Val
1               5                   10                  15

Arg Met Ile Ala Ala Glu Ala Pro Val Val Phe Ala Arg Ala Cys Glu
                20                  25                  30

Met Phe Ile Leu Glu Leu Thr His Arg Gly Trp Ala His Ala Glu Glu
            35                  40                  45

Asn Lys Arg Arg Thr Leu Gln Lys Ser Asp Ile Ala Ala Ala Ile Ala
        50                  55                  60

Arg Thr
65
```

```
<210> SEQ ID NO 103
<211> LENGTH: 66
<212> TYPE: PRT
<213> ORGANISM: Oryza sativa
<220> FEATURE:
<223> OTHER INFORMATION: G3546 conserved domain

<400> SEQUENCE: 103

Leu Pro Leu Ala Arg Ile Lys Lys Ile Met Lys Ala Asp Glu Asp Val
1               5                   10                  15

Arg Met Ile Ala Ala Glu Ala Pro Val Val Phe Ala Arg Ala Cys Glu
            20                  25                  30

Met Phe Ile Leu Glu Leu Thr His Arg Gly Trp Ala His Ala Glu Glu
        35                  40                  45

Asn Lys Arg Arg Thr Leu Gln Lys Ser Asp Ile Ala Ala Ala Ile Ala
    50                  55                  60

Arg Thr
65

<210> SEQ ID NO 104
<211> LENGTH: 66
<212> TYPE: PRT
<213> ORGANISM: Zea mays
<220> FEATURE:
<223> OTHER INFORMATION: G3909 conserved domain

<400> SEQUENCE: 104

Leu Pro Leu Ala Arg Ile Lys Lys Ile Met Lys Ala Asp Glu Asp Val
1               5                   10                  15

Arg Met Ile Ala Ala Glu Ala Pro Val Val Phe Ser Arg Ala Cys Glu
            20                  25                  30

Met Phe Ile Leu Glu Leu Thr His Arg Gly Trp Ala His Ala Glu Glu
        35                  40                  45

Asn Lys Arg Arg Thr Leu Gln Lys Ser Asp Ile Ala Ala Ala Val Ala
    50                  55                  60

Arg Thr
65

<210> SEQ ID NO 105
<211> LENGTH: 66
<212> TYPE: PRT
<213> ORGANISM: Zea mays
<220> FEATURE:
<223> OTHER INFORMATION: G3552 conserved domain

<400> SEQUENCE: 105

Leu Pro Leu Ala Arg Ile Lys Lys Ile Met Lys Ala Asp Glu Asp Val
1               5                   10                  15

Arg Met Ile Ser Ala Glu Ala Pro Val Val Phe Ala Lys Ala Cys Glu
            20                  25                  30

Ile Phe Ile Leu Glu Leu Thr Leu Arg Ser Trp Met His Thr Glu Glu
        35                  40                  45

Asn Lys Arg Arg Thr Leu Gln Lys Asn Asp Ile Ala Ala Ala Ile Thr
    50                  55                  60

Arg Thr
65

<210> SEQ ID NO 106
<211> LENGTH: 66
```

```
<212> TYPE: PRT
<213> ORGANISM: Arabidopsis thaliana
<220> FEATURE:
<223> OTHER INFORMATION: G483 conserved domain

<400> SEQUENCE: 106
```

Leu Pro Leu Ala Arg Ile Lys Lys Ile Met Lys Ala Asp Glu Asp Val
1               5                   10                  15

Arg Met Ile Ser Ala Glu Ala Pro Val Ile Phe Ala Lys Ala Cys Glu
            20                  25                  30

Met Phe Ile Leu Glu Leu Thr Leu Arg Ala Trp Ile His Thr Glu Glu
        35                  40                  45

Asn Lys Arg Arg Thr Leu Gln Lys Asn Asp Ile Ala Ala Ile Ser
    50                  55                  60

Arg Thr
65

```
<210> SEQ ID NO 107
<211> LENGTH: 66
<212> TYPE: PRT
<213> ORGANISM: Glycine max
<220> FEATURE:
<223> OTHER INFORMATION: G3547 conserved domain

<400> SEQUENCE: 107
```

Leu Pro Leu Ala Arg Ile Lys Lys Ile Met Lys Ala Asp Glu Asp Val
1               5                   10                  15

Arg Met Ile Ser Ala Glu Ala Pro Val Ile Phe Ala Arg Ala Cys Glu
            20                  25                  30

Met Phe Ile Leu Glu Leu Thr Leu Arg Ser Trp Asn His Thr Glu Glu
        35                  40                  45

Asn Lys Arg Arg Thr Leu Gln Lys Asn Asp Ile Ala Ala Ala Ile Thr
    50                  55                  60

Arg Thr
65

```
<210> SEQ ID NO 108
<211> LENGTH: 66
<212> TYPE: PRT
<213> ORGANISM: Arabidopsis thaliana
<220> FEATURE:
<223> OTHER INFORMATION: G714 conserved domain

<400> SEQUENCE: 108
```

Leu Pro Leu Ala Arg Ile Lys Lys Ile Met Lys Ala Asp Glu Asp Val
1               5                   10                  15

Arg Met Ile Ser Ala Glu Ala Pro Val Val Phe Ala Arg Ala Cys Glu
            20                  25                  30

Met Phe Ile Leu Glu Leu Thr Leu Arg Ser Trp Asn His Thr Glu Glu
        35                  40                  45

Asn Lys Arg Arg Thr Leu Gln Lys Asn Asp Ile Ala Ala Ala Val Thr
    50                  55                  60

Arg Thr
65

```
<210> SEQ ID NO 109
<211> LENGTH: 66
<212> TYPE: PRT
<213> ORGANISM: Oryza sativa
<220> FEATURE:
<223> OTHER INFORMATION: G3542 conserved domain
```

<400> SEQUENCE: 109

Leu Pro Leu Ala Arg Ile Lys Lys Ile Met Lys Ala Asp Glu Asp Val
1               5                   10                  15

Arg Met Ile Ser Ala Glu Ala Pro Val Val Phe Ala Lys Ala Cys Glu
            20                  25                  30

Val Phe Ile Leu Glu Leu Thr Leu Arg Ser Trp Met His Thr Glu Glu
        35                  40                  45

Asn Lys Arg Arg Thr Leu Gln Lys Asn Asp Ile Ala Ala Ala Ile Thr
    50                  55                  60

Arg Thr
65

<210> SEQ ID NO 110
<211> LENGTH: 66
<212> TYPE: PRT
<213> ORGANISM: Arabidopsis thaliana
<220> FEATURE:
<223> OTHER INFORMATION: G489 conserved domain

<400> SEQUENCE: 110

Leu Pro Leu Ala Arg Ile Lys Lys Ile Met Lys Ala Asp Glu Asp Val
1               5                   10                  15

Arg Met Ile Ser Ala Glu Ala Pro Val Val Phe Ala Arg Ala Cys Glu
            20                  25                  30

Met Phe Ile Leu Glu Leu Thr Leu Arg Ser Trp Asn His Thr Glu Glu
        35                  40                  45

Asn Lys Arg Arg Thr Leu Gln Lys Asn Asp Ile Ala Ala Ala Val Thr
    50                  55                  60

Arg Thr
65

<210> SEQ ID NO 111
<211> LENGTH: 66
<212> TYPE: PRT
<213> ORGANISM: Oryza sativa
<220> FEATURE:
<223> OTHER INFORMATION: G3544 conserved domain

<400> SEQUENCE: 111

Leu Pro Leu Ala Arg Ile Lys Lys Ile Met Lys Ala Asp Glu Asp Val
1               5                   10                  15

Arg Met Ile Ser Ala Glu Ala Pro Val Ile Phe Ala Lys Ala Cys Glu
            20                  25                  30

Ile Phe Ile Leu Glu Leu Thr Leu Arg Ser Trp Met His Thr Glu Glu
        35                  40                  45

Asn Lys Arg Arg Thr Leu Gln Lys Asn Asp Ile Ala Ala Ala Ile Thr
    50                  55                  60

Arg Thr
65

<210> SEQ ID NO 112
<211> LENGTH: 66
<212> TYPE: PRT
<213> ORGANISM: Glycine max
<220> FEATURE:
<223> OTHER INFORMATION: G3550 conserved domain

<400> SEQUENCE: 112

Leu Pro Leu Ala Arg Ile Lys Lys Ile Met Lys Ala Asp Glu Asp Val

```
                1               5                  10                 15
Arg Met Ile Ser Ala Glu Ala Pro Val Ile Phe Ala Lys Ala Cys Glu
                20                 25                 30

Met Phe Ile Leu Glu Leu Thr Leu Arg Ser Trp Ile His Thr Glu Glu
            35                 40                 45

Asn Lys Arg Arg Thr Leu Gln Lys Asn Asp Ile Ala Ala Ala Ile Ser
        50                 55                 60

Arg Asn
65

<210> SEQ ID NO 113
<211> LENGTH: 66
<212> TYPE: PRT
<213> ORGANISM: Glycine max
<220> FEATURE:
<223> OTHER INFORMATION: G3548 conserved domain

<400> SEQUENCE: 113

Leu Pro Leu Ala Arg Ile Lys Lys Ile Met Lys Ala Asp Glu Asp Val
1               5                  10                 15

Arg Met Ile Ser Ala Glu Ala Pro Val Ile Phe Ala Lys Ala Cys Glu
                20                 25                 30

Met Phe Ile Leu Glu Leu Thr Leu Arg Ser Trp Ile His Thr Glu Glu
            35                 40                 45

Asn Lys Arg Arg Thr Leu Gln Lys Asn Asp Ile Ala Ala Ala Ile Ser
        50                 55                 60

Arg Asn
65

<210> SEQ ID NO 114
<211> LENGTH: 66
<212> TYPE: PRT
<213> ORGANISM: Arabidopsis thaliana
<220> FEATURE:
<223> OTHER INFORMATION: G715 conserved domain

<400> SEQUENCE: 114

Leu Pro Leu Ala Arg Ile Lys Lys Ile Met Lys Ala Asp Glu Asp Val
1               5                  10                 15

Arg Met Ile Ser Ala Glu Ala Pro Ile Leu Phe Ala Lys Ala Cys Glu
                20                 25                 30

Leu Phe Ile Leu Glu Leu Thr Ile Arg Ser Trp Leu His Ala Glu Glu
            35                 40                 45

Asn Lys Arg Arg Thr Leu Gln Lys Asn Asp Ile Ala Ala Ala Ile Thr
        50                 55                 60

Arg Thr
65

<210> SEQ ID NO 115
<211> LENGTH: 66
<212> TYPE: PRT
<213> ORGANISM: Glycine max
<220> FEATURE:
<223> OTHER INFORMATION: G3886 conserved domain

<400> SEQUENCE: 115

Leu Pro Leu Ala Arg Ile Lys Lys Ile Met Lys Ala Asp Glu Asp Val
1               5                  10                 15

Arg Met Ile Ser Ala Glu Ala Pro Ile Leu Phe Ala Lys Ala Cys Glu
                20                 25                 30
```

-continued

Leu Phe Ile Leu Glu Leu Thr Ile Arg Ser Trp Leu His Ala Glu Glu
            35                  40                  45

Asn Lys Arg Arg Thr Leu Gln Lys Asn Asp Ile Ala Ala Ile Thr
    50                  55                  60

Arg Thr
65

<210> SEQ ID NO 116
<211> LENGTH: 66
<212> TYPE: PRT
<213> ORGANISM: Zea mays
<220> FEATURE:
<223> OTHER INFORMATION: G3889 conserved domain

<400> SEQUENCE: 116

Leu Pro Leu Ala Arg Ile Lys Lys Ile Met Lys Ala Asp Glu Asp Val
1               5                   10                  15

Arg Met Ile Ser Ala Glu Ala Pro Val Leu Phe Ala Lys Ala Cys Glu
            20                  25                  30

Leu Phe Ile Leu Glu Leu Thr Ile Arg Ser Trp Leu His Ala Glu Glu
            35                  40                  45

Asn Lys Arg Arg Thr Leu Gln Arg Asn Asp Val Ala Ala Ile Ala
    50                  55                  60

Arg Thr
65

<210> SEQ ID NO 117
<211> LENGTH: 66
<212> TYPE: PRT
<213> ORGANISM: Arabidopsis thaliana
<220> FEATURE:
<223> OTHER INFORMATION: G1646 conserved domain

<400> SEQUENCE: 117

Leu Pro Leu Ala Arg Ile Lys Lys Ile Met Lys Ala Asp Glu Asp Val
1               5                   10                  15

Arg Met Ile Ser Ala Glu Ala Pro Ile Leu Phe Ala Lys Ala Cys Glu
            20                  25                  30

Leu Phe Ile Leu Glu Leu Thr Ile Arg Ser Trp Leu His Ala Glu Glu
            35                  40                  45

Asn Lys Arg Arg Thr Leu Gln Lys Asn Asp Ile Ala Ala Ile Thr
    50                  55                  60

Arg Thr
65

<210> SEQ ID NO 118
<211> LENGTH: 66
<212> TYPE: PRT
<213> ORGANISM: Oryza sativa
<220> FEATURE:
<223> OTHER INFORMATION: G3543 conserved domain

<400> SEQUENCE: 118

Leu Pro Leu Ala Gly Ile Lys Lys Ile Met Lys Ala Asp Glu Asp Val
1               5                   10                  15

Arg Met Ile Ser Ala Glu Ala Pro Val Leu Phe Ala Lys Ala Cys Glu
            20                  25                  30

Leu Phe Ile Leu Glu Leu Thr Ile Arg Ser Trp Leu His Ala Glu Glu
            35                  40                  45

```
                                    -continued

Asn Lys Arg Arg Thr Leu Gln Arg Lys Asp Val Ala Ala Ala Ile Ala
     50                  55                  60

Arg Thr
 65

<210> SEQ ID NO 119
<211> LENGTH: 66
<212> TYPE: PRT
<213> ORGANISM: Arabidopsis thaliana
<220> FEATURE:
<223> OTHER INFORMATION: G1820 conserved domain

<400> SEQUENCE: 119

Leu Pro Leu Ala Arg Ile Lys Lys Ile Met Lys Ala Asp Pro Asp Val
 1               5                  10                  15

His Met Val Ser Ala Glu Ala Pro Ile Ile Phe Ala Lys Ala Cys Glu
                20                  25                  30

Met Phe Ile Val Asp Leu Thr Met Arg Ser Trp Leu Lys Ala Glu Glu
            35                  40                  45

Asn Lys Arg His Thr Leu Gln Lys Ser Asp Ile Ser Asn Ala Val Ala
     50                  55                  60

Ser Ser
 65

<210> SEQ ID NO 120
<211> LENGTH: 66
<212> TYPE: PRT
<213> ORGANISM: Arabidopsis thaliana
<220> FEATURE:
<223> OTHER INFORMATION: G1836 conserved domain

<400> SEQUENCE: 120

Leu Pro Ile Thr Arg Ile Lys Lys Ile Met Lys Tyr Asp Pro Asp Val
 1               5                  10                  15

Thr Met Ile Ala Ser Glu Ala Pro Ile Leu Leu Ser Lys Ala Cys Glu
                20                  25                  30

Met Phe Ile Met Asp Leu Thr Met Arg Ser Trp Leu His Ala Gln Glu
            35                  40                  45

Ser Lys Arg Val Thr Leu Gln Lys Ser Asn Val Asp Ala Ala Val Ala
     50                  55                  60

Gln Thr
 65

<210> SEQ ID NO 121
<211> LENGTH: 65
<212> TYPE: PRT
<213> ORGANISM: Arabidopsis thaliana
<220> FEATURE:
<223> OTHER INFORMATION: G1819 conserved domain

<400> SEQUENCE: 121

Phe Pro Leu Thr Arg Ile Lys Lys Ile Met Lys Ser Asn Pro Glu Val
 1               5                  10                  15

Asn Met Val Thr Ala Glu Ala Pro Val Leu Ile Ser Lys Ala Cys Glu
                20                  25                  30

Met Leu Ile Leu Asp Leu Thr Met Arg Ser Trp Leu His Thr Val Glu
            35                  40                  45

Gly Gly Arg Gln Thr Leu Lys Arg Ser Asp Leu Thr Arg Ser Asp
     50                  55                  60

Ile
```

-continued

<210> SEQ ID NO 122
<211> LENGTH: 65
<212> TYPE: PRT
<213> ORGANISM: Arabidopsis thaliana
<220> FEATURE:
<223> OTHER INFORMATION: G1818 conserved domain

<400> SEQUENCE: 122

Pro Ile Ser Arg Ile Lys Arg Ile Met Lys Phe Asp Pro Asp Val Ser
1               5                   10                  15

Met Ile Ala Ala Glu Ala Pro Asn Leu Leu Ser Lys Ala Cys Glu Met
            20                  25                  30

Phe Val Met Asp Leu Thr Met Arg Ser Trp Leu His Ala Gln Glu Ser
        35                  40                  45

Asn Arg Leu Thr Ile Arg Lys Ser Asp Val Asp Ala Val Val Ser Gln
    50                  55                  60

Thr
65

<210> SEQ ID NO 123
<211> LENGTH: 66
<212> TYPE: PRT
<213> ORGANISM: Arabidopsis thaliana
<220> FEATURE:
<223> OTHER INFORMATION: G490 conserved domain

<400> SEQUENCE: 123

Leu Pro Leu Ser Arg Val Arg Lys Ile Leu Lys Ser Asp Pro Glu Val
1               5                   10                  15

Lys Lys Ile Ser Cys Asp Val Pro Ala Leu Phe Ser Lys Ala Cys Glu
            20                  25                  30

Tyr Phe Ile Leu Glu Val Thr Leu Arg Ala Trp Met His Thr Gln Ser
        35                  40                  45

Cys Thr Arg Glu Thr Ile Arg Arg Cys Asp Ile Phe Gln Ala Val Lys
    50                  55                  60

Asn Ser
65

<210> SEQ ID NO 124
<211> LENGTH: 64
<212> TYPE: PRT
<213> ORGANISM: Arabidopsis thaliana
<220> FEATURE:
<223> OTHER INFORMATION: G3074 conserved domain

<400> SEQUENCE: 124

Pro Ala Ala Arg Ile Lys Lys Ile Met Gln Ala Asp Glu Asp Val Gly
1               5                   10                  15

Lys Ile Ala Leu Ala Val Pro Val Leu Val Ser Lys Ser Leu Glu Leu
            20                  25                  30

Phe Leu Gln Asp Leu Cys Asp Arg Thr Tyr Glu Ile Thr Leu Glu Arg
        35                  40                  45

Gly Ala Lys Thr Val Ser Ser Leu His Leu Lys His Cys Val Glu Arg
    50                  55                  60

<210> SEQ ID NO 125
<211> LENGTH: 64
<212> TYPE: PRT
<213> ORGANISM: Arabidopsis thaliana
<220> FEATURE:
<223> OTHER INFORMATION: G1249 conserved domain

<400> SEQUENCE: 125

Pro Ile Gly Arg Val Lys Lys Ile Met Lys Leu Asp Lys Asp Ile Asn
1               5                   10                  15

Lys Ile Asn Ser Glu Ala Leu His Val Ile Thr Tyr Ser Thr Glu Leu
            20                  25                  30

Phe Leu His Phe Leu Ala Glu Lys Ser Ala Val Val Thr Ala Glu Lys
        35                  40                  45

Lys Arg Lys Thr Val Asn Leu Asp His Leu Arg Ile Ala Val Lys Arg
    50                  55                  60

<210> SEQ ID NO 126
<211> LENGTH: 63
<212> TYPE: PRT
<213> ORGANISM: Arabidopsis thaliana
<220> FEATURE:
<223> OTHER INFORMATION: G3075 conserved domain

<400> SEQUENCE: 126

Pro Met Asn Arg Ile Arg Arg Ile Met Arg Ser Asp Asn Ser Ala Pro
1               5                   10                  15

Gln Ile Met Gln Asp Ala Val Phe Leu Val Asn Lys Ala Thr Glu Met
            20                  25                  30

Phe Ile Glu Arg Phe Ser Glu Glu Ala Tyr Asp Ser Ser Val Lys Asp
        35                  40                  45

Lys Lys Lys Phe Ile His Tyr Lys His Leu Ser Ser Val Val Ser
    50                  55                  60

<210> SEQ ID NO 127
<211> LENGTH: 953
<212> TYPE: DNA
<213> ORGANISM: Artificial sequence
<220> FEATURE:
<223> OTHER INFORMATION: synthetic sequence
<220> FEATURE:
<223> OTHER INFORMATION: P399 overexpression construct (35S::G929)

<400> SEQUENCE: 127
ggagagacct taacaatttt tctgagggta agatccagag attgattgaa tcagcttact      60
attttatata attcagtttg ttgttcctca gacttgtaac taggacagtc ttctcatgaa     120
tcatgacttc ttcagtacat gagctctctg ataacaatga aagtcatgcg aagaaagaac     180
gtccagattc ccaaacccga ccacaggttc cttcaggacg aagttcggaa tctattgata     240
caaactctgt ctactcagag cccatggcac atggattata cccgtatcca gatccttact     300
acagaagcgt ctttgcacag caagcgtatc ttccacatcc ctatcctggg gtccaattgc     360
agttaatggg aatgcagcag ccaggagttc cattgcaatg tgatgcagtc gaggaacctg     420
ttttttgttaa cgcaaagcaa taccatggta tactcaggcg caggcaatcc cgggcaaaac     480
ttgaggcacg aaatagagcc atcaaagcaa aaaagccata catgcatgaa tctcggcatt     540
tacatgcgat aagacggcca agaggatgtg gtggccggtt tctcaatgcc aagaaggaaa     600
atggagacca caaggaggag gaggaggcaa cctctgatga aacacttca gaagcaagtt      660
ccagcctcag gtccgagaaa ttagctatgg ctacttctgg tcctaatggt agatcttgag     720
gaaggtttct gcacaaccac aagtttagtt tctattttgg gtggatgttc tcagggcatc     780
atcgtcttta gtgttttttgg atacgctgtg tacaggttat ttgctagggt aaactttgtt     840

```
ttagcgatta gaaataaaac taagcaaaga aatgaaaagt gtgattggaa gtattgttgt    900
accaaattga tattctttgc caatgaactc atgttttgga aagtaaaaaa aaa           953

<210> SEQ ID NO 128
<211> LENGTH: 812
<212> TYPE: DNA
<213> ORGANISM: Artificial sequence
<220> FEATURE:
<223> OTHER INFORMATION: synthetic sequence
<220> FEATURE:
<223> OTHER INFORMATION: P1627 overexpression construct (35S::G2344)

<400> SEQUENCE: 128
ttattctaag tagcttgact tgtttagttt aaatatgagg ttaatgattt tgtggggatt    60
tgatagttct ggttcttgag tttatttaaa ataggtttac caggatcatg tactgactct   120
gttctttgga acttttcaga attctgcttc ggacattaag ctcatgagtc atgacttctt   180
caatccatga gctttctgat aacattggaa gtcatgagaa gcaagaacag agagattctc   240
atttccaacc accaatccct tctgcaagaa attatgaatc aattgttaca agtttagtct   300
actcagaccc ggggactaca aattccatgg cacctggaca atatccatat ccagatcctt   360
actacagaag catatttgca ccgcctccac aaccgtatac cggggtacat ctacagttga   420
tgggagtgca gcaacaaggc gttcctttac catctgatgc agtcgaggaa cctgtttttg   480
ttaacgcaaa gcaataccac ggtatactaa ggcgcagaca atcaagagca agacttgagt   540
ctcagaataa agtcatcaag tcacgtaagc cgtatttgca tgaatctcgg catttgcatg   600
cgataagacg accaagagga tgtggcgggc ggtttctaaa tgccaagaag gaggatgagc   660
atcacgaaga cagtagtcat gaagaaaaat ccaaccttag cgctggtaaa tccgccatgg   720
ctgcttctag tggtacatct tgagaaggtc ctacaagtag ctttgttgta ttttggctct   780
gtttggtctc agatcatcta tgtcttttag tg                                 812

<210> SEQ ID NO 129
<211> LENGTH: 1138
<212> TYPE: DNA
<213> ORGANISM: Artificial sequence
<220> FEATURE:
<223> OTHER INFORMATION: synthetic sequence
<220> FEATURE:
<223> OTHER INFORMATION: P1608 overexpression construct (35S::G931)

<400> SEQUENCE: 129
tgacagacac atgtatcatc aatcttctct gttgaagcag agagagagag agctaattgt    60
tgcctctgag tcacatggat aagaaagttt catttactag ctctgtggca cattcaactc   120
caccatacct tagtacttcc atctcatggg gacttccaac caaatccaat ggtgtgactg   180
aatcactgag tttgaaggtg gtagatgcaa gaccagaacg tcttataaac acaaagaata   240
tcagtttcca ggaccaggat tcatcttcaa ctctgtcctc tgctcaatct tctaacgatg   300
ttacaagtag tggagatgat aaccccctcaa gacaaatctc attttagca cattcagatg   360 tttgtaaagg atttgaagaa actcaaagga agcgatttgc aattaaatca ggctcctcca   420
cggcaggaat cgctgatatt cactcttctc cttccaaggc taacttctca tttcactatg   480
ccgatccaca ttttggtggt ttaatgcctg cggcttacct accacaggca acaatatgga   540
atccccaaat gactcgagtt ccgctaccat tcgatctcat agagaatgag cctgtctttg   600
tcaatgcaaa gcaattccat gcaattatga ggaggaggca acagcgtgct aagctagagg   660
cgcaaaacaa actaatcaaa gcccgtaagc cgtatcttca tgaatctcga catgttcacg   720
```

```
ctcttaaacg acctagagga tctggtggaa gattcctaaa caccaaaaag cttcaagaat    780
ctacagatcc aaaacaagac atgccaatcc aacagcaaca cgcaacggga aacatgtcaa    840
gatttgtgct ttatcagttg cagaacagca atgactgtga ttgttcaacc acttctcgct    900
ctgacatcac atctgcttct gacagcgtta atctctttgg acactctgaa tttctgatat    960
cagattgccc atctcagaca aacccaacaa tgtatgttca tggtcaatca aatgacatgc   1020
atggaggtag gaacacacac catttctctg tccatatctg agccggtgga atctggtaat   1080
gtgtacgttc ctacaaaaaa agggaagtca tccttggctg ctacttcgct tattagct    1138

<210> SEQ ID NO 130
<211> LENGTH: 956
<212> TYPE: DNA
<213> ORGANISM: Artificial sequence
<220> FEATURE:
<223> OTHER INFORMATION: synthetic sequence
<220> FEATURE:
<223> OTHER INFORMATION: P26608 overexpression construct (35S::G3920)

<400> SEQUENCE: 130
agttggtgct aagatgccag ggaaacctga cactgatgat tggcgtgtag agcgtgggga     60
gcagattcag tttcagtctt ccatttactc tcatcatcag ccttggtggc gcggagtggg    120
ggaaaatgcc tccaaatcat cttcagatga tcagttaaat ggttcaatcg tgaatggtat    180
cacgcggtct gagaccaatg ataagtcagg cggaggtgtt gccaagaat accaaaacat     240 caaacatgcc atgttgtcaa ccccatttac catggagaaa catcttgctc caaatcccca    300
gatggaactt gttggtcatt cagttgtttt aacatctcct tattcagatg cacagtatgg    360
tcaaatcttg actacttacg ggcaacaagt tatgataaat cctcagttgt atggaatgca    420
tcatgctaga atgcctttgc cacttgaaat ggaagaggag cctgtttatg tcaatgcgaa    480
gcagtatcat ggtatttga ggcgaagaca gtcacgtgct aaggctgaga ttgaaaagaa    540
agtaatcaaa acaggaagc catacctcca tgaatcccgt caccttcatg caatgagaag    600
ggcaagaggc aacggtggtc gctttctcaa cacaaagaag cttgaaaata caattctaa    660 ttccacttca gacaaaggca acaatactcg tgcaaacgcc tcaacaaact cgcctaacac    720
tcaacttttg ttcaccaaca atttgaatct aggctcatca aatgtttcac aagccacagt    780
tcagcacatg cacacagagc agagtttcac tataggttac cataatgaa atggtcttac    840 agcactatac cgttcacaag caaatgggaa aaggaggga aactgctttg gtaaagagag    900
ggaccctaat ggggattca aataacactt ccctcagcca tacagcaaga gttagg       956

<210> SEQ ID NO 131
<211> LENGTH: 1486
<212> TYPE: DNA
<213> ORGANISM: Artificial sequence
<220> FEATURE:
<223> OTHER INFORMATION: synthetic sequence
<220> FEATURE:
<223> OTHER INFORMATION: P143 overexpression construct (35S::G928)

<400> SEQUENCE: 131
cccaggaaag gtaaaagaga cggagacgaa ccaaaacaag gaagaaagaa gaagatctta     60
catacgaaga tcactctctg attcactctg agagacaaac tggtttactt tggttctgtt    120
tgacaaaagg agacatgcaa aaataaatct ctatcccttg ttttcttct tcgcttcatc    180 gattactcaa agaggttgtt ggttgtgaga ataattagct tgttaaggaa gacgttatga    240
```

| | |
|---|---|
| tgcatcagat gttgaataag aaagattcag ctactcattc cactttgcca taccttaata | 300 |
| ctagcatctc ttggggagtg gttccaactg attccgttgc taatcgtcgc ggtcctgctg | 360 |
| aatcactaag cttgaaggtt gattcaagac ctgggcatat acaaactaca aagcaaatca | 420 |
| gttttcagga ccaagattca tcttcaacac agtccactgg tcaatcttat actgaagttg | 480 |
| ctagtagtgg tgatgataat ccttccagac aaatctcctt ttcggctaaa tcaggatctg | 540 |
| aaataactca acggaagggg tttgcaagta atcctaaaca aggctcgatg actggatttc | 600 |
| cgaatattca ctttgctcct gcacaggcta atttctcatt tcactatgct gatccacatt | 660 |
| atggtggttt attagctgca acttacctac cacaggcacc aacatgcaat cctcaaatgg | 720 |
| tgagtatgat tcctggtcgt gttcctttac cagcagagct cacagaaact gatccagtct | 780 |
| ttgtcaatgc gaagcaatac cacgcaatta tgaggaggag acagcaacgt gctaagcttg | 840 |
| aggctcaaaa caaactaatc agagcccgta agccctatct tcatgagtct cgacatgttc | 900 |
| atgctcttaa aaggccaaga ggatctggtg gaagattcct aaacaccaaa aaacttcttc | 960 |
| aagaatccga acaggctgct gctagagaac aagaacagga caagttaggc caacaggtaa | 1020 |
| acagaaagac caacatgtct agattcgaag ctcatatgct gcagaacaac aaagaccgca | 1080 |
| gctcaaccac ttctggctca gacatcacct ctgtttccga cggtgctgat atctttggac | 1140 |
| acactgaatt ccagttttca ggtttcccaa ctccgataaa ccgagccatg cttgttcatg | 1200 |
| gtcagtctaa tgacatgcat ggaggtggag acatgccacca tttctctgtc catatctgag | 1260 |
| acagtggatc ttggtgctgt gttcatgttc ccaccaagaa ggggaagtca tccttggcta | 1320 |
| ctactagttc tttcgcttgt tgtaacttca gtgtttttat ttcatattat gtctgtgtta | 1380 |
| gacatcacaa gaacgaccaa gatcttcact ttgaaacact ctattacctt ttcatcttct | 1440 |
| gttaccatgg atctcttgtc taaactagtg atatgattct tctgat | 1486 |

<210> SEQ ID NO 132
<211> LENGTH: 1007
<212> TYPE: DNA
<213> ORGANISM: Artificial sequence
<220> FEATURE:
<223> OTHER INFORMATION: synthetic sequence
<220> FEATURE:
<223> OTHER INFORMATION: P966 overexpression construct (35S::G1782)

<400> SEQUENCE: 132

| | |
|---|---|
| gatttgtgac tggacttgtt ggtttggaca tttagtttat tgaagtaaag atttgaagac | 60 |
| aatgcaagtg tttcaaagga aagaagattc atcttgggga aactcaatgc ctacaacaaa | 120 |
| ttcaaatatt caaggatctg aatctttcag cttgactaag gatatgataa tgtctacaac | 180 |
| acaattaccc gcgatgaaac attcgggttt gcagctgcaa aatcaagatt caacctcatc | 240 |
| acaatctact gaagaagaat caggcggcgg tgaagttgca agctttggag aatataagcg | 300 |
| ttatggatgc agcattgtta ataacaatct ctcaggttac atcgaaaact tgggaaagcc | 360 |
| tattgaaaat tatactaagt caattactac ctcgtcgatg gtgtctcaag actctgtgtt | 420 |
| tcctgctcct acttctggtc aaatatcttg gtctcttcaa tgtgctgaaa cgtcacattt | 480 |
| caatggtttc ttggctcctg aatatgcatc aacaccaacg gcgctgccac atttagagat | 540 |
| gatgggtttg gtttcttcaa gagtgccatt gcctcatcac attcaagaga atgaaccaat | 600 |
| atttgtcaat gcgaaacagt atcatgcgat tctccgtcgc aggaagcacc gtgctaaact | 660 |
| cgaagctcag aacaaactca tcaaatgccg taaaccgtac cttcatgagt ctcgccatct | 720 |
| tcatgctttta aagagagcta gaggctccgg tggacgtttc ctcaatacaa agaagcttca | 780 |

```
agaatcatca aactcactgt gttcttctca aatggcaaat ggacaaaatt tctctatgag    840
ccctcacggt ggtggaagcg gaatcgggtc tagttcgatc tcaccgagct ccaattcaaa    900
ctgtatcaac atgttccaaa acccgcagtt cagattctca ggttatccgt caacacacca    960
tgcctcagct ctcatgtcag ggacttgagg cacatgagaa gaccttg                 1007

<210> SEQ ID NO 133
<211> LENGTH: 1671
<212> TYPE: DNA
<213> ORGANISM: Artificial sequence
<220> FEATURE:
<223> OTHER INFORMATION: synthetic sequence
<220> FEATURE:
<223> OTHER INFORMATION: P26121 overexpression construct (35S::G1363::
      (9A)YFP)

<400> SEQUENCE: 133
atgcaagagt tccatagtag caaagattca ttgccttgtc ctgcaacttc ttgggataac     60
tctgtcttca ccaactcaaa tgtccaagga tcatcatcct tgaccgataa caacacttta    120
agcttgacaa tggagatgaa acaaactggt tttcaaatgc agcactatga ttcctcctct    180
actcaatcca ctggaggaga atcatatagt gaagttgcta gcttaagtga acctactaat    240
cgttatggcc acaacattgt tgtcactcat ctctcaggtt acaaagaaaa cccggaaaat    300
cctattggaa gtcattcgat atcaaggtgt ctcaagatt cagtggttct tcctattgag     360
gcggcttctt ggcctttaca cggcaatgta acgccacatt tcaatggttt cttgtctttt    420
ccttatgcat cacaacacac ggtgcagcat cctcaaatca gagggttggt tccgtctaga    480
atgcctttgc ctcacaacat tccagagaac gaaccaattt tcgtcaatgc aaaacagtac    540
caagccattc tccgccgcag agagcgccgt gcaaagcttg aagctcagaa caagctcatc    600
aaagtccgca aaccatatct tcacgagtcg cggcacctcc atgcactaaa gagagttaga    660
ggctctggtg gacgtttcct caacacaaag aagcatcaag aatcaaattc ctcactatct    720
cctccattct tgattccacc tcatgtcttc aagaactctc aggaaagtt ccggcaaatg     780 gacatttcaa ggggtggggt tgtgtctagt gtctcgacaa catcttgctc ggacataacc    840
gggaacaaca acgacatgtt ccagcaaaac ccacaattca ggttctcagg ttatccatca    900
aaccaccatg tctcagtcct catggcggcc gctgccgctg cggcagcggc catggtgagc    960
aagggcgagg agctgttcac cggggtggtg cccatcctgg tcgagctgga cggcgacgta   1020
aacgccacca gttcagcgt gtccggcgag ggcgagggcg atgccaccta cggcaagctg    1080
accctgaagt tcatctgcac caccggcaag ctgcccgtgc cctggcccac cctcgtgacc   1140
accttcggct acggcctgca gtgcttcgcc cgctacccg accacatgaa gcagcacgac    1200
ttcttcaagt ccgccatgcc cgaaggctac gtccaggagc gcaccatctt cttcaaggac   1260
gacggcaact acaagacccg cgccgaggtg aagttcgagg gcgacaccct ggataaccga   1320
atcgagctga aggcatcga cttcaaggag gacggcaaca tcctggggca caagctggag    1380
tacaactaca acagccacaa cgtctatatc atggccgaca gcagaagaa cggcatcaag    1440 gtgaacttca gatccgcca caacatcgag gacggcagct gcagctcgc cgaccactac    1500 cagcagaaca cccccatcgg cgacggcccc gtggtgctgc cgacaaccca ctacctgagc   1560
taccagtccg ccctgagcaa agaccccaac gagaagcgcg atcacatggt cctgctggag   1620
ttcgtgaccg ccgccgggat cactctcggc atggacgagc tgtacaagta a            1671
```

<210> SEQ ID NO 134
<211> LENGTH: 824
<212> TYPE: DNA
<213> ORGANISM: Artificial sequence
<220> FEATURE:
<223> OTHER INFORMATION: synthetic sequence
<220> FEATURE:
<223> OTHER INFORMATION: P26602 overexpression construct (35S::G3924)

<400> SEQUENCE: 134

```
gcattccgag gtgagcgagc atggagtcga ggccgggggg aaccaacctc gtggagccga      60
gggggcaggg cgcgctgccg tccggcatac cgatccagca gccgtggtgg acgacctccg     120
ccggggtcgg ggcggtgtcg cccgccgtcg tggcgccggg gagcggtgcg gggatcagcc     180
tgtcgggcag ggatggcggc ggcgacgacg cggcagagga gagcagcgat gactcacgaa     240
gatcagggga gaccaaagat ggaagcactg atcaagaaaa gcatcatgca acatcgcaga     300
tgactgcttt ggcatcagac tatttaacac cattttcaca gctggaacta aaccaaccaa     360
ttgcttcggc agcataccag taccctgact cttactatat gggcatggtt ggtccctatg     420
gacctcaagc tatgtccgca cagactcatt ccagctacc  tggattaact cactctcgta     480
tgccgttgcc tcttgaaata tctgaggagc ctgtttatgt aaatgctaag caatatcatg     540
gaattttaag acggaggcag tcacgtgcga aggctgaact tgagaaaaaa gttgttaaat     600
caagaaagcc ctatcttcat gagtctcgtc atcaacatgc tatgcgaagg gcaagaggaa     660
cgggtggacg cttcctgaac acaaagaaaa atgaagatgg tgctcccagt gagaaagccg     720
aaccaaacaa aggagagcag aactccgggt atcgccggat ccctcctgac ttacagctcc     780
tacagaagga aacatgaagt agcggctcga aacctagaac agtg                     824
```

<210> SEQ ID NO 135
<211> LENGTH: 1000
<212> TYPE: DNA
<213> ORGANISM: Artificial sequence
<220> FEATURE:
<223> OTHER INFORMATION: synthetic sequence
<220> FEATURE:
<223> OTHER INFORMATION: P26600 overexpression construct (35S::G3926)

<400> SEQUENCE: 135

```
gtggatcttg agtaatgcct tctaataatg ataatgctgt tgcaagaaat ggagaatcat      60
cctgtccaat gcatggccaa gaccaactat gattttcttg ccaggaataa ctatccaatg     120
aaacagttag ttcagaggaa ctctgatggt gactcgtcac caacaaagtc tggggagtct     180
caccaagaag catctgcagt aagtgacagc agtctcaacg acaacacac  ctcaccacaa     240
tcagtgtttg tccoctcaga tattaacaac aatgatagtt gtggggagcg ggaccatggc     300
actaagtcgg tattgtcttt ggggaacaca gaagctgcct ttcctccttc aaagttcgat     360
tacaaccagc cttttgcatg tgtttcttat ccatatggta ctgatccata ttatggtgga     420
gtattaacag gatacacttc acatgcattt gttcatcctc aaattactgg tgctgcaaac     480
tctaggatgc cattgcctgt tgatccttct gtagaagagc ccatatttgt caatgcaaag     540
caatacaatg cgatccttag aagaaggcaa acgcgtgcaa aattggaggc ccaaaataag     600
gcggtgaaag gtcggaagcc ttacctccat gaatctcgac atcatcatgc tatgaagcga     660
gcccgtggat caggtggtcg gttccttacc aaaaaggagc tgctggaaca gcagcagcag     720
cagcagcagc agaagccacc accggcatca gctcagtctc caacaggtag agccagaacg     780
agcggcggtg ccgttgtcct tggcaagaac ctgtgcccag agaacagcac atcctgctcg     840
```

```
ccatcgacac cgacaggctc cgagatctcc agcatctcat ttgggggcgg catgctggct    900
caccaagagc acatcagctt cgcatccgct gatcgccacc ccacaatgaa ccagaaccac    960
cgtgtccccg tcatgaggtg aaaacctcgg gatcgcggga                         1000

<210> SEQ ID NO 136
<211> LENGTH: 756
<212> TYPE: DNA
<213> ORGANISM: Artificial sequence
<220> FEATURE:
<223> OTHER INFORMATION: synthetic sequence
<220> FEATURE:
<223> OTHER INFORMATION: P26597 overexpression construct (35S::G3925)

<400> SEQUENCE: 136
ggaggaggtt tgccggagag gggacatgct ccctcctcat ctcacagaaa atggcacagt     60
aatgattcag tttggtcata aaatgcctga ctacgagtca tcagctaccc aatcaactag    120
tggatctcct cgtgaagtgt ctggaatgag cgaaggaagc ctcaatgagc agaatgatca    180
atctggtaat cttgatggtt acacgaagag tgatgaaggt aagatgatgt cagctttatc    240
tctgggcaaa tcagaaactg tgtatgcaca ttcggaacct gaccgtagcc aaccctttgg    300
catatcatat ccatatgctg attcgttcta tggtggtgct gtagcgactt atggcacaca    360
tgctattatg catccccaga ttgtgggcgt gatgtcatcc tcccgagtcc cgctaccaat    420
agaaccagcc accgaagagc ctatttatgt aaatgcaaag caataccatg cgattctccg    480
aaggagacag ctccgtgcaa agttagaggc tgaaaacaag ctggtgaaaa accgcaagcc    540
gtacctccat gaatcccggc atcaacacgc gatgaagaga gctcggggaa cagggggag    600 attcctcaac acaaagcagc agcctgaagc ttcagatggt ggcaccccaa ggctcgtctc    660
tgcaaacggc gttgtgttct caaagcacga gcacagcttg tcgtccagtg atctccatca    720
tcgtcgtgcg aaagagggcg cttgagatcc tcgccg                              756

<210> SEQ ID NO 137
<211> LENGTH: 1091
<212> TYPE: DNA
<213> ORGANISM: Artificial sequence
<220> FEATURE:
<223> OTHER INFORMATION: synthetic sequence
<220> FEATURE:
<223> OTHER INFORMATION: P26593 overexpression construct (35S::G4264)

<400> SEQUENCE: 137
agatcatctg atttctcaga agcaaaatgt tgtttggagc tcagtgacac catcttgtaa     60
tgcctgtgat tttacgggaa atggaggatc attctgtcca tcccatgtct aagtctaacc    120
atggctcctt gtcaggaaat ggttatgaga tgaaacattc aggccataaa gtttgcgata    180
gggattcatc atcggagtct gatcggtctc accaagaagc atcagcagca agtgaaagca    240
gtccaaatga acacacatca actcaatcag acaatgatga agatcatggg aaagataatc    300
aggacacaat gaagccagta ttgtccttgg ggaaggaagg ctctgccttt ttggccccaa    360
aattacatta cagcccatct tttgcttgta ttccttatac ttctgatgct tattatagtg    420
cggttggggt cttgacagga tatcctccac atgccattgt ccatcccag caaaatgata    480 caacgaacac tccgggtatg ttacctgtgg aacctgcaga agaaccaata tatgttaatg    540
caaaacaata ccatgcaatc cttaggagga ggcaaacacg tgctaaattg gaggcccaga    600
acaagatggt gaaaaatcgg aagccatatc ttcatgagtc ccgacatcgt catgccatga    660
aacgggctcg tggatcagga ggacggttcc tcaacacaaa gcagctccag gagcagaacc    720
```

```
agcagtatca ggcatcgagt ggttcattgt gctcaaagat cattgccaac agcataatct        780
cccaaagtgg ccccacctgc acgccctctt ctggcactgc aggtgcttca acagccggcc        840
aggaccgcag ctgcttgccc tcagttggct tccgccccac gacaaacttc agtgaccaag        900
gtcgaggagc cttgaagctg gccgtgatcg gcatgcagca gcgtgtttcc accataaggt        960
gaagagaagt gggcacaaca ccattcccag gcacactgcc tgtggcaact catccttggc       1020
tcttggaact ttgaatatgc aatcgacatg tagcttgagt tcctcagaat aaccaaaccg       1080
tgaagaatat g                                                            1091

<210> SEQ ID NO 138
<211> LENGTH: 1149
<212> TYPE: DNA
<213> ORGANISM: Artificial sequence
<220> FEATURE:
<223> OTHER INFORMATION: synthetic sequence
<220> FEATURE:
<223> OTHER INFORMATION: P15494 overexpression construct (35S::G2632)

<400> SEQUENCE: 138
agatcgtttc atcgtccaag cggaagaagc gtctccttca atcaccgtgg acacctccga         60
gactgtctcc gattgaatgg gaattgaaga catgcattca aaatctgaca gtggtgggaa        120
caaggttgat tcagaggttc atggtacagt atcgtcgtcg ataaatagtt taaacccttg        180
gcatcgtgct gctgctgctt gcaatgcaaa ttctagtgtg gaagctggag ataaatcttc        240
taagtcaata gcattagcat tggaatcaaa cggttccaaa tcaccatcca atagagataa        300
tactgttaac aaggaatcac aagtcacaac gtctccacaa tcagctggag attatagtga        360
taaaaaccaa gaatctctgc atcatggcat cacacaacct cctcctcacc ctcaacttgt        420
tggccacaca gttgtaactt cccaatatag atatattgtt cttatcattt cctttgggaa        480
aattttagct atggttgctt acaatttagt ttttttcccgg ttatgaatca tgcagggatg       540
ggcatcctca aatccatacc aggatccata ttatgcagga gtgatgggag cctatggaca        600
tcatcccctg gggtttgttc catatggtgg gatgcctcat tcaagaatgc cactgccgcc        660
tgagatggca caagaaccag ttttcgtgaa tgctaaacag taccaggcga ttctgaggcg        720
aaggcaggca cgcgccaagg cagagctaga gaagaagcta ataaaatcca gaaagcctta        780
tctacatgaa tctcggcatc aacatgctat gaggaggcca aggggtactg gaggacggtt        840
tgcaaagaaa accaacaccg aagcttcaaa gcgtaaagct gaagaaaaga gcaatggtca        900
tgttactcag tccccgtcat catctaattc tgatcaaggt gaagcttgga atggtgacta        960
tagaacacct cagggagatg agatgcagag ctcagcttat aagagaaggg aagaaggaga       1020
gtgttcaggg cagcaatgga acagcctttc ctcaaaccat ccttctcaag ctcgtctagc       1080
cattaaatga cctcacaagg cggcaattca ttcttggctt tctctttgtt ggcttattcg       1140
gtagcagcc                                                              1149

<210> SEQ ID NO 139
<211> LENGTH: 873
<212> TYPE: DNA
<213> ORGANISM: Artificial sequence
<220> FEATURE:
<223> OTHER INFORMATION: synthetic sequence
<220> FEATURE:
<223> OTHER INFORMATION: P714 overexpression construct (35S::G1334)

<400> SEQUENCE: 139
```

```
ccattggact tttggaacat aagctatgca aactgaggag cttttgtcgc caccacagac      60
tccttggtgg aatgcttttg gatctcagcc gttgactaca gagagccttt ccggcgaagc     120
ttctgattca ttcaccggag ttaaggcagt tactacggag gcagaacaag gtgtggtgga     180
taaacaaact tctacaactc tcttcacttt ctcacctggt ggtgaaaaga gttcaagaga     240
tgtgccaaag cctcatgttg ctttcgcgat gcaatcagct tgcttcgagt ttggatttgc     300
tcagccaatg atgtacacaa agcatcctca tgttgaacaa tactatggag ttgtttcagc     360
atacggatct cagaggtctt cgggccgagt aatgattcca ctgaagatgg agacagaaga     420
agatggtacc atctatgtga actcaaagca gtaccatgga attatcaggc gacgccagtc     480
ccgagcaaag gctgaaaaac tgagtagatg ccgtaagcca tatatgcatc actcacgcca     540
tctccatgct atgcgccgtc ctagaggatc tggcgggcgt ttcttgaaca ccaagacagc     600
tgatgcggct aagcagtcta agccgagtaa ttctcagagt tctgaagtct ttcatccgga     660
aaatgagacc ataaactcat cgagggaagc aaatgagtca atctctcgg attctgcagt      720 tacaagtatg gattactttc taagttcgtc ggcttattct cctggtggca tggtcatgcc     780
tatcaagtgg aatgcagcag caatggatat tggctgctgc aaacttaata tatgatcagc     840 agataggga caagacatga ttggtcacca gtc                                  873
```

<210> SEQ ID NO 140
<211> LENGTH: 1394
<212> TYPE: DNA
<213> ORGANISM: Artificial sequence
<220> FEATURE:
<223> OTHER INFORMATION: synthetic sequence
<220> FEATURE:
<223> OTHER INFORMATION: P15491 overexpression construct (35S::G926)

<400> SEQUENCE: 140

```
tgtttgatct ttgtccagag aactccaaga tagaccaaaa aggttcaacc tcaaaacaaa      60
caacacaaaa acagccaaat agctagagac caagatgaga tcaagcagcc aaaattctga     120
aaactccaag acttgtctat ctaacaacat caaagcaacc accaagaatg aagaagataa     180
agatgaagag gatgatgaag aaggcgaaga ggatgaagaa gagagatctg gagatcagag     240
cccatctagc aatagctatg aggaagagag tgggagtcac caccatgatc agaacaagaa     300
gaatggagga tccgtgaggc cgtacaaccg ctcaaagact ccgaggctgc gatggacgcc     360
ggagctccat atttgctttc ttcaagctgt ggagagattg ggtggcccag atagagcaac     420
accgaagctt gttctccaat tgatgaacgt caaggggcta agtattgccc atgttaagag     480
tcatcttcag atgtacagaa gcaagaagac cgatgagcct aatgaaggag atcaaggatt     540
ttcgtttgaa cacggagctg gttacactta caacccttagc caacttccaa tgctacaaag     600
ttttgatcaa aggccttctt ctagtttagg atatggtggt ggttcgtgga ctgaccacag     660
acgacagatc taccgtagcc cttggagagg attaacgaca cgagaaaata caagaacaag     720
acaaacaatg tttagctcac agcctggtga gagatatcac ggagttagca atagtattct     780
taacgataag aacaaaacta tttcatttcg aatcaattct catgaagggg ttcatgataa     840
caatggagta gctggagctg ttccaagaat tcatagaagt tttcttgaag gtatgaaaac     900
gtttaacaaa tcatggggac agagcctctc ttccaatctt aagtcctcca ccgcaacaat     960
accacaagat catattgcta caacgctaaa ttcttatcaa tgggagaatg ctggagtggc    1020
agaaggatca gagaatgttt tgaagaggaa gaggttatta ttttctgatg actgcaataa    1080
gtcagaccaa gatttggatc taagcttgtc ccttaaggta cctcggacac acgacaatct    1140
```

```
tggagaatgc ttgttagaag atgaagtaaa agaacatgat gatcatcaag atatcaagag    1200
tttgtctctt tcgttatcat cttcaggttc atcaaaactc gaccgaacca ttaggaaaga    1260
agatcaaact gatcacaaaa agagaaagat ttcggtcttg gcaagtcccc ttgatctcac    1320
tctgtgaata tgtataacaa cttatatacg tatattctaa gtgagatctt gtggtacttg    1380
ttgatggaag acgg                                                      1394
```

<210> SEQ ID NO 141
<211> LENGTH: 1560
<212> TYPE: DNA
<213> ORGANISM: Artificial sequence
<220> FEATURE:
<223> OTHER INFORMATION: synthetic sequence
<220> FEATURE:
<223> OTHER INFORMATION: P26217 overexpression construct (35S::G926::
      (9A)YFP)

<400> SEQUENCE: 141

```
atgcaatcaa aaccgggaag agaaaacgaa gaggaagtca ataatcacca tgctgttcag     60
cagccgatga tgtatgcaga gccctggtgg aaaaacaact cctttggtgt tgtacctcaa    120
gcgagacctt ctggaattcc atcaaattcc tcttctttgg attgccccaa tggttccgag    180
tcaaacgatg ttcattcagc atctgaagac ggtgcgttga atggtgaaaa cgatggcact    240
tggaaggatt cacaagctgc aacttcctct cgttcagata tcacggaat ggaaggaaat     300 gacccagcgc tctctatccg taacatgcat gatcagccac ttgtacaacc accagagctt    360
gttggacact atatcgcttg tgtcccaaac ccatatcagg atccatatta tggggattg     420 atgggagcat atggtcatca gcaattgggt tttcgtccat atcttggaat gcctcgtgaa    480
agaacagctc tgccacttga catggcacaa gagcccgttt atgtgaatgc aaagcagtac    540
gagggaattc taaggcgaag aaaagcacgt gccaaggcag agctagagag gaaagtcatc    600
cgggacagaa agccatatct tcacgagtca agacacaagc atgcaatgag aagggcacga    660
gcgagtggag gccggtttgc gaagaaaagt gaggtagaag cgggagagga tgcaggaggg    720
agagacagag aaagggttc agcaaccaac tcatcaggct ctgaacaagt tgagacagac    780
tctaatgaga ccctgaattc ttctggtgca ccagcggccg ctgccgctgc ggcagcggcc    840
atggtgagca agggcgagga gctgttcacc ggggtggtgc ccatcctggt cgagctggac    900
ggcgacgtaa acggccacaa gttcagcgtg tccggcgagg gcgagggcga tgccacctac    960
ggcaagctga ccctgaagtt catctgcacc accggcaagc tgcccgtgcc ctggcccacc   1020
ctcgtgacca cctctcggcta cggcctgcag tgcttcgccc gctaccccga ccacatgaag   1080
cagcacgact tcttcaagtc cgccatgccc gaaggctacg tccaggagcg caccatcttc   1140
ttcaaggacg acggcaacta caagacccgc gccgaggtga agttcgaggg cgacaccctg   1200
gataaccgaa tcgagctgaa gggcatcgac ttcaaggagg acggcaacat cctgggcac    1260 aagctggagt acaactacaa cagccacaac gtctatatca tggccgacaa gcagaagaac   1320
ggcatcaagg tgaacttcaa gatccgccac aacatcgagg acggcagcgt gcagctcgcc   1380
gaccactacc agcagaacac ccccatcggc gacggccccg tgctgctgcc cgacaaccac   1440
tacctgagct accagtccgc cctgagcaaa gaccccaacg agaagcgcga tcacatggtc   1500
ctgctggagt tcgtgaccgc cgccgggatc actctcggca tggacgagct gtacaagtaa   1560
```

<210> SEQ ID NO 142
<211> LENGTH: 1304

```
<212> TYPE: DNA
<213> ORGANISM: Artificial sequence
<220> FEATURE:
<223> OTHER INFORMATION: synthetic sequence
<220> FEATURE:
<223> OTHER INFORMATION: P142 overexpression construct (35S::G927)

<400> SEQUENCE: 142
ggaatctgaa gctcttctct actctctact ctatcactcc atctgtgaac atatctttct      60
tattcttcta ggcactatct attttcact ttttgtaatt ggaatttgga gatggctatg     120
caaactgtga gagaaggtct cttctctgct ccacagactt cttggtggac tgcttttgga     180
tctcagccgt tggctccgga gagtctcgcc ggcgattctg actcattcgc cggagttaag     240
gtcggatctg tcggagagac aagacaacgt gtggataaac agagcaactc tgcaacgcac     300
ttagctttct cacttggtga tgtaaagagt ccaagacttg tgccaaagcc tcatggagct     360
actttctcaa tgcaatcacc ttgcttggaa cttggatttt ctcagccacc gatctataca     420
aagtatccct atggagaaca acaatactat ggagttgttt cagcctatgg atctcagagc     480
agggtaatgc ttcctctaaa catggaaacg gaagatagta ccatctatgt gaactcaaag     540
cataccatg gaatcataag gagacgccaa tcccgcgcaa aggctgctgc tgttcttgat     600
cagaagaaat tgagtagtag atgccgcaag ccatatatgc atcattcgcg ccatctccat     660
gcattgcggc gtcctagagg atccggtggg agattcttga acactaaaag tcagaacttg     720
gaaaatagcg gaaccaatgc aaagaaaggt gatggaagta tgcagattca gtctcagcct     780
aagcctcagc aaagtaactc tcagaattct gaagttgttc atccggaaaa cgggaccatg     840
aacttatcga acggattaaa tgtgtcggga tcagaagtta ctagcatgaa ctacttccta     900
agttctcccg ttcattctct tggtggcatg gtaatgccta gcaagtggat agcagcagca     960
gcagcaatgg ataatggctg ctgcaatttc aaaacctgat cctttaccgt tcacagtca    1020
aacggagaga gataaagaac tcttgccttg gtataaagga tttcctttt tgccaatccg    1080
ctttggctgt gaacaggcaa atcatctttg gctcattctc tattaaggta acttcgccgt    1140
gaggtgaaaa aagctttgat atatttatct tcagtgtaaa agtagttaaa actggtgaag    1200
aacaatgatg tgtttggtca ctaaacccac ttgttccaac tagtagtgtg tgttttaaga    1260
aaactctgtt atctgatttt gtagctctct ctggctttgt gtgt                     1304

<210> SEQ ID NO 143
<211> LENGTH: 627
<212> TYPE: DNA
<213> ORGANISM: Artificial sequence
<220> FEATURE:
<223> OTHER INFORMATION: synthetic sequence
<220> FEATURE:
<223> OTHER INFORMATION: P26591 overexpression construct (35S::G3911)

<400> SEQUENCE: 143
acaaccctag ctgccccga atccatggat cctaacaaat ccagcacccc gccgccgcct       60
ccagtcatgg gtgccccgt tgcctaccct ccgcctgcgt accctcccgg tgtggccgcc      120
ggcgccggcg cctacccgcc gcagctctac gcaccgccgg ctgctgccgc ggcccagcag      180
gcggcggccg cgcagcagca gcagctgcag atattctggg cggagcagta ccgcgagatc      240
gaggccacta ccgacttcaa gaatcacaac ctcccgctcg cccgcatcaa gaagatcatg      300
aaagccgacg aggacgtccg catgatcgcc gccgaggctc ccgtggtgtt cgcccgggcc      360
tgcgagatgt tcatcctcga gctcacccat cgcggctggg cgcacgccga agagaacaag      420
```

```
cgccgcacgc tccagaaatc cgacattgcc gctgccatcg cccgcaccga ggtattcgac    480
ttccttgtgg acatcgttcc gcgcgacgac ggtaaagacg ctgatgcggc ggccgccgca    540
gctgccgcgg ctgccgggat cccgcgcccc gccgccggag taccagccac cgaccctctc    600
gcctactact acgtgcctca gcagtaa                                        627

<210> SEQ ID NO 144
<211> LENGTH: 649
<212> TYPE: DNA
<213> ORGANISM: Artificial sequence
<220> FEATURE:
<223> OTHER INFORMATION: synthetic sequence
<220> FEATURE:
<223> OTHER INFORMATION: P26603 overexpression construct (35S::G3546)

<400> SEQUENCE: 144 gagaaacccct agcaatggag cccaaatcca ccaccctcc tccgcctcct ccgcccccg     60 tgctgggcgc cccgtccct taccgccgg cgggagccta ccccccaccc gtcgggccct    120
acgcccacgc gccgccgctc tacgcccgc ctccccccgc cgccgccgcc gcctccgccg    180
ccgccaccgc cgcctcgcag caggccgccg ccgcgcagct ccagaacttc tgggcggagc    240
agtaccgcga gatcgagcac accaccgact tcaagaacca caacctcccc ctcgcccgca    300
tcaagaagat catgaaggcc gacgaggacg tccgcatgat cgccgccgag gcccccgtcg    360
tgttcgccag ggcgtgcgag atgttcatcc tcgagctcac ccaccgcggc tgggcgcacg    420
ccgaggagaa caagcgccgc acgctccaga agtccgacat cgccgccgcc atcgcccgca    480
ccgaggtctt cgacttcctc gtcgacatcg tgccccgcga cgaggccaag gacgccgagg    540
ccgccgccgc cgttgccgcc gggatccccc acccgccgc cggtttgccc gccaccgacc    600
ccatggccta ctactatgtc cagccgcagt aacatttcc taccgtata                649

<210> SEQ ID NO 145
<211> LENGTH: 638
<212> TYPE: DNA
<213> ORGANISM: Artificial sequence
<220> FEATURE:
<223> OTHER INFORMATION: synthetic sequence
<220> FEATURE:
<223> OTHER INFORMATION: P26596 overexpression construct (35S::G3909)

<400> SEQUENCE: 145
tgaccgccgt aacaccctag gcaatggagc ccaaatccac cacccctccc ccgcccccg     60 tgatgggcgc gcccatcgcg tatcctcccc gccccggcgc cgcgtacccc gccgggccgt    120
acgtgcacgc gccggcggcc gcgctctacc ctcctcctcc cctgccgccg gcgccccct    180 cctcgcagca gggcgccgcg gcggcgcacc agcagcagct attctgggcg gagcaatacc    240
gcgagatcga ggccaccacc gacttcaaga accacaacct gccgctcgcc cgcatcaaga    300
agatcatgaa ggccgacgag gacgtgcgca tgatcgccgc cgaggcgccc gtcgtcttct    360
cccgcgcctg cgagatgttc atcctcgagc tcacccaccg cggctgggca cacgccgagg    420
agaacaagcg ccgcacgctg cagaagtccg acatcgccgc cgcgtcgcg cgcaccgagg    480 tcttcgactt cctcgtcgac atcgtgccgc gggacgaggc caaggacgcc gactccgccg    540
ccatgggagc agccgggatc ccgcaccccg ccgccggcct gccgccgcc gatcccatgg    600 gctactacta cgtccagccg ccgcagtaac gaatttgc                           638

<210> SEQ ID NO 146
<211> LENGTH: 778
```

<212> TYPE: DNA
<213> ORGANIsM: Artificial sequence
<220> FEATURE:
<223> OTHER INFORMATION: synthetic sequence
<220> FEATURE:
<223> OTHER INFORMATION: P26595 overexpression construct (35S::G3552)

<400> SEQUENCE: 146

```
gagtggatat ggaaccatcc cctcagccta tgggtgtcgc tgccggtggg tcacaagtgt      60
atcctgcctc tgcctatccg cctgcagcaa cagtagctcc tgcttctgtt gtatctgctg     120
gtttacagtc agggcagcca ttcccagcca atcctggtca tatgagtgct cagcaccaga     180
ttgtctacca acaagctcaa caattccacc aacagctcca gcagcaacaa caacagcagc     240
ttcagcagtt ctgggttgaa cgcatgactg aaattgaggc gacgactgat ttcaagaacc     300
acaacttgcc acttgcgagg ataaagaaga tcatgaaggc cgatgaagat gttcgcatga     360
tctcagctga agctcctgta gtctttgcaa aagcttgtga gatattcata ctggagctga     420
cacttaggtc gtggatgcac actgaggaga acaagcgccg caccttgcaa aagaatgaca     480
ttgcagcagc gatcactagg actgacattt atgacttctt ggtcgacatt gttcccaggg     540
atgagatgaa ggaggacgga attgggcttc ctagggctgg tctgccaccc atgggagccc     600
cagctgatgc atatccatac tactacatgc cacagcagca ggtgcctggt tctggaatgg     660
tttatggtgc ccagcaaggg cacccagtga cttatttgtg gcaggagcct cagcaacagc     720
aggagcaagc tcctgaagag cagcaatctg catgaaagtg gctgagaata ttgctcag      778
```

<210> SEQ ID NO 147
<211> LENGTH: 553
<212> TYPE: DNA
<213> ORGANISM: Artificial sequence
<220> FEATURE:
<223> OTHER INFORMATION: synthetic sequence
<220> FEATURE:
<223> OTHER INFORMATION: P48 overexpression construct (35S::G483)

<400> SEQUENCE: 147

```
tgggctaacc aaatgcaaga gatcgagcat accactgatt tcaagaacca caccttccc      60
ctagcccgca tcaagaagat catgaaagct gatgaagatg tgaggatgat ctctgcggag     120
gctcctgtga tttttgccaa ggcctgtgag atgttcattt tggagctcac tctacgtgct     180
tggatccaca ccgaggagaa caagaggagg accttgcaga agaacgacat cgccgctgcc     240
atttccagga ccgacgtgtt tgatttcctt gtggacataa tcccgaggga cgagctgaaa     300
gaagaaggtt taggcgtgac caaagggacc ataccatcgg tggtgggttc cccgccatac     360
tattacttgc aacaacaggg gatgatgcaa cactggcccc aggagtaaca ccctgatgag     420
tcttaaaact tttcccctttt cgtttgtttg gttgtatcgt agtaaggtag ctctgctctg     480
ctgggaacca tttctattgt gttctgtaat gacatgttag tatatcccca gtctatatct     540
atggcaatgc agt                                                        553
```

<210> SEQ ID NO 148
<211> LENGTH: 806
<212> TYPE: DNA
<213> ORGANISM: Artificial sequence
<220> FEATURE:
<223> OTHER INFORMATION: synthetic sequence
<220> FEATURE:
<223> OTHER INFORMATION: P26758 overexpression construct (35S::G3547)

<400> SEQUENCE: 148

```
gggaagaatg gatcatcaag ggcatagcca gaacccatct atgggggttg ttggtagtgg      60
agctcaatta gcatatggtt ctaacccata tcagccaggc caaataactg ggccaccggg     120
gtctgttgtg acatcagttg ggaccattca atccaccggt caacctgctg gagctcagct     180
tggacagcat caacttgctt atcagcatat tcatcagcaa caacagcacc agcttcagca     240
acagctccaa caattttggt caagccagta ccaagaaatt gagaaggtta ctgattttaa     300
gaaccacagt cttcccctgg caaggatcaa gaagattatg aaggctgacg aggatgttag     360
gatgatatca gctgaagcac cagtcatttt tgcaagggca tgtgaaatgt tcatattaga     420
gttaaccctg cgctcttgga atcacactga agagaacaaa aggcgaacac ttcagaaaaa     480
tgatattgct gctgctatca caaggactga catctttgat ttcttggttg acattgtgcc     540
tcgtgaggac ttgaaagatg aagtgcttgc atcaatccca agaggaacaa tgcctgttgc     600
agggcctgct gatgcccttc atactgctca catgccgcct cagcatccgt cccaagttgg     660
agctgctggt gtcataatgg gtaagcctgt gatggaccca acatgtatg ctcagcagtc     720 tcacccttac atggcaccac aaatgtggcc acagccacca gaccaacgac agtcatctcc     780
agaacattag ctgatgtgtc gtggaa                                          806

<210> SEQ ID NO 149
<211> LENGTH: 925
<212> TYPE: DNA
<213> ORGANISM: Artificial sequence
<220> FEATURE:
<223> OTHER INFORMATION: synthetic sequence
<220> FEATURE:
<223> OTHER INFORMATION: P111 overexpression construct (35S::G714)

<400> SEQUENCE: 149
ccacgcgtcc gcgtcaatct ttgagtttgg tagagaaatg gatcaacaag gacaatcatc      60
agctatgaac tatggttcaa acccatatca aaccaacgcc atgaccacta caccaaccgg     120
ttcagaccat ccagcttacc atcagatcca ccagcaacaa caacaacagc tcactcaaca     180
gcttcaatct ttctgggaga ctcaattcaa agagattgag aaaaccactg atttcaagaa     240
ccatagcctt ccattggcaa gaatcaagaa aatcatgaaa gctgatgaag atgtgcgtat     300
gatctcggcc gaggcgcctg ttgtgttcgc cagggcctgc gagatgttta ttctggagct     360
tacgttaagg tcttggaacc atactgagga gaacaagaga aggacgttgc agaagaatga     420
tatcgcggct gcggtgacta gaactgatat ttttgatttt cttgtggata ttgttcctcg     480
ggaggatctt cgtgatgaag tcttgggtgg tgttggtgct gaagctgcta cagctgcggg     540
ttatccgtat ggatacttgc ctcctggaac agctccaatt gggaacccgg aatggttat     600 gggtaacccg ggcgcgtatc cgccgaaggc gtatatgggt cagccaatgt ggcaacaacc     660
aggacctgag cagcaggatc ctgacaatta gcttggccta ataaactagc cgtctaattc     720
gaagctctcc ccggtggatc tactcaagaa gaagaatgtt aatagaaaac tattgcgaca     780
taaaaagttt ggtgtagtag aataatttct gttttatgat ccatggattt atcaattgtt     840
attcagtttg gtttatcttg tcatcaaact gttttcggtc aatgtaacaa attcataaat     900
tgagaattga acttacaaaa ggcta                                           925

<210> SEQ ID NO 150
<211> LENGTH: 798
<212> TYPE: DNA
<213> ORGANISM: Artificial sequence
<220> FEATURE:
<223> OTHER INFORMATION: synthetic sequence
```

<220> FEATURE:
<223> OTHER INFORMATION: P26604 overexpression construct (35S::G3542 )

<400> SEQUENCE: 150

```
agctgacatg gaaccatcct cacagcctca gcctgtgatg ggtgttgcca ctggtgggtc      60
acaagcatat cctcctcctg ctgctgcata tccacctcaa gccatggttc ctggagctcc     120
tgctgttgtt cctcctggct cacagccatc agcaccattc cccactaatc agctcaact     180
cagtgctcag caccagctag tctaccaaca agcccagcaa tttcatcagc agctgcagca     240
acagcaacag cagcaactcc gtgagttctg ggctaaccaa atggaagaga ttgagcaaac     300
aaccgacttc aagaaccaca gcttgccact cgcaaggata agaagataa tgaaggctga     360
tgaggatgtc cggatgatct cggcagaagc ccccgttgtc ttcgcaaagg catgcgaggt     420
attcatatta gagttaacat tgaggtcgtg gatgcacacg gaggagaaca gcgccggac     480
cttgcagaag aatgacattg cagctgccat caccaggact gatatctatg acttcttggt     540
ggacatagtt cccagggatg aaatgaaaga agaagggctt gggcttccga gggttggcct     600
accgcctaat gtggggggcg cagcagacac atatccatat tactacgtgc agcgcagca     660
ggggcctgga tcaggaatga tgtacggtgg acagcaaggt cacccggtga cgtatgtgtg     720
gcagcagcct caagagcaac aggaagaggc ccctgaagag cagcactctc tgccagaaag     780
tagctaaaga tgatacag                                                  798
```

<210> SEQ ID NO 151
<211> LENGTH: 1407
<212> TYPE: DNA
<213> ORGANISM: Artificial sequence
<220> FEATURE:
<223> OTHER INFORMATION: synthetic sequence
<220> FEATURE:
<223> OTHER INFORMATION: P26060 overexpression construct (35S::G489::
      (9A)YFP)

<400> SEQUENCE: 151

```
atgaactatg gcacaaaccc ataccaaacc aacccgatga gcaccactgc tgctactgta      60
gcaggaggtg cggcacaacc aggccagctg gcgttccacc agatccatca gcagcagcag    120
cagcaacagc tggcacagca gcttcaagca ttttgggaga accaattcaa agagattgag    180
aagactaccg atttcaagaa ccacagccct ccccttgcga gaatcaagaa atcatgaaa    240
gcggatgaag atgtccgtat gatctcggct gaggcgcctg tcgtgtttgc aagggcctgt    300
gagatgttca tcctggagct gacactcagg tcgtggaacc acactgagga gaataagagg    360
cggacgttgc agaagaacga tattgctgct gctgtgacta gaaccgatat tttttgatttc    420
cttgtggata ttgttccccg ggaggatctc cgagatgaag tcttgggaag tattccgagg    480
ggcactgtcc cggaagctgc tgctgctggt tacccgtatg gatacttgcc tgcaggaact    540
gctccaatag gaaatccggg aatggttatg ggtaatcccg gtggtgcgta tccacctaat    600
ccttatatgg gtcaaccaat gtggcaacaa caggcacctg accaacctga ccaggaaaat    660
gcggccgctg ccgctgcggc agcggccatg gtgagcaagg gcgaggagct gttcaccggg    720
gtggtgccca tcctggtcga gctggacggc gacgtaaacg gccacaagtt cagcgtgtcc    780
ggcgagggcg agggcgatgc cacctacggc aagctgaccc tgaagttcat ctgcaccacc    840
ggcaagctgc ccgtgccctg gcccaccctc gtgaccacct tcggctacgg cctgcagtgc    900
ttcgcccgct accccgacca catgaagcag cacgacttct tcaagtccgc catgcccgaa    960
ggctacgtcc aggagcgcac catcttcttc aaggacgacg gcaactacaa gacccgcgcc   1020
```

```
gaggtgaagt tcgagggcga caccctggat aaccgaatcg agctgaaggg catcgacttc    1080
aaggaggacg gcaacatcct ggggcacaag ctggagtaca actacaacag ccacaacgtc    1140
tatatcatgg ccgacaagca gaagaacggc atcaaggtga acttcaagat ccgccacaac    1200
atcgaggacg gcagcgtgca gctcgccgac cactaccagc agaacacccc catcggcgac    1260
ggccccgtgg tgctgcccga caaccactac ctgagctacc agtccgccct gagcaaagac    1320
cccaacgaga gcgcgatca catggtcctg ctggagttcg tgaccgccgc cgggatcact     1380
ctcggcatgg acgagctgta caagtaa                                        1407
```

<210> SEQ ID NO 152
<211> LENGTH: 760
<212> TYPE: DNA
<213> ORGANISM: Artificial sequence
<220> FEATURE:
<223> OTHER INFORMATION: synthetic sequence
<220> FEATURE:
<223> OTHER INFORMATION: P26599 overexpression construct (35S::G3544)

<400> SEQUENCE: 152

```
agaggacatg gagccatcat cacaacctca gccggcaatt ggtgttgttg ctggtggatc     60
acaagtgtac cctgcatacc ggcctgcagc aacagtgcct acagctcctg ctgtcattcc    120
tgccggttca cagccagcac cgtcgttccc tgccaaccct gatcaactga gtgctcagca    180
ccagctcgtc tatcagcaag cccagcaatt tcaccagcag cttcagcagc agcaacagcg    240
tcaactccag cagttttggg ctgaacgtct ggtcgatatt gaacaaacta ctgacttcaa    300
gaaccacagc ttgccacttg ctaggataaa gaagatcatg aaggcagatg aggacgttcg    360
catgatctcc gcagaggctc ctgtgatctt tgcgaaagca tgtgagatat tcatactgga    420
gctgaccctg agatcatgga tgcacacgga ggagaacaag cgccgtacct tgcagaagaa    480
tgacatagca gctgccatca ccaggacgga tatgtacgat ttcttggtag atatagttcc    540
cagggatgac ttgaaggagg agggagttgg gctccctagg gctggattgc cgcccttggg    600
tgtccctgct gactcatatc cgtatggcta ctatgtgcca cagcagcagg tcccaggtgc    660
aggaatagcg tatggtggtc agcaaggtca tccggggtat ctgtggcagg atcctcagga    720
acagcaggaa gagcctcctg cagagcagca aagtgattaa                          760
```

<210> SEQ ID NO 153
<211> LENGTH: 847
<212> TYPE: DNA
<213> ORGANISM: Artificial sequence
<220> FEATURE:
<223> OTHER INFORMATION: synthetic sequence
<220> FEATURE:
<223> OTHER INFORMATION: P26606 overexpression construct (35S::G3550)

<400> SEQUENCE: 153

```
agtaagtcat catggataaa tcagagcaga ctcaacagca gcagcagcaa caacagcatg     60
tgatgggagt tgccgcaggg gctagccaaa tggcctattc ttctcactac ccgactgctt    120
ccatggtggc ttctggcacg cccgctgtaa ctgctccttc cccaactcag gctccagctg    180
ccttctctag ttctgctcac cagcttgcat accagcaagc acagcatttc caccaccaac    240
agcagcaaca ccaacaacag cagcttcaaa tgttctggtc aaaccaaatg caagaaattg    300
agcaaacaat tgactttaaa aaccatagcc ttcctcttgc tcggataaaa aagataatga    360
aagctgatga agatgtccgg atgatttcag cagaagctcc ggtcatattt gcaaaagctt    420
```

```
gtgaaatgtt catattagag ttgacgttgc gatcttggat ccacacagaa gagaacaaga      480
ggagaactct acaaaagaat gatatagcag ctgctatttc gagaaacgat gttttttgatt     540 tcttggttga tattattcca agagatgagt tgaaagagga aggacttgga ataaccaagg      600
ctactattcc gttagtgggt tctccagctg atatgccata ttactatgtc cctccacagc     660
atcctgttgt aggaccacct gggatgatca tgggcaagcc cattggcgct gagcaagcaa     720
cactatattc tacacagcag cctcgacctc ctgtggcgtt catgccatgg cctcatacac    780
aacccctgca acagcagcca ccccaacatc aacaaacaga ctcatgatga ctatgcaatt    840
caattag                                                              847

<210> SEQ ID NO 154
<211> LENGTH: 786
<212> TYPE: DNA
<213> ORGANISM: Artificial sequence
<220> FEATURE:
<223> OTHER INFORMATION: synthetic sequence
<220> FEATURE:
<223> OTHER INFORMATION: P26610 overexpression construct (35S::G3548 )

<400> SEQUENCE: 154
aacatcaggg gatgggcgtt gccacaggtg ctagccaaat ggcctattct tctcactacc      60
cgactgctcc catggtggct tctggcacgc ctgctgtagc tgttccttcc ccaactcagg     120
ctccagctgc cttctctagt tctgctcacc agcttgcata ccagcaagca cagcatttcc     180
accaccaaca gcagcaacac caacaacagc agcttcaaat gttctggtca aaccaaatgc     240
aagaaattga gcaaacaatt gactttaaaa accacagtct tcctcttgct cggataaaaa     300
agataatgaa agctgatgaa gatgtccgga tgatttctgc agaagctcca gtcatatttg     360
caaaagcatg tgaaatgttc atattagagt tgacgttgag atcttggatc cacacagaag     420
agaacaagag gagaactcta caaaagaatg atatagcagc tgctatttcg agaaacgatg     480
tttttgattt cttggttgat attatcccaa gagatgagtt gaaagaggaa ggacttggaa     540
taaccaaggc tactattcca ttggtgaatt ctccagctga tatgccatat tactatgtcc     600
ctccacagca tcctgttgta ggacctcctg ggatgatcat gggcaagccc gttggtgctg     660
agcaagcaac gctgtattct acacagcagc ctcgacctcc catggcgttc atgccatggc     720
cccatacaca accccagcaa cagcagccac cccaacatca caaacagac tcatgatgac    780 catgca                                                               786

<210> SEQ ID NO 155
<211> LENGTH: 748
<212> TYPE: DNA
<213> ORGANISM: Artificial sequence
<220> FEATURE:
<223> OTHER INFORMATION: synthetic sequence
<220> FEATURE:
<223> OTHER INFORMATION: P15502 overexpression construct (35S::G715)

<400> SEQUENCE: 155
ccgaccaatg gataccaaca accagcaacc acctccctcc gccgccggaa tcctcctcc       60 accacctgga accaccatct ccgccgcagg aggaggagct tcttaccacc accttctcca    120
acaacaacaa caacagctcc aactattctg gacctaccaa cgccaagaga tcgaacaagt    180
taacgatttc aaaaaccatc agcttccact agctaggata aaaaagatca tgaaagccga    240
tgaagatgtt cgtatgatct ccgcagaagc accgattctc ttcgcgaaag cttgtgagct    300
tttcattctc gagctcacga tcagatcttg gcttcacgct gaggagaata aacgtcgtac    360
```

```
gcttcagaaa aacgatatcg ctgctgcgat tactaggact gatatcttcg atttccttgt    420
tgatattgtt cctagagatg agattaagga cgaagccgca gtcctcggtg gtggaatggt    480
ggtggctcct accgcgagcg gcgtgcctta ctattatccg ccgatgggac aaccagctgg    540
tcctggaggg atgatgattg ggagaccagc tatggatccg aatggtgttt atgtccagcc    600
tccgtctcag gcgtggcaga gtgtttggca gacttcgacg gggacgggag atgatgtctc    660
ttatggtagt ggtggaagtt ccggtcaagg gaatctcgac ggccaaggtt aagctcagag    720
tattccagat gatgcttgac ctgcttga                                       748
```

<210> SEQ ID NO 156
<211> LENGTH: 750
<212> TYPE: DNA
<213> ORGANISM: Artificial sequence
<220> FEATURE:
<223> OTHER INFORMATION: synthetic sequence
<220> FEATURE:
<223> OTHER INFORMATION: P26607 overexpression construct (35S::G3886)

<400> SEQUENCE: 156

```
attgggggaa tggagaccaa caaccagcaa caacaacaac aaggagctca agcccaatcg     60
ggaccctacc ccgtcgccgg cgccggcggc agtgcaggtg caggtgcagg cgctcctccc    120
cctttccagc accttctcca gcagcagcag cagcagctcc agatgttctg gtcttaccag    180
cgtcaagaaa tcgagcacgt gaacgacttt aagaatcacc agctccctct tgcccgcatc    240
aagaagatca tgaaggccga cgaggatgtc cgcatgatct ccgccgaggc ccccatcctc    300
ttcgccaagg cctgcgagct cttcatcctc gagctcacca tccgctcctg gctccacgcc    360
gaggagaaca agcgccgcac cctccagaag aacgacatcg ccgccgccat cacccgcacc    420
gacattttcg acttcctcgt tgatattgtc ccccgcgacg agatcaagga cgacgctgct    480
cttgtggggg ccaccgccag tggggtgcct tactactacc cgcccattgg acagcctgcc    540
gggatgatga ttggccgccc cgccgtcgat cccgccaccg gggtttatgt ccagccgccc    600
tcccaggcat ggcagtccgt ctggcagtcc gctgccgagg acgcttccta tggcaccggc    660
ggggccggtg cccagcggag ccttgatggc cagagttgag tgacatcgat gccgatgatg    720
gacagtcagg agttatgaag attctgaact                                     750
```

<210> SEQ ID NO 157
<211> LENGTH: 768
<212> TYPE: DNA
<213> ORGANISM: Artificial sequence
<220> FEATURE:
<223> OTHER INFORMATION: synthetic sequence
<220> FEATURE:
<223> OTHER INFORMATION: P26590 overexpression construct (35S::G3889)

<400> SEQUENCE: 157

```
aatccatgga caaccagccg ctgccctact ccacaggcca gccccctgcc cccggaggag     60
ccccggtggc gggcatgcct ggcgcggccg gcctcccacc cgtgccgcac caccacctgc    120
tccagcagca gcaggcccag ctgcaggcgt tctgggcgta ccagcgccag gaggcggagc    180
gcgcgtccgc gtcggacttc aagaaccacc agctgcctct ggcccggatc aagaagatca    240
tgaaggccga cgaggacgtg cgcatgatct ccgccgaggc gcccgtgctg ttcgccaagg    300
cctgcgagct cttcatcctc gagctcacta tccgctcctg gctccacgcc gaggagaaca    360
agcgccgcac cctgcagcgc aacgacgtcg ccgcggccat cgcgcgcacc gacgtcttcg    420
```

-continued

```
atttcctcgt cgacatcgtg ccccgcgagg aggccaagga ggagcccggc agcgccctcg    480
gcttcgcggc gcctgggacc ggcgtcgtcg gggctggcgc cccgggcggg cgccagccg    540 ccgggatgcc ctactactat ccgccgatgg ggcagccggc gccgatgatg ccggcctggc    600
atgttccggc ctgggacccg gcctggcagc aaggggcagc ggatgtcgat cagagcggca    660
gcttcagcga ggaaggacaa gggtttggag caggccatgg cggcgccgct agcttccctc    720
ctgcgcctcc gacctccgag tgatcgatcg gcgcgtctct tggtcctg              768
```

<210> SEQ ID NO 158
<211> LENGTH: 800
<212> TYPE: DNA
<213> ORGANISM: Artificial sequence
<220> FEATURE:
<223> OTHER INFORMATION: synthetic sequence
<220> FEATURE:
<223> OTHER INFORMATION: P964 overexpression construct (35S::G1646)

<400> SEQUENCE: 158

```
gatcttttga tccaatcaca aggcaaagat ccaatggaca ataacaacaa caacaacaac     60
cagcaaccac caccaacctc cgtctatcca cctggctccg ccgtcacaac cgtaatccct    120
cctccaccat ctggatctgc atcaatagtc accggaggag gagcgacata ccaccacctc    180
ctccagcaac aacagcaaca gcttcaaatg ttctggacat accagagaca agagatcgaa    240
caggtaaacg atttcaaaaa ccatcagctc cctctagctc gtatcaaaaa aatcatgaaa    300
gctgatgaag atgtgcgtat gatctccgcc gaagcaccga ttctcttcgc gaaagcttgt    360
gagcttttca ttctcgaact tacgattaga tcttggcttc acgctgaaga gaacaaacgt    420
cgtacgcttc agaaaaacga tatcgctgct gcgattacta gaaccgatat cttcgatttc    480
cttgttgata ttgttcctag ggaagagatc aaggaagagg aagatgcagc atcggctctt    540
ggtggaggag gtatggttgc tcccgccgcg agcggtgttc cttattatta ccaccgatg    600 ggacaaccgg cggttcctgg agggatgatg attggaagac cggcgatgga tcctagcggt    660
gtttatgctc agcctccttc tcaggcatgg caaagcgttt ggcagaattc agctggtggt    720
ggtgatgatg tgtcttatgg aagtggagga agtagcggcc atggtaatct cgatagccaa    780
gggtaagtga attctagtag                                                 800
```

<210> SEQ ID NO 159
<211> LENGTH: 762
<212> TYPE: DNA
<213> ORGANISM: Artificial sequence
<220> FEATURE:
<223> OTHER INFORMATION: synthetic sequence
<220> FEATURE:
<223> OTHER INFORMATION: P26598 overexpression construct (35S::G3543)

<400> SEQUENCE: 159

```
ggtgacaatg gacaaccagc agctacccta cgccggtcag ccggcggccg caggcgccgg     60
agccccggtg ccgggcgtgc ctggcgcggg cgggccgccg gcggtgccgc accaccacct    120
gctccagcag cagcaggcgc agctgcaggc gttctgggcg taccagcggc aggaggcgga    180
gcgcgcgtcg gcgtcggact tcaagaacca ccagctgccg ctggcgcgga tcaagaagat    240
catgaaggcg gacgaggacg tgcgcatgat ctcggcggag gcgcccgtgc tgttcgccaa    300
ggcgtgcgag ctcttcatcc tggagctcac catccgctcg tggctgcacg ccgaggagaa    360
caagcgccgc accctgcagc gcaacgacgt cgccgccgcc atcgcgcgca ccgacgtgtt    420
cgacttcctc gtcgacatcg tgccgcggga ggaggccaag gaggagcccg gcagcgcgct    480
```

```
cgggttcgcg gcgggagggc ccgccggcgc cgttggagcg gccggccccg ccgcggggct    540
gccgtactac tacccgccga tggggcagcc ggcgccgatg atgccggcgt ggcatgttcc    600
ggcgtgggac ccggcgtggc agcaaggagc agcgccggat gtggaccagg gcgccgccgg    660
cagcttcagc gaggaagggc agcaaggttt tgcaggccat ggcggtgcgg cagctagctt    720
ccctcctgca cctccaagct ccgaatagtg atgatccata tg                       762
```

<210> SEQ ID NO 160
<211> LENGTH: 734
<212> TYPE: DNA
<213> ORGANISM: Artificial sequence
<220> FEATURE:
<223> OTHER INFORMATION: synthetic sequence
<220> FEATURE:
<223> OTHER INFORMATION: P1284 overexpression construct (35S::G1820)

<400> SEQUENCE: 160

```
tctcacttcc aacatccaaa tccctagaaa ttgtaaatgg ctgagaacaa caacaacaac     60
ggcgacaaca tgaacaacga caaccaccag caaccaccgt cgtactcgca gctgccgccg    120
atggcatcat ccaaccctca gttacgtaat tactggattg agcagatgga aaccgtctcg    180
gatttcaaaa accgtcagct tccattggct cgaattaaga agatcatgaa ggctgatcca    240
gatgtgcaca tggtctccgc agaggctccg atcatcttcg caaggcttg cgaaatgttc    300 atcgttgatc tcacgatgcg gtcgtggctc aaagccgagg agaacaaacg ccacacgctt    360
cagaaatcgg atatctccaa cgcagtggct agctctttca cctacgattt ccttcttgat    420
gttgtcccta aggacgagtc tatcgccacc gctgatcctg gctttgtggc tatgccacat    480
cctgacggtg gaggagtacc gcaatattat tatccaccgg gagtggtgat gggaactcct    540
atggttggta gtggaatgta cgcgccatcg caggcgtggc cagcagcggc tggtgacggg    600
gaggatgatg ctgaggataa tggaggaaac ggcggcggaa attgaagtgt agatttaggg    660
tttgtaaccg cctatgtggg aaatttgaaa tttggtggtg tttattaggg ttcttcaatt    720
cgtcggattt gctt                                                      734
```

<210> SEQ ID NO 161
<211> LENGTH: 668
<212> TYPE: DNA
<213> ORGANISM: Artificial sequence
<220> FEATURE:
<223> OTHER INFORMATION: synthetic sequence
<220> FEATURE:
<223> OTHER INFORMATION: P973 overexpression construct (35S::G1836)

<400> SEQUENCE: 161

```
ataacaagcc tagaacacta gaaacttcaa aaaagaaaaa aatcttatgg agaacaacaa     60
cggcaacaac cagctgccac cgaaaggtaa cgagcaactg aagagtttct ggtcaaaaga    120
gatggaaggt aacttagatt tcaaaaatca cgaccttcct ataactcgta tcaagaagat    180
tatgaagtat gatccggatg tgactatgat agctagtgag gctccaatcc tcctctcgaa    240
agcatgtgag atgtttatca tggatctcac gatgcgttcg tggctccatg ctcaggaaag    300
caaacgagtc acgctacaga aatctaatgt cgatgccgca gtggctcaaa ctgttatctt    360
tgatttcttg cttgatgatg acattgaggt aaagagagag tctgttgccg ccgctgctga    420
tcctgtggcc atgccaccta ttgacgatgg agagctgcct ccaggaatgg taattggaac    480
tcctgtttgt tgtagtcttg gaatccacca accacaacca caaatgcagg catggcctgg    540
```

```
agcttggacc tcggtgtctg gtgaggagga agaagcgcgt gggaaaaaag gaggtgacga    600
cggaaactaa taagtggaat acgttttagg gtattttcaa gggaatatgt agtaaatagt    660
catggatc                                                            668

<210> SEQ ID NO 162
<211> LENGTH: 800
<212> TYPE: DNA
<213> ORGANISM: Artificial sequence
<220> FEATURE:
<223> OTHER INFORMATION: synthetic sequence
<220> FEATURE:
<223> OTHER INFORMATION: P1285 overexpression construct (35S::G1819)

<400> SEQUENCE: 162
aatagttggg ctgatttcgt agcccactta atcagccttt aaatatggaa accctagcct     60
agaaagtgaa caagaaaaac gtaaagatca aatggaaga gaacaacggc aacaacaacc    120
actacctgcc gcaaccatcg tcttcccaac tgccgccgcc accattgtat tatcaatcaa    180
tgccgttgcc gtcatattca ctgccgctgc cgtactcacc gcagatgcgg aattattgga    240
ttgcgcagat gggaaacgca actgatgtta agcatcatgc gtttccacta accaggataa    300
agaaaatcat gaagtccaac ccggaagtga acatggtcac tgcagaggct ccggtcctta    360
tatcgaaggc ctgtgagatg ctcattcttg atctcacaat gcgatcgtgg cttcataccg    420
tggagggcgg tcgccaaact ctcaagagat ccgatacgct cacgagatcc gatatctccg    480
ccgcaacgac tcgtagtttc aaatttacct tccttggcga cgttgtccca agagacccctt    540 ccgtcgttac cgatgatccc gtgctacatc cggacggtga agtacttcct ccgggaacgg    600
tgataggata tccggtgttt gattgtaatg gtgtgtacgc gtcaccgcca cagatgcagg    660
agtggccggc ggtgcctggt gacggagagg aggcagctgg ggaaattgga ggaagcagcg    720
gcggtaattg aaaagtgttg attgggtttt agggttgtaa tgcttttgtg agaatttgta    780
tctctatgga gtcatgtttg                                               800

<210> SEQ ID NO 163
<211> LENGTH: 736
<212> TYPE: DNA
<213> ORGANISM: Artificial sequence
<220> FEATURE:
<223> OTHER INFORMATION: synthetic sequence
<220> FEATURE:
<223> OTHER INFORMATION: P1677 overexpression construct (35S::G1818)

<400> SEQUENCE: 163
taggttgaga ttcatatatg taaagagatc acttcttaat cttatcctac catatcttat     60
atacgcttaa ttttccttta tatatgcaaa cctccacata aaatatctc aaacccaaac    120 acttcaaaca aaaaaaaaat ggagaacaac aacaacaacc accaacagcc accgaaagat    180
aacgagcaac taaagagttt ctggtcaaag gggatggaag gtgacttgaa tgtcaagaat    240
cacgagttcc ccatctctcg tatcaagagg ataatgaagt ttgatccgga tgtgagtatg    300
atcgctgctg aggctccaaa tctcttatct aaggcttgtg aaatgtttgt catggacctc    360
acgatgcgtt catggctcca tgctcaagag agcaaccgac tcacgatacg gaaatctgat    420
gttgatgccg tagtgtctca aaccgtcatc tttgatttct tgcgtgatga tgtccctaag    480
gacgagggag agcccgttgt cgccgctgct gatcctgtgg acgatgttgc tgatcatgtg    540
gctgtgccaa atcttaacaa tgaagaactg ccgccgggaa cggtgatagg aactccggtt    600
tgttacggtt taggaataca cgcgccacac ccgcagatgc ctggagcttg gaccgaggag    660
```

```
gatgcgactg gggcaaatgg aggaaacggt gggaattaat atttggattg ggttttgtaa    720
ccgctgttgt gagaac                                                    736

<210> SEQ ID NO 164
<211> LENGTH: 779
<212> TYPE: DNA
<213> ORGANISM: Artificial sequence
<220> FEATURE:
<223> OTHER INFORMATION: synthetic sequence
<220> FEATURE:
<223> OTHER INFORMATION: P912 overexpression construct (35S::G490)

<400> SEQUENCE: 164
acccttgttc ttgccaaact ctacatcttc aaagattttt catcatctgt tgtgaaatat     60
aacatgagga ggccaaagtc atctcacgtc aggatggaac ctgttgcgcc tcgttcacat    120
aacacgatgc caatgcttga tcaatttcga tctaatcatc ctgaaacaag caagatcgag    180
ggggtctctt cgttggacac agctctgaag gtgttttgga ataatcaaag ggagcagcta    240
ggaaactttg caggccaaac tcatttgccg ctatctaggg tcagaaagat tttgaaatct    300
gatcctgaag tcaagaagat aagctgtgat gttcctgctt tgttttcgaa agcctgtgaa    360
tacttcattc tagaggtaac attacgagct tggatgcata ctcaatcatg cactcgtgag    420
accatccggc gttgtgatat cttccaggcc gtaaagaact caggaactta tgatttcctg    480
attgatcgtg tcccttttgg accgcactgt gtcacccatc agggtgtgca acctcctgct    540
gaaatgattt tgccggatat gaatgttcca atcgatatgg accagattga ggaggagaat    600
atgatggaag agcgctctgt cgggtttgac ctcaactgtg atctccagtg aacatgaagc    660
tgctctggaa gacaaaaact tgaagaagag aagaaatctg aagaggaatc acccaacaac    720
tctatgttat gttcacctta taatagttta tcataaactc attcactaaa ctatgtgta    779

<210> SEQ ID NO 165
<211> LENGTH: 715
<212> TYPE: DNA
<213> ORGANISM: Artificial sequence
<220> FEATURE:
<223> OTHER INFORMATION: synthetic sequence
<220> FEATURE:
<223> OTHER INFORMATION: P2712 overexpression construct (35S::G3074)

<400> SEQUENCE: 165
cattgtgtgg aaagatataa cgtgtttgat tttctgaggg aagttgtgag taaggtgcct     60
gactatggcc attcccaagg gcaaggacat ggtgatgtta ccatggatga tcgcagcatc    120
tccaagagaa ggaagcccat cagcgatgaa gtgaatgaca gtgacgagga atataagaaa    180
agcaaaacgc aagagatagg gagtgctaag accagtggca ggggtggtag aggaagaggg    240
cgaggaagag gtcgtggtgg acgagctgca aaagcagccg aaagagaggg tctcaaccgc    300
gagatggaag tagaagccgc caattctgga cagccaccac cagaagacaa tgtcaagatg    360
catgcgtcag agtcatcacc acaagaggat gagaagaaag gcatcgacgg cacagcagca    420
tcgaacgaag acaccaagca acaccttcaa agtcccaaag aaggcattga ctttgatctc    480
aacgctgaat ccctcgacct aaacgagacc aaactggcac cagccacagg cacaaccaca    540
accacaactg cagcaacaga ctctgaggag tattcgggct ggcctatgat ggacataagc    600
aaaatggatc cagcacagct tgctagtctg ggtaagagga tagacgagga tgaggaagat    660
tatgacgaag aaggctaagt cataacagca ctataggata tatagagtag cagcg          715
```

<210> SEQ ID NO 166
<211> LENGTH: 738
<212> TYPE: DNA
<213> ORGANISM: Artificial sequence
<220> FEATURE:
<223> OTHER INFORMATION: synthetic sequence
<220> FEATURE:
<223> OTHER INFORMATION: P1184 overexpression construct (35S::G1249)

<400> SEQUENCE: 166

```
tcgaccgttc ttctcaatct caccaatcgg tttaagctga aaacccgaat tagcaaaatc      60
ttcgttcggg ctgttttggt taatccggtt tacatgtttt ctcattgctc attttcattt     120
tcccgccgtg acagagcgcg taaatctcaa acccctaaaa atgtcgaaca tatacaattc     180
attaccttaa tcagattttc tcaacagaat caaaatcaaa atccatggag gaagaagaag     240
gatcaatccg accagagttt ccaatcggaa gagtaaagaa gataatgaaa ctggacaaag     300
acatcaacaa aatcaactca gaagctcttc acgtcatcac ttactccacc gaactcttcc     360
tccacttcct cgccgagaaa tctgctgttg ttacggcgga gaagaagcgt aagactgtta     420
atctcgatca tttaagaatc gccgtgaaaa gacaccaacc tactagtgat ttcctcttag     480
actcgcttcc gttgccggct cagcctgtca aacataccaa atcggtttcc gacaagaaga     540
ttccggcgcc gccaattggg actcgtcgta tcgatgattt cttcagtaaa gggaaagcaa     600
agactgattc agcctaaagt aaaatttctc attttgttca caattgcaaa ttttactctg     660
ttctcaaatc aaaatcttgt tttgctaaaa gtgtagtgag aatgtatgga tcatgaggaa     720
cttttatagg aagcggcc                                                   738
```

<210> SEQ ID NO 167
<211> LENGTH: 1461
<212> TYPE: DNA
<213> ORGANISM: Artificial sequence
<220> FEATURE:
<223> OTHER INFORMATION: synthetic sequence
<220> FEATURE:
<223> OTHER INFORMATION: P2797 overexpression construct (35S::G3075)

<400> SEQUENCE: 167

```
ggcgaaaggg tgaaacatac tgtagttcta aaaaattaat ggtgtcgtca agaaaccca      60
aggagaagaa ggcgaggagc gatgtcgtcg tcaataaagc gagtggtcgg agtaaacgca    120
gctccggttc cagaacgaag aagacgtcga acaaggttaa cattgtgaag aagaagccgg    180
agatttacga gatctcagaa tcatcgagca gtgactctgt ggaagaagca ataagaggcg    240
atgaggcgaa gaaaagtaac ggcgtcgtga gcaagagggg taacggaaag agtgtaggaa    300
ttccgacgaa gacgagtaaa aatcgagaag aggacgatgg aggcgcggaa gatgctaaga    360
tcaagtttcc gatgaatcgg attcggcgga tcatgagaag cgataattct gctcctcaga    420
ttatgcagga tgctgtattt cttgtcaaca aagccacggt atagtactaa ttagacatat    480
aaatttagct tgaggaactt aatttcacat ggtttttgat gaatttggga gtatcaattg    540
ctagtcagtg ttaattgggc gttataatct cgcaaattgc tacagtaatg agattgtttc    600
tgttaattaa gccgggaatt aacgttattg cttcatctcc atgtgtgttt gatgaaaccg    660
tagttactgt gcttgattgt cataggttta gcttttacat ccagaacttg tagacaccta    720
acacatgaga aagtcctttat atatgattta ggttcatatt ttcaaagctt aagtgatgag    780
tgtttaattt tcctgtattg gaacttggca ttgttttttc tttcttttga tttcatcttg    840
tgttcatcga aattgatgtt cattgcgttt acagtacatt aactggtttt tgtgattgaa    900
```

```
ggagatgttc attgagcggt tttctgaaga agcttatgat agttccgtca aggacaaaaa      960
gaaattcatc cactacaaac acctctgtaa gctctaatct cgtccctatt tgccaatatc     1020
tggttacctc aatactgaat cccatgtcga aaatctcatg ctgctgcacc aattgctgaa     1080
cttaggattt ctggcttctg cacaagggcc agtagttagt cttaggaaga gtttagataa     1140
tgagttaatc cgttcgtatc acttgcaaga tttgttgcac tcctaacata attgatgaca     1200
ctgtcatttc tactcgttgg cagcatccgt agtgagtaac gaccagagat acgagttcct     1260
tgcaggtact taataacctc tgaagtattc gttttatgag ttccatgtgg tttacgaaca     1320
gcattttaat acctgtaata tcttgaatgc agatagtgtt cccgagaaac ttaaagcaga     1380
ggccgcgttg gaggaatggg aaagaggcat gacagatgca ggctgaaata aatccggttg     1440
gaatcgaact gaaccatttg g                                               1461

<210> SEQ ID NO 168
<211> LENGTH: 747
<212> TYPE: DNA
<213> ORGANISM: Artificial sequence
<220> FEATURE:
<223> OTHER INFORMATION: synthetic sequence
<220> FEATURE:
<223> OTHER INFORMATION: P25800 overexpression construct (35S::MCS::(9A)YFP)

<400> SEQUENCE: 168
gcggccgctg ccgctgcggc agcggccatg gtgagcaagg gcgaggagct gttcaccggg       60
gtggtgccca tcctggtcga gctggacggc gacgtaaacg gccacaagtt cagcgtgtcc      120
ggcgagggcg agggcgatgc cacctacggc aagctgaccc tgaagttcat ctgcaccacc      180
ggcaagctgc ccgtgccctg gcccaccctc gtgaccacct tcggctacgg cctgcagtgc      240
ttcgcccgct accccgacca catgaagcag cacgacttct tcaagtccgc catgcccgaa      300
ggctacgtcc aggagcgcac catcttcttc aaggacgacg gcaactacaa gacccgcgcc      360
gaggtgaagt tcgagggcga cacactggtg aaccgcatcg agctgaaggg catcgacttc      420
aaggaggacg gcaacatcct ggggcacaag ctggagtaca actacaacag ccacaacgtc      480
tatatcatgg ccgacaagca gaagaacggc atcaaggtga acttcaagat ccgccacaac      540
atcgaggacg gcagcgtgca gctcgccgac cactaccagc agaacacccc catcggcgac      600
ggccccgtgc tgctgcccga caaccactac ctgagctacc agtccgccct gagcaaagac      660
cccaacgaga gcgcgatca catggtcctg ctggagttcg tgaccgccgc cgggatcact      720
ctcggcatgg acgagctgta caagtaa                                         747

<210> SEQ ID NO 169
<211> LENGTH: 4856
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (17)..(52)
<223> OTHER INFORMATION: n is a, c, g, or t
<220> FEATURE:
<223> OTHER INFORMATION: pMEN1963 overexpression construct (35S::attR1::
      CAT::ccdB::attR2::E9)

<400> SEQUENCE: 169
```

```
aagcttnnnn ctgcagnnnn nnnnnnnnnn nnnnnnnnnn nnnnnnnnnn nntcggattc    60
cattgcccag ctatctgtca ctttattgtg aagatagtga aaaagaaggt ggctcctaca   120
aatgccatca ttgcgataaa ggaaaggcca tcgttgaaga tgcctctgcc gacagtggtc   180
ccaaagatgg accccaccc acgaggagca tcgtggaaaa agaagacgtt ccaaccacgt    240
cttcaaagca agtggattga tgtgatggtc cgattgagac ttttcaacaa agggtaatat   300
ccggaaacct cctcggattc cattgcccag ctatctgtca ctttattgtg aagatagtgg   360
aaaaggaagg tggctcctac aaatgccatc attgcgataa aggaaaggcc atcgttgaag   420
atgcctctgc cgacagtggt cccaaagatg gaccccacc cacgaggagc atcgtggaaa    480
aagaagacgt tccaaccacg tcttcaaagc aagtggattg atgtgatatc tccactgacg   540
taagggatga cgcacaatcc cactatcctt cgcaagaccc ttcctctata taaggaagtt   600
catttcattt ggagaggaca cgctgacaag ctgactctag cagatctggt accgtcgaat   660
cacaagtttg tacaaaaaag ctgaacgaga acgtaaaat gatataaata tcaatatatt    720
aaattagatt ttgcataaaa aacagactac ataatactgt aaaacacaac atatccagtc   780
actatggcgg ccgcattagg caccccaggc tttacacttt atgcttccgg ctcgtataat   840
gtgtggattt tgagttagga tccgtcgaga ttttcaggag ctaaggaagc taaaatggag   900
aaaaaaatca ctggatatac caccgttgat atatcccaat ggcatcgtaa agaacatttt   960
gaggcatttc agtcagttgc tcaatgtacc tataaccaga ccgttcagct ggatattacg  1020
gcctttttaa agaccgtaaa gaaaaataag cacaagtttt atccggcctt tattcacatt  1080
cttgcccgcc tgatgaatgc tcatccggaa ttccgtatgg caatgaaaga cggtgagctg  1140
gtgatatggg atagtgttca cccttgttac accgttttcc atgagcaaac tgaaacgttt  1200
tcatcgctct ggagtgaata ccacgacgat ttccggcagt ttctacacat atattcgcaa  1260
gatgtggcgt gttacggtga aaacctggcc tatttcccta aagggtttat tgagaatatg  1320
tttttcgtct cagccaatcc ctgggtgagt ttcaccagtt ttgatttaaa cgtggccaat  1380
atggacaact tcttcgcccc cgttttcacc atgggcaaat attatacgca aggcgacaag  1440
gtgctgatgc cgctggcgat tcaggttcat catgccgtct gtgatggctt ccatgtcggc  1500
agaatgctta tgaattaca acagtactgc gatgagtggc agggcggggc gtaaagatct  1560
ggatccggct tactaaaagc cagataacag tatgcgtatt tgcgcgctga ttttgcggt   1620
ataagaatat atactgatat gtatacccga agtatgtcaa aaagaggtat gctatgaagc  1680
agcgtattac agtgacagtt gacagcgaca gctatcagtt gctcaaggca tatatgatgt  1740
caatatctcc ggtctggtaa gcacaaccat gcagaatgaa gcccgtcgtc tgcgtgccga  1800
acgctggaaa gcggaaaatc aggaagggat ggctgaggtc gcccggttta ttgaaatgaa  1860
cggctctttt gctgacgaga acaggggctg gtgaaatgca gtttaaggtt tacacctata  1920
aaagagagag ccgttatcgt ctgtttgtgg atgtacagag tgatattatt gacacgcccg  1980
ggcgacggat ggtgatcccc ctggccagtg cacgtctgct gtcagataaa gtctcccgtg  2040
aactttaccc ggtggtgcat atcggggatg aaagctggcg catgatgacc accgatatgg  2100
ccagtgtgcc ggtctccgtt atcggggaag aagtggctga tctcagccac cgcgaaaatg  2160
acatcaaaaa cgccattaac ctgatgttct ggggaatata aatgtcaggc tcccttatac  2220
acagccagtc tgcaggtcga ccatagtgac tggatatgtt gtgttttaca gtattatgta  2280
gtctgttttt tatgcaaaat ctaatttaat atattgatat ttatatcatt ttacgtttct  2340
```

```
cgttcagctt tcttgtacaa agtggtgatg ccgctctag acaggcctcg taccggatcc   2400
tctagctaga gctttcgttc gtatcatcgg tttcgacaac gttcgtcaag ttcaatgcat   2460
cagtttcatt gcgcacacac cagaatccta ctgagtttga gtattatggc attgggaaaa   2520
ctgttttttct tgtaccattt gttgtgcttg taatttactg tgtttttat tcggttttcg    2580
ctatcgaact gtgaaatgga aatggatgga gaagagttaa tgaatgatat ggtccttttg    2640
ttcattctca aattaatatt atttgttttt tctcttattt gttgtgtgtt gaatttgaaa    2700
ttataagaga tatgcaaaca ttttgttttg agtaaaaatg tgtcaaatcg tggcctctaa    2760
tgaccgaagt taatatgagg agtaaaacac ttgtagttgt accattatgc ttattcacta    2820
ggcaacaaat atattttcag acctagaaaa gctgcaaatg ttactgaata caagtatgtc    2880
ctcttgtgtt ttagacattt atgaactttc ctttatgtaa ttttccagaa tccttgtcag    2940
attctaatca ttgctttata attatagtta tactcatgga tttgtagttg agtatgaaaa    3000
tatttttttaa tgcattttat gacttgccaa ttgattgaca acatgcatca atcgacctgc    3060
agccactcga agcggccggc cgccactcga gatcatgagc ggagaattaa gggagtcacg    3120
ttatgacccc cgccgatgac gcgggacaag ccgttttacg tttggaactg acagaaccgc    3180
aacgttgaag gagccactca gccgcgggtt tctggagttt aatgagctaa gcacatacgt    3240
cagaaaccat tattgcgcgt tcaaaagtcg cctaaggtca ctatcagcta gcaaatattt    3300
cttgtcaaaa atgctccact gacgttccat aaattcccct cggtatccaa ttagagtctc    3360
atattcactc tcaatccaaa taatctgcac cggatctgga tcgtttcgca tgattgaaca    3420
agatggattg cacgcaggtt ctccggccgc ttgggtggag aggctattcg gctatgactg    3480
ggcacaacag acaatcggct gctctgatgc cgccgtgttc cggctgtcag cgcaggggcg    3540
cccggttctt tttgtcaaga ccgacctgtc cggtgccctg aatgaactgc aggacgaggc    3600
agcgcggcta tcgtggctgg ccacgacggg cgttccttgc gcagctgtgc tcgacgttgt    3660
cactgaagcg ggaagggact ggctgctatt gggcgaagtg ccggggcagg atctcctgtc    3720
atctcacctt gctcctgccg agaaagtatc catcatggct gatgcaatgc ggcggctgca    3780
tacgcttgat ccggctacct gcccattcga ccaccaagcg aaacatcgca tcgagcgagc    3840
acgtactcgg atggaagccg gtcttgtcga tcaggatgat ctggacgaag agcatcaggg    3900
gctcgcgcca gccgaactgt tcgccaggct caaggcgcgc atgcccgacg gcgaggatct    3960
cgtcgtgacc catggcgatg cctgcttgcc gaatatcatg gtggaaaatg gccgcttttc    4020
tggattcatc gactgtggcc ggctgggtgt ggcggaccgc tatcaggaca tagcgttggc    4080
tacccgtgat attgctgaag agcttggcgg cgaatgggct gaccgcttcc tcgtgcttta    4140
cggtatcgcc gctcccgatt cgcagcgcat cgccttctat cgccttcttg acgagttctt    4200
ctgagcggga ctctggggtt cgaaatgacc gaccaagcga cgcccaacct gccatcacga    4260
gatttcgatt ccaccgccgc cttctatgaa aggttgggct tcggaatcgt tttccgggac    4320
gccggctgga tgatcctcca gcgcgggat ctcatgctgg agttcttcgc ccacgggatc    4380
tctgcggaac aggcggtcga aggtgccgat atcattacga cagcaacggc cgacaagcac    4440
aacgccacga tcctgagcga caatatgatc gggcccggcg tccacatcaa cggcgtcggc    4500
ggcgactgcc caggcaagac cgagatgcac cgcgatatct gctgcgttc ggatattttc    4560
gtggagttcc cgccacagac ccggatgatc ccgatcgtt caaacatttg gcaataaagt    4620
ttcttaagat tgaatcctgt tgccggtctt gcgatgatta tcatataatt ctgttgaat    4680
tacgttaagc atgtaataat taacatgtaa tgcatgacgt tatttatgag atgggttttt    4740
```

<210> SEQ ID NO 170
<211> LENGTH: 1394
<212> TYPE: DNA
<213> ORGANISM: Artificial sequence
<220> FEATURE:
<223> OTHER INFORMATION: synthetic sequence
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (17)..(52)
<223> OTHER INFORMATION: n is a, c, g, or t
<220> FEATURE:
<223> OTHER INFORMATION: pMEN20 vector (35S::MCS::E9)

<400> SEQUENCE: 170

```
atgattagag tcccgcaatt atacatttaa tacgcgatag aaaacaaaat atagcgcgca    4800
aactaggata aattatcgcg cgcggtgtca tctatgttac tagatcgggc tcgaga        4856
```

```
aagcttnnnn ctgcagnnnn nnnnnnnnnn nnnnnnnnnn nnnnnnnnnn nntcggattc      60
cattgcccag ctatctgtca ctttattgtg aagatagtga aaaagaaggt ggctcctaca    120
aatgccatca ttgcgataaa ggaaaggcca tcgttgaaga tgcctctgcc gacagtggtc    180
ccaaagatgg accccaccc acgaggagca tcgtggaaaa agaagacgtt ccaaccacgt     240
cttcaaagca agtggattga tgtgatatc tcgattgagac tttctcaacaa agggtaatat   300 ccggaaacct cctcggattc cattgcccag ctatctgtca ctttattgtg aagatagtgg    360
aaaaggaagg tggctcctac aaatgccatc attgcgataa aggaaaggcc atcgttgaag    420
atgcctctgc cgacagtggt cccaaagatg gaccccacc cacgaggagc atcgtggaaa    480
aagaagacgt tccaaccacg tcttcaaagc aagtggattg atgtgatatc tccactgacg    540
taagggatga cgcacaatcc cactatcctt cgcaagaccc ttcctctata taaggaagtt   600
catttcattt ggagaggaca cgctgacaag ctgactctag cagatctggt accgtcgacg   660
gtgagctccg cggccgctct agacaggcct cgtaccggat cctctagcta gagctttcgt   720
tcgtatcatc ggtttcgaca acgttcgtca agttcaatgc atcagtttca ttgcgcacac   780
accagaatcc tactgagttt gagtattatg cattgggaa aactgttttt cttgtaccat    840
ttgttgtgct tgtaatttac tgtgtttttt attcggtttt cgctatcgaa ctgtgaaatg   900
gaaatggatg gagaagagtt aatgaatgat atggtccttt tgttcattct caaattaata  960
ttatttgttt tttctcttat ttgttgtgtg ttgaatttga aattataaga gatatgcaaa 1020 catttgttt tgagtaaaaa tgtgtcaaat cgtggcctct aatgaccgaa gttaatatga   1080 ggagtaaaaac acttgtagtt gtaccattat gcttattcac taggcaacaa atatattttc 1140
agacctagaa aagctgcaaa tgttactgaa tacaagtatg tcctcttgtg ttttagacat 1200
ttatgaactt tcctttatgt aattttccag aatccttgtc agattctaat cattgcttta 1260
taattatagt tatactcatg gatttgtagt tgagtatgaa aatatttttt aatgcatttt 1320
atgacttgcc aattgattga caacatgcat caatcgacct gcagccactc gaagcggccg 1380
gccgccactc gaga                                                    1394
```

<210> SEQ ID NO 171
<211> LENGTH: 3158
<212> TYPE: DNA
<213> ORGANISM: Artificial sequence
<220> FEATURE:

```
<223> OTHER INFORMATION: synthetic sequence
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: misc_feature
<222> LOCATION: (17)..(52)
<223> OTHER INFORMATION: n is a, c, g, or t
<220> FEATURE:
<223> OTHER INFORMATION: pMEN65 vector (35S::MCS::E9)

<400> SEQUENCE: 171
```

| | | | | | |
|---|---|---|---|---|---|
| aagcttnnnn | ctgcagnnnn | nnnnnnnnnn | nnnnnnnnnn | nnnnnnnnnn | nntcggattc | 60 |
| cattgcccag | ctatctgtca | ctttattgtg | aagatagtga | aaaagaaggt | ggctcctaca | 120 |
| aatgccatca | ttgcgataaa | ggaaaggcca | tcgttgaaga | tgcctctgcc | gacagtggtc | 180 |
| ccaaagatgg | accccacccc | acgaggagca | tcgtggaaaa | agaagacgtt | ccaaccacgt | 240 |
| cttcaaagca | agtggattga | tgtgatggtc | cgattgagac | ttttcaacaa | agggtaatat | 300 |
| ccggaaacct | cctcggattc | cattgcccag | ctatctgtca | ctttattgtg | aagatagtgg | 360 |
| aaaaggaagg | tggctcctac | aaatgccatc | attgcgataa | aggaaaggcc | atcgttgaag | 420 |
| atgcctctgc | cgacagtggt | cccaaagatg | gaccccacc | cacgaggagc | atcgtggaaa | 480 |
| aagaagacgt | tccaaccacg | tcttcaaagc | aagtggattg | atgtgatatc | tccactgacg | 540 |
| taagggatga | cgcacaatcc | cactatcctt | cgcaagaccc | ttcctctata | taaggaagtt | 600 |
| catttcattt | ggagaggaca | cgctgacaag | ctgactctag | cagatctggt | accgtcgacg | 660 |
| gtgagctccg | cggccgctct | agacaggcct | cgtaccggat | cctctagcta | gagctttcgt | 720 |
| tcgtatcatc | ggtttcgaca | acgttcgtca | agttcaatgc | atcagtttca | ttgcgcacac | 780 |
| accagaatcc | tactgagttt | gagtattatg | gcattgggaa | aactgttttt | cttgtaccat | 840 |
| ttgttgtgct | tgtaatttac | tgtgtttttt | attcggtttt | cgctatcgaa | ctgtgaaatg | 900 |
| gaaatggatg | gagaagagtt | aatgaatgat | atggtccttt | tgttcattct | caaattaata | 960 |
| ttatttgttt | tttctcttat | tgttgtgtg | ttgaatttga | aattataaga | gatatgcaaa | 1020 |
| catttttgttt | tgagtaaaaa | tgtgtcaaat | cgtggcctct | aatgaccgaa | gttaatatga | 1080 |
| ggagtaaaac | acttgtagtt | gtaccattat | gcttattcac | taggcaacaa | atatattttc | 1140 |
| agacctagaa | aagctgcaaa | tgttactgaa | tacaagtatg | tcctcttgtg | ttttagacat | 1200 |
| ttatgaactt | tcctttatgt | aattttccag | aatccttgtc | agattctaat | cattgcttta | 1260 |
| taattatagt | tatactcatg | gatttgtagt | tgagtatgaa | atatttttt | aatgcatttt | 1320 |
| atgacttgcc | aattgattga | caacatgcat | caatcgacct | gcagccactc | gaagcggccg | 1380 |
| gccgccactc | gagatcatga | gcggagaatt | aagggagtca | cgttatgacc | ccgccgatg | 1440 |
| acgcgggaca | agccgtttta | cgtttggaac | tgacagaacc | gcaacgttga | aggagccact | 1500 |
| cagccgcggg | tttctggagt | ttaatgagct | aagcacatac | gtcagaaacc | attattgcgc | 1560 |
| gttcaaaagt | cgcctaaggt | cactatcagc | tagcaaatat | ttcttgtcaa | aaatgctcca | 1620 |
| ctgacgttcc | ataaattccc | ctcggtatcc | aattagagtc | tcatattcac | tctcaatcca | 1680 |
| aataatctgc | accggatctg | gatcgtttcg | catgattgaa | caagatggat | tgcacgcagg | 1740 |
| ttctccggcc | gcttgggtgg | agaggctatt | cggctatgac | tgggcacaac | agacaatcgg | 1800 |
| ctgctctgat | gccgccgtgt | tccggctgtc | agcgcagggg | cgcccggttc | tttttgtcaa | 1860 |
| gaccgacctg | tccggtgccc | tgaatgaact | gcaggacgag | gcagcgcggc | tatcgtggct | 1920 |
| ggccacgacg | ggcgttcctt | gcgcagctgt | gctcgacgtt | gtcactgaag | cgggaaggga | 1980 |

-continued

```
ctggctgcta ttgggcgaag tgccggggca ggatctcctg tcatctcacc ttgctcctgc    2040
cgagaaagta tccatcatgg ctgatgcaat gcggcggctg catacgcttg atccggctac    2100
ctgcccattc gaccaccaag cgaaacatcg catcgagcga gcacgtactc ggatggaagc    2160
cggtcttgtc gatcaggatg atctggacga agagcatcag gggctcgcgc cagccgaact    2220
gttcgccagg ctcaaggcgc gcatgcccga cggcgaggat ctcgtcgtga cccatggcga    2280
tgcctgcttg ccgaatatca tggtggaaaa tggccgcttt tctggattca tcgactgtgg    2340
ccggctgggt gtggcggacc gctatcagga catagcgttg gctacccgtg atattgctga    2400
agagcttggc ggcgaatggg ctgaccgctt cctcgtgctt tacggtatcg ccgctcccga    2460
ttcgcagcgc atcgccttct atcgccttct tgacgagttc ttctgagcgg gactctgggg    2520
ttcgaaatga ccgaccaagc gacgcccaac ctgccatcac gagatttcga ttccaccgcc    2580
gccttctatg aaaggttggg cttcggaatc gttttccggg acgccggctg gatgatcctc    2640
cagcgcgggg atctcatgct ggagttcttc gcccacggga tctctgcgga acaggcggtc    2700
gaaggtgccg atatcattac gacagcaacg gccgacaagc acaacgccac gatcctgagc    2760
gacaatatga tcgggcccgg cgtccacatc aacggcgtcg gcggcgactg cccaggcaag    2820
accgagatgc accgcgatat cttgctgcgt tcggatattt tcgtggagtt cccgccacag    2880
acccggatga tccccgatcg ttcaaacatt tggcaataaa gtttcttaag attgaatcct    2940
gttgccggtc ttgcgatgat tatcatataa tttctgttga attacgttaa gcatgtaata    3000
attaacatgt aatgcatgac gttatttatg agatgggttt ttatgattag agtcccgcaa    3060
ttatacattt aatacgcgat agaaaacaaa atatagcgcg caaactagga taaattatcg    3120
cgcgcggtgt catctatgtt actagatcgg gctcgaga                            3158
```

<210> SEQ ID NO 172
<211> LENGTH: 230
<212> TYPE: PRT
<213> ORGANISM: Lycopersicon esculentum
<220> FEATURE:
<223> OTHER INFORMATION: G3553 polypeptide

<400> SEQUENCE: 172

```
Met Asp Gln His Gly Asn Gly Gln Pro Pro Val Ser Ala Gly Ala Ile
1               5                   10                  15

Gln Ser Pro Gln Ala Ala Gly Leu Ala Ala Ser Ser Ala Gln Met Ala
            20                  25                  30

Gln His Gln Leu Ala Tyr Gln His Ile His Gln Gln Gln Gln Gln Gln
        35                  40                  45

Leu Gln Gln Gln Leu Gln Thr Phe Trp Ala Asn Gln Tyr Gln Glu Ile
    50                  55                  60

Glu His Val Thr Asp Phe Lys Asn His Ser Leu Pro Leu Ala Arg Ile
65                  70                  75                  80

Lys Lys Ile Met Lys Ala Asp Glu Asp Val Arg Met Ile Ser Ala Glu
                85                  90                  95

Ala Pro Val Val Phe Ala Arg Ala Cys Glu Met Phe Ile Leu Glu Leu
            100                 105                 110

Thr Leu Arg Ala Trp Asn His Thr Glu Glu Asn Lys Arg Arg Thr Leu
        115                 120                 125

Gln Lys Asn Asp Ile Ala Ala Ala Ile Thr Arg Thr Asp Ile Phe Asp
    130                 135                 140

Phe Leu Val Asp Ile Val Pro Arg Glu Asp Leu Lys Asp Glu Val Leu
```

```
145                 150                 155                 160
Ala Thr Ile Pro Arg Gly Thr Leu Pro Val Gly Gly Pro Thr Glu Gly
                165                 170                 175

Leu Pro Phe Tyr Tyr Gly Met Pro Pro Gln Ser Ala Gln Pro Ile Gly
                180                 185                 190

Ala Pro Gly Met Tyr Met Gly Lys Pro Val Asp Gln Ala Leu Tyr Ala
                195                 200                 205

Gln Gln Pro Arg Pro Tyr Met Ala Gln Pro Ile Trp Pro Gln Gln Gln
            210                 215                 220

Gln Pro Pro Ser Asp Ser
225                 230

<210> SEQ ID NO 173
<211> LENGTH: 271
<212> TYPE: PRT
<213> ORGANISM: Lycopersicon esculentum
<220> FEATURE:
<223> OTHER INFORMATION: G3554 polypeptide

<400> SEQUENCE: 173

Met Asp Gln His Gly Asn Gly Gln Pro Pro Gly Ile Gly Val Val Thr
1               5                   10                  15

Ser Ser Ala Pro Ile Tyr Gly Ala Pro Tyr Gln Ala Asn Gln Met Ala
                20                  25                  30

Gly Pro Ser Pro Pro Ala Val Ser Ala Gly Ala Ile Gln Ser Pro Gln
            35                  40                  45

Ala Ala Gly Leu Ala Ala Ser Ser Ala Gln Met Ala Gln His Gln Leu
50                  55                  60

Ala Tyr Gln His Ile His Gln Gln Gln Gln Gln Leu Gln Gln Gln
65                  70                  75                  80

Leu Gln Thr Phe Trp Ala Asn Gln Tyr Gln Glu Ile Glu His Val Thr
                85                  90                  95

Asp Phe Lys Asn His Ser Leu Pro Leu Ala Arg Ile Lys Lys Ile Met
                100                 105                 110

Lys Ala Asp Glu Asp Val Arg Met Ile Ser Ala Glu Ala Pro Val Val
            115                 120                 125

Phe Ala Arg Ala Cys Glu Met Phe Ile Leu Glu Leu Thr Leu Arg Ala
130                 135                 140

Trp Asn His Thr Glu Glu Asn Lys Arg Arg Thr Leu Gln Lys Asn Asp
145                 150                 155                 160

Ile Ala Ala Ala Ile Thr Arg Thr Asp Ile Phe Asp Phe Leu Val Asp
                165                 170                 175

Ile Val Pro Arg Glu Asp Leu Lys Asp Glu Val Leu Ala Thr Ile Pro
                180                 185                 190

Arg Gly Thr Leu Pro Val Gly Pro Thr Glu Gly Leu Pro Phe Tyr
            195                 200                 205

Tyr Gly Met Pro Pro Gln Ser Ala Gln Pro Ile Gly Ala Pro Gly Met
            210                 215                 220

Tyr Met Gly Lys Ala Cys Arg Ser Ser Val Cys Pro Ala Ala Pro
225                 230                 235                 240

Pro Ile Tyr Gly Thr Ala Asn Leu Ala Pro Ala Ala Thr Thr Leu
                245                 250                 255

Arg Phe Leu Ser Ser Ser Lys Leu Arg Leu Gln Glu Ser Arg Ser
                260                 265                 270
```

-continued

```
<210> SEQ ID NO 174
<211> LENGTH: 258
<212> TYPE: PRT
<213> ORGANISM: Lycopersicon esculentum
<220> FEATURE:
<223> OTHER INFORMATION: G3894 polypeptide

<400> SEQUENCE: 174

Met Asp Gln His Gly Asn Gly Gln Pro Pro Gly Ile Gly Val Val Thr
1               5                   10                  15

Ser Ser Ala Pro Ile Tyr Gly Ala Pro Tyr Gln Ala Asn Gln Met Ala
            20                  25                  30

Gly Pro Ser Pro Pro Ala Val Ser Ala Gly Ala Ile Gln Ser Pro Gln
        35                  40                  45

Ala Ala Gly Leu Ala Ala Ser Ser Ala Gln Met Ala Gln His Gln Leu
    50                  55                  60

Ala Tyr Gln His Ile His Gln Gln Gln Gln Leu Gln Gln Gln
65                  70                  75                  80

Leu Gln Thr Phe Trp Ala Asn Gln Tyr Gln Glu Ile Glu His Val Thr
                85                  90                  95

Asp Phe Lys Asn His Ser Leu Pro Leu Ala Arg Ile Lys Lys Ile Met
            100                 105                 110

Lys Ala Asp Glu Asp Val Arg Met Ile Ser Ala Glu Ala Pro Val Val
        115                 120                 125

Phe Ala Arg Ala Cys Glu Met Phe Ile Leu Glu Leu Thr Leu Arg Ala
    130                 135                 140

Trp Asn His Thr Glu Glu Asn Lys Arg Arg Thr Leu Gln Lys Asn Asp
145                 150                 155                 160

Ile Ala Ala Ala Ile Thr Arg Thr Asp Ile Phe Asp Phe Leu Val Asp
                165                 170                 175

Ile Val Pro Arg Glu Asp Leu Lys Asp Glu Val Leu Ala Thr Ile Pro
            180                 185                 190

Arg Gly Thr Leu Pro Val Gly Gly Pro Thr Glu Gly Leu Pro Phe Tyr
        195                 200                 205

Tyr Gly Met Pro Pro Gln Ser Ala Gln Pro Ile Gly Ala Pro Gly Met
    210                 215                 220

Tyr Met Gly Lys Pro Val Asp Gln Ala Leu Tyr Ala Gln Gln Pro Arg
225                 230                 235                 240

Pro Tyr Met Ala Gln Pro Ile Trp Pro Gln Gln Gln Pro Pro Ser
                245                 250                 255

Asp Ser

<210> SEQ ID NO 175
<211> LENGTH: 230
<212> TYPE: PRT
<213> ORGANISM: Solanum tuberosum
<220> FEATURE:
<223> OTHER INFORMATION: G3892 polypeptide

<400> SEQUENCE: 175

Met Asp His His Gly Asn Gly Gln Pro Pro Val Ser Ala Gly Ala Ile
1               5                   10                  15

Gln Ser Pro Gln Ala Ala Gly Leu Ser Ala Ser Ser Ala Gln Met Ala
            20                  25                  30

Gln His Gln Leu Ala Tyr Gln His Ile His Gln Gln Gln Gln Gln Gln
        35                  40                  45

Leu Gln Gln Gln Leu Gln Thr Phe Trp Ala Asn Gln Tyr Gln Glu Ile
```

```
                 50                  55                  60
Glu His Val Thr Asp Phe Lys Asn His Ser Leu Pro Leu Ala Arg Ile
 65                  70                  75                  80

Lys Lys Ile Met Lys Ala Asp Glu Asp Val Arg Met Ile Ser Ala Glu
                 85                  90                  95

Ala Pro Val Val Phe Ala Arg Ala Cys Glu Met Phe Ile Leu Glu Leu
                100                 105                 110

Thr Leu Arg Ala Trp Asn His Thr Glu Glu Asn Lys Arg Arg Thr Leu
                115                 120                 125

Gln Lys Asn Asp Ile Ala Ala Ala Ile Thr Arg Thr Asp Ile Phe Asp
            130                 135                 140

Phe Leu Val Asp Ile Val Pro Arg Glu Asp Leu Lys Asp Glu Val Leu
145                 150                 155                 160

Ala Thr Ile Pro Arg Gly Thr Leu Pro Val Gly Gly Pro Thr Glu Gly
                165                 170                 175

Leu Pro Phe Tyr Tyr Gly Met Pro Pro Gln Ser Ala Gln Pro Ile Gly
                180                 185                 190

Ala Pro Gly Met Tyr Met Gly Lys Pro Val Asp Gln Ala Leu Tyr Ala
            195                 200                 205

Gln Gln Pro Arg Pro Phe Met Ala Gln Pro Ile Trp Pro Gln Gln Gln
    210                 215                 220

Gln Pro Pro Ser Asp Ser
225                 230

<210> SEQ ID NO 176
<211> LENGTH: 228
<212> TYPE: PRT
<213> ORGANISM: Solanum tuberosum
<220> FEATURE:
<223> OTHER INFORMATION: G3893 polypeptide

<400> SEQUENCE: 176

Met Asp His His Gly Asn Gly Gln Pro Pro Gly Ile Gly Val Val Thr
  1               5                  10                  15

Ser Ser Ala Pro Ile Tyr Gly Ala Pro Tyr Gln Ala Asn Gln Met Ala
                 20                  25                  30

Gly Pro Pro Ala Val Ser Ala Gly Ala Ile Gln Ser Pro Gln Ala Ala
             35                  40                  45

Gly Leu Ser Ala Ser Ser Ala Gln Met Ala Gln His Gln Leu Ala Tyr
         50                  55                  60

Gln His Ile His Gln Gln Gln Gln Leu Gln Gln Gln Leu Gln
 65                  70                  75                  80

Thr Phe Trp Ala Asn Gln Tyr Gln Glu Ile Glu His Val Thr Asp Phe
                 85                  90                  95

Lys Asn His Ser Leu Pro Leu Ala Arg Ile Lys Lys Ile Met Lys Ala
                100                 105                 110

Asp Glu Asp Val Arg Met Ile Ser Ala Glu Ala Pro Val Val Phe Ala
            115                 120                 125

Arg Ala Cys Glu Met Phe Ile Leu Glu Leu Thr Leu Arg Ala Trp Asn
130                 135                 140

His Thr Glu Glu Asn Lys Arg Arg Thr Leu Gln Lys Asn Asp Ile Ala
145                 150                 155                 160

Ala Ala Ile Thr Arg Thr Asp Ile Phe Asp Phe Leu Val Asp Ile Val
                165                 170                 175

Pro Arg Glu Asp Leu Lys Asp Glu Val Leu Ala Thr Ile Pro Arg Gly
```

```
                180             185             190
Thr Leu Pro Val Gly Pro Thr Glu Gly Leu Pro Phe Tyr Tyr Gly
        195                 200                 205

Met Pro Pro Gln Ser Ala Gln Pro Ile Gly Ala Pro Gly Met Tyr Met
    210                 215                 220

Gly Lys Pro Val
225

<210> SEQ ID NO 177
<211> LENGTH: 260
<212> TYPE: PRT
<213> ORGANISM: Medicago truncatula
<220> FEATURE:
<223> OTHER INFORMATION: G3896 polypeptide

<400> SEQUENCE: 177

Met Asp His Gln Gly His Asn Gln Asn Pro Gln Met Gly Val Val Gly
1               5                   10                  15

Ser Gly Ser Gln Met Pro Tyr Gly Ser Asn Pro Tyr Gln Ser Asn Gln
            20                  25                  30

Met Thr Gly Ala Pro Gly Ser Val Val Thr Ser Val Gly Gly Met Gln
        35                  40                  45

Ser Thr Gly Gln Pro Ala Gly Ala Gln Leu Gly Gln His Gln Leu Ala
    50                  55                  60

Tyr Gln His Ile His Gln Gln Gln Gln Leu Gln Gln Gln Leu
65                  70                  75                  80

Gln Ser Phe Trp Ser Asn Gln Tyr Gln Glu Ile Glu Lys Val Thr Asp
                85                  90                  95

Phe Lys Asn His Ser Leu Pro Leu Ala Arg Ile Lys Lys Ile Met Lys
            100                 105                 110

Ala Asp Glu Asp Val Arg Met Ile Ser Ala Glu Ala Pro Val Ile Phe
        115                 120                 125

Ala Arg Ala Cys Glu Met Phe Ile Leu Glu Leu Thr Leu Arg Ser Trp
    130                 135                 140

Asn His Thr Glu Glu Asn Lys Arg Arg Thr Leu Gln Lys Asn Asp Ile
145                 150                 155                 160

Ala Ala Ala Ile Thr Arg Thr Asp Ile Phe Asp Phe Leu Val Asp Ile
                165                 170                 175

Val Pro Arg Glu Asp Leu Lys Asp Glu Val Leu Ala Ser Ile Pro Arg
            180                 185                 190

Gly Thr Met Pro Val Ala Gly Pro Ala Asp Ala Leu Pro Tyr Cys Tyr
        195                 200                 205

Met Pro Pro Gln His Ala Ser Gln Val Gly Thr Ala Gly Val Ile Met
    210                 215                 220

Gly Lys Pro Val Met Asp Pro Asn Met Tyr Ala Gln Gln Pro His Pro
225                 230                 235                 240

Tyr Met Ala Pro Gln Met Trp Pro Gln Pro Glu Gln Arg Pro Pro
                245                 250                 255

Ser Pro Asp His
            260

<210> SEQ ID NO 178
<211> LENGTH: 248
<212> TYPE: PRT
<213> ORGANISM: Zea mays
<220> FEATURE:
<223> OTHER INFORMATION: G3551 polypeptide
```

<400> SEQUENCE: 178

```
Met Glu Pro Ser Pro Gln Pro Met Gly Val Ala Ala Gly Gly Ser Gln
1               5                   10                  15

Val Tyr Pro Ala Ser Ala Tyr Pro Pro Ala Ala Thr Val Ala Pro Ala
            20                  25                  30

Ser Val Val Ser Ala Gly Leu Gln Ser Gly Gln Pro Phe Pro Ala Asn
        35                  40                  45

Pro Gly His Met Ser Ala Gln His Gln Ile Val Tyr Gln Gln Ala Gln
    50                  55                  60

Gln Phe His Gln Gln Leu Gln Gln Gln Gln Gln Gln Leu Gln Gln
65                  70                  75                  80

Phe Trp Val Glu Arg Met Thr Glu Ile Glu Ala Thr Thr Asp Phe Lys
                85                  90                  95

Asn His Asn Leu Pro Leu Ala Arg Ile Lys Lys Ile Met Lys Ala Asp
            100                 105                 110

Glu Asp Val Arg Met Ile Ser Ala Glu Ala Pro Val Val Phe Ala Lys
            115                 120                 125

Ala Cys Glu Ile Phe Ile Leu Glu Leu Thr Leu Arg Ser Trp Met His
130                 135                 140

Thr Glu Val Asn Lys Arg Thr Leu Gln Lys Asn Asp Ile Ala Ala
145                 150                 155                 160

Ala Ile Thr Arg Thr Asp Ile Tyr Asp Phe Leu Val Asp Ile Val Pro
            165                 170                 175

Arg Asp Glu Met Lys Glu Asp Gly Ile Gly Leu Pro Arg Ala Gly Leu
            180                 185                 190

Pro Pro Met Gly Ala Pro Ala Asp Ala Tyr Pro Tyr Tyr Met Pro
        195                 200                 205

Gln Gln Gln Val Pro Gly Ser Gly Met Val Tyr Gly Ala Gln Gln Gly
    210                 215                 220

His Pro Val Thr Tyr Leu Trp Gln Glu Pro Gln Gln Gln Glu Gln
225                 230                 235                 240

Ala Pro Glu Glu Gln Gln Ser Ala
245
```

<210> SEQ ID NO 179
<211> LENGTH: 249
<212> TYPE: PRT
<213> ORGANISM: Daucus carota
<220> FEATURE:
<223> OTHER INFORMATION: G3899 polypeptide

<400> SEQUENCE: 179

```
Met Asp Glu Ser Glu Glu Pro Gln Gln Gln Glu Ala Val Ile Asp
1               5                   10                  15

Ser Ala Ser Gln Met Thr Tyr Gly Val Pro His Tyr His Ala Val Gly
            20                  25                  30

Leu Gly Val Ala Thr Gly Thr Pro Val Val Pro Val Ser Ala Pro Thr
        35                  40                  45

Gln His Pro Thr Gly Thr Thr Ser Gln Gln Pro Glu Tyr Tyr Glu
    50                  55                  60

Ala Gln His Val Tyr Gln Gln Gln Leu Gln Leu Arg Thr Gln Leu
65                  70                  75                  80

Gln Ala Phe Trp Ala Asn Gln Ile Gln Glu Ile Gly Gln Thr Pro Asp
                85                  90                  95
```

```
Phe Lys Asn His Ser Leu Pro Leu Ala Arg Ile Lys Lys Ile Met Lys
                100                 105                 110

Ala Asp Glu Asp Val Arg Met Ile Ser Ser Glu Ala Pro Val Ile Phe
            115                 120                 125

Ala Lys Ala Cys Glu Met Phe Ile Leu Glu Leu Thr Met Arg Ser Trp
130                 135                 140

Leu Leu Thr Glu Glu Asn Lys Arg Arg Thr Leu Gln Lys Asn Asp Ile
145                 150                 155                 160

Ala Ala Ala Ile Ser Arg Thr Asp Ile Phe Asp Phe Leu Val Asp Ile
                165                 170                 175

Ile Pro Arg Asp Glu Leu Lys Glu Gly Leu Gly Ile Thr Lys Ala
            180                 185                 190

Thr Ile Pro Leu Leu Gly Ser Pro Ala Asp Ser Ala Pro Tyr Tyr Tyr
            195                 200                 205

Val Pro Gln Gln His Ala Val Glu Gln Ala Gly Phe Tyr Pro Asp Gln
            210                 215                 220

Gln Ala His Pro Gln Leu Pro Tyr Met Ser Trp Gln Gln Pro His Glu
225                 230                 235                 240

His Lys Asp Gln Glu Glu Asn Gly Asp
                245

<210> SEQ ID NO 180
<211> LENGTH: 229
<212> TYPE: PRT
<213> ORGANISM: Daucus carota
<220> FEATURE:
<223> OTHER INFORMATION: G3900 polypeptide

<400> SEQUENCE: 180

Met Asp His Ser Glu Glu Ser Gln Gln Gln Gln Glu Glu Val Ile Asp
1               5                   10                  15

Ile Ala Tyr Gly Met Pro Gln Tyr His Ala Gly Pro Gly Val Ala Thr
                20                  25                  30

Gly Thr Pro Val Val Pro Val Ser Ala Ala Thr Gln Ala Gln His Phe
            35                  40                  45

Phe Gln Gln Lys Leu Gln Leu Gln Gln Gln Asp Gln Leu Gln Ala Phe
        50                  55                  60

Trp Ala Asn Gln Met Gln Glu Ile Glu Gln Thr Thr Asp Phe Lys Asn
65                  70                  75                  80

His Ser Leu Pro Leu Ala Arg Ile Lys Lys Ile Met Lys Ala Asp Glu
                85                  90                  95

Asp Val Arg Met Ile Ser Ser Glu Ala Pro Val Val Phe Ala Lys Ala
            100                 105                 110

Cys Glu Met Phe Ile Met Asp Leu Thr Met Arg Ser Trp Ser His Thr
        115                 120                 125

Glu Glu Asn Lys Arg Arg Thr Leu Gln Lys Asn Asp Ile Ala Ala Ala
    130                 135                 140

Val Ser Arg Thr Asp Val Phe Asp Phe Leu Val Asp Ile Ile Pro Lys
145                 150                 155                 160

Asp Glu Met Lys Glu Asp Thr Arg Ala Ser Ile Pro Leu Met Gly Gln
                165                 170                 175

Pro Pro Ala Asp Ser Val Pro Tyr Tyr Tyr Val Pro Gln Gln His Ala
            180                 185                 190

Ala Gly Gln Ala Gly Phe Tyr Pro Asp Gln His Gln Gln Gln Pro Leu
        195                 200                 205
```

```
Pro Tyr Met Gln Trp Gln Gln Pro Gln Gln Asp Gln Asn Gln Gln Gln
    210                 215                 220

Gln Glu Asn Gly Asn
225
```

<210> SEQ ID NO 181
<211> LENGTH: 184
<212> TYPE: PRT
<213> ORGANISM: Gossypium arboreum
<220> FEATURE:
<223> OTHER INFORMATION: G3907 polypeptide

<400> SEQUENCE: 181

```
Met Asp Gln Arg Glu Lys Thr Gln Gln Gln Gln Gln Pro Val Met
1               5                   10                  15

Gly Val Val Pro Gly Ala Gly Gln Met Gly Tyr Ser Thr Ala Tyr Gln
                20                  25                  30

Thr Ala Ser Met Val Ala Ser Gly Thr Thr Gly Val Ala Val Pro Ile
            35                  40                  45

Gln Thr Gln Pro Ser Ala Thr Phe Ser Ser Ser Pro His Gln Leu Ala
    50                  55                  60

Tyr Gln Gln Ala Gln His Phe His His Gln Gln Gln Gln Gln Gln Gln
65                  70                  75                  80

Gln Gln Leu Gln Met Phe Trp Ala Asn Gln Met His Glu Ile Glu Gln
                85                  90                  95

Thr Thr Asp Phe Lys Asn His Ser Leu Pro Leu Ala Arg Ile Lys Lys
            100                 105                 110

Ile Met Lys Ala Asp Glu Asp Val Arg Met Ile Ser Ala Glu Ala Pro
        115                 120                 125

Val Ile Phe Ala Lys Ala Cys Glu Met Phe Val Leu Glu Leu Thr Leu
    130                 135                 140

Arg Ser Trp Ile His Thr Glu Glu Asn Lys Arg Thr Leu Gln Lys
145                 150                 155                 160

Asn Asp Ile Ala Ala Ala Ile Ser Arg Thr Asp Val Phe Asp Phe Leu
                165                 170                 175

Val Asp Ile Ile Pro Gly Thr Glu
            180
```

<210> SEQ ID NO 182
<211> LENGTH: 270
<212> TYPE: PRT
<213> ORGANISM: Glycine max
<220> FEATURE:
<223> OTHER INFORMATION: G3549 polypeptide

<400> SEQUENCE: 182

```
Met Asp Lys Ser Glu Gln Thr Gln Gln Gln Gln Gln Gln His Val
1               5                   10                  15

Met Gly Val Ala Ala Gly Ala Ser Gln Met Ala Tyr Ser Ser His Tyr
                20                  25                  30

Pro Thr Ala Ser Met Val Ala Ser Gly Thr Pro Ala Val Thr Ala Pro
            35                  40                  45

Ser Pro Thr Gln Ala Pro Ala Ala Phe Ser Ser Ser Ala His Gln Leu
    50                  55                  60

Ala Tyr Gln Gln Ala Gln His Phe His His Gln Gln Gln Gln His Gln
65                  70                  75                  80

Gln Gln Gln Leu Gln Met Phe Trp Ser Asn Gln Met Gln Glu Ile Glu
                85                  90                  95
```

-continued

```
Gln Thr Ile Asp Phe Lys Asn His Ser Leu Pro Leu Ala Arg Ile Lys
            100                 105                 110

Lys Ile Met Lys Ala Asp Glu Asp Val Arg Met Ile Ser Ala Glu Ala
        115                 120                 125

Pro Val Ile Phe Ala Lys Ala Cys Glu Met Phe Ile Leu Glu Leu Thr
    130                 135                 140

Leu Arg Ser Trp Ile His Thr Glu Asn Lys Arg Arg Thr Leu Gln
145                 150                 155                 160

Lys Asn Asp Ile Ala Ala Ile Ser Arg Asn Asp Val Phe Asp Phe
                165                 170                 175

Leu Val Asp Ile Ile Pro Arg Asp Glu Leu Lys Glu Glu Gly Leu Gly
                180                 185                 190

Ile Thr Lys Ala Thr Ile Pro Leu Val Asn Ser Pro Ala Asp Met Pro
            195                 200                 205

Tyr Tyr Tyr Val Pro Pro Gln His Pro Val Val Gly Pro Pro Gly Met
        210                 215                 220

Ile Met Gly Lys Pro Val Gly Ala Glu Gln Ala Thr Leu Tyr Ser Thr
225                 230                 235                 240

Gln Gln Pro Arg Pro Pro Met Ala Phe Met Pro Trp Pro His Thr Gln
                245                 250                 255

Pro Gln Gln Gln Gln Pro Pro Gln His Gln Gln Thr Asp Ser
            260                 265                 270

<210> SEQ ID NO 183
<211> LENGTH: 201
<212> TYPE: PRT
<213> ORGANISM: Sorghum bicolor
<220> FEATURE:
<223> OTHER INFORMATION: G3910 polypeptide

<400> SEQUENCE: 183

Met Glu Pro Lys Ser Thr Thr Pro Pro Pro Pro Val Met Gly Ala
1               5                   10                  15

Pro Val Ala Tyr Pro Pro Pro Gly Ala Ala Tyr Pro Ala Gly Pro
            20                  25                  30

Tyr Ala His Ala Pro Ala Ala Ala Leu Tyr Pro Pro Pro Pro Pro
        35                  40                  45

Pro Ala Pro Pro Thr Ser Gln Gln Gly Ala Ala Ala Gln Gln Leu
    50                  55                  60

Gln Leu Phe Trp Ala Glu Gln Tyr Arg Glu Ile Glu Ala Thr Thr Asp
65                  70                  75                  80

Phe Lys Asn His Asn Leu Pro Leu Ala Arg Ile Lys Lys Ile Met Lys
                85                  90                  95

Ala Asp Glu Asp Val Arg Met Ile Ala Ala Glu Ala Pro Val Val Phe
            100                 105                 110

Ala Arg Ala Cys Glu Met Phe Ile Leu Glu Leu Thr His Arg Gly Trp
        115                 120                 125

Ala His Ala Glu Glu Asn Lys Arg Arg Thr Leu Gln Lys Ser Asp Ile
    130                 135                 140

Ala Ala Ala Val Ala Arg Thr Glu Val Phe Asp Phe Leu Val Asp Ile
145                 150                 155                 160

Val Pro Arg Asp Glu Ala Lys Glu Ala Asp Ser Ala Ala Ala Met Gly
                165                 170                 175

Pro Ala Gly Ile Pro His Pro Ala Ala Gly Leu Pro Ala Thr Asp Pro
                180                 185                 190
```

```
Met Gly Tyr Tyr Tyr Val Gln Pro Gln
        195                 200
```

<210> SEQ ID NO 184
<211> LENGTH: 232
<212> TYPE: PRT
<213> ORGANISM: Lycopersicon esculentum
<220> FEATURE:
<223> OTHER INFORMATION: G3555 polypeptide

<400> SEQUENCE: 184

```
Met Asp Asn Asn Pro His Gln Ser Pro Thr Glu Ala Ala Ala Ala Ala
1               5                   10                  15

Ala Ala Ala Ala Ala Ala Ala Gln Ser Ala Thr Tyr Pro Ser Gln Thr
            20                  25                  30

Pro Tyr His His Leu Leu Gln Gln Gln Gln Gln Leu Gln Met Phe
        35                  40                  45

Trp Thr Tyr Gln Arg Gln Glu Ile Glu Gln Val Asn Asp Phe Lys Asn
    50                  55                  60

His Gln Leu Pro Leu Ala Arg Ile Lys Lys Ile Met Lys Ala Asp Glu
65                  70                  75                  80

Asp Val Arg Met Ile Ser Ala Glu Ala Pro Val Leu Phe Ala Lys Ala
                85                  90                  95

Cys Glu Leu Phe Ile Leu Glu Leu Thr Ile Arg Ser Trp Leu His Ala
            100                 105                 110

Glu Glu Asn Lys Arg Arg Thr Leu Gln Lys Asn Asp Ile Ala Ala Ala
        115                 120                 125

Ile Thr Arg Thr Asp Ile Phe Asp Phe Leu Val Asp Ile Val Pro Arg
130                 135                 140

Asp Glu Ile Lys Asp Glu Gly Val Gly Leu Pro Gly Ile Val Gly
145                 150                 155                 160

Ser Thr Ala Ser Gly Val Pro Tyr Tyr Pro Pro Met Gly Gln Pro
                165                 170                 175

Ala Pro Gly Gly Val Met Leu Gly Arg Pro Ala Val Pro Gly Val Asp
            180                 185                 190

Pro Ser Met Tyr Val His Pro Pro Ser Gln Ala Trp Gln Ser Val
        195                 200                 205

Trp Gln Thr Gly Asp Asp Asn Ser Tyr Ala Ser Gly Gly Ser Ser Gly
    210                 215                 220

Gln Gly Asn Leu Asp Gly Gln Ile
225                 230
```

<210> SEQ ID NO 185
<211> LENGTH: 232
<212> TYPE: PRT
<213> ORGANISM: Solanum tuberosum
<220> FEATURE:
<223> OTHER INFORMATION: G3885 polypeptide

<400> SEQUENCE: 185

```
Met Asp Asn Asn Pro His Gln Ser Pro Thr Glu Ala Ala Ala Ala
1               5                   10                  15

Ala Ala Ala Ala Ala Ala Ala Gln Ser Ala Thr Tyr Pro Pro Gln Thr
            20                  25                  30

Pro Tyr His His Leu Leu Gln Gln Gln Gln Gln Leu Gln Met Phe
        35                  40                  45

Trp Thr Tyr Gln Arg Gln Glu Ile Glu Gln Val Asn Asp Phe Lys Asn
```

```
            50                  55                  60
His Gln Leu Pro Leu Ala Arg Ile Lys Lys Ile Met Lys Ala Asp Glu
 65                  70                  75                  80

Asp Val Arg Met Ile Ser Ala Glu Ala Pro Val Leu Phe Ala Lys Ala
                 85                  90                  95

Cys Glu Leu Phe Ile Leu Glu Leu Thr Ile Arg Ser Trp Leu His Ala
                100                 105                 110

Glu Glu Asn Lys Arg Arg Thr Leu Gln Lys Asn Asp Ile Ala Ala Ala
            115                 120                 125

Ile Thr Arg Thr Asp Ile Phe Asp Phe Leu Val Asp Ile Val Pro Arg
        130                 135                 140

Asp Glu Ile Lys Asp Glu Gly Val Val Leu Gly Pro Gly Ile Val Gly
145                 150                 155                 160

Ser Thr Ala Ser Gly Val Pro Tyr Tyr Tyr Pro Pro Met Gly Gln Pro
                165                 170                 175

Ala Pro Gly Gly Val Met Leu Gly Arg Pro Ala Val Pro Gly Val Asp
            180                 185                 190

Pro Ser Met Tyr Val His Pro Pro Ser Gln Ala Trp Gln Ser Val
        195                 200                 205

Trp Gln Thr Gly Asp Asp Asn Ser Tyr Ala Ser Gly Ser Ser Gly
    210                 215                 220

Gln Gly Asn Leu Asp Gly Gln Ile
225                 230

<210> SEQ ID NO 186
<211> LENGTH: 233
<212> TYPE: PRT
<213> ORGANISM: Gossypium raimondii
<220> FEATURE:
<223> OTHER INFORMATION: G3883 polypeptide

<400> SEQUENCE: 186

Met Asp Ser Asn Gln Gln Thr Gln Ser Thr Pro Tyr Pro Pro Gln Pro
  1               5                  10                  15

Pro Thr Ser Ala Ile Thr Pro Pro Ser Ser Ala Thr Ala Thr Ala Pro
                 20                  25                  30

Pro Phe His His Leu Leu Gln Gln Gln Gln Gln Leu Gln Met Phe
             35                  40                  45

Trp Ser Tyr Gln Arg Gln Glu Ile Glu Gln Val Asn Asp Phe Lys Asn
 50                  55                  60

His Gln Leu Pro Leu Ala Arg Ile Lys Lys Ile Met Lys Ala Asp Glu
 65                  70                  75                  80

Asp Val Arg Met Ile Ser Ala Glu Ala Pro Ile Leu Phe Ala Lys Ala
                 85                  90                  95

Cys Glu Leu Phe Ile Leu Glu Leu Thr Ile Arg Ser Trp Leu His Ala
                100                 105                 110

Glu Glu Asn Lys Arg Arg Thr Leu Gln Lys Asn Asp Ile Ala Ala Ala
            115                 120                 125

Ile Thr Arg Thr Asp Ile Phe Asp Phe Leu Val Asp Ile Val Pro Arg
        130                 135                 140

Asp Glu Ile Lys Asp Glu Thr Gly Leu Ala Pro Met Val Gly Ala Thr
145                 150                 155                 160

Ala Ser Gly Val Pro Tyr Phe Tyr Pro Pro Met Gly Gln Pro Ala Ala
                165                 170                 175

Gly Gly Pro Gly Gly Met Met Ile Gly Arg Pro Ala Val Asp Pro Thr
```

```
                180              185                190
Gly Gly Ile Tyr Gly Gln Pro Pro Ser Gln Ala Trp Gln Ser Val Trp
            195                  200                 205

Gln Thr Ala Gly Thr Asp Asp Gly Ser Tyr Gly Ser Gly Val Thr Gly
            210                  215                 220

Gly Gln Gly Asn Leu Asp Gly Gln Gly
225                 230

<210> SEQ ID NO 187
<211> LENGTH: 227
<212> TYPE: PRT
<213> ORGANISM: Nicotiana benthamiana
<220> FEATURE:
<223> OTHER INFORMATION: G3884 polypeptide

<400> SEQUENCE: 187

Met Glu Asn Asn Gln Gln Ser Ala Ala Asn Ala Ala Ala Ala Ala Ala
1               5                   10                  15

Ala Ala Ala Ala Tyr Pro Ala Gln Pro Pro Tyr His His Leu Leu Gln
            20                  25                  30

Gln Gln Gln Gln Gln Leu Gln Met Phe Trp Thr Tyr Gln Arg Gln Glu
        35                  40                  45

Ile Glu Gln Val Asn Asp Phe Lys Asn His Gln Leu Pro Leu Ala Arg
    50                  55                  60

Ile Lys Lys Ile Met Lys Ala Asp Glu Asp Val Arg Met Ile Ser Ala
65                  70                  75                  80

Glu Ala Pro Ile Leu Phe Ala Lys Ala Cys Glu Leu Phe Ile Leu Glu
                85                  90                  95

Leu Thr Ile Arg Ser Trp Leu His Ala Glu Glu Asn Lys Arg Arg Thr
            100                 105                 110

Leu Gln Lys Asn Asp Ile Ala Ala Ile Thr Arg Thr Asp Ile Phe
        115                 120                 125

Asp Phe Leu Val Asp Ile Val Pro Arg Asp Glu Ile Lys Glu Glu Gly
    130                 135                 140

Gly Val Gly Leu Gly Pro Ala Gly Ile Val Gly Ser Thr Ala Ser Gly
145                 150                 155                 160

Val Pro Tyr Tyr Tyr Pro Pro Met Gly Gln Pro Ala Pro Pro Gly Val
                165                 170                 175

Met Met Gly Arg Pro Ala Met Pro Gly Val Asp Pro Ser Met Tyr Val
            180                 185                 190

Gln Pro Pro Pro Ser Gln Ala Trp Gln Ser Val Trp Gln Thr Ala Glu
        195                 200                 205

Asp Asn Ser Tyr Ala Ser Gly Gly Ser Ser Gly Gln Gly Asn Leu Asp
    210                 215                 220

Gly Gln Ser
225

<210> SEQ ID NO 188
<211> LENGTH: 214
<212> TYPE: PRT
<213> ORGANISM: Physcomitrella patens
<220> FEATURE:
<223> OTHER INFORMATION: G3867 polypeptide

<400> SEQUENCE: 188

Met Ser His Pro Gly Ala Val Met Pro Leu Gln Met His Tyr Pro Gln
1               5                   10                  15
```

```
Ala Gln Gln Gln Met Met Pro Gln Leu Gly Asp Gln Gln Met Gln Pro
             20                  25                  30

Gln Leu His Tyr Gln Gln Ile Gln Lys Gln Gln Leu Ser Gln Phe Trp
         35                  40                  45

Gln Gln Gln Met Gln Glu Met Glu Gln Val Asn Asp Phe Lys Thr His
 50                  55                  60

Gln Leu Pro Leu Ala Arg Ile Lys Lys Ile Met Lys Ser Asp Glu Asp
 65                  70                  75                  80

Val Lys Met Ile Ala Ala Glu Ala Pro Val Leu Phe Ser Lys Ala Cys
                 85                  90                  95

Glu Met Phe Ile Leu Glu Leu Thr Leu Arg Ser Trp Ile His Thr Glu
                100                 105                 110

Glu Asn Lys Arg Arg Thr Leu Gln Arg Asn Asp Ile Ala Gly Ala Ile
            115                 120                 125

Thr Arg Gly Asp Ile Phe Asp Phe Leu Val Asp Ile Val Pro Arg Asp
        130                 135                 140

Glu Leu Lys Glu Glu Asp Leu Gly Val Pro Trp Thr Gly Val Pro Gly
145                 150                 155                 160

Asp Gly Ser Val Pro Tyr Gly Gly Ile Phe Tyr Pro Pro Met Ala Gly
                165                 170                 175

Gln Gln Met His His Ser Met Gly Ala Pro Glu Met Met Val Gly Gln
            180                 185                 190

Pro Pro Asn Pro Gln Met Met Tyr Gln Pro Pro Gln Thr Ala Phe Val
        195                 200                 205

Pro Glu Gln Gln Gln Gln
    210

<210> SEQ ID NO 189
<211> LENGTH: 249
<212> TYPE: PRT
<213> ORGANISM: Oryza sativa
<220> FEATURE:
<223> OTHER INFORMATION: G3545 polypeptide

<400> SEQUENCE: 189

Met Asp Pro His Ser His Lys Lys Ala His Glu Gly Leu Ile Gly Asp
1               5                   10                  15

Asn Pro Asp Ala Tyr Ala Val Thr Thr Tyr Gln Pro Val Leu Met Val
            20                  25                  30

Glu Pro Ser Ala Ala Ala Ala Phe Pro Pro Ala Pro Gln Val Ala Pro
        35                  40                  45

Ala Tyr Pro Val Asn Pro Met Gln Leu Pro Glu His Gln Gln His Ala
 50                  55                  60

Ile Gln Gln Val Gln Gln Leu Gln Gln Gln Lys Glu Gln Leu Gln
 65                  70                  75                  80

Ala Phe Trp Ala Asp Gln Met Ala Glu Val Glu Gln Met Thr Glu Phe
                 85                  90                  95

Lys Leu Pro Asn Leu Pro Leu Ala Arg Ile Lys Lys Ile Met Lys Ala
                100                 105                 110

Asp Glu Asp Val Lys Met Ile Ala Gly Glu Ala Pro Ala Leu Phe Ala
            115                 120                 125

Lys Ala Cys Glu Met Phe Ile Leu Asp Met Thr Leu Arg Ser Trp Gln
        130                 135                 140

His Thr Glu Glu Gly Arg Arg Arg Thr Leu Gln Arg Ser Asp Val Glu
145                 150                 155                 160
```

```
Ala Val Ile Lys Lys Thr Asp Ile Phe Asp Phe Leu Val Asp Ile Ile
            165                 170                 175

Thr Asp Asp Lys Met Lys Asp Asp Gly Met Gly Ser Gln Ala Ala Ser
            180                 185                 190

Met Val Ser Pro Tyr Thr Ser Gly Gly Met Gly Phe Ser Phe Asp Leu
            195                 200                 205

Tyr Pro Asn Gln His His Leu Ala Tyr Met Trp Pro Pro Gln Glu Gln
            210                 215                 220

Gln Glu Gln Trp Pro Gln Glu Gln Gln Gln Lys Gln Lys Gln
225                 230                 235                 240

Asp Ser Asp Gly Gly Gly Gln Asp Glu
            245
```

<210> SEQ ID NO 190
<211> LENGTH: 275
<212> TYPE: PRT
<213> ORGANISM: Arabidopsis thaliana
<220> FEATURE:
<223> OTHER INFORMATION: G2637 polypeptide

<400> SEQUENCE: 190

```
Met Glu Ser Glu Lys Val Val Asp Glu Leu Pro Leu Ala Ile Val
1               5                   10                  15

Arg Arg Val Val Lys Lys Lys Leu Ser Glu Cys Ser Pro Asp Tyr Asp
            20                  25                  30

Val Ser Ile His Lys Glu Ala Leu Leu Ala Phe Ser Glu Ser Ala Arg
            35                  40                  45

Ile Phe Ile His Tyr Leu Ser Ala Thr Ala Asn Asp Phe Cys Lys Asp
50                  55                  60

Ala Arg Arg Gln Thr Met Lys Ala Asp Asp Val Phe Lys Ala Leu Glu
65                  70                  75                  80

Glu Met Asp Phe Ser Glu Phe Leu Glu Pro Leu Lys Ser Ser Leu Glu
            85                  90                  95

Asp Phe Lys Lys Lys Asn Ala Gly Lys Lys Ala Gly Ala Ala Ala Ala
            100                 105                 110

Ser Tyr Pro Ala Gly Gly Ala Ala Leu Lys Ser Ser Ser Gly Thr Ala
            115                 120                 125

Ser Lys Pro Lys Glu Thr Lys Lys Arg Lys Gln Glu Glu Pro Ser Thr
130                 135                 140

Gln Lys Gly Ala Arg Lys Ser Lys Ile Asp Glu Glu Thr Lys Arg Asn
145                 150                 155                 160

Asp Glu Glu Thr Glu Asn Asp Asn Thr Glu Glu Asn Gly Asn Asp
            165                 170                 175

Glu Glu Asp Glu Asn Gly Asn Asp Glu Glu Asp Glu Asn Asp Asp Glu
            180                 185                 190

Asn Thr Glu Glu Asn Gly Asn Asp Glu Glu Asn Asp Asp Glu Asn Thr
            195                 200                 205

Glu Glu Asn Gly Asn Asp Glu Asn Glu Lys Glu Asp Glu Glu Asn
            210                 215                 220

Ser Met Glu Glu Asn Gly Asn Glu Ser Glu Ser Gly Asn Glu Asp
225                 230                 235                 240

His Ser Met Glu Glu Asn Gly Ser Gly Val Gly Glu Asp Asn Glu Asn
            245                 250                 255

Glu Asp Gly Ser Val Ser Gly Ser Gly Glu Val Gly Ser Asp Glu
            260                 265                 270
```

Glu Asp Glu
    275

<210> SEQ ID NO 191
<211> LENGTH: 3446
<212> TYPE: DNA
<213> ORGANISM: Artificial sequence
<220> FEATURE:
<223> OTHER INFORMATION: synthetic sequence
<220> FEATURE:
<223> OTHER INFORMATION: P5326 driver construct in 2-component system
      (AP1::LexA-GAL4TA)

<400> SEQUENCE: 191

```
cacggacctt ggatctgaag ttatgaacaa taacatattt ggcaaaacaa agaaaaaaga      60
aacaacaata ctaacatatt ttggtaaaag aacattgaga agtctcaaaa attaacttct     120
tcttattttg tttcctaata agaccgtttg cttcatttca agttcttagg aaataatttc     180
atgtaacgtg tatgtagata tgtttatgta cagataaaga gagatctgaa aatgatatat     240
agagcttttg tggtgataag tgcaacaagc aggatatata tatcgaacgt ggtggttaga     300
agatagcgtc aaaatagatg ctagctgctg cgtatacatc atattcatat catatgtact     360
tctcttttgt gatttctcat gtgattgaac atactacata aatcttgata gatttataaa     420
aatgcaacaa attgttgttt atataagaaa aataaaacac tgatatgata tttcattagt     480
tattatcaaa tttgcaatat aatgtttaac atccaagatt tgttttacat aatcgttacg     540
gttactaaag tttaatttat gatgttttaa acaaattga gactaaattt ctaaaagaaa      600
catatacgta catgtgtgta gctgcgtata tatatagaat ggtggggcta aaagctaatg     660
atgtgtacat taattggaca tttgatgtgg ctggattgga cccaacttgc tctttgatag     720
agacctaact aagacaattt tgctcttcat tcatttctcc cgtatacata attgaattaa     780
ctgtacataa tgtttcacaa caagcgatct agctatatat ttcaaaataa cagagactga     840
tattttaatc tggtcttcta agctctaacg tcaaattaaa aaaaaaatcc gatcttctaa     900
ttaattagaa gaaatcaatt atagaacctc tctctttaat ttcatttatt taaaactgct     960
tggaaattta attattcact aaagactcac tattctcctt aatttatgat aatttgtaga    1020
tcatatgttc agttttttatt tatttgccat tcgaatgttg agttttaatt aaaccaatat    1080
gttaatattc gaattaaaaa aacttaccta taattcactt atttaaaaac ataaaataat    1140
aataattgca tcaccgtgat acaaagcaac ctcacaagtc acaactctcg tgactacaaa    1200
gatcactcat taaacaaacc ttcctgcctt ctttttttct acttgggcac ctcgaccgat    1260
cgaagactat tcttgggatc tgcttcaaaa acgactatat gttctaaatc cacttcgtat    1320
gatgacgaac atttggttta ctactgaaga tagagattac gtccttctaa ttagaagtaa    1380
ttaattattt tagtatttgg aagctaatgg tggagatgta accgtatctt agtggatcga    1440
gatattgtat ataaaatatg tatgctacat cgaataataa actgaaagag agtaaaaagg    1500
gatatttaat gggaagaaaa gaagggtgga gatgtaacaa aggcgaagat aatggatatt    1560
cttgggatgt tgtcttcaag gccacgagct tagattcttt tagttttgct caatttgtta    1620
agtttctact tttcctttttg ttgcttacta cttttgctca tgatctccat atacatatca    1680
tacatatata tagtatacta tctttagact gatttctcta tacactatct tttaacttat    1740
gtatcgtttc aaaactcagg acgtacatgt ttaaatttgg ttatataacc acgaccattt    1800
caagtatata tgtcatacca taccagattt aatataactt ctatgaagaa aatacataaa    1860
gttggattaa aatgcaagtg acatctttttt agcataggtt catttggcat agaagaaata    1920
```

```
tataactaaa aatgaacttt aacttaaata gattttacta tattacaatt ttttcttttt      1980
acatggtcta atttatttt ctaaaattag tataattgtt gttttgatga aacaataata       2040
ccgtaagcaa tagttgctaa aagatgtcca aatatttata aattacaaag taaatcaaat      2100
aaggaagaag acacgtggaa aacaccaaat aagagaagaa atggaaaaaa cagaaagaaa     2160 tttttttaaca agaaaaatca attagtcctc aaacctgaga tatttaaagt aatcaactaa    2220
aacaggaaca cttgactaac aaagaaattt gaaacgtggt ccaactttca cttaattata    2280
ttgttttctc taaggcttat gcaatatatg ccttaagcaa atgccgaatc tgtttttttt    2340
ttttttgtta ttggatattg actgaaaata aggggttttt tcacacttga agatctcaaa    2400
agagaaaact attacaacgg aaattcattg taaaagaagt gattaagcaa attgagcaaa    2460 ggttttatg tggtttattt cattatatga ttgacatcaa attgtatata tatggttgtt     2520
ttatttaaca atatatatgg atataacgta caaactaaat atgtttgatt gacgaaaaaa   2580
aatatatgta tgtttgatta acaacatagc acatattcaa ctgattttg tcctgatcat     2640 ctacaactta ataagaacac acaacattga acaaatcttt gacaaaatac tattttggg    2700 tttgaaattt tgaatactta caattattct tctcgatctt cctctctttc cttaaatcct    2760
gcgtacaaat ccgtcgacgc aatacattac acagttgtca attggttctc agctctacca    2820 aaaacatctca ttgccaaaag aaaggtctat ttgtacttca ctgttacagc tgagaacatt  2880
aaatataata agcaaatttg ataaaacaaa gggttctcac cttattccaa aagaatagtg   2940
taaaataggg taatagagaa atgttaataa aaggaaatta aaaatagata ttttggttgg   3000
ttcagatttt gtttcgtaga tctacaggga atctccgcc gtcaatgcaa agcgaaggtg    3060
acacttgggg aaggaccagt ggtccgtaca atgttactta cccatttctc ttcacgagac   3120
gtcgataatc aaattgttta ttttcatatt tttaagtccg cagtttatt aaaaaatcat   3180 ggacccgaca ttagtacgag atataccaat gagaagtcga cacgcaaatc ctaaagaaac   3240
cactgtggtt tttgcaaaca agagaaacca gctttagctt ttccctaaaa ccactcttac    3300
ccaaatctct ccataaataa agatcccgag actcaaacac aagtcttttt ataaggaaa    3360 gaaagaaaaa cttttcctaat tggttcatac caaagtctga gctcttcttt atatctctct   3420
tgtagtttct tattgggggt ctttgt                                         3446
```

<210> SEQ ID NO 192
<211> LENGTH: 800
<212> TYPE: DNA
<213> ORGANISM: Artificial sequence
<220> FEATURE:
<223> OTHER INFORMATION: synthetic sequence
<220> FEATURE:
<223> OTHER INFORMATION: P6063 transcription factor component of 2-
      component system (opLexA::G1819)

<400> SEQUENCE: 192

```
aatagttggg ctgatttcgt agcccactta atcagccttt aaatatggaa accctagcct     60
agaaagtgaa caagaaaaac gtaaagatca aaatggaaga gaacaacggc aacaacaacc   120
actacctgcc gcaaccatcg tcttcccaac tgccgccgcc accattgtat tatcaatcaa    180
tgccgttgcc gtcatattca ctgccgctgc cgtactcacc gcagatgcgg aattattgga    240
ttgcgcagat gggaaacgca actgatgtta agcatcatgc gtttccacta accaggataa    300
agaaaatcat gaagtccaac ccggaagtga acatggtcac tgcagaggct ccggtcctta   360
tatcgaaggc ctgtgagatg ctcattcttg atctcacaat gcgatcgtgg cttcataccg    420
```

```
tggagggcgg tcgccaaact ctcaagagat ccgatacgct cacgagatcc gatatctccg      480
ccgcaacgac tcgtagtttc aaatttacct tccttggcga cgttgtccca agagaccctt      540
ccgtcgttac cgatgatccc gtgctacatc cggacggtga agtacttcct ccgggaacgg      600
tgataggata tccggtgttt gattgtaatg gtgtgtacgc gtcaccgcca cagatgcagg      660
agtggccggc ggtgcctggt gacggagagg aggcagctgg ggaaattgga ggaagcagcg      720
gcggtaattg aaaagtgttg attgggtttt agggttgtaa tgcttttgtg agaatttgta      780
tctctatgga gtcatgtttg                                                  800
```

<210> SEQ ID NO 193
<211> LENGTH: 1183
<212> TYPE: DNA
<213> ORGANISM: Artificial sequence
<220> FEATURE:
<223> OTHER INFORMATION: synthetic sequence
<220> FEATURE:
<223> OTHER INFORMATION: P5287 driver construct in 2-component system
    (LTP1::LexA-GAL4TA)

<400> SEQUENCE: 193

```
gatatgacca aaatgattaa cttgcattac agttgggaag tatcaagtaa acaacatttt       60 gttttttgttt gatatcggga atctcaaaac caaagtccac actagttttt ggactatata     120
atgataaaag tcagatatct actaatacta gttgatcagt atattcgaaa acatgacttt     180
ccaaatgtaa gttatttact ttttttttgc tattataatt aagatcaata aaaatgtcta     240
agttttaaat ctttatcatt atatccaaac aatcataatc ttattgttaa tctctcatca     300
acacacagtt tttaaaataa attaattacc ctttgcatga taccgaagag aaacgaattc     360
gttcaaataa ttttataaca ggaaataaaa tagataaccg aaataaacga tagaatgatt     420
tcttagtact aactcttaac aacagtttta tttaaatgac ttttgtaaaa aaaacaaagt     480
taacttatac acgtacacgt gtcgaaaata ttattgacaa tggatagcat gattcttatt     540
agagtcatgt aaaagataaa cacatgcaaa tatatatatg aataatatgt tgttaagata     600
aactagacga ttagaatata tagcacatct atagtttgta aaataactat ttctcaacta     660
gacttaagtc ttcgaaatac ataaatacaa ccaaactataa aaattcagaa aaaacatga     720 gagtacgtta gtaaaatgta tttttttggt aaaataatca cttttcatca ggtcttttgt     780
aaagcagttt tcatgttaga taaacgagat tttaatttt tttaaaaaaa gaagtaaact     840
aactatgttc ctatctacac acctataatt ttgaacaatt acaaaacaac aatgaaatgc     900
aaagaagacg tagggcactg tcacactaca atacgattaa taaatgtatt ttggtcgaat     960
taataacttt ccatacgata aagttgaatt aacatgtcaa acaaagaga tgagtggtcc   1020 tatacatagt taggaattag gaacctctaa attaaatgag tacaaccacc aactactcct   1080
tccctctata atctatcgca ttcacaccac ataacatata cgtacctact ctatataaca   1140
ctcactcccc aaactctctt catcatccat cactacacac atc                      1183
```

<210> SEQ ID NO 194
<211> LENGTH: 812
<212> TYPE: DNA
<213> ORGANISM: Artificial sequence
<220> FEATURE:
<223> OTHER INFORMATION: synthetic sequence
<220> FEATURE:
<223> OTHER INFORMATION: P6063 transcription factor component of 2-
    component system (opLexA::G2344)

<400> SEQUENCE: 194

```
ttattctaag tagcttgact tgtttagttt aaatatgagg ttaatgattt tgtggggatt      60
tgatagttct ggttcttgag tttatttaaa ataggtttac caggatcatg tactgactct     120
gttctttgga acttttcaga attctgcttc ggacattaag ctcatgagtc atgacttctt     180
caatccatga gctttctgat aacattggaa gtcatgagaa gcaagaacag agagattctc     240
atttccaacc accaatccct tctgcaagaa attatgaatc aattgttaca agtttagtct     300
actcagaccc ggggactaca aattccatgg cacctggaca atatccatat ccagatcctt     360
actacagaag catatttgca ccgcctccac aaccgtatac cggggtacat ctacagttga     420
tgggagtgca gcaacaaggc gttcctttac catctgatgc agtcgaggaa cctgttttg      480 ttaacgcaaa gcaataccac ggtatactaa ggcgcagaca atcaagagca agacttgagt     540
ctcagaataa agtcatcaag tcacgtaagc cgtatttgca tgaatctcgg catttgcatg     600
cgataagacg accaagagga tgtggcgggc ggtttctaaa tgccaagaag gaggatgagc     660
atcacgaaga cagtagtcat gaagaaaaat ccaaccttag cgctggtaaa tccgccatgg     720
ctgcttctag tggtacatct tgagaaggtc ctacaagtag cttgttgta ttttggctct      780 gtttggtctc agatcatcta tgtcttttag tg                                   812
```

<210> SEQ ID NO 195
<211> LENGTH: 1110
<212> TYPE: DNA
<213> ORGANISM: Artificial sequence
<220> FEATURE:
<223> OTHER INFORMATION: synthetic sequence
<220> FEATURE:
<223> OTHER INFORMATION: pMEN48 2-component driver vector (MCS::m35S::
     oEnh::LexAGal4)

<400> SEQUENCE: 195

```
aagctttgag ctccgcggcc gcaagaccct tcctctatat aaggaagttc atttcatttg      60
gagaggacac gctcgagtat aagagctcat ttttacaaca attaccaaca acaacaaaca     120
acaaacaaca ttacaattac atttacaatt accatggaag cgttaacggc caggcaacaa     180
gaggtgtttg atctcatccg tgatcacatc agccagacag gtatgccgcc gacgcgtgcg     240
gaaatcgcgc agcgtttggg gttccgttcc ccaaacgcgg ctgaagaaca tctgaaggcg     300
ctggcacgca aaggcgttat tgaaattgtt tccggcgcat cacgcgggat tcgtctgttg     360
caggaagagg aagaagggtt gccgctggta ggtcgtgtgg ctgccggtga accacttctg     420
gcgcaacagc atattgaagg tcattatcag gtcgatcctt ccttattcaa gccgaatgct     480
gatttcctgc tgcgcgtcag cgggatgtcg atgaaagata tcggcattat ggatggtgac     540
ttgctggcag tgcataaaac tcaggatgta cgtaacggtc aggtcgttgt cgcacgtatt     600
gatgacgaag ttaccgttaa gcgcctgaaa aaacagggca taaagtcga actgttgcca     660 gaaaatagcg agtttaaacc aattgtcgta gatcttcgtc agcagagctt caccattgaa     720
gggctggcgg ttgggttat tcgcaacggc gactggctgg aattccccaa tttttaatcaa     780 agtgggaata ttgctgatag ctcattgtcc ttcactttca ctaacagtag caacggtccg     840
aacctcataa caactcaaac aaattctcaa gcgctttcac aaccaattgc ctcctctaac     900
gttcatgata acttcatgaa taatgaaatc acggctagta aaattgatga tggtaataat     960
tcaaaaccac tgtcacctgg ttggacggac caaactgcgt ataacgcgtt tggaatcact    1020
acagggatgt ttaataccac tacaatggat gatgtatata actatctatt cgatgatgaa    1080
```

```
gataccccac caaacccaaa aaaagagtag                                     1110

<210> SEQ ID NO 196
<211> LENGTH: 333
<212> TYPE: DNA
<213> ORGANISM: Artificial sequence
<220> FEATURE:
<223> OTHER INFORMATION: synthetic sequence
<220> FEATURE:
<223> OTHER INFORMATION: pMEN53 LexA operator and polylinker sequence
      two component target vector (opLexA::MCS::E9)

<400> SEQUENCE: 196
acatatccat atctaatctt acctcgactg ctgtatataa aaccagtggt tatatgtcca     60
gtactgctgt atataaaacc agtggttata tgtacagtac gtcgatcgat cgacgactgc   120
tgtatataaa accagtggtt atatgtacag tactgctgta tataaaacca gtggttatat   180
gtacagtacg tcgaggggat gatcaagacc cttcctctat ataaggaagt tcatttcatt   240
tggagaggac acgctgacaa gctgactcta gcagatctgg taccgtcgac ggtgagctcc   300
gcggccgctc tagacaggcc tcgtaccgga tcc                                333

<210> SEQ ID NO 197
<211> LENGTH: 1098
<212> TYPE: DNA
<213> ORGANISM: Gossypium raimondii
<220> FEATURE:
<223> OTHER INFORMATION: G3883

<400> SEQUENCE: 197
aaataataat aataaacaaa gccagcgccc attacaatgg ccgctgtacc ttatcccatc     60
catatctgac ctttaaaaat atccaccgcc gccaccacca ccacgatcac caccgccaca   120
tccccatctc ccgccatttg ttcaccagcc aatggacagt aaccagcaaa ctcaatccac   180 cccatacccca cctcagcctc ccacatccgc cattacccct ccttcatccg ccacagcaac   240
cgcgcctcct ttccaccacc tccttcaaca acaacagcaa cagctccaaa tgttttggtc   300
ataccaacgc caagaaatcg agcaagttaa cgattttaag aaccaccaac tcccattagc   360
tcgcattaag aagataatga agccgacga agacgtccgt atgatctccg ccgaggctcc   420
cattctcttc gccaaagctt gtgagctttt cattttggaa ctcactatcc gttcttggct   480
tcacgccgag gaaacaagc gacggacact tcagaaaaac gacatcgctg cggctattac   540
gaggaccgac attttcgatt tcttggtaga tattgtgcct agggatgaga tcaaggatga   600
aactggtttg gctccgatgg ttggggctac cgccagtggg gtaccttact tttatccccc   660
tatgggtcaa cctgctgctg gtggtcctgg tgggatgatg attggccggc ctgccgtcga   720
tcccaccgga ggtatttacg gtcagccacc ttctcaggct tggcagagtg tttggcagac   780
ggcgggaact gatgatggct cgtatggcag tggagttacc ggtggtcaag gaatcttga   840 cggtcaaggc taacctaaaa tcatgggtcc gatatcgtac agtggatggt gtggaaaacg   900
cgtggaactc aggtgatcta ctggggaatt tatgcttttg tgcttattga tttatgaatg   960
cagttgtgtt ggtattgttt atgggaaaaa agaaaagcta ccttgaattt gatgacactt  1020
ctatagtaac ttgttaaaaa aacaaactct tttaactcat ttttagtgca gctaaaacaa  1080
tatcttgctg ccatgcca                                                1098

<210> SEQ ID NO 198
<211> LENGTH: 233
<212> TYPE: PRT
```

<213> ORGANISM: Gossypium raimondii
<220> FEATURE:
<223> OTHER INFORMATION: G3883 polypeptide (domain in aa coordinates: 67-132)

<400> SEQUENCE: 198

Met Asp Ser Asn Gln Gln Thr Gln Ser Thr Pro Tyr Pro Pro Gln Pro
1               5                   10                  15

Pro Thr Ser Ala Ile Thr Pro Pro Ser Ser Ala Thr Ala Thr Ala Pro
            20                  25                  30

Pro Phe His His Leu Leu Gln Gln Gln Gln Gln Leu Gln Met Phe
        35                  40                  45

Trp Ser Tyr Gln Arg Gln Glu Ile Glu Gln Val Asn Asp Phe Lys Asn
        50                  55                  60

His Gln Leu Pro Leu Ala Arg Ile Lys Lys Ile Met Lys Ala Asp Glu
65                  70                  75                  80

Asp Val Arg Met Ile Ser Ala Glu Ala Pro Ile Leu Phe Ala Lys Ala
                85                  90                  95

Cys Glu Leu Phe Ile Leu Glu Leu Thr Ile Arg Ser Trp Leu His Ala
            100                 105                 110

Glu Glu Asn Lys Arg Arg Thr Leu Gln Lys Asn Asp Ile Ala Ala Ala
        115                 120                 125

Ile Thr Arg Thr Asp Ile Phe Asp Phe Leu Val Asp Ile Val Pro Arg
130                 135                 140

Asp Glu Ile Lys Asp Glu Thr Gly Leu Ala Pro Met Val Gly Ala Thr
145                 150                 155                 160

Ala Ser Gly Val Pro Tyr Phe Tyr Pro Pro Met Gly Gln Pro Ala Ala
                165                 170                 175

Gly Gly Pro Gly Gly Met Met Ile Gly Arg Pro Ala Val Asp Pro Thr
            180                 185                 190

Gly Gly Ile Tyr Gly Gln Pro Pro Ser Gln Ala Trp Gln Ser Val Trp
        195                 200                 205

Gln Thr Ala Gly Thr Asp Asp Gly Ser Tyr Gly Ser Gly Val Thr Gly
    210                 215                 220

Gly Gln Gly Asn Leu Asp Gly Gln Gly
225                 230

<210> SEQ ID NO 199
<211> LENGTH: 66
<212> TYPE: PRT
<213> ORGANISM: Gossypium raimondii
<220> FEATURE:
<223> OTHER INFORMATION: G3883 conserved domain

<400> SEQUENCE: 199

Leu Pro Leu Ala Arg Ile Lys Lys Ile Met Lys Ala Asp Glu Asp Val
1               5                   10                  15

Arg Met Ile Ser Ala Glu Ala Pro Ile Leu Phe Ala Lys Ala Cys Glu
            20                  25                  30

Leu Phe Ile Leu Glu Leu Thr Ile Arg Ser Trp Leu His Ala Glu Glu
        35                  40                  45

Asn Lys Arg Arg Thr Leu Gln Lys Asn Asp Ile Ala Ala Ala Ile Thr
    50                  55                  60

Arg Thr
65

<210> SEQ ID NO 200

<211> LENGTH: 719
<212> TYPE: DNA
<213> ORGANISM: Artificial sequence
<220> FEATURE:
<223> OTHER INFORMATION: synthetic sequence
<220> FEATURE:
<223> OTHER INFORMATION: P26821 overexpression construct (35S::3883)

<400> SEQUENCE: 200

| | | | | | |
|---|---|---|---|---|---|
| gttcaccagc | caatggacag | taaccagcaa | actcaatcca | ccccatacccc | acctcagcct | 60 |
| cccacatccg | ccattacccc | tccttcatcc | gccacagcaa | cagcgcctcc | tttccaccac | 120 |
| ctccttcaac | aacaacagca | acagctccaa | atgttttggt | cataccaacg | ccaagaaatc | 180 |
| gagcaagtta | acgattttaa | gaaccaccaa | ctcccattag | ctcgcattaa | gaagataatg | 240 |
| aaagccgacg | aagacgtccg | tatgatctcc | gccgaggctc | ccattctctt | cgccaaagct | 300 |
| tgtgagcttt | tcattttgga | actcactatc | cgttcttggc | ttcacgccga | ggaaaacaag | 360 |
| cgacggacac | ttcagaaaaa | cgacatcgct | gcggctatta | cgaggaccga | cattttcgat | 420 |
| ttcttggtag | atattgtgcc | tagggatgag | atcaaggatg | aaactgcttt | ggctccgatg | 480 |
| gtcggtgcta | ccgccagtgg | ggtaccttac | ttttatcccc | ctatgggtca | acctgctggt | 540 |
| ggtggtcctg | gtgggatgat | gattggccgg | cctgccgtcg | atcccaccgg | agttatttac | 600 |
| ggtcagccac | cttctcaggc | ttggcagagt | gtttggcaga | cggcggggac | tgatgatggc | 660 |
| tcgtatggca | gtggagttac | cggtggtcaa | gggaatcttg | acggtcaagg | ctaacctaa | 719 |

<210> SEQ ID NO 201
<211> LENGTH: 1221
<212> TYPE: DNA
<213> ORGANISM: Lycopersicon esculentum
<220> FEATURE:
<223> OTHER INFORMATION: G3894

<400> SEQUENCE: 201

| | | | | | |
|---|---|---|---|---|---|
| tatcaatcat | ctacctcttt | gattgaaccc | tagctctcac | tctctctttc | tctctctaaa | 60 |
| aaaaaagcat | aaaagtttca | atctttcagg | taatttgatt | ggagaggcgt | atccagaatt | 120 |
| tggagcttca | atcagtgggg | agcctaagtt | agctttggat | tctccaaaag | ggaatcttgc | 180 |
| tcaaaatgga | tcaacatgga | aatggacagc | ctccaggtat | tggagtcgtt | actagctcag | 240 |
| ctccaatata | tggtgctcca | taccaagcta | accaaatggc | agggccctct | cctcctgcag | 300 |
| tttcagctgg | tgcaattcaa | tctcctcaag | cagctggtct | tgctgcttcg | tcagctcaga | 360 |
| tggcgcaaca | tcagctcgct | tatcagcaca | ttcatcagca | gcagcaacaa | cagttgcagc | 420 |
| aacaactcca | gactttctgg | gcaaatcaat | atcaagaaat | cgagcatgtt | actgatttca | 480 |
| agaatcatag | cttgccattg | gcaaggatca | agaaaatcat | gaaagcggat | gaagatgtta | 540 |
| ggatgatatc | tgctgaagca | ccagtcgtat | tgctcgtgc | ctgtgagatg | ttcatacttg | 600 |
| aattgacact | gcgtgcatgg | aaccacactg | aggagaacaa | aaggaggacg | ctgcagaaaa | 660 |
| atgatatcgc | tgcagccata | acaaggactg | acatatttga | tttcttagtt | gacattgtcc | 720 |
| caagagagga | cttgaaagat | gaggtgcttg | caacaattcc | tagaggaacg | cttcctgttg | 780 |
| gaggcccaac | tgagggtctg | ccattctatt | atggcatgcc | accacaatct | gctcaaccga | 840 |
| ttggagctcc | agggatgtac | atgggaaagc | ctgtcgatca | agctctgtat | gcccagcagc | 900 |
| cccgcccata | tatggcacag | ccaatttggc | cccagcagca | gcaaccaccc | tcagattctt | 960 |
| aagcagctca | aagcttagat | tacaggaatc | cagaagctag | gagcagtgag | tagtctgagt | 1020 |
| agcgaagtac | tggagaacac | atagcagtct | gcatactttg | aactttattt | taatatatat | 1080 |

```
cgacatgaag cactagttat taaaagtcga gtgttcccttt agtgtagcta aaactttaca    1140
ccatgagctt gatgttcttg gtgatgttta tgaacaaata tgttttttaag tgtgtgattt    1200 aaaagtaaaa aaaaaaaaaa a                                               1221
```

<210> SEQ ID NO 202
<211> LENGTH: 258
<212> TYPE: PRT
<213> ORGANISM: Lycopersicon esculentum
<220> FEATURE:
<223> OTHER INFORMATION: G3894 polypeptide (domain in aa coordinates: 103-168)

<400> SEQUENCE: 202

```
Met Asp Gln His Gly Asn Gly Gln Pro Pro Gly Ile Gly Val Val Thr
 1               5                   10                  15

Ser Ser Ala Pro Ile Tyr Gly Ala Pro Tyr Gln Ala Asn Gln Met Ala
            20                  25                  30

Gly Pro Ser Pro Pro Ala Val Ser Ala Gly Ala Ile Gln Ser Pro Gln
        35                  40                  45

Ala Ala Gly Leu Ala Ala Ser Ser Ala Gln Met Ala Gln His Gln Leu
    50                  55                  60

Ala Tyr Gln His Ile His Gln Gln Gln Gln Gln Leu Gln Gln Gln
65                  70                  75                  80

Leu Gln Thr Phe Trp Ala Asn Gln Tyr Gln Glu Ile Glu His Val Thr
                85                  90                  95

Asp Phe Lys Asn His Ser Leu Pro Leu Ala Arg Ile Lys Lys Ile Met
            100                 105                 110

Lys Ala Asp Glu Asp Val Arg Met Ile Ser Ala Glu Ala Pro Val Val
        115                 120                 125

Phe Ala Arg Ala Cys Glu Met Phe Ile Leu Glu Leu Thr Leu Arg Ala
    130                 135                 140

Trp Asn His Thr Glu Glu Asn Lys Arg Arg Thr Leu Gln Lys Asn Asp
145                 150                 155                 160

Ile Ala Ala Ala Ile Thr Arg Thr Asp Ile Phe Asp Phe Leu Val Asp
                165                 170                 175

Ile Val Pro Arg Glu Asp Leu Lys Asp Glu Val Leu Ala Thr Ile Pro
            180                 185                 190

Arg Gly Thr Leu Pro Val Gly Gly Pro Thr Glu Gly Leu Pro Phe Tyr
        195                 200                 205

Tyr Gly Met Pro Pro Gln Ser Ala Gln Pro Ile Gly Ala Pro Gly Met
    210                 215                 220

Tyr Met Gly Lys Pro Val Asp Gln Ala Leu Tyr Ala Gln Gln Pro Arg
225                 230                 235                 240

Pro Tyr Met Ala Gln Pro Ile Trp Pro Gln Gln Gln Pro Pro Ser
                245                 250                 255

Asp Ser
```

<210> SEQ ID NO 203
<211> LENGTH: 66
<212> TYPE: PRT
<213> ORGANISM: Lycopersicon esculentum
<220> FEATURE:
<223> OTHER INFORMATION: G3894 conserved domain

<400> SEQUENCE: 203

```
Leu Pro Leu Ala Arg Ile Lys Lys Ile Met Lys Ala Asp Glu Asp Val
```

```
                1               5                  10                 15
            Arg Met Ile Ser Ala Glu Ala Pro Val Val Phe Ala Arg Ala Cys Glu
                           20                  25                  30

Met Phe Ile Leu Glu Leu Thr Leu Arg Ala Trp Asn His Thr Glu Glu
                       35                  40                  45

Asn Lys Arg Arg Thr Leu Gln Lys Asn Asp Ile Ala Ala Ala Ile Thr
                     50                  55                  60

Arg Thr
            65

<210> SEQ ID NO 204
<211> LENGTH: 799
<212> TYPE: DNA
<213> ORGANISM: Artificial sequence
<220> FEATURE:
<223> OTHER INFORMATION: synthetic sequence
<220> FEATURE:
<223> OTHER INFORMATION: P26611 overexpression construct (35S::G3894)

<400> SEQUENCE: 204
gctcaaaatg gatcaacatg gaaatggaca gcctccaggt attggagtcg ttactagctc      60
agctccaata tatggtgctc cataccaagc taaccaaatg gcagggccct ctcctcctgc     120
agtttcagct ggtgcaattc aatctcctca agcagctggt cttgctgctt cgtcagctca     180
gatggcgcaa catcagctcg cttatcagca cattcatcag cagcagcaac aacagttgca     240
gcaacaactc cagactttct gggcaaatca atatcaagaa atcgagcatg ttactgattt     300
caagaatcat agcttgccat ggcaaggat caagaaaatc atgaaagcgg atgaagatgt      360
taggatgata tctgctgaag caccagtcgt atttgctcgt gcctgtgaga tgttcatact     420
tgaattgaca ctgcgtgcat ggaaccacac tgaggagaac aaaaggagga cgctgcagaa     480
aaatgatatc gctgcagcca taacaaggac tgacatattt gatttcttag ttgacattgt     540
cccaagagag gacttgaaag atgaggtgct tgcaacaatt cctagaggaa cgcttcctgt     600
tggaggccca actgagggtc tgccattcta ttatggcatg ccaccacaat ctgctcaacc     660
gattggagct ccaggatgt acatgggaaa gcctgtcgat caagctctgt atgcccagca      720
gccccgccca tatatggcac agccaatttg gccccagcag cagcaaccac cctcagattc     780
ttaagcagct caaagctta                                                  799

<210> SEQ ID NO 205
<211> LENGTH: 1109
<212> TYPE: DNA
<213> ORGANISM: Artificial sequence
<220> FEATURE:
<223> OTHER INFORMATION: synthetic sequence
<220> FEATURE:
<223> OTHER INFORMATION: P5324 driver construct in 2-component system
      (CRU::LexA-GAL4TA)

<400> SEQUENCE: 205
ctacacgttt tgaaaagtta acctgttggt taaatggtta gctatgactc tcgcaacaaa      60 cccaacccttt aagatgatga tggtttaaca tttgacaaca tagttaagac tgtgtctata    120
taatagtcaa caaattcaga ttgtagtatt atggagtcaa catatttcga gatcaaaaac     180
attcaaaacg taaatctatc gacgtctcac atagtttttgt tatgaagctg atgaaaaaag    240
ttggaagaca tagttttgca aacatcattt gttgctaacg tataaacgtt ggtttgatta     300
aatgtaatag gataaggata tccgtttgtt catataattg agttaaatta tattttggtt    360
```

| | |
|---|---|
| attataatat gttaagttga aaataaatag gtccaacaac cttgtttaaa tagatttttt | 420 |
| aggagtgatt cccttttaat agtatagatt atactctctt cctaatcgac cttccgtggg | 480 |
| gtaaagtggt caattatatt ctttatggat gagcttgatt gagaatgggt ttatgggtta | 540 |
| tgacaagggc atgtacaaat gtcactgcct cttgacatgc aaccgaacag ttggcgactc | 600 |
| aagtcgcaga agatacaacg gaccaaaccc tccgagtgtc gccgcgtctg ttatgtgtca | 660 |
| cctttttgtc tcctttcctt aaaaattggt aactcatttt tcaaaaaaag aagaggatag | 720 |
| ttttggctgt atctcctaaa ctattcgatc acaacgccag atattttaat actggatact | 780 |
| agtgatgtaa tttgatttgt taattgtcaa aaagtagatt ctcctatctc gttttttagtt | 840 |
| caattattat atggttaaat gaatttaagt cgattagaaa tgattagtta atcaaccaga | 900 |
| gttgctctat aagtctatac tgataacatg aaccattttc taaaaatgag atagatacat | 960 |
| ttgaattttg tcgtggtttg gagtatgcgg agatagtcgt acgcgcatga acatcatgag | 1020 |
| acacttgctt cagctcacag agtgacgtgt aaagaccata gacccacgac ttcatgcaaa | 1080 |
| cccattccta cgtggcacaa accttcatg | 1109 |

<210> SEQ ID NO 206
<211> LENGTH: 1341
<212> TYPE: DNA
<213> ORGANISM: Artificial sequence
<220> FEATURE:
<223> OTHER INFORMATION: synthetic sequence
<220> FEATURE:
<223> OTHER INFORMATION: P9107 transcription factor component of 2-
      component system (opLexA::G929)

<400> SEQUENCE: 206

| | |
|---|---|
| atgacttctt cagtacatga gctctctgat aacaatgaaa gtcatgcgaa gaaagaacgt | 60 |
| ccagattccc aaacccgacc acaggttcct tcaggacgaa gttcggaatc tattgataca | 120 |
| aactctgtct actcagagcc catggcacat ggattatacc cgtatccaga tccttactac | 180 |
| agaagcgtct tgcacagca agcgtatctt ccacatccct atcctggggt ccaattgcag | 240 |
| ttaatgggaa tgcagcagcc aggagttcca ttgcaatgtg atgcagtcga ggaacctgtt | 300 |
| tttgttaacg caaagcaata ccatggtata ctcaggcgca ggcaatcccg ggcaaaactt | 360 |
| gaggcacgaa atagagccat caaagcaaaa aagccataca tgcatgaatc tcggcattta | 420 |
| catgcgataa gacggccaag aggatgtggt ggccggtttc tcaatgccaa gaggaaaat | 480 |
| ggagaccaca aggaggagga ggaggcaacc tctgatgaga acacttcaga agcaagttcc | 540 |
| agcctcaggt ccgagaaatt agctatggct acttctggtc ctaatggtag atctgcggcc | 600 |
| gctgccgctg cggcagcggc catggtgagc aagggcgagg agctgttcac cggggtggtg | 660 |
| cccatcctgg tcgagctgga cggcgacgta acggccaca gttcagcgt gtccggcgag | 720 |
| ggcgagggcg atgccaccta cggcaagctg accctgaagt tcatctgcac caccggcaag | 780 |
| ctgcccgtgc cctggcccac cctcgtgacc accttcggct acggcctgca gtgcttcgcc | 840 |
| cgctacccg accacatgaa gcagcacgac ttcttcaagt ccgccatgcc cgaaggctac | 900 |
| gtccaggagc gcaccatctt cttcaaggac gacggcaact acaagacccg cgccgaggtg | 960 |
| aagttcgagg gcgacaccct ggataaccga atcgagctga agggcatcga cttcaaggag | 1020 |
| gacggcaaca tcctggggca caagctggag tacaactaca acagccacaa cgtctatatc | 1080 |
| atggccgaca gcagaagaa cggcatcaag gtgaacttca agatccgcca caacatcgag | 1140 |
| gacggcagcg tgcagctcgc cgaccactac cagcagaaca cccccatcgg cgacggcccc | 1200 |

```
gtggtgctgc cgacaacca ctacctgagc taccagtccg ccctgagcaa agaccccaac    1260
gagaagcgcg atcacatggt cctgctggag ttcgtgaccg ccgccgggat cactctcggc    1320
atggacgagc tgtacaagta a                                              1341
```

<210> SEQ ID NO 207
<211> LENGTH: 1386
<212> TYPE: DNA
<213> ORGANISM: Artificial sequence
<220> FEATURE:
<223> OTHER INFORMATION: synthetic sequence
<220> FEATURE:
<223> OTHER INFORMATION: P5562 transcription factor component of 2-
      component system (opLexA::G926)

<400> SEQUENCE: 207

```
ccaaaatcta gggttttctt ctcgcccaat ttcacttttc ttctacgaaa ttctccattc      60
ctgccggctg tcgggttttc tgaatcgatt ctccttcacc aacttcttct ctggttctgt     120
tcgattctga ttttttttca aggtcaattt tttcttctct ttaaactctg caaaatcgtg     180
atcgattaaa ttcacctcag ggttttttga tttctgaaag aagttaatct tcttcgaagg     240
cgattgcaaa agagtgctct gctgtgaatt tccactgaga tgcaatcaaa accgggaaga     300
gaaaacgaag aggaagtcaa taatcaccat gctgttcagc agccgatgat gtatgcagag     360
ccctggtgga aaaacaactc cttggtgtt gtacctcaag cgagaccttc tggaattcca      420
tcaaattcct cttctttgga ttgccccaat ggttccgagt caaacgatgt tcattcagca     480
tctgaagacg gtgcgttgaa tggtgaaaac gatggcactt ggaaggattc acaagctgca     540
acttcctctc gttcagataa tcacggaatg gaaggaaatg acccagcgct ctctatccgt     600
aacatgcatg atcagccact tgtacaacca ccagagcttg ttggacacta tatcgcttgt     660
gtcccaaacc catatcagga tccatattat gggggattga tgggagcata tggtcatcag     720
caattgggtt ttcgtccata tcttggaatg cctcgtgaaa aacagctct gcccacttgac    780 atggcacaag agcccgttta tgtgaatgca aagcagtacg agggaattct aaggcgaaga     840
aaagcacgtg ccaaggcaga gctagagagg aaagtcatcc gggacagaaa gccatatctt     900
cacgagtcaa gacacaagca tgcaatgaga agggcacgag cgagtggagg ccggtttgcg     960
aagaaaagtg aggtagaagc gggagaggat gcaggaggga gagacagaga aaggggttca    1020
gcaaccaact catcaggctc tgaacaagtt gagacagact ctaatgagac cctgaattct    1080
tctggtgcac cataataaaa aaagccaaag ctctgagagg agagagagac acacactttg    1140
gctaatataa tccattgcct caaaccggca aatcattctt ggcttttcg tttttgtgtt     1200 tgctagttgt tcttgtcaga gtctcatatt gtgtgggttt aacagttatg atgaatgtac    1260
aaagagcgag ttatgttagg tgttagattt tggagacaag agacaaagga atagcaagta    1320
ggtcttgttt ttattctttg accttttttt tctcttttgc aaaattgaaa aatacgtttg    1380
cttaaa                                                               1386
```

<210> SEQ ID NO 208
<211> LENGTH: 4361
<212> TYPE: DNA
<213> ORGANISM: Artificial sequence
<220> FEATURE:
<223> OTHER INFORMATION: synthetic sequence
<220> FEATURE:
<223> OTHER INFORMATION: P5318 driver construct in 2-component system
      (STM::LexA-GAL4TA)

<400> SEQUENCE: 208

-continued

```
agaatgtagc aatacaaata tatgacggta ccgttatcca tcaccattat atgtatatat        60
gtataatttg ataaatattc actttgtgtt tcgtcgtttg cttaataaac agctcatttc       120
catggtattg agtcttctat atgcgagaga atcagattcc cgctgggata acaaaagaac       180
aaggtactga aaaaaataga caaaactttt ttttaaatta tataagctat aaaagaaaag       240
agtatagaga gagattagcc ctactgttta agagggagag agtagggtca ttagggcttt       300
agagagagaa gacattcgga ctgtccccac ttgcttttct gtagaataac attatttaaa       360
tcttattttt aattaaatat tacaactaaa agaagaaacc aactttttaaa ataaatgcag      420 attatatgct ctgacttgga ctaaataaaa cttgcaagta acagtttcaa gtccttttgt       480
tttagaactt tttctttcgt agaagtgata aatgattgcc ctagacctga tagattctct       540
aaaattctac gtattacagc ataagttacc tcctttattt gactattaga ccatccatat       600
tggtgggctt ttagcaaatg ttcttaacaa taattttata atttatttta atgttaagag       660
gtttgataat ttttttttt taagagtgta ttttgtttat taaatgtgt tttgtttctt         720 atataagaac caaatcttaa ctattttacc aattaaacat taaatttaaa ttttaatatc       780
tctaagaatt atattaagag ccaatataga tgcttttaaa accattggtt gaataaataa       840
atctaacctt cttaattatt tctgtgtgaa tattttctaa attttcattt taatttagca       900
caatataatc catgttctaa aaagaacaat taacataata tttacaaacc taaaaagatt       960
ataaaacaca attttatttt ttacagctta taatgtttta aagttcaggt ttatttttta      1020
aaagttcagg tttattacat taggtttgac ttgtaatcat catttatcac aacgatcaaa      1080
ctattattac aatcacaata gtagacaaaa tttaggatat atatatatat atataattat      1140 gtataaaacta tgaacattta aagtgagatt tttcaaaata atatataaat tcaaatagaa     1200
atagactatt tggttcttaa atgagagacc cccgaaaaaa tcttttttttt tttctcatca    1260 agctgtttac atttttagat ataaaatcat attctttata gtttagaata tgaattaaat      1320
agttttatat gttattaact tatcataaga tatgcgtgag gttggccaaa aactcatcaa      1380
ttaaccaaat aagaaaagta aaattgtatt ttgctttgct aaaaatgtaa atatttcatt      1440
gaaaaatgaa aaaggtttag gtaatacaat taagtaaatc ctacaatttt ggttccatgg      1500
caaaagaata aaattgtatt gctttggtaa aagttgatcc aactaatata ttcagtagaa      1560
actgcaaaac tgaagaaata agtttgttta gtagaattgc tttcggttat gtaatgaata      1620
tacatccaaa atggcttttt agtaatgatg tcttttcata ctctttccaa tccctactac      1680
tttcagatta tttgtcctac tattatagag atatacgttc gttttcaata atatgaaaag      1740
tgatatatat ttaaatagtg tgatatatat ataagttttg caagtgcatc acttcccaaa      1800
atcgcataaa tcattaatca tattgtcgaa aacagtataa taacttctta aacgaaaacg      1860
cagcgcaatt aaaaataaca actagagata attgacaaaa cattgattaa tatttaccta      1920
taagttaatt attgtatttta aaatttattt aaagttcata aggaaaacat atgcaaaaat     1980
atttatatct aatatttgc tatgttatcc ttttttttttt ttacgttatc ctaattttgt      2040
ttatcctaat ttgttgtggt taaaatctta ttattgataa aaagagaact ttttttttg       2100 tcatcataaa aaagagaact tattacttcg attttaaaat tctatgagcg taggagacaa      2160
agaaaaaaaa aataaaaaaa aaaagaagag aaaaatcact tcttttcttc tttttagtcc      2220
agatccaaca tattttggat aactaaatga agatttttta aaaaaatata ttttagggta      2280
tatataaatc ataatttgaa gcaaatgaaa taaaatccag tttggtaata tataaatatg      2340
```

```
atttgatggg ttccttgtaa tctctctcta tctattagtt tctcagttat cttttctttg      2400
ccagaaatgg cagtgaaggc agtggctgag gagagagttt tttttcttct ttcatgggga      2460
aagtaaaact ttgccttgaa gatttctctc ttcaatattt ttctaagact tttgatttca      2520
acgaatcact gtccttaacc taaaagcaag aaaaattagc tttatactgg tctttacttt      2580
tttttaacat atttatttt atatagttta cttataaaca tagacatacg agtatgggaa       2640
tatatagtat atccaacttc taaataatat ttcgaatagt gataacaaaa ttagcaatac      2700
atacggctag tgaaatgttg atcgaataaa cggcactgat gtaatgtact tatcaattt      2760 gataattta attgtattgt tttctttt ttcccacagt attgaactag acaattaaat        2820
ttaaagtaaa attatacatt tctttcgttg tgtattaaag taacatgcat aatatcattt      2880
tccttcgtac aatcctccaa attgacaatt gatgaattac tttgtcaatc gtaaatgaat     2940
ttttctcaag tctgtatact atttcaggg ataaacaggt acaggtgtcc catgcttatt      3000
ctcttgatag taacatgtgt cctatgttga gtcaattcta cgttcgaaga agtgctaaca     3060
attgttaata gcctcgtata ttattctaat taaaatgcct cgatagattt ggttagtggt    3120
ctgaatgtga ttggttattt tttcaagtgg caagaggtct accatctaat attacaatca    3180
atcgaccaaa aaggtcgaga acatgataat ggtggcaaat acaaatggtt cattgttgtc     3240
taatataaca agccatcagt tgtcactttt taaaaacaat acagaataca agatactttt     3300
tttttaaggt aaaatgtgtg tttaatattt tcgtttatat aacaaataaa cagttacatg     3360
ttttactcta tgattatatt tatgacattt ttcttcttct taacaacatt ttttcccat      3420 aagaacattt acaatagtat taaaactttg attgcaatca aatgttagat cacttattat    3480
aaaattacta agactgctat cttttcctat tgacaaaagc gaatccaata tatgttactg     3540
aaacaaatgc gtaaattata ctatatggag atctatcggt taattattga gagaatctaa     3600
gaaagttttt gagtacaaca gtcctaataa tatcttcaca taccatataa tatacatata    3660
tacatataca caaatgtact ttttaaacca acatcagcat acgtatatcc catcaggaaa    3720
cttagacttt tgggaattca tggtatgaaa accaaaacca aatgacaaca ttcgatttga    3780
tactcccgac ccatggtaaa gaaataacaa attccaatat atctttcact ggactttccg    3840
aggcacattc cggttttctc catttcaaga aattgtcaaa aataaattga gatccggttt    3900
attacctcaa aaaagaagaa gagaaattac aacattaatt tccgaaaagg cataaatgag    3960
aaatcatatt tcagcagaag aacacaaaag agttaagaac ccacagatca cacaacctct    4020
gtccatgtct gcttttaca cttttttaaa ataagtttct cctaaaaagt tatttcctat     4080
ttataataat ttccttagat ttatcttcct ggtctctctt ctgctgcttc cctctccccc    4140
ataactatca ctatttagaa ttttcaatgt ggaaaaggaa gctgattgtt gaagcataaa    4200
tcccgggaga ccacttttgc atttcaaat aattaaatta aaccatagat acacacacac    4260
agttacttac tcttttaggg tttcccaata aatttatagt actttaatgt gtttcatgat   4320
attgatgata aatgctagct gtatttacaa tgggggctcc t                        4361
```

<210> SEQ ID NO 209
<211> LENGTH: 1243
<212> TYPE: DNA
<213> ORGANISM: Zea mays
<220> FEATURE:
<223> OTHER INFORMATION: G4259

<400> SEQUENCE: 209

```
aaaaaaagaa gcttgccatt tcgctcaggg ccctgcaacg cgcggcagcg cgccacgcgc       60
```

```
cgagcttggc ttgggactgg gccgcccggc cgcgaggaat aaactcactc ctgccttcat    120
acgtatccaa atagccgcgg cagtacgtgt atgtggttag ctatacgcga cctcagctcg    180
ggcgcaagct acaacgccga ccaggcgaga agaagcatcg atagtgtgac gagctaaccc    240
accagcagca acgtaatcca aatccatgga caaccagccg ctgccctact ccacaggcca    300
gcccctgcc cccggaggag ccccggtggc gggcatgcct ggcgcggccg gcctcccacc     360
cgtgccgcac caccacctgc tccagcagca gcaggcccag ctgcaggcgt tctgggcgta    420
ccagcgccag gaggcggagc gcgcgtccgc gtcggacttc aagaaccacc agctgcctct    480
ggcccggatc aagaagatca tgaaggccga cgaggacgtg cgcatgatct ccgccgaggc    540
gcccgtgctg ttcgccaagg cctgcgagct cttcatcctc gagctcacta tccgctcctg    600
gctccacgcc gaggagaaca agcgccgcac cctgcagcgc aacgacgtcg ccgcggccat    660
cgcgcgcacc gacgtcttcg atttcctcgt agacatcgtg ccccgcgagg aggccaagga    720
ggagcccggc agcgccctcg gcttcgcggc gcctgggacc ggcgtcgtcg gggctggcgc    780
cccgggcggg gcgccagccg ccgggatgcc ctactactat ccgccgatgg ggcagccggc    840
gccgatgatg ccgccctggc atgttccggc ctgggacccg gcctggcagc aaggggcagc    900
ggatgtcgat cagagcggca gcttcagcga ggaaggacaa gggtttggag caggccatgg    960
cggcgccgct agcttccctc ctgcgcctcc gacctccgag tgatcgatcg gcgcgtctct   1020
tggtcctggc ctcctggctt agctacatgt gcatgatgtc aatcgttcaa tgtgccatgc   1080
tgtgtatatt ctacagcaaa cgtggtaatg gagctgctat gcatacagaa cgaataaggc   1140
gtgacgtgtg agaccgtaag agtacgtagt actaatatgt agatgcacgt gacgtgccaa   1200
ttaatcaaag attaacatgc agttaattaa ttagatcctc cct                     1243
```

<210> SEQ ID NO 210
<211> LENGTH: 245
<212> TYPE: PRT
<213> ORGANISM: Zea mays
<220> FEATURE:
<223> OTHER INFORMATION: G4259 polypeptide (domain in aa coordinates: 70-135)

<400> SEQUENCE: 210

```
Met Asp Asn Gln Pro Leu Pro Tyr Ser Thr Gly Gln Pro Ala Pro
 1               5                  10                  15

Gly Gly Ala Pro Val Ala Gly Met Pro Gly Ala Ala Gly Leu Pro Pro
             20                  25                  30

Val Pro His His His Leu Leu Gln Gln Gln Ala Gln Leu Gln Ala
             35                  40                  45

Phe Trp Ala Tyr Gln Arg Gln Glu Ala Glu Arg Ala Ser Ala Ser Asp
     50                  55                  60

Phe Lys Asn His Gln Leu Pro Leu Ala Arg Ile Lys Lys Ile Met Lys
65                   70                  75                  80

Ala Asp Glu Asp Val Arg Met Ile Ser Ala Glu Ala Pro Val Leu Phe
                 85                  90                  95

Ala Lys Ala Cys Glu Leu Phe Ile Leu Glu Leu Thr Ile Arg Ser Trp
            100                 105                 110

Leu His Ala Glu Glu Asn Lys Arg Arg Thr Leu Gln Arg Asn Asp Val
        115                 120                 125

Ala Ala Ala Ile Ala Arg Thr Asp Val Phe Asp Phe Leu Val Asp Ile
    130                 135                 140
```

```
Val Pro Arg Glu Glu Ala Lys Glu Glu Pro Gly Ser Ala Leu Gly Phe
145                 150                 155                 160

Ala Ala Pro Gly Thr Gly Val Val Gly Ala Gly Ala Pro Gly Gly Ala
                165                 170                 175

Pro Ala Ala Gly Met Pro Tyr Tyr Tyr Pro Pro Met Gly Gln Pro Ala
            180                 185                 190

Pro Met Met Pro Ala Trp His Val Pro Ala Trp Asp Pro Ala Trp Gln
        195                 200                 205

Gln Gly Ala Ala Asp Val Asp Gln Ser Gly Ser Phe Ser Glu Glu Gly
    210                 215                 220

Gln Gly Phe Gly Ala Gly His Gly Gly Ala Ala Ser Phe Pro Pro Ala
225                 230                 235                 240

Pro Pro Thr Ser Glu
            245

<210> SEQ ID NO 211
<211> LENGTH: 66
<212> TYPE: PRT
<213> ORGANISM: Zea mays
<220> FEATURE:
<223> OTHER INFORMATION: G4259 conserved domain

<400> SEQUENCE: 211

Leu Pro Leu Ala Arg Ile Lys Lys Ile Met Lys Ala Asp Glu Asp Val
1               5                   10                  15

Arg Met Ile Ser Ala Glu Ala Pro Val Leu Phe Ala Lys Ala Cys Glu
                20                  25                  30

Leu Phe Ile Leu Glu Leu Thr Ile Arg Ser Trp Leu His Ala Glu Glu
            35                  40                  45

Asn Lys Arg Arg Thr Leu Gln Arg Asn Asp Val Ala Ala Ala Ile Ala
        50                  55                  60

Arg Thr
65

<210> SEQ ID NO 212
<211> LENGTH: 1505
<212> TYPE: DNA
<213> ORGANISM: Zea mays
<220> FEATURE:
<223> OTHER INFORMATION: G4261

<400> SEQUENCE: 212
gcgcgaggga gagacagagt gaggaaacga gggaaggaga cgacgcgctc gcctattggc    60
cgccggctcc gctccttcgc gcccagtgcg acggccacgg cctgagcggc gctgccagca   120
aggcggctag tatgagcagc atggagtcgc ggccgggccg aacgaacctg gtggagccca   180
tagggcacgg cgccgcgctg ccgtccggcg gccaggcagt gcagccgtgg tggacgagct   240
ccggggctgt gctcggtgca gtctcgccag ccgtcgtggc ggtggcgccc gggagcggga   300
cggggattag cctgtcgagc agcccggcag gtggtagtgg tggtggcggc gcggctaaag   360
gagccgcgag tgacgagagc agcgaggatt cacggagatc tggggaacca aaagatggaa   420
gcgctagtca agaaaagaac catgccacat cgcagatacc cgctctggcg ccagagtatt   480
tggcaccata ctcgcagctg gaactgaacc aatcaattgc ttctgcagca tatcagtacc   540
cagatcctta ctatgcaggc atggttgctc cctatggaag tcatgctgtg gctcattttc   600
agctacctgg actaactcaa tctcgaatgc cattacctct tgaagtatcc gaggagcctg   660
tttatgtaaa tgccaagcag taccatggta tcttaagacg acggcagtcc cgtgctaagg   720
```

```
ctgaacttga gaaaaaggtg gtcaaagcca gaaagccata ccttcacgag tctcgtcatc    780
agcacgcgat gaggagggca agaggaaacg ggggacgctt cctgaacaca agaaaagtg     840 acagtggtgc tcccaatgga ggcgaaaacg ccgagcatct ccatgtccct cccgacttac    900
tacagctacg acagaacgag gcttgaagta gcggtatggc tctggcatcc ttgaacagca    960
gttcctgtcc acgggcgtag gcattcgaga ccggattcat atagctctcc acagcatacg   1020
cgcagccatc tctgcggtaa cgcacgttct cctgaacgag ctttgtagcg agataggtat   1080
gcaagtgcaa tctgggcgca ggaatccatc atcaagtgcc caatgcccat ggggtaggta   1140
cgctgtttca ggcaattcat tcttggcttt cacgttccac ccttgtgtaa ctggtgtgtt   1200
gtaaatgtgt ggaaaactaa gcttgtgctc tgtatcgggc cgttcagcgg aactgcaaaa   1260
cgcctgtata attaagatcg aactttggat taactcggta atgctttgtc tggttttctt   1320
ttagcttttc aactgtaaca cggccacagc tgattcatgt gatgtgcttg ctaatattta   1380
aataaacacc ttgacccggc cgggcgcgga gtaattttat attttttata ttcgggagtc   1440
cacacaatcg tgtaaggttc ctgcgaacca gttctgactt taattgaacc gcccggattc   1500
atatg                                                               1505

<210> SEQ ID NO 213
<211> LENGTH: 264
<212> TYPE: PRT
<213> ORGANISM: Zea mays
<220> FEATURE:
<223> OTHER INFORMATION: G4261 polypeptide (domain in aa coordinates:
      175-231)

<400> SEQUENCE: 213

Met Ser Ser Met Glu Ser Arg Pro Gly Arg Thr Asn Leu Val Glu Pro
1               5                   10                  15

Ile Gly His Gly Ala Ala Leu Pro Ser Gly Gln Ala Val Gln Pro
            20                  25                  30

Trp Trp Thr Ser Ser Gly Ala Val Leu Gly Ala Val Ser Pro Ala Val
        35                  40                  45

Val Ala Val Ala Pro Gly Ser Gly Thr Gly Ile Ser Leu Ser Ser Ser
    50                  55                  60

Pro Ala Gly Gly Ser Gly Gly Gly Ala Ala Lys Gly Ala Ala Ser
65                  70                  75                  80

Asp Glu Ser Ser Glu Asp Ser Arg Arg Ser Gly Glu Pro Lys Asp Gly
                85                  90                  95

Ser Ala Ser Gln Glu Lys Asn His Ala Thr Ser Gln Ile Pro Ala Leu
            100                 105                 110

Ala Pro Glu Tyr Leu Ala Pro Tyr Ser Gln Leu Glu Leu Asn Gln Ser
        115                 120                 125

Ile Ala Ser Ala Ala Tyr Gln Tyr Pro Asp Pro Tyr Tyr Ala Gly Met
    130                 135                 140

Val Ala Pro Tyr Gly Ser His Ala Val Ala His Phe Gln Leu Pro Gly
145                 150                 155                 160

Leu Thr Gln Ser Arg Met Pro Leu Pro Leu Glu Val Ser Glu Pro
                165                 170                 175

Val Tyr Val Asn Ala Lys Gln Tyr His Gly Ile Leu Arg Arg Arg Gln
            180                 185                 190

Ser Arg Ala Lys Ala Glu Leu Glu Lys Lys Val Val Lys Ala Arg Lys
        195                 200                 205
```

```
Pro Tyr Leu His Glu Ser Arg His Gln His Ala Met Arg Arg Ala Arg
    210             215                 220

Gly Asn Gly Gly Arg Phe Leu Asn Thr Lys Lys Ser Asp Ser Gly Ala
225             230                 235             240

Pro Asn Gly Gly Glu Asn Ala Glu His Leu His Val Pro Pro Asp Leu
                245                 250             255

Leu Gln Leu Arg Gln Asn Glu Ala
            260

<210> SEQ ID NO 214
<211> LENGTH: 57
<212> TYPE: PRT
<213> ORGANISM: Zea mays
<220> FEATURE:
<223> OTHER INFORMATION: G4261 conserved domain

<400> SEQUENCE: 214

Glu Pro Val Tyr Val Asn Ala Lys Gln Tyr His Gly Ile Leu Arg Arg
1               5                   10                  15

Arg Gln Ser Arg Ala Lys Ala Glu Leu Glu Lys Lys Val Val Lys Ala
            20                  25                  30

Arg Lys Pro Tyr Leu His Glu Ser Arg His Gln His Ala Met Arg Arg
        35                  40                  45

Ala Arg Gly Asn Gly Gly Arg Phe Leu
    50                  55

<210> SEQ ID NO 215
<211> LENGTH: 16
<212> TYPE: PRT
<213> ORGANISM: Artificial sequence
<220> FEATURE:
<223> OTHER INFORMATION: derived from wheat, rye, and tomato
<220> FEATURE:
<221> NAME/KEY: MISC_FEATURE
<222> LOCATION: (3)..(3)
<223> OTHER INFORMATION: Arg or Lys
<220> FEATURE:
<221> NAME/KEY: MISC_FEATURE
<222> LOCATION: (8)..(8)
<223> OTHER INFORMATION: any unknown amino acid
<220> FEATURE:
<221> NAME/KEY: MISC_FEATURE
<222> LOCATION: (11)..(11)
<223> OTHER INFORMATION: any unknown amino acid

<400> SEQUENCE: 215

Pro Lys Xaa Pro Ala Gly Arg Xaa Lys Phe Xaa Glu Thr Arg His Pro
1               5                   10                  15

<210> SEQ ID NO 216
<211> LENGTH: 5
<212> TYPE: PRT
<213> ORGANISM: arabidopsis thaliana

<400> SEQUENCE: 216

Asp Ser Ala Trp Arg
1               5
```

PLANTS WITH ENHANCED SIZE AND GROWTH RATE

RELATED APPLICATION

This is a U.S. National Phase patent application of PCT/US2007/017,321, filed Aug. 3, 2007, which claims priority to U.S. Provisional patent application Ser. No. 60/836,243, filed Aug. 7, 2006, all of which are hereby incorporated by reference in the present disclosure in their entirety.

JOINT RESEARCH AGREEMENT

The claimed invention, in the field of functional genomics and the characterization of plant genes for the improvement of plants, was made by or on behalf of Mendel Biotechnology, Inc. and Monsanto Corporation as a result of activities undertaken within the scope of a joint research agreement in effect on or before the date the claimed invention was made.

FIELD OF THE INVENTION

The present invention relates to plant genomics and plant improvement.

BACKGROUND OF THE INVENTION

Increasing the size or growth rate of a commercially valuable plant provides a number of important practical applications, and may contribute to an increase in yield. For example, increasing the size of a cultivar may generate higher yield of the edible vegetative portion a crop plant. Increasing the size and/or growth rate of a plant may also provide a competitive advantage in the field. Many weeds outgrow slow-growing young crops or out-compete them for nutrients, and thus it is usually desirable to use plants that establish themselves quickly. Seedlings and young plants are also particularly susceptible to stress conditions such as salinity or disease. Increasing seedling growth rate and shortening the time to emergence from soil contributes to seedling vigor, aids seedlings in coping with these stresses, and may allow these crops to be planted earlier in the season. Early planting helps add days to a critical seed or grain-filling period and increases yield. Modification of the biomass of other tissues, such as root tissue, may be useful to improve a plant's ability to grow under harsh environmental conditions, including drought, high salt or nutrient deprivation, because larger roots may better reach or take up water or nutrients.

For many plants, including fruit-bearing trees, plants that are used for biofuels, trees that are used for lumber production, or trees and shrubs that serve as view or wind screens, increased stature provides improved benefits in the forms of greater yield or improved screening.

Increased leaf size may also be of particular interest. Increasing leaf biomass can be used to increase production of plant-derived pharmaceutical or industrial products. An increase in total plant photosynthesis is typically achieved by increasing leaf area of the plant. Additional photosynthetic capacity may be used to increase yield derived from particular plant tissue, including leaves, roots, fruits or seed, or permit better growth of a plant under both decreased and high light intensity.

However, increasing the size or growth rate of a plant may require controlling a number of regulatory and synthetic pathways. Transcription factors are proteins that influence the expression of a particular gene or sets of genes. Altering the expression of one or more transcription factors may provide the necessary control to manipulate complex biochemical or morphological traits in a plant, and thus multiple cellular processes. This application demonstrates that transformed plants that comprise cells having altered levels of at least one of the closely-related transcription factors of the invention exhibit increased size and/or growth rate relative to control plants.

SUMMARY OF THE INVENTION

An object of this invention is to provide plants that can express genes to increase the yield of commercially significant plants by increasing the growth rate, yield, and/or mass of the plants. A plant of the invention is transformed with an expression vector that encodes a CCAAT family transcription factor polypeptide of the invention, and the polypeptide is then overexpressed in the plant. Due to the function of these polynucleotides and their encoded polypeptides, the transgenic plant will have greater yield and/or increased size and/or growth rate at one or more stages of growth as compared to a control plant.

Methods for producing transgenic plants having increased size, yield and/or growth rate are also encompassed by the invention. These method steps include first providing an expression vector comprising a recombinant polynucleotide of the invention. The expression vector may also include at least one regulatory element flanking the polynucleotide sequence. Generally, the regulatory element(s) control expression of the recombinant polynucleotide in a target plant. The expression vector is then introduced into plant cells. The plant cells overexpress a polypeptide encoded by the recombinant polynucleotide, resulting in increased size and/or growth rate of the plant. Those plants that have increased yield, size and/or growth rate may be identified and possibly selected on the basis of the extent to which yield, size and/or growth rate is increased.

The recombinant polynucleotides, expression vectors and transgenic plants of the invention may comprise any of the following sequences:

(a) the nucleotide sequences found in the sequence listing;
(b) nucleotide sequences encoding polypeptides found in the sequence listing;
(c) sequence variants that are at least 35% sequence identical to any of the nucleotide sequences of (a) or (b);
(d) polypeptide sequences that are at least 35%, at least 36%, at least 37%, at least 38%, at least 39%, at least 40%, at least 41%, at least 42%, at least 45%, at least 46%, at least 47%, at least 49%, at least 50%, at least 53%, at least 54%, at least 55%, at least 56%, at least 57%, at least 58%, at least 61%, at least 62%, at least 63%, at least 72%, at least 78%, at least 79%, or at least 86% identical in their amino acid sequence to any of SEQ ID NOs: 2n, where n=1 to 42, or SEQ ID NOs: 198, 202, 210 or 213;
(e) orthologous and paralogous nucleotide sequences that are at least 35% identical to any of the nucleotide sequences of (a) or (b);
(f) nucleotide sequence that hybridize to any of the nucleotide sequences of (a) or (b) under stringent conditions, which may include, for example, hybridization with wash steps of 6×SSC and 65° C. for ten to thirty minutes per wash step; and
(g) polypeptides, and the nucleotide sequences that encode them, having a conserved CCAAT family domain required for the function of regulating transcription and increasing size or biomass in a transgenic plant, the conserved domain being at least 34%, at least 37%, at least 39%, at least 44%, at least 47%, at least 52%, at least 55%, at least 61%, at least 63%, at least 64%, at least 65%, at least 66%, at least 67%, at least 70%, at least 71%, at least 72%, at least 73%, at least 75%, at least 76%, at least 78%, at least 80%, at least 81%, at least 83%, at least 84%, at least 85%, at least 86%, at least 87%, at least 89%, at least 90%, at least 91%, at least 92%, at least 96%, or 100% identical to any of the phylogenetically-related conserved domains of SEQ ID NO: 85-126, or SEQ ID NOs: 199, 203, 211 or 214. The polypeptides of the invention, SEQ ID NO: 2n, where n=1 to 42, or 198, 202, 210 or 213 are listed in Tables 1-4. Each polypeptide of the invention comprises a conserved domain required for the function of regulating transcription and altering a trait in a transgenic plant, said trait selected from the group consisting of increased size (for example, seedling size or size of the mature plant), increased growth rate, increased yield, increased biomass, and increased height, as compared to the control plant.

The expression vectors, and hence the transgenic plants of the invention, comprise putative transcription factor polynucleotides sequences and, in particular, CCAAT family HAP2-like (NF-YA) and HAP5-like (NF-YC) sequences comprising conserved domains that are required for subunit association and/or DNA binding, and hence the regulatory activity of the CCAAT-box transcription factor complex. When any of the polypeptides of the invention is overexpressed in a plant, the polypeptide confers at least one transcriptional regulatory activity to the plant, which in turn is manifested in a trait selected from the group consisting of increased growth rate, increased size, increased biomass, increased yield, and increased height as compared to the control plant.

The invention is also directed to transgenic seed produced by any of the transgenic plants of the invention, and to methods for making transgenic seed.

BRIEF DESCRIPTION OF THE SEQUENCE
LISTING AND DRAWINGS

The Sequence Listing provides exemplary polynucleotide and polypeptide sequences of the invention. The traits associated with the use of the sequences are included in the Examples.

CD-ROMs Copy 1 and Copy 2, as well as Copy 3, the latter being a CRF copy of the Sequence Listing under CFR Section 1.821(e), are read-only memory computer-readable compact discs. Each contains a copy of the Sequence Listing in ASCII text format. The Sequence Listing is named "MBI-0072P.ST25.txt", the electronic file of the Sequence Listing contained on each of these CD-ROMs was created on Aug. 4, 2006, and the file is 331 kilobytes in size. The copies of the Sequence Listing on the CD-ROM discs are hereby incorporated by reference in their entirety.

FIG. 1 shows a conservative estimate of phylogenetic relationships among the orders of flowering plants (modified from Angiosperm Phylogeny Group (1998) *Ann. Missouri Bot. Gard.* 84: 1-49). Those plants with a single cotyledon (monocots) are a monophyletic Glade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al., 2001).

Figure 2:
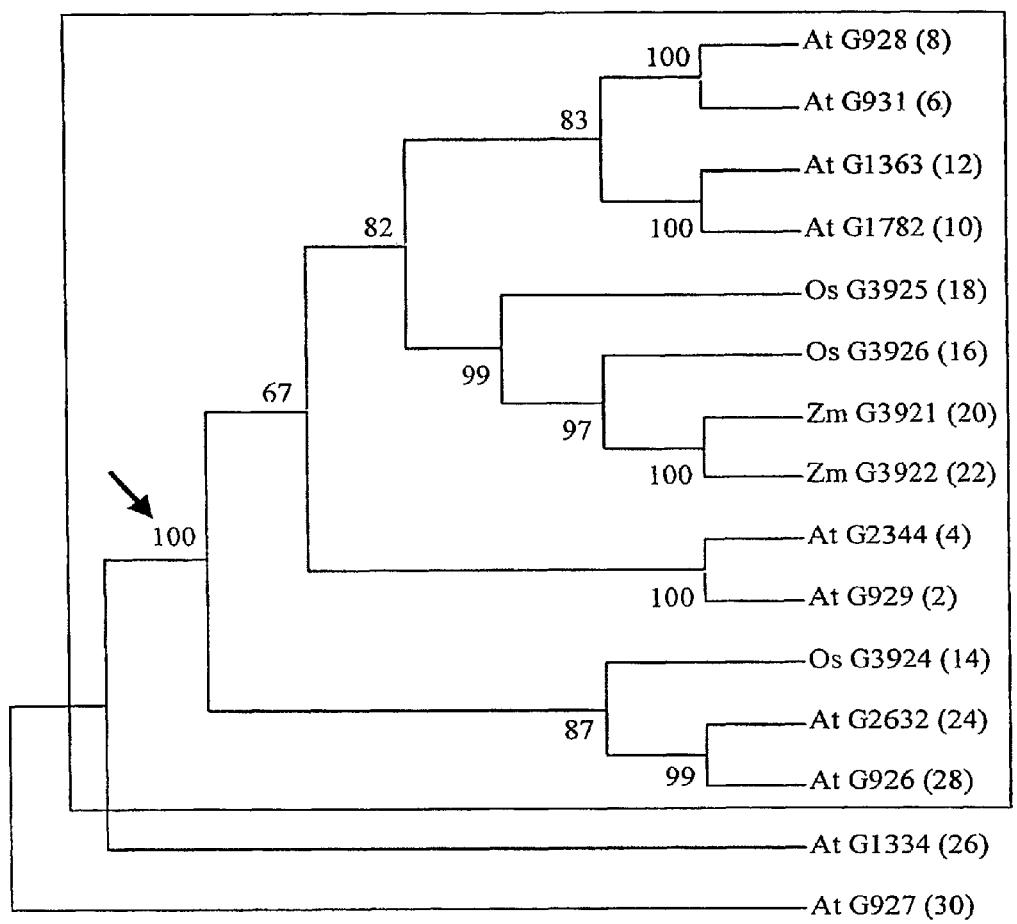
Figure 3:
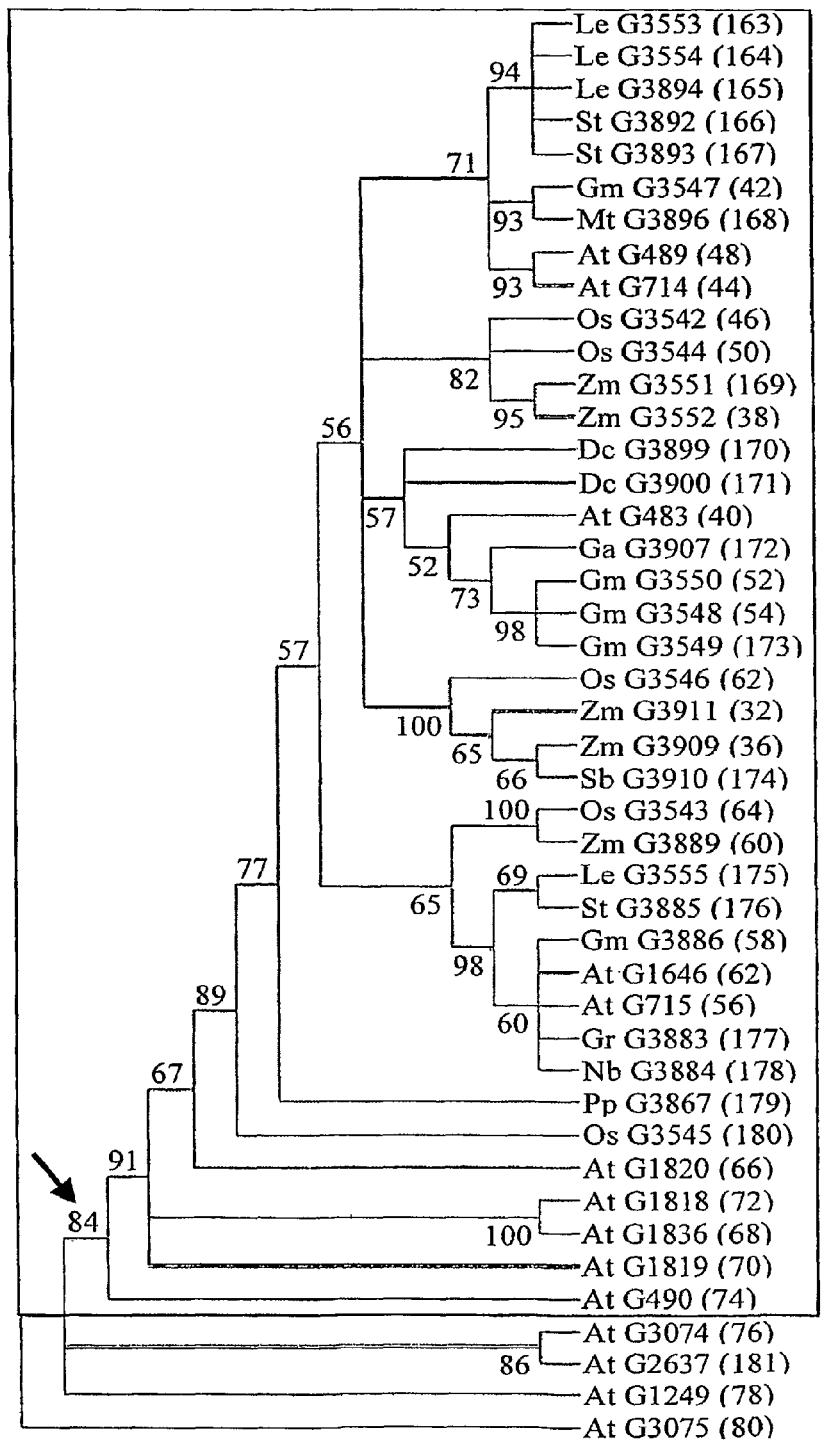

In FIGS. 2 and 3, phylogenetic trees and multiple sequence alignments of related transcription factors in the HAP2 and HAP5 CCAAT binding families, respectively, were constructed using ClustalW (CLUSTAL W Multiple Sequence Alignment Program version 1.83, 2003). ClustalW multiple alignment parameters were:
Gap Opening Penalty: 10.00
Gap Extension Penalty: 0.20
Delay divergent sequences: 30%
DNA Transitions Weight: 0.50
Protein weight matrix: Gonnet series
DNA weight matrix: IUB
Use negative matrix: OFF A FastA formatted alignment was then used to generate phylogenetic trees in MEGA2 software (MEGA2 (www.megasoftware.net) using the neighbor joining algorithm and a p-distance model. A test of phylogeny was done via bootstrap with 1000 replications and Random Seed set to default. Cut off values of the bootstrap tree were set to 50%. Closely-related homologs of G929 (SEQ ID NO: 2) or G3911 (SEQ ID NO: 36) are considered as being those proteins descending from ancestral sequences indicated by strong nodes of the trees. In FIGS. 2 and 3, two ancestral nodes are indicated by arrows have bootstrap values of 100 and 84, respectively. Sequences of closely related homologs that descended from these ancestral nodes are shown within the large boxes in these figures. As indicated in the experiments found in the Examples, many of these sequences have been overexpressed in plants and have been shown to retain the function of increasing size and/or growth rate. SEQ ID NOs. appear in parentheses. Abbreviations: At—*Arabidopsis thaliana*; Dc—*Daucus carota*; Ga—*Gossypium arboreum*; Gm—*Glycine max*; Gr—*Gossypium raimondii*; Le—*Lycopersicon esculentum*; Mt—*Medicago truncatula*; Nb *Nicotiana benthamiana*; Os—*Oryza sativa*; Pp—*Physcomitrella patens*; Sb—*Sorghum bicolor*; St—*Solanum tuberosum*; Zm—*Zea mays*.

FIGS. 4A-4G show a Clustal W alignment of HAP2 transcription factors. SEQ ID NOs: appear in parentheses after each Gene IDentifier (GID). GIDs representing HAP2 polypeptides that are closely related to G929 and G3926 appear in the boxes along the left margin in FIGS. 4A-4G. Highly conserved domains comprising the contiguous subunit association domains and DNA binding domains (Edwards et al., 1998) are identified in FIGS. 4D-4E by the large boxes surrounding the residues within these domains.

Figure 5C:
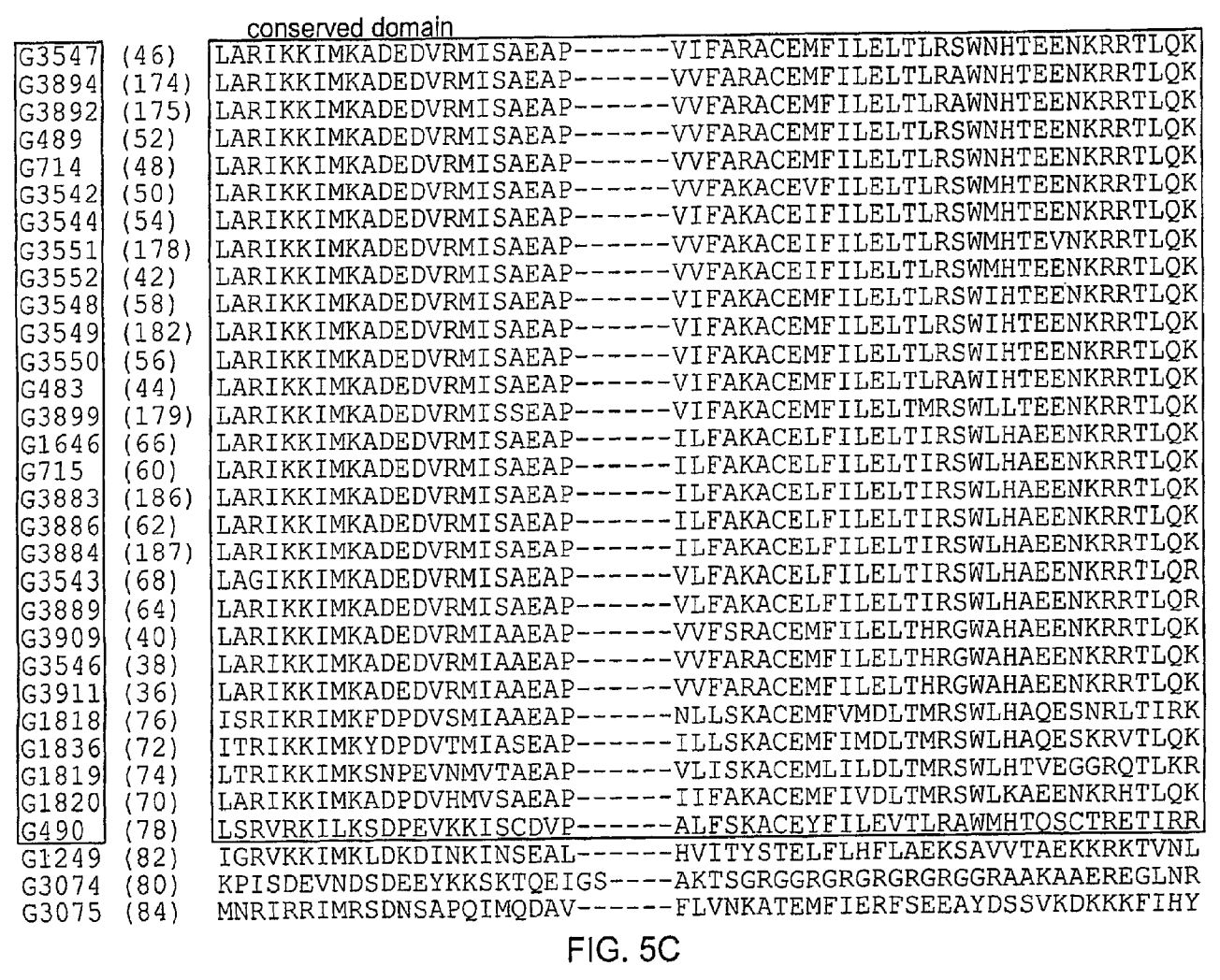
Figure 5E:
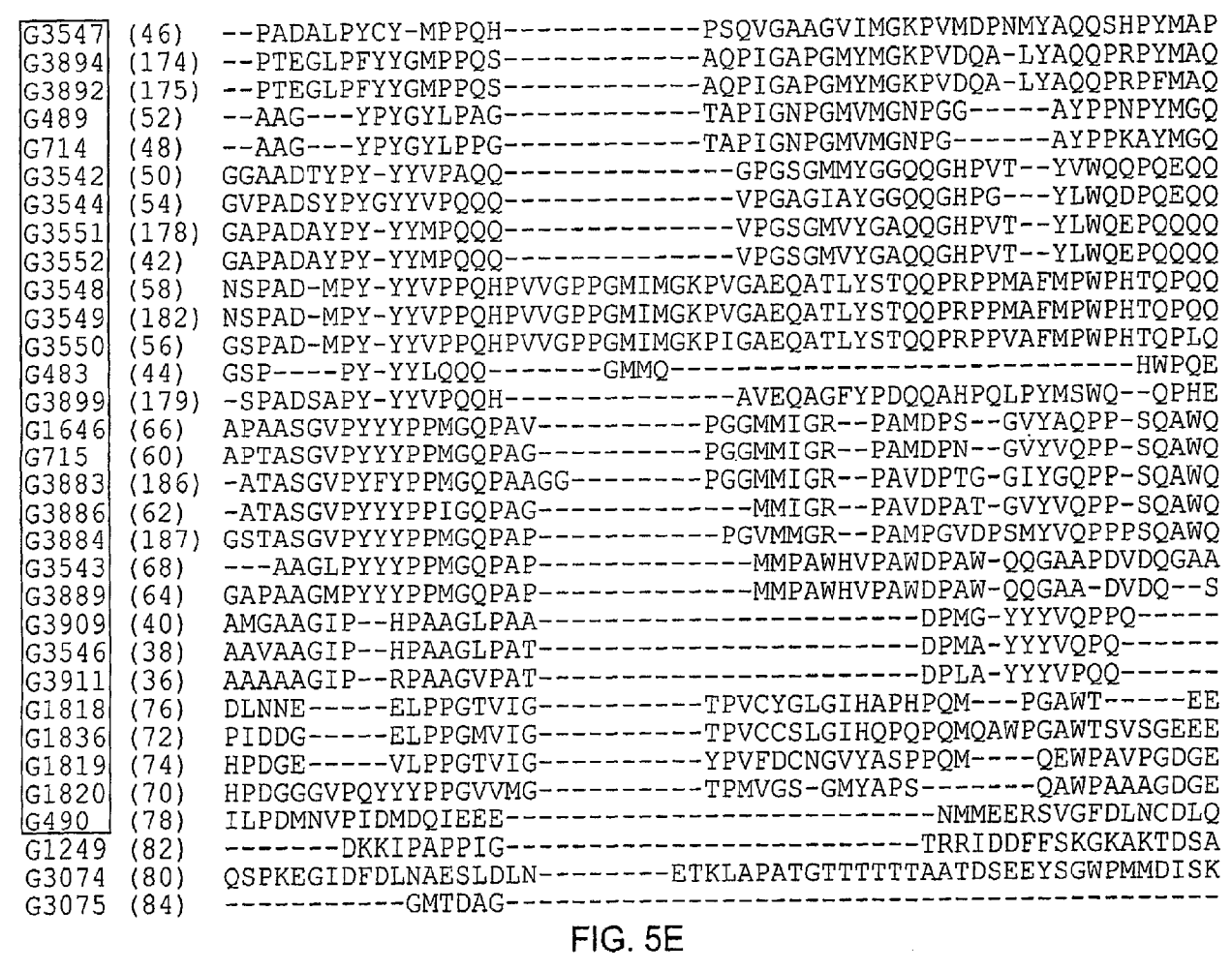

FIGS. 5A-5G show a Clustal W alignment of HAP5 transcription factors. SEQ ID NOs: appear in parentheses after each Gene IDentifier (GID). GIDs representing HAP5 polypeptides that are closely related to G3911 and G3543 appear in the boxes along the left margin in FIGS. 5A-5G. The highly conserved "core sequence" domains first described in related sequences by Edwards et al. (1998) are identified in FIGS. 5B-5D by the large boxes surrounding the residues within these domains.

Figure 6:

FIG. 6 shows a field of transgenic tomato plants overexpressing a number of different promoter and transcription factor combinations. Of particular note is a transgenic plant in the center of this photograph, indicated by the arrow, overexpressing G929 under the regulatory control of the cruciferin promoter. This plant was transformed with a two component expression system consisting of SEQ ID NO: 205 (a driver vector comprising the cruciferin promoter, a LexA DNA binding domain, and a GAL4 transactivation (TA) domain) and SEQ ID NO: 206 (comprising a LexA operator (opLexA) and the G929 transcription factor sequence). The transgenic plant was much larger than virtually all of its neighboring plants, including wild-type and empty vector control plants, and was particularly noted for its high vigor, upright stems, and no noticeable loss in fruit production.

DETAILED DESCRIPTION

The present invention relates to polynucleotides and polypeptides for modifying phenotypes of plants, particularly those associated with increased yield with respect to a control plant (for example, a wild-type plant). Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al., 1976). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide, or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 4A-4G and specifically 4D-4E may be used to identify conserved domains and relatedness within these domains. An alignment may suitably be determined by means of computer programs known in the art, such as MACVECTOR software (1999) (Accelrys, Inc., San Diego, Calif.).

A "conserved domain" or "conserved region" as used herein refers to a region in heterologous polynucleotide or polypeptide sequences where there is at least one similar conserved function and a relatively high degree of sequence identity between the distinct sequences. Subunit association domains and DNA binding domains such as are found in a polypeptide member of HAP2 transcription factors, or HAP5 core sequences from HAP2 transcription factors (Edwards, 1998) are examples of a conserved domain. With respect to polynucleotides encoding presently disclosed polypeptides, a conserved domain is preferably at least nine base pairs (bp) in length. A conserved domain with respect to presently disclosed polypeptides refers to a domain within a polypeptide family that exhibits similar function and a higher degree of sequence homology, such as at least about 34%, at least about 37%, at least about 39%, at least about 44%, at least about 47%, at least about 52%, at least about 55%, at least about 61%, at least about 63%, at least about 64%, at least about 65%, at least about 66%, at least about 67%, at least about 70%, at least about 71%, at least about 72%, at least about 73%, at least about 75%, at least about 76%, at least about 78%, at least about 80%, at least about 81%, at least about 83%, at least about 84%, at least about 85%, at least about 86%, at least about 87%, at least about 89%, at least about 90%, at least about 91%, at least about 92%, at least about 96%, or 100% amino acid sequence identity to the similar conserved domains of SEQ ID NO: 85-126, 199, 203, 211, or 214. Sequences that possess or encode for conserved domains that meet these criteria of percentage identity, and that have comparable biological activity to the present polypeptide sequences, thus being members of the HAP2 and HAP5 polypeptides, are encompassed by the invention. A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al., 2000a, 2000b). Edwards (1998) defined conserved domains of HAP2 transcription factor sequences, and identified these contiguous domains as comprising subunit association and DNA binding activity. Edwards (1998) also defined conserved "core sequence" domains of HAP5 transcription factors that comprise a predicted histone fold triple helix for dimerization and are required for formation of the CCAAT-box transcription factor complex. Thus, by using alignment methods well known in the art, the conserved domains of the CCAAT binding transcription factor proteins may be determined. The conserved domains for many of the polypeptide sequences of the invention are listed in Tables 1-4. Also, the polypeptides of Tables 1-4 have conserved domains specifically indicated by amino acid coordinates of the full length polypeptides. It is expected that these conserved domains are required for the functions of subunit association and/or DNA binding (Edwards, 1998).

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al., 1985, Sambrook et al., 1989, and by Haymes et al., 1985), which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known related polynucleotide sequences. Numerous variations are possible in the conditions and means by which nucleic acid hybridization can be performed to isolate related polynucleotide sequences having similarity to sequences known in the art and are not limited to those explicitly disclosed herein. Such an approach may be used to isolate polynucleotide sequences having various degrees of similarity with disclosed polynucleotide sequences, such as, for example, encoded transcription factors having 34% or greater identity with a conserved domain of disclosed sequences as provided in SEQ ID NOs: 85-126, 199, 203, 211, or 214.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, under "www.tigr.org/TIGRFAMs/Explanations.shtml" for the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent polypeptides. Thus, it will be readily appreciated by those of skill in the art, that any of a variety of polynucleotide sequences is capable of encoding the polypeptides and homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840, 544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the polynucleotides listed in the Sequence Listing. Exemplary fragments also include fragments that comprise a region that encodes an conserved domain of a polypeptide. Exemplary fragments also include fragments that comprise a conserved domain of a polypeptide. Exemplary fragments include fragments that comprise an conserved domain of a polypeptide, for example, amino acid residues 98-157 of G929 (SEQ ID NO: 2), amino acid residues 164-222 of 03926 (SEQ ID NO: 18), amino acid residues 83-148 of G3911 (SEQ ID NO: 36) or amino acid residues 70-135 of G3543 (SEQ ID NO: 68).

Fragments may also include subsequences of polypeptides and protein molecules, or a subsequence of the polypeptide. Fragments may have uses in that they may have antigenic potential. In some cases, the fragment or domain is a subsequence of the polypeptide that performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode polypeptides and derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding polypeptides or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae (see for example, FIG. 1, adapted from Daly et al., 2001, and see also Tudge, 2000).

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, that is, a vector that does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant of the invention generally contains an expression vector or cassette. The expression cassette typically comprises a polypeptide-encoding sequence operably linked (i.e., under regulatory control of) to appropriate inducible or constitutive regulatory sequences that allow for the controlled expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, e.g., in that it has been knocked out, overexpressed, or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular polypeptide in a suspension cell is the expression levels of a set of genes in a cell knocking out or overexpressing that polypeptide compared with the expression levels of that same set of genes in a suspension cell that has normal levels of that polypeptide. The transcript profile can be presented as a list of those genes whose expression level is significantly different between the two treatments, and the difference ratios. Differences and similarities between expression levels may also be evaluated and calculated using statistical and clustering methods.

With regard to gene knockouts as used herein, the term "knockout" refers to a plant or plant cell having a disruption in at least one gene in the plant or cell, where the disruption results in a reduced expression or activity of the polypeptide encoded by that gene compared to a control cell. The knockout can be the result of, for example, genomic disruptions, including transposons, tilling, and homologous recombination, antisense constructs, sense constructs, RNA silencing constructs, or RNA interference. A T-DNA insertion within a gene is an example of a genotypic alteration that may abolish expression of that gene.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression in a wild-type plant, cell or tissue, at any developmental or temporal stage for the gene. Overexpression can occur when, for example, the genes encoding one or more polypeptides are under the control of a strong promoter (e.g., the cauliflower mosaic virus 35S transcription initiation region). Overexpression may also under the control of an inducible or tissue specific promoter. Thus, overexpression may occur throughout a plant, in specific tissues of the plant, or in the presence or absence of particular environmental signals, depending on the promoter used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors possess a conserved domain. The transcription factors also comprise an amino acid subsequence that forms a transcription activation domain that regulates expression of one or more yield-related genes in a plant when the transcription factor binds to the regulating region.

"Yield" or "plant yield" refers to increased plant growth, increased crop growth, increased biomass, and/or increased plant product production, and is dependent to some extent on temperature, plant size, organ size, planting density, light, water and nutrient availability, and how the plant copes with various stresses, such as through temperature acclimation and water or nutrient use efficiency. Relative indicators of yield may include volume per land area (e.g. bushels per acre) or weight per land area (e.g., kilograms per hectare) measurements.

"Planting density" refers to the number of plants that can be grown per acre. For crop species, planting or population density varies from a crop to a crop, from one growing region to another, and from year to year. Using corn as an example, the average prevailing density in 2000 was in the range of 20,000-25,000 plants per acre in Missouri, USA. A desirable higher population density (a measure of yield) would be at least 22,000 plants per acre, and a more desirable higher population density would be at least 28,000 plants per acre, more preferably at least 34,000 plants per acre, and most preferably at least 40,000 plants per acre. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre (Cheikh et al., 2003) U.S. Patent Application No. 20030101479). A desirable higher population density for each of these examples, as well as other valuable species of plants, would be at least 10% higher than the average prevailing density or yield.

DESCRIPTION OF THE SPECIFIC EMBODIMENTS

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding motif (see, for example, Riechmann et al., 2000a). The plant transcription factors of the present invention belong to the CCAAT binding HAP2 or HAP5 families.

Generally, transcription factors are involved in cell differentiation and proliferation and the regulation of growth. Accordingly, one skilled in the art would recognize that by expressing the present sequences in a plant, by, for example, introducing into the plant a polynucleotide sequence encoding a transcription factor of the invention, one may change the expression of autologous genes or induce the expression of introduced genes and thus alter the plant's phenotype to one with improved traits related to size, growth rate and/or yield. Plants may then be selected for those that produce the most desirable degree of over- or under-expression of target genes of interest and coincident trait improvement.

The sequences of the present invention may be derived from any species, particularly plant species, in a naturally occurring form or from any source whether natural, synthetic, semi-synthetic or recombinant. The sequences of the invention may also include functional fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode polypeptides that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) and Peng et al. (1999). In addition, many others have demonstrated that an *Arabidopsis* transcription factor expressed in an exogenous plant species elicits the same or very similar phenotypic response (see, for example, Fu et al., 2001; Nandi et al., 2000; Coupland, 1995; and Weigel and Nilsson, 1995).

In another example, Mandel et al. (1992b) and Suzuki et al. (2001) teach that a transcription factor expressed in another plant species elicits the same or very similar phenotypic response of the endogenous sequence, as often predicted in earlier studies of *Arabidopsis* transcription factors in *Arabidopsis* (see Mandel et al., 1992a; and Suzuki et al., 2001). Other examples include Müller et al. (2001); Kim et al., (2001); Kyozuka and Shimamoto (2002); Boss and Thomas (2002); He et al. (2000); and Robson et al. (2001).

In yet another example, Gilmour et al. (1998) teach that an *Arabidopsis* AP2 transcription factor, CBF1, which, when overexpressed in transgenic plants, increases plant freezing tolerance. Jaglo et al. (2001) further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis*, *B. napus*, wheat, rye, and tomato revealed the presence of conserved consecutive amino acid residues, PICK/RPAGRxKFxETRHP (SEQ ID NO: 215) and DSAWR (SEQ ID NO: 216), which bracket the AP2/EREBP DNA binding domains of the proteins and distinguish them from other members of the AP2/EREBP protein family. (Jaglo et al., 2001)

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al., 2000; and Borevitz et al., 2000). Further, global transcript profiles have been used successfully as diagnostic tools for specific cellular states (e.g., cancerous vs. non-cancerous; Bhattacharjee et al., 2001; and Xu et al., 2001). Consequently, it is evident to one skilled in the art that similarity of transcript profile upon overexpression of different transcription factors would indicate similarity of transcription factor function.

Polypeptides and Polynucleotides of the Invention

The present invention includes putative transcription factors (TFs), and isolated or recombinant polynucleotides encoding the polypeptides, or novel sequence variant polypeptides or polynucleotides encoding novel variants of polypeptides derived from the specific sequences provided in the Sequence Listing; the recombinant polynucleotides of the invention may be incorporated in expression vectors for the purpose of producing transformed plants. Also provided are methods for modifying yield from a plant by modifying the mass, size or number of plant organs or seed of a plant by controlling a number of cellular processes. These methods are based on the ability to alter the expression of transcription factors, critical regulatory molecules that may be conserved between diverse plant species. Related conserved regulatory molecules may be originally discovered in a model system such as *Arabidopsis* and homologous, functional molecules may then be discovered in other plant species. The latter may then be used to confer increased yield in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known polypeptides. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known polypeptides.

Additional polynucleotides of the invention were identified by screening *Arabidopsis thaliana* and/or other plant cDNA libraries with probes corresponding to known polypeptides under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE were performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

Many of the sequences in the Sequence Listing, derived from diverse plant species, have been ectopically expressed in transgenic plants. Therefore, the present polynucleotides and polypeptides can be used to change expression levels of genes, polynucleotides, and/or proteins of plants or plant cells. The changes in the characteristic(s) or trait(s) of the plants were then observed and found to confer increased growth rate and/or size.

Background Information for HAP2 and HAP5 Related Sequences; the Role of the CCAAT-box Element and CCAAT-box Binding Proteins Transcriptional regulation of most eukaryotic genes occurs through the binding of transcription factors to sequence specific binding sites in their promoter regions. Many of these protein binding sites have been conserved through evolution and are found in the promoters of diverse eukaryotic organisms. One element that shows a high degree of conservation is the CCAAT-box (Gelinas et al., 1985). This cis-acting regulatory element is found in all eukaryotic species and is present in the promoter and enhancer regions of approximately 30% of genes (Bucher and Trifonov, 1988; Bucher, 1990). The CCAAT-box can function in either orientation, and operates alone, or in possible cooperation with other cis regulatory elements (Tasanen et al., 1992).

Proteins that bind the CCAAT-box element were first identified in yeast, and function as a hetero-tetrameric complex called the HAP complex (heme activator protein complex) or the CCAAT binding factor (Forsburg and Guarente, 1988). The yeast HAP complex is composed of at least four subunits, HAP2, HAP3, HAP4, and HAP5, each of which is encoded by a single gene. The yeast HAP4 polypeptide does not bind to DNA but associates with the HAP2, 3, 5 complex and activates transcription through an acidic domain. (Forsburg and Guarente, 1989). The yeast HAP complex has a key role in the regulation of energy metabolism. In particular, the HAP complex is required for growth on non-fermentable carbon sources and is involved in the activation of genes involved in mitochondrial biogenesis (Mazon et al., 1982; Dang et al., 1996; Gancedo, 1998).

CCAAT binding factors of the HAP2-like, HAP3-like and HAP5-like classes are found in plant proteomes, and as in mammals, HAP4-like factors are absent (Edwards et al., 1998). In vertebrates, the three sequences of the CCAAT-binding factor are known as NF-YA, NF-YB, and NF-YC, respectively, and are homologous to HAP2, HAP3 and HAP5 subunits, respectively. In plants, the HAP2-like, HAP3-like and HAP5-like proteins are each encoded by small gene families and likely play a more complex role in regulating gene transcription than in yeast. We have identified 36 CCAAT family genes in the *Arabidopsis* genome, and these are approximately equally divided into each of the three subfamilies. In *Arabidopsis* there are 10 members of the HAP2 (NF-YA) subfamily, 12 members of the HAP3 (NF-YB) subfamily, and 11 members of the HAP5 (NF-YC) subfamily. Three additional *Arabidopsis* proteins were also identified that did not clearly fit into any of the three sub-groups, but that have some similarity to HAPs; we have designated these as HAP-like factors.

The three types of subunits in plants have the same kind of structural organization as their counterparts from mammals. For example, G481 (found in PCT patent publication WO2004076638) encodes a 141 amino acid protein of the HAP3 (NF-YB) class. In the case of the HAP3 class, the central conserved region, which confers the DNA binding and subunit interaction properties, is termed the B domain. The more variable N and C terminal regions are called the A and C domains, respectively (Li et al., 1992).

Like their mammalian counterparts, plant CCAAT binding factors most likely bind DNA as heterotrimers composed of HAP2-like, HAP3-like and HAP5-like subunits. All subunits contain regions that are required for DNA binding and subunit association. However, regions that might have an activation domain function are less apparent than in the mammalian proteins, where Q-rich regions within the HAP2 and HAP5 subunits are thought to fulfill such a role. Nonetheless, some of the HAP2 and HAP5 class proteins that we have identified do have Q-rich regions within the N and C-termini. However, these regions have not been confirmed yet as having such activation domain properties.

There is some support for the notion that HAP subunits might function in close association with other transcription factors on target promoters as part of a larger complex. This is evidenced by that fact that the CCAAT box is generally found in close proximity to other promoter elements. In particular, a HAP3-like protein from rice, OsNF-YB1, interacts with a MADS-box protein OsMADS18 in vitro as part of a ternary complex (Masiero et al., 2002). It was also shown that the in vitro interaction between these two types of transcription factors requires that OsNF-YB1 dimerizes with a HAP5-like protein, and that OsMADS18 forms a heterodimer with another MADS-box protein. Interestingly, the OsNF-YB1/HAP5 protein dimer is incapable of interacting with HAP2-like subunits and therefore cannot bind the CCAAT element. The authors therefore speculated that there is a select set of HAP3-like proteins in plants that act on non-CCAAT promoter elements by virtue of their interaction with other non-CCAAT transcription factors (Masiero et al., 2002). In support of this, HAP3/HAP5 subunit dimers have been shown to be able to interact with TFIID in the absence of HAP2 subunits (Romier et al., 2003).

A number of phylogenetically-related sequences from diverse plant species are listed in Tables 1-4 for HAP2 (Tables 1 and 2) and HAP5 (Tables 3 and 4) proteins, respectively. These tables include the SEQ ID NO: (Column 1 of each table), the species from which the sequence was derived and the Gene Identifier ("GID"; Column 2 of each table), the percent identity of each polypeptide to the full length polypeptide of G929, SEQ ID NO: 2 (Table 1, Column 3), G3926, SEQ ID NO: 18 (Table 2, column 3), G3911, SEQ ID NO: 36 (Table 3, Column 3) and G3543, SEQ ID NO: 68 (Table 4, Column 3), as determined by a BLASTp analysis with a wordlength (W) of 3, an expectation (E) of 10, and the BLOSUM62 scoring matrix Henikoff & Henikoff (1989). The numbers in parentheses in Column 3 in each of these tables indicate the number of identical residues over the number of residues in the length of sequence compared in the BLAST analysis. Tables 1-4 also list the amino acid residue coordinates for the conserved domains, in coordinates beginning at the N-terminus of each of the sequences (Column 4 of each table), the conserved domain sequences of the respective polypeptides (Column 5 of each table); the SEQ ID NO: of each of the conserved domains (Column 6 of each table), the percentage identity of each conserved domain in each Column 5 to the conserved domain of G929, SEQ ID NO: 85 (Table 1, Column 7), G3926, SEQ ID NO: 93 (Table 2, Column 7), G3911, SEQ ID NO: 102 (Table 3, Column 7), or G3543, SEQ ID NO: 118 (Table 4, Column 7), and in the assays performed thus far, whether a transgenic plant overexpressing the CCAAT-binding transcription factor was larger, had greater biomass, and/or a faster growth rate relative to a control plant at the seedling stage or adult stage (Column 8 of each table). Positive results are reported when more than one line (except in Tables 3 and 4 for G3886 and G3894 as noted) had larger size, biomass and/or faster growth rate than wild type controls or control plants harboring an empty vector. Transgenic plants generated with the sequences in Tables 1-4 overexpressed the transcription factor under the regulatory control of the constitutive CaMV 35S promoter, unless otherwise noted for certain tissue-specific promoters. "OE" refers to a transgenic plant overexpressing a CCAAT-binding transcription factor of Column 1. Species abbreviations used in these tables included: At—*Arabidopsis thaliana*; Gm—*Glycine max*; Gr—*Gossypium raimondii*; Le—*Lycopersicon esculentum*; Os—*Oryza sativa*; Zm—*Zea mays*.

At the time of evaluation, plants were given one of the following scores:

(+) Enhanced size, biomass and/or growth rate compared to controls. The response was consistent but was only moderately above the normal levels of variability observed for that assay.

(−) No detectable difference from wild-type controls, or impaired size, biomass and/or growth rate compared to controls.

(n/d) Experiment failed, data not obtained, or assay not performed.

TABLE 1

Sequential and functional similarity of G929-related HAP2 polypeptides and conserved domains

| Col. 1 Polypeptide SEQ ID NO: | Col. 2 Species/ GID No. | Col. 3 Percent identity of polypeptide in Column 1 to G929 | Col. 4 Conserved domain in amino acid coordinates | Col. 5 HAP2 conserved domain | Col. 6 SEQ ID NO: of conserved domain | Col. 7 Percent identity of conserved domain in Column 5 to conserved domain of G929 | Col. 8 OE had greater size, biomass or faster growth rate |
|---|---|---|---|---|---|---|---|
| 2 | At/G929 | 100% (198/198) | 98-157 | EPVFVNAKQ YHGILRRRQS RAKLEARNR AIKAKKPYM HESRHLHAIR RPRGCGGRF LNAK | 85 | 100% (60/60) | + |
| 4 | At/G2344 | 63% (126/197) | 100-159 | EPVFVNAKQ YHGILRRRQS RARLESQNK VIKSRKPYLH ESRHLHAIRR PRGCGGRFL NAK | 86 | 86% (52/60) | + |
| 6 | At/G931 | 47% (73/155) | 172-231 | EPVFVNAKQ FHAIMRRRQ QRAKLEAQN KLIKARKPYL HESRHVHAL KRPRGSGGR FLNTK | 87 | 76% (46/60) | + |

TABLE 1-continued

Sequential and functional similarity of G929-related HAP2 polypeptides and conserved domains

| Col. 1 Polypeptide SEQ ID NO: | Col. 2 Species/ GID No. | Col. 3 Percent identity of polypeptide in Column 1 to G929 | Col. 4 Conserved domain in amino acid coordinates | Col. 5 HAP2 conserved domain | Col. 6 SEQ ID NO: of conserved domain | Col. 7 Percent identity of conserved domain in Column 5 to conserved domain of G929 | Col. 8 OE had greater size, biomass or faster growth rate |
|---|---|---|---|---|---|---|---|
| 8 | Gm/G3920 | 50% (69/136) | 149-208 | EPVYVNAKQ YHGILRRRQS RAKAEIEKK VIKNRKPYL HESRHLHAM RRARGNGGR FLNTK | 88 | 76% (46/60) | + |
| 10 | At/G928 | 45% (68/151) | 179-238 | DPVFVNAKQ YHAIMRRRQ QRAKLEAQN KLIRARKPYL HESRHVHAL KRPRGSGGR FLNTK | 89 | 75% (45/60) | + |
| 12 | At/G1782 | 58% (56/96) | 178-237 | EPIFVNAKQY HAILRRRKH RAKLEAQNK LIKCRKPYLH ESRHLHALK RARGSGGRF LNTK | 90 | 75% (45/60) | + |
| 213 | Zm/G4261 | 55% (64/116) | 175-231 | EPVYVNAKQ YHGILRRRQS RAKAELEKK VVKARKPYL HESRHQHAM RRARGNGGR FL | 214 | 75% (45/60) | n/d |
| 14 | At/G1363 | 42% (66/156) | 171-230 | EPIFVNAKQY QAILRRRERR AKLEAQNKL IKVRKPYLHE SRHLHALKR VRGSGGRFL NTK | 91 | 73% (44/60) | + |
| 16 | Os/G3924 | 42% (74/174) | 163-222 | EPVYVNAKQ YHGILRRRQS RAKAELEKK VVKSRKPYL HESRHQHAM RRARGTGGR FLNTK | 92 | 73% (44/60) | + |
| 28 | At/G2632 | 50% (67/134) | 166-223 | EPVFVNAKQ YQAILRRRQ ARAKAELEK KLIKSRKPYL HESRHQHAM RRPRGTGGR FAK | 98 | 73% (41/56) | − |
| 18 | Os/G3926 | 42% (79/184) | 164-222 | EPIFVNAKQY NAILRRRQTR AKLEAQNKA VKGRKPYLH ESRHHHAMK RARGSGGRF LTK | 93 | 71% (43/60) | + |
| 20 | Os/G3925 | 42% (67/158) | 138-197 | EPIYVNAKQ YHAILRRRQL RAKLEAENK | 94 | 71% (43/60) | + |

TABLE 1-continued

Sequential and functional similarity of G929-related HAP2 polypeptides and conserved domains

| Col. 1 Polypeptide SEQ ID NO: | Col. 2 Species/ GID No. | Col. 3 Percent identity of polypeptide in Column 1 to G929 | Col. 4 Conserved domain in amino acid coordinates | Col. 5 HAP2 conserved domain | Col. 6 SEQ ID NO: of conserved domain | Col. 7 Percent identity of conserved domain in Column 5 to conserved domain of G929 | Col. 8 OE had greater size, biomass or faster growth rate |
|---|---|---|---|---|---|---|---|
| | | | | LVKNRKPYL HESRHQHAM KRARGTGGR FLNTK | | | |
| 22 | Zm/G3921 | 41% (71/170) | 148-207 | EPIYVNAKQ YHAILRRRQT RAKLEAQNK MVKGRKPYL HESRHRHAM KRARGSGGR FLNTK | 95 | 71% (43/60) | n/d |
| 24 | Zm/G3922 | (69/193) | 171-230 | EPIYVNAKQ YHAILRRRQT RAKLEAQNK MVKNRKPYL HESRHRHAM KRARGSGGR FLNTK | 96 | 71% (43/60) | n/d |
| 26 | Zm/G4264 | 38% (74/193) | 155-214 | EPIYVNAKQ YHAILRRRQT RAKLEAQNK MVKNRKPYL HESRHRHAM KRARGSGGR FLNTK | 97 | 71% (43/60) | + |
| 30 | At/G1334 | 40% (60/149) | 133-190 | DGTIYVNSK QYHGIIRRRQ SRAKAEKLS RCRKPYMHH SRHLHAMRR PRGSGGRFL NTK | 99 | 70% (41/58) | + |
| 32 | At/G926 | 44% (58/131) | 171-228 | EPVYVNAKQ YEGILRRRKA RAKAELERK VIRDRKPYLH ESRHKHAMR RARASGGRF AK | 100 | 66% (37/56) | +[1] |
| 34 | At/G927 | 37% (59/156) | 136-199 | STIYVNSKQY HGIIRRRQSR AKAAAVLDQ KKLSSRCRKP YMHHSRHLH ALRRPRGSG GRFLNTK | 101 | 64% (40/62) | − |

TABLE 2

Sequential and functional similarity of G3926-related HAP2 polypeptides and conserved domains

| Col. 1 Polypeptide SEQ ID NO: | Col. 2 Species/ GID No. | Col. 3 Percent identity of polypeptide in Column 1 to G3926 | Col. 4 Conserved domain in amino acid coordinates | Col. 5 HAP2 conserved domain | Col. 6 SEQ ID NO: of conserved domain | Col. 7 Percent identity of conserved domain in Column 5 to conserved domain of G3926 | Col. 8 OE had greater size, biomass or faster growth rate |
|---|---|---|---|---|---|---|---|
| 18 | Os/G3926 | 100% (317/317) | 164-222 | EPIFVNAKQY NAILRRRQTR AKLEAQNKA VKGRKPYLH ESRHHHAMK RARGSGGRF LTK | 93 | 100% (59/59) | + |
| 22 | Zm/G3921 | 47% (143/304) | 148-207 | EPIYVNAKQ YHAILRRRQT RAKLEAQNK MVKGRKPYL HESRHRHAM KRARGSGGR FLNTK | 95 | 92% (53/57) | n/d |
| 24 | Zm/G3922 | 47% (140/295) | 171-230 | EPIYVNAKQ YHAILRRRQT RAKLEAQNK MVKNRKPYL HESRHRHAM KRARGSGGR FLNTK | 96 | 91% (52/57) | n/d |
| 26 | Zm/G4264 | 46% (146/311) | 155-214 | EPIYVNAKQ YHAILRRRQT RAKLEAQNK MVKNRKPYL HESRHRHAM KRARGSGGR FLNTK | 97 | 91% (52/57) | + |
| 12 | At/G1782 | 37% (89/236) | 178-237 | EPIFVNAKQY HAILRRRKH RAKLEAQNK LIKCRKPYLH ESRHLHALK RARGSGGRF LNTK | 90 | 85% (49/57) | + |
| 20 | Os/G3925 | 50% (104/204) | 138-197 | EPIYVNAKQ YHAILRRRQL RAKLEAENK LVKNRKPYL HESRHQHAM KRARGTGGR FLNTK | 94 | 85% (49/57) | + |
| 14 | At/G1363 | 37% (98/259) | 171-230 | EPIFVNAKQY QAILRRRERR AKLEAQNKL IKVRKPYLHE SRHLHALKR VRGSGGRFL NTK | 91 | 84% (48/57) | + |
| 6 | At/G931 | 37% (104/278) | 172-231 | EPVFVNAKQ FHAIMRRRQ QRAKLEAQN KLIKARKPYL HESRHVHAL KRPRGSGGR FLNTK | 87 | 80% (46/57) | + |
| 10 | At/G928 | 35% (94/262) | 179-238 | DPVFVNAKQ YHAIMRRRQ QRAKLEAQN | 89 | 78% (45/57) | |

TABLE 2-continued

Sequential and functional similarity of G3926-related HAP2 polypeptides and conserved domains

| Col. 1 Polypeptide SEQ ID NO: | Col. 2 Species/ GID No. | Col. 3 Percent identity of polypeptide in Column 1 to G3926 | Col. 4 Conserved domain in amino acid coordinates | Col. 5 HAP2 conserved domain | Col. 6 SEQ ID NO: of conserved domain | Col. 7 Percent identity of conserved domain in Column 5 to conserved domain of G3926 | Col. 8 OE had greater size, biomass or faster growth rate |
|---|---|---|---|---|---|---|---|
| | | | | KLIRARKPYL HESRHVHAL KRPRGSGGR FLNTK | | | |
| 4 | At/G2344 | 49% (66/134) | 100-159 | EPVFVNAKQ YHGILRRRQS RARLESQNK VIKSRKPYLH ESRHLHAIRR PRGCGGRFL NAK | 86 | 75% (43/57) | + |
| 16 | Os/G3924 | 45% (76/167) | 163-222 | EPVYVNAKQ YHGILRRRQS RAKAELEKK VVKSRKPYL HESRHQHAM RRARGTGGR FLNTK | 92 | 75% (43/57) | + |
| 213 | Zm/G4261 | 47% (87/183) | 175-231 | EPVYVNAKQ YHGILRRRQS RAKAELEKK VVKARKPYL HESRHQHAM RRARGNGGR FL | 214 | 75% (43/57) | n/d |
| 2 | At/G929 | 42% (79/184) | 98-157 | EPVFVNAKQ YHGILRRRQS RAKLEARNR AIKAKKPYM HESRHLHAIR RPRGCGGRF LNAK | 85 | 73% (42/57) | + |
| 28 | At/G2632 | 40% (87/217) | 166-223 | EPVFVNAKQ YQAILRRRQ ARAKAELEK KLIKSRKPYL HESRHQHAM RRPRGTGGR FAK | 98 | 72% (43/59) | − |
| 8 | Gm/G3920 | 36% (76/209) | 149-208 | EPVYVNAKQ YHGILRRRQS RAKAEIEKK VIKNRKPYL HESRHLHAM RRARGNGGR FLNTK | 88 | 73% (42/57) | + |
| 32 | At/G926 | 39% (75/192) | 171-228 | EPVYVNAKQ YEGILRRRKA RAKAELERK VIRDRKPYLH ESRHKHAMR RARASGGRF AK | 100 | 67% (40/59) | +[1] |
| 30 | At/G1334 | 39% (54/136) | 133-190 | DGTIYVNSK QYHGIIRRRQ SRAKAEKLS RCRKPYMHH | 99 | 65% (36/55) | + |

TABLE 2-continued

Sequential and functional similarity of G3926-related HAP2 polypeptides and conserved domains

| Col. 1 Polypeptide SEQ ID NO: | Col. 2 Species/ GID No. | Col. 3 Percent identity of polypeptide in Column 1 to G3926 | Col. 4 Conserved domain in amino acid coordinates | Col. 5 HAP2 conserved domain | Col. 6 SEQ ID NO: of conserved domain | Col. 7 Percent identity of conserved domain in Column 5 to conserved domain of G3926 | Col. 8 OE had greater size, biomass or faster growth rate |
|---|---|---|---|---|---|---|---|
| | | | | SRHLHAMRR PRGSGGRFL NTK | | | |
| 34 | At/G927 | 34% (73/213) | 136-199 | STIYVNSKQY HGIIRRRQSR AKAAAVLDQ KKLSSRCRKH YMHHSRHLH ALRRPRGSG GRFLNTK | 101 | 57% (34/59) | — |

Specific notes for Tables 1 and 2:
[1]Assays with 35S::G926 *Arabidopsis* plants have not yet been performed. However, 35S::G926 overexpressing tomato plants produced increased average fruit weight in the top 5% and cruciferin::G926 tomato plants produced increased average fruit weight in the top 10% of 3,217 tomato lines tested that overexpressed many different *Arabidopsis* transcription factors. *Arabidopsis* plants overexpressing G926-YFP fusion proteins (YFP or "yellow fluorescent protein" is a red-shifted spectral variant of green fluorescent protein (GFP)) were not larger and did not appear to have a faster growth rate than controls.

TABLE 3

Sequential and functional similarity of G3911-related HAP5 polypeptides and conserved domains

| Col. 1 Polypeptide SEQ ID NO: | Col. 2 Species/ GID No. | Col. 3 Percent identity of polypeptide in Column 1 to G3911 | Col. 4 Conserved domain in amino acid coordinates | Col. 5 Conserved domain | Col. 6 SEQ ID NO: of conserved domain | Col. 7 Percent identity of conserved domain in Column 5 to conserved domain of G3911 | Col. 8 OE had greater size, biomass or faster growth rate |
|---|---|---|---|---|---|---|---|
| 36 | Zm/G3911 | 100% (200/200) | 83-148 | LPLARIKKIM KADEDVRMI AAEAPVVFA RACEMFILEL THRGWAHA EENKRRTLQ KSDIAAAIART | 102 | 100% (66/66) | + |
| 38 | Os/G3546 | 79% (167/211) | 91-156 | LPLARIKKIM KADEDVRMI AAEAPVVFA RACEMFILEL THRGWAHA EENKRRTLQ KSDIAAAIART | 103 | 100% (66/66) | + |
| 40 | Zm/G3909 | 78% (159/203) | 86-151 | LPLARIKKIM KADEDVRMI AAEAPVVFS RACEMFILEL THRGWAHA EENKRRTLQ KSDIAAAVA RT | 104 | 96% (64/66) | + |
| 202 | Le/G3894 | 54% (119/220) | 103-168 | LPLARIKKIM KADEDVRMI SAEAPVVFA RACEMFILEL TLRAWNHTE ENKRRTLQK NDIAAAITRT | 203 | 89% (59/66) | +[1] |

TABLE 3-continued

Sequential and functional similarity of G3911-related HAP5 polypeptides and conserved domains

| Col. 1 Polypeptide SEQ ID NO: | Col. 2 Species/ GID No. | Col. 3 Percent identity of polypeptide in Column 1 to G3911 | Col. 4 Conserved domain in amino acid coordinates | Col. 5 Conserved domain | Col. 6 SEQ ID NO: of conserved domain | Col. 7 Percent identity of conserved domain in Column 5 to conserved domain of G3911 | Col. 8 OE had greater size, biomass or faster growth rate |
|---|---|---|---|---|---|---|---|
| 46 | Gm/G3547 | 55% (125/226) | 102-167 | LPLARIKKIM KADEDVRMI SAEAPVIFAR ACEMFILELT LRSWNHTEE NKRRTLQKN DIAAAITRT | 107 | 87% (58/66) | + |
| 48 | At/G714 | 72% (96/132) | 71-136 | LPLARIKKIM KADEDVRMIS AEAPVVFARA CEMFILELTLR SWNHTEENK RRTLQKNDIA AAVTRT | 108 | 87% (58/66) | + |
| 52 | At/G489 | 58% (107/182) | 81-146 | LPLARIKKIM KADEDVRMIS AEAPVVFARA CEMFILELTLR SWNHTEENK RRTLQKNDIA AAVTRT | 110 | 87% (58/66) | +[2] |
| 42 | Zm/G3552 | 55% (121/218) | 100-165 | LPLARIKKIM KADEDVRMI SAEAPVVFA KACEIFILELT LRSWMHTEE NKRRTLQKN DIAAAITRT | 105 | 86% (57/66) | + |
| 44 | At/G483 | 65% (95/144) | 77-142 | LPLARIKKIM KADEDVRMI SAEAPVIFAK ACEMFILELT LRAWIHTEE NKRRTLQKN DIAAAISRT | 106 | 86% (57/66) | − |
| 50 | Os/G3542 | 54% (124/228) | 106-171 | LPLARIKKIM KADEDVRMIS AEAPVVFAKA CEVFILELTLR SWMHTEENK RRTLQKNDIA AAITRT | 109 | 86% (57/66) | + |
| 56 | Gm/G3550 | 56% (108/191) | 107-172 | LPLARIKKIM KADEDVRMIS AEAPVIFAKA CEMFILELTLR SWIHTEENKR RTLQKNDIAA AISRN | 112 | 86% (56/65) | + |
| 58 | Gm/G3548 | 56% (112/198) | 90-155 | LPLARIKKIM KADEDVRMIS AEAPVIFAKA CEMFILELTLR SWIHTEENKR RTLQKNDIAA AISRN | 113 | 86% (56/65) | + |
| 54 | Os/G3544 | 56% (111/198) | 102-167 | LPLARIKKIM KADEDVRMIS AEAPVIFAKA | 111 | 84% (56/66) | + |

TABLE 3-continued

Sequential and functional similarity of G3911-related HAP5 polypeptides and conserved domains

| Col. 1 Polypeptide SEQ ID NO: | Col. 2 Species/ GID No. | Col. 3 Percent identity of polypeptide in Column 1 to G3911 | Col. 4 Conserved domain in amino acid coordinates | Col. 5 Conserved domain | Col. 6 SEQ ID NO: of conserved domain | Col. 7 Percent identity of conserved domain in Column 5 to conserved domain of G3911 | Col. 8 OE had greater size, biomass or faster growth rate |
|---|---|---|---|---|---|---|---|
| | | | | CEIFILELTLRS WMHTEENKR RTLQKNDIAA AITRT | | | |
| 60 | At/G715 | 54% (117/215) | 66-131 | LPLARIKKIM KADEDVRMIS AEAPILFAKA CELFILELTIRS WLHAEENKR RTLQKNDIAA AITRT | 114 | 84% (56/66) | + |
| 62 | Gm/G3886 | 61% (114/186) | 72-137 | LPLARIKKIM KADEDVRMIS AEAPILFAKA CELFILELTIRS WLHAEENKR RTLQKNDIAA AITRT | 115 | 84% (56/66) | +[1] |
| 64 | Zm/G3889 | 55% (114/206) | 69-134 | LPLARIKKIM KADEDVRMIS AEAPVLFAKA CELFILELTIRS WLHAEENKR RTLQRNDVA AAIART | 116 | 84% (56/66) | + |
| 66 | At/G1646 | 53% (111/206) | 79-144 | LPLARIKKIM KADEDVRMIS AEAPILFAKA CELFILELTIRS WLHAEENKR RTLQKNDIAA AITRT | 117 | 84% (56/66) | + |
| 198 | Gr/G3883 | 61% (104/168) | 67-132 | LPLARIKKIM KADEDVRMIS AEAPILFAKA CELFILELTIRS WLHAEENKR RTLQKNDIAA AITRT | 199 | 84% (56/66) | − |
| 210 | Zm/4259 | 57% (115/201) | 70-135 | LPLARIKKIM KADEDVRMIS AEAPVLFAKA CELFILELTIRS WLHAEENKR RTLQRNDVA AAIART | 211 | 84% (56/66) | n/d |
| 68 | Os/G3543 | 55% (108/193) | 70-135 | LPLAGIKKIM KADEDVRMIS AEAPVLFAKA CELFILELTIRS WLHAEENKR RTLQRKDVA AAIART | 118 | 83% (55/66) | + |
| 70 | At/G1820 | 52% (76/145) | 55-120 | LPLARIKKIM KADPDVHMV SAEAPIIFAKA CEMFIVDLTM | 119 | 73% (47/64) | − |

TABLE 3-continued

Sequential and functional similarity of G3911-related HAP5 polypeptides and conserved domains

| Col. 1 Polypeptide SEQ ID NO: | Col. 2 Species/ GID No. | Col. 3 Percent identity of polypeptide in Column 1 to G3911 | Col. 4 Conserved domain in amino acid coordinates | Col. 5 Conserved domain | Col. 6 SEQ ID NO: of conserved domain | Col. 7 Percent identity of conserved domain in Column 5 to conserved domain of G3911 | Col. 8 OE had greater size, biomass or faster growth rate |
|---|---|---|---|---|---|---|---|
| | | | | RSWLKAEEN KRHTLQKSDI SNAVASS | | | |
| 72 | At/G1836 | 53% (65/122) | 37-102 | LPITRIKKIMK YDPDVTMIAS EAPILLSKACE MFIMDLTMRS WLHAQESKR VTLQKSNVDA AVAQT | 120 | 63% (42/66) | + |
| 74 | At/G1819 | 37% (64/169) | 64-135 | FPLTRIKKIMK SNPEVNMVTA EAPVLISKACE MLILDLTMRS WLHTVEGGR QTLKRSDTLT RSDISAATTRS | 121 | 52% (37/71) | + |
| 76 | At/G1818 | 47% (57/119) | 38-102 | PISRIKRIMKF DPDVSMIAAE APNLLSKACE MFVMDLTMR SWLHAQESNR LTIRKSDVDA VVSQT | 122 | 55% (36/65) | + |
| 78 | At/G490 | 41% (41/99) | 68-133 | LPLSRVRKILK SDPEVKKISC DVPALFSKAC EYFILEVTLRA WMHTQSCTR ETIRRCDIFQA VKNS | 123 | 44% (28/63) | + |
| 80 | At/G3074 | 38% (30/77) | 9-73 | FPAARIKKIM QADEDVGKIA LAVPVLVSKS LELFLQDLCD RTYEITLERG AKTVSSLHLK HCVER | 124 | 37% (24/64) | + |
| 82 | At/G1249 | 35% (27/77) | 12-76 | FPIGRVKKIM KLDKDINKIN SEALHVITYST ELFLHFLAEK SAVVTAEKKR KTVNLDHLRI AVKR | 125 | 34% (22/64) | + |
| 84 | At/G3075 | 25% (19/76) | 110-173 | FPMNRIRRIM RSDNSAPQIM QDAVFLVNK ATEMFIERFSE EAYDSSVKDK KKFIHYKHLS SVVS | 126 | 22% (14/63) | − |

TABLE 4

Sequential and functional similarity of G3543-related HAP5 polypeptides and conserved domains

| Col. 1 Polypeptide SEQ ID NO: | Col. 2 Species/ GID No. | Col. 3 Percent identity of polypeptide in Column 1 to G3543 | Col. 4 Conserved domain in amino acid coordinates | Col. 5 Conserved domain | Col. 6 SEQ ID NO: of conserved domain | Col. 7 Percent identity of conserved in Column 5 to conserved domain of G3543 | Col. 8 OE had greater size, biomass or faster growth rate |
|---|---|---|---|---|---|---|---|
| 68 | Os/G3543 | 100% (246/246) | 70-135 | LPLAGIKKIM KADEDVRMI SAEAPVLFA KACELFILEL TIRSWLHAEE NKRRTLQRK DVAAAIART | 118 | 100% (66/66) | + |
| 210 | Zm/4259 | 87% (219/251) | 70-135 | LPLARIKKIM KADEDVRMI SAEAPVLFA KACELFILEL TIRSWLHAEE NKRRTLQRN DVAAAIART | 211 | 96% (64/66 | n/d |
| 64 | Zm/G3889 | 86% (218/251) | 69-134 | LPLARIKKIM KADEDVRMI SAEAPVLFA KACELFILEL TIRSWLHAEE NKRRTLQRN DVAAAIART | 116 | 96% (64/66) | + |
| 60 | At/G715 | 58% (144/248) | 66-131 | LPLARIKKIM KADEDVRMI SAEAPILFAK ACELFILELTI RSWLHAEEN KRRTLQKND IAAAITRT | 114 | 90% (60/66) | + |
| 62 | Gm/G3886 | 58% (142/243) | 72-137 | LPLARIKKIM KADEDVRMI SAEAPILFAK ACELFILELTI RSWLHAEEN KRRTLQKND IAAAITRT | 115 | 90% (60/66) | +[1] |
| 66 | At/G1646 | 56% (143/253) | 79-144 | LPLARIKKIM KADEDVRMI SAEAPILFAK ACELFILELTI RSWLHAEEN KRRTLQKND IAAAITRT | 117 | 90% (60/66) | + |
| 198 | Gr/G3883 | 58% (142/244) | 67-132 | LPLARIKKIM KADEDVRMI SAEAPILFAK ACELFILELTI RSWLHAEEN KRRTLQKND IAAAITRT | 199 | 90% (60/66) | − |
| 56 | Gm/G3550 | 63% (98/154) | 107-172 | LPLARIKKIM KADEDVRMI SAEAPVIFAK ACEMFILELT LRSWIHTEEN KRRTLQKND IAAAISRN | 112 | 84% (55/65) | + |
| 58 | Gm/G3548 | 62% (97/154) | 90-155 | LPLARIKKIM KADEDVRMI SAEAPVIFAK ACEMFILELT | 113 | 84% (55/65) | + |

TABLE 4-continued

Sequential and functional similarity of G3543-related HAP5 polypeptides and conserved domains

| Col. 1 Polypeptide SEQ ID NO: | Col. 2 Species/ GID No. | Col. 3 Percent identity of polypeptide in Column 1 to G3543 | Col. 4 Conserved domain in amino acid coordinates | Col. 5 Conserved domain | Col. 6 SEQ ID NO: of conserved domain | Col. 7 Percent identity of conserved in Column 5 to conserved domain of G3543 | Col. 8 OE had greater size, biomass or faster growth rate |
|---|---|---|---|---|---|---|---|
| | | | | LRSWIHTEEN KRRTLQKND IAAAISRN | | | |
| 50 | Os/G3542 | 55% (113/205) | 106-171 | LPLARIKKIM KADEDVRMI SAEAPVVFA KACEVFILEL TLRSWMHTE ENKRRTLQK NDIAAAITRT | 109 | 84% (56/66) | + |
| 42 | Zm/G3552 | 56% (110/194) | 100-165 | LPLARIKKI MKADEDVR MISAEAPVV FAKACEIFIL ELTLRSWM HTEENKRRT LQKNDIAAA ITRT | 105 | 84% (56/66) | + |
| 54 | Os/G3544 | 54% (108/198) | 102-167 | LPLARIKKIM KADEDVRMI SAEAPVIFAK ACEIFILELTL RSWMHTEEN KRRTLQKND IAAAITRT | 111 | 84% (56/66) | + |
| 44 | At/G483 | 65% (105/161) | 77-142 | LPLARIKKI MKADEDVR MISAEAPVI FAKACEMFI LELTLRAWI HTEENKRRT LQKNDIAAA ISRT | 106 | 83% (55/66) | − |
| 46 | Gm/G3547 | 53% (117/220) | 102-167 | LPLARIKKI MKADEDVR MISAEAPVI FARACEMFI LELTLRSWN HTEENKRRT LQKNDIAAA ITRT | 107 | 83% (55/66) | + |
| 36 | Zm/G3911 | 55% (108/193) | 83-148 | LPLARIKKI MKADEDVR MIAAEAPVV FARACEMFI LELTHRGW AHAEENKR RTLQKSDIA AAIART | 102 | 83% (55/66) | + |
| 38 | Os/G3546 | 56% (110/194) | 91-156 | LPLARIKKI MKADEDVR MIAAEAPVV FARACEMFI LELTHRGW AHAEENKR RTLQKSDIA AAIART | 103 | 83% (55/66) | + |
| 48 | At/G714 | 57% (106/185) | 71-136 | LPLARIKKIM KADEDVRMI SAEAPVVFA | 108 | 81% (54/66) | + |

TABLE 4-continued

Sequential and functional similarity of G3543-related HAP5 polypeptides and conserved domains

| Col. 1 Polypeptide SEQ ID NO: | Col. 2 Species/ GID No. | Col. 3 Percent identity of polypeptide in Column 1 to G3543 | Col. 4 Conserved domain in amino acid coordinates | Col. 5 Conserved domain | Col. 6 SEQ ID NO: of conserved domain | Col. 7 Percent identity of conserved in Column 5 to conserved domain of G3543 | Col. 8 OE had greater size, biomass or faster growth rate |
|---|---|---|---|---|---|---|---|
| | | | | RACEMFILEL TLRSWNHTE ENKRRTLQK NDIAAAVTRT | | | |
| 52 | At/G489 | 53% (117/220) | 81-146 | LPLARIKKIM KADEDVRMI SAEAPVVFA RACEMFILEL TLRSWNHTE ENKRRTLQK NDIAAAVTRT | 110 | 81% (54/66) | +[2] |
| 202 | Le/G3894 | 59% (108/182) | 103-168 | LPLARIKKI MKADEDVR MISAEAPVV FARACEMFI LELTLRAW NHTEENKR RTLQKNDIA AAITRT | 203 | 81% (54/64) | +[1] |
| 40 | Zm/G3909 | 55% (108/193) | 86-151 | LPLARIKKI MKADEDVR MIAAEAIPVV FSRACEMFI LELTHRGW AHAEENKR RTLQKSDIA AAVART | 104 | 80% (53/66) | + |
| 70 | At/G1820 | 43% (85/195) | 55-120 | LPLARIKKIM KADPDVHM VSAEAPIIFA KACEMFIVD LTMRSWLKA EENKRHTLQ KSDISNAVASS | 119 | 71% (46/64) | - |
| 72 | At/G1836 | 46% (72/154) | 37-102 | LPITRIKKIM KYDPDVTMI ASEAPILLSK ACEMFIMDL TMRSWLHAQ ESKRVTLQK SNVDAAVAQT | 120 | 63% (42/66) | + |
| 74 | At/G1819 | 38% (67/174) | 64-135 | FPLTRIKKIM KSNPEVNMV TAEAPVLISK ACEMLILDLT MRSWLHTVE GGRQTLKRS DTLTRSDISA ATTRS | 121 | 61% (35/57) | + |
| 76 | At/G1818 | 35% (70/195) | 38-102 | PISRIKRIMKF DPDVSMIAA EAPNLLSKA CEMFVMDLT MRSWLHAQE SNRLTIRKSD VDAVVSQT | 122 | 55% (36/65) | + |
| 78 | At/G490 | 40% (41/101) | 68-133 | LPLSRVRKIL KSDPEVKKIS CDVPALFSK ACEYFILEVT | 123 | 47% (30/63) | + |

TABLE 4-continued

Sequential and functional similarity of G3543-related HAP5 polypeptides and conserved domains

| Col. 1 Polypeptide SEQ ID NO: | Col. 2 Species/ GID No. | Col. 3 Percent identity of polypeptide in Column 1 to G3543 | Col. 4 Conserved domain in amino acid coordinates | Col. 5 Conserved domain | Col. 6 SEQ ID NO: of conserved domain | Col. 7 Percent identity of conserved in Column 5 to conserved domain of G3543 | Col. 8 OE had greater size, biomass or faster growth rate |
|---|---|---|---|---|---|---|---|
| | | | | LRAWMHTQS CTRETIRRCD IFQAVKNS | | | |
| 80 | At/G3074 | 39% (31/79) | 9-73 | FPAARIKKIM QADEDVGKI ALAVPVLVS KSLELFLQDL CDRTYEITLE RGAKTVSSL HLKHCVER | 124 | 39% (25/64) | + |
| 82 | At/G1249 | 34% (27/79) | 12-76 | FPIGRVKKIM KLDKDINKIN SEALHVITYS TELFLHFLAE KSAVVTAEK KRKTVNLDH LRIAVKR | 125 | 34% (22/64) | + |
| 84 | At/G3075 | 26% (27/101) | 110-173 | FPMNRIRRIM RSDNSAPQIM QDAVFLVNK ATEMFIERFS EEAYDSSVK DKKKFIHYK HLSSVVS | 126 | 23% (15/63) | - |

Specific notes for Tables 3 and 4:
[1] One of ten lines had larger seedlings
[2] Numerous plants overexpressing G489-YFP fusion proteins had larger rosettes than controls; YFP or "yellow fluorescent protein is a red-shifted spectral variant of green fluorescent protein (GFP)

Orthologs and Paralogs

Homologous sequences as described above can comprise orthologous or paralogous sequences. Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen (1998), evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis; functional predictions can be greatly improved by focusing on how the genes became similar in sequence, i.e., by evolutionary processes, rather than on the sequence similarity itself (Eisen, 1998). In fact, many specific examples exist in which gene function has been shown to correlate well with gene phylogeny (Eisen, 1998). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, 1998).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same Glade (a group of similar genes) when a gene family phylogeny is analyzed using programs such as CLUSTAL (Thompson et al., 1994; Higgins et al., 1996). Groups of similar genes can also be identified with pair-wise BLAST analysis (Feng and Doolittle, 1987). For example, a Glade of very similar MADS domain transcription factors from *Arabidopsis* all share a related function in flowering time (Ratcliffe et al., 2001, 2003), and a group of very similar AP2 domain transcription factors from *Arabidopsis* are involved in tolerance of plants to freezing (Gilmour et al., 1998). Analysis of groups of similar genes with similar function that fall within one Glade can yield sub-sequences that are particular to the Glade. These sub-sequences, known as consensus sequences, can not only be used to define the sequences within each Glade, but define the functions of these genes; genes within a Glade may contain paralogous sequences, or orthologous sequences that share the same function (see also, for example, Mount, 2001).

Transcription factor gene sequences are conserved across diverse eukaryotic species lines (Goodrich et al., 1993; Lin et al., 1991; Sadowski et al., 1988). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al., 1994; Higgins et al., 1996) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

By using a phylogenetic analysis, one skilled in the art would recognize that the ability to predict similar functions conferred by closely-related polypeptides is predictable. This predictability has been confirmed by our own many studies in which we have found that a wide variety of polypeptides have orthologous or closely-related homologous sequences that function as does the first, closely-related reference sequence. For example, distinct transcription factors, including:

(i) AP2 family *Arabidopsis* G47 (found in US patent publication 20040019925A1), a phylogenetically-related sequence from soybean, and two phylogenetically-related homologs from rice all conferred greater tolerance to drought, hyperosmotic stress, or delayed flowering in transgenic plants as compared to control plants;

(ii) CCAAT family and HAP3 *Arabidopsis* G481 (found in PCT patent publication WO2004076638), and numerous phylogenetically-related sequences from dicots and monocots conferred greater tolerance to drought-related stress as compared to control plants;

(iii) Myb-related *Arabidopsis* G682 (found in PCT patent publication WO2004076638) and numerous phylogenetically-related sequences from dicots and monocots conferred greater tolerance to heat, drought-related stress, cold, and salt as compared to control plants;

(iv) WRKY family *Arabidopsis* G1274 (found in U.S. patent application Ser. No. 10/666,642) and numerous closely-related sequences from dicots and monocots have been shown to confer increased water deprivation tolerance, and (v) AT-hook family soy sequence G3456 (found in US patent publication 20040128712A1) and numerous phylogenetically-related sequences from dicots and monocots, increased biomass compared to control plants when these sequences were overexpressed in plants.

The polypeptide sequences belong to distinct clades of polypeptides that include members from diverse species. In each case, most or all of the Glade member sequences derived from both dicots and monocots have been shown to confer increased yield or tolerance to one or more abiotic stresses when the sequences were overexpressed. These studies and others demonstrate that evolutionarily conserved genes from diverse species are likely to function similarly (i.e., by regulating similar target sequences and controlling the same traits), and that polynucleotides from one species may be transformed into closely-related or distantly-related plant species to confer or improve traits.

As shown in Tables 1-4, polypeptides that are phylogenetically related homologs of the polypeptides of the invention may have conserved domains that share at least 34%, at least 37%, at least 39%, at least 44%, at least 47%, at least 52%, at least 55%, at least 61%, at least 63%, at least 64%, at least 65%, at least 66%, at least 67%, at least 70%, at least 71%, at least 72%, at least 73%, at least 75%, at least 76%, at least 78%, at least 80%, at least 81%, at least 83%, at least 84%, at least 85%, at least 86%, at least 87%, at least 89%, at least 90%, at least 91%, at least 92%, at least 96%, or 100% amino acid sequence identity to similar conserved domains of any of SEQ ID NO: 85-126, 199, 203, 211, or 214, and have similar functions in that the polypeptides of the invention may, when overexpressed, confer at least one regulatory activity selected from the group consisting of greater yield, more rapid growth, greater size, and increased biomass as compared to a control plant.

At the nucleotide level, the sequences of the invention will typically share at least about 30% or 35% nucleotide sequence identity, or 40% nucleotide sequence identity, preferably at least about 50%, or about 60%, or about 70% or about 80% sequence identity, or more preferably about 85%, or about 90%, or about 95% or about 97% or more sequence identity to one or more of the listed full-length sequences, or to a listed sequence but excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp (1988). The clustal algorithm groups sequences into clusters by examining the distances between all pairs. The clusters are aligned pairwise and then in groups. Other alignment algorithms or programs may be used, including FASTA, or BLAST, and which may be used to calculate percent similarity. These are available as a part of the GCG sequence analysis package (University of Wisconsin, Madison, Wis.), and can be used with or without default settings. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Software for performing BLAST analyses is publicly available, e.g., through the National Center for Biotechnology Information (see internet website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, 1990; Altschul et al., 1993). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at www.ncbi.nlm.nih.gov/).

Other techniques for alignment are described by Doolittle (1996). Preferably, an alignment program that permits gaps in the sequence is utilized to align the sequences. The Smith-Waterman is one type of algorithm that permits gaps in sequence alignments (see Shpaer (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity.

Percent identity between polynucleotide sequences can also be counted or calculated by other methods known in the art, e.g., the Jotun Hein method (see, for example, Hein, 1990). Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al., 1997), PFAM, and other databases which contain previously identified and annotated motifs, sequences and gene functions. Methods that search for primary sequence patterns with secondary structure gap penalties (Smith et al., 1992) as well as algorithms such as Basic Local Alignment Search Tool (BLAST; Altschul, 1990; Altschul et al., 1993), BLOCKS (Henikoff and Henikoff, 1991), Hidden Markov Models (HMM; Eddy, 1996; Sonnhammer et al., 1997), and the like, can be used to manipulate and analyze polynucleotide and polypeptide sequences encoded by polynucleotides. These databases, algorithms and other methods are well known in the art and are described in Ausubel et al. (1997) and in Meyers (1995).

A further method for identifying or confirming that specific homologous sequences control the same function is by comparison of the transcript profile(s) obtained upon overexpression or knockout of two or more related polypeptides. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler and Thomashow (2002) have shown that three paralogous AP2 family genes (CBF1, CBF2 and CBF3) are induced upon cold treatment, and each of which can condition improved freezing tolerance, and all have highly similar transcript profiles. Once a polypeptide has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and conserved (e.g., CCAAT binding) domains. Such manual methods are well-known by those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of *Arabidopsis* polypeptide sequences and functionally similar and phylogenetically-related sequences are listed in Tables 1-4 and the Sequence Listing. In addition to the sequences in Tables 1-4 and the Sequence Listing, the invention encompasses isolated nucleotide sequences that are phylogenetically and structurally similar to sequences listed in the Sequence Listing) and can function in a plant by increasing yield and/or and abiotic stress tolerance when ectopically expressed in a plant.

Since a significant number of these sequences are phylogenetically and sequentially related to each other and have been shown to increase yield from a plant and/or abiotic stress tolerance, one skilled in the art would predict that other similar, phylogenetically related sequences falling within the present clades of polypeptides would also perform similar functions when ectopically expressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency under which two polynucleotide strands hybridize, the more similar are the two strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al., 1989; Berger and Kimmel, 1987; and Anderson and Young, 1985).

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger, 1987; and Kimmel, 1987). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art (see, for example, Sambrook et al., 1989; Berger, 1987, pages 467-469; and Anderson and Young, 1985).

Stability of DNA duplexes is affected by such factors as base composition, length, and degree of base pair mismatch. Hybridization conditions may be adjusted to allow DNAs of different sequence relatedness to hybridize. The melting temperature I is defined as the temperature when 50% of the duplex molecules have dissociated into their constituent single strands. The melting temperature of a perfectly matched duplex, where the hybridization buffer contains formamide as a denaturing agent, may be estimated by the following equations:

DNA-DNA: $T_m(°C.)=81.5+16.6(\log [Na+])+0.41(\% G+C)−0.62(\% \text{formamide})−500/L$ (I)

DNA-RNA: $T_m(°C.)=79.8+18.5(\log [Na+])+0.58(\% G+C)+0.12(\% G+C)^2−0.5(\% \text{formamide})−820/L$ (II)

RNA-RNA: $T_m(°C.)=79.8+18.5(\log [Na+])+0.58(\% G+C)+0.12(\% G+C)^2−0.35(\% \text{formamide})−820/L$ (III)

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young, 1985). In addition, one or more of the following may be used to reduce non-specific hybridization: sonicated salmon sperm DNA or another non-complementary DNA, bovine serum albumin, sodium pyrophosphate, sodium dodecyl sulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guideline, high stringency is typically performed at $T_m$-5° C. to $T_m$-20° C., moderate stringency at $T_m$-20° C. to $T_m$-35° C. and low stringency at $T_m$-35° C. to $T_m$-50° C. for duplex >150 base pairs. Hybridization may be performed at low to moderate stringency (25-50° C. below $T_m$), followed by post-hybridization washes at increasing stringencies. Maximum rates of hybridization in solution are determined empirically to occur at $T_m$-25° C. for DNA-DNA duplex and $T_m$-15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point I for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present polypeptides include, for example:

6×SSC at 65° C.;
50% formamide, 4×SSC at 42° C.; or
0.5×SSC, 0.1% SDS at 65° C.;
with, for example, two wash steps of 10-30 minutes each. Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a polypeptide known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a polypeptide that is associated with a particular first trait may also be associated with at least one other, unrelated and inherent second trait that was not predicted by the first trait.

Example I

Project Types and Vector and Cloning Information

A number of constructs were used to modulate the activity of sequences of the invention. An individual project was defined as the analysis of transgenic plant lines for a particular construct (for example, this might include G929, G3926, G3911 or G3543 lines that constitutively overexpressed a sequence of the invention). In the present study, each gene was directly fused to a promoter that drove its expression in transgenic plants. Such a promoter could be the native promoter of that gene, or the cauliflower mosaic 35S promoter. Alternatively, a promoter that drives tissue specific or conditional expression could be used in similar studies.

In the present study, expression of a given polynucleotide from a particular promoter was achieved by either a direct-promoter fusion construct in which that sequence was cloned directly behind the promoter of interest, or a two-component system, described below. A direct fusion approach has the advantage of allowing for simple genetic analysis if a given promoter-polynucleotide line is to be crossed into different genetic backgrounds at a later date. The two-component method potentially allows for stronger expression to be obtained via an amplification of transcription.

For the two-component system, two separate constructs were used: Promoter::LexA-GAL4TA and opLexA::TF. The first of these (Promoter::LexA-GAL4TA) comprised a desired promoter (for example, the floral meristem-specific AP1 promoter, the epidermis and vascular tissue-specific LTP1 promoter, the shoot apical meristem-specific STM promoter, or the embryo-, endosperm-, and fruit-specific cruciferin promoter (SEQ ID NOs: 191, 193, 208 or 205, respectively) cloned in front of a LexA DNA binding domain fused to a GAL4 activation domain. The construct vector backbone (pMEN48, SEQ ID NO: 195) also carried a kanamycin resistance marker along with an opLexA::GFP reporter. Transgenic lines were obtained containing this first component, and a line was selected that showed reproducible expression of the reporter gene in the desired pattern through a number of generations. A homozygous population was established for that line, and the population was supertransformed with the second construct (opLexA::TF) carrying the transcription factor of interest cloned behind a LexA operator site, for example, G1819 (SEQ ID NO: 192), G2344 (SEQ ID NO: 194) or G929 (SEQ ID NO: 206). The backbone of these second construct vectors (pMEN53, SEQ ID NO: 196) also contained a sulfonamide resistance marker. After supertransformation, the LexA-GAL4 transcript was translated, and the resulting fusion protein activated the second component construct causing transcription of the transcription factor of interest.

For analysis of HAP2- or HAP5-overexpressing plants, transgenic lines were created with an expression vector, for example, P399 (SEQ ID NO: 127) or P26600 (SEQ ID NO: 135) containing HAP2 DNA clones, or P26591 (SEQ ID NO: 143) or P26598 (SEQ ID NO: 159) which contained HAP5 cDNA clones. These constructs constituted 35S::0929, 35S::G3926, 35S::G3911 or 35S::G3543 direct promoter-fusions, respectively in these examples, each carrying a kanamycin resistance marker. The constructs were introduced into Arabidopsis plants as indicated in following Examples.

A list of constructs (PIDs), indicating the promoter fragment that was used to drive the transgene, along with the cloning vector backbone, is provided in Table 5. Compilations of the sequences of promoter fragments and the expressed transgene sequences within the PIDs are provided in the Sequence Listing.

TABLE 5

Expression constructs, sequences of promoter fragments and the expressed transgene sequences

| Gene Identifier | Construct (PID) | SEQ ID NO: of PID | Promoter | Project type | Vector |
|---|---|---|---|---|---|
| G929 | P399 | 127 | 35S | Direct promoter-fusion | pMEN20 |
| G2344 | P1627 | 128 | 35S | Direct promoter-fusion | pMEN65 |
| G931 | P1608 | 129 | 35S | Direct promoter-fusion | pMEN65 |
| G3920 | P26608 | 130 | 35S | Direct promoter-fusion | pMEN65 |
| G928 | P143 | 131 | 35S | Direct promoter-fusion | pMEN20 |
| G1782 | P966 | 132 | 35S | Direct promoter-fusion | pMEN65 |
| G1363 | P26121 | 133 | 35S | Protein-YFP-C-fusion | P25800 |
| G3924 | P26602 | 134 | 35S | Direct promoter-fusion | pMEN65 |
| G3926 | P26600 | 135 | 35S | Direct promoter-fusion | pMEN65 |
| G3925 | P26597 | 136 | 35S | Direct promoter-fusion | pMEN65 |
| G4264 | P26593 | 137 | 35S | Direct promoter-fusion | pMEN65 |
| G2632 | P15494 | 138 | 35S | Direct promoter-fusion | pMEN65 |
| G1334 | P714 | 139 | 35S | Direct promoter-fusion | pMEN20 |
| G926 | P26217 | 140 | 35S | Direct promoter-fusion | pMEN65 |
| G926 | P26217 | 141 | 35S | Protein-YFP-C-fusion | P25800 |
| G927 | P142 | 142 | 35S | Direct promoter-fusion | pMEN20 |
| G3911 | P26591 | 143 | 35S | Direct promoter-fusion | pMEN65 |
| G3546 | P26603 | 144 | 35S | Direct promoter-fusion | pMEN65 |
| G3909 | P26596 | 145 | 35S | Direct promoter-fusion | pMEN20 |
| G3552 | P26595 | 146 | 35S | Direct promoter-fusion | pMEN65 |
| G483 | P48 | 147 | 35S | Direct promoter-fusion | pMEN20 |
| G3547 | P26758 | 148 | 35S | Direct promoter-fusion | pMEN65 |
| G714 | P111 | 149 | 35S | Direct promoter-fusion | pMEN20 |
| G3542 | P26604 | 150 | 35S | Direct promoter-fusion | pMEN65 |

TABLE 5-continued

Expression constructs, sequences of promoter fragments and the expressed transgene sequences

| Gene Identifier | Construct (PID) | SEQ ID NO: of PID | Promoter | Project type | Vector |
|---|---|---|---|---|---|
| G489 | P26060 | 151 | 35S | Protein-YFP-C-fusion | P25800 |
| G3544 | P26599 | 152 | 35S | Direct promoter-fusion | pMEN65 |
| G3550 | P26606 | 153 | 35S | Direct promoter-fusion | pMEN65 |
| G3548 | P26610 | 154 | 35S | Direct promoter-fusion | pMEN65 |
| G715 | P15502 | 155 | 35S | Direct promoter-fusion | pMEN65 |
| G3886 | P26607 | 156 | 35S | Direct promoter-fusion | pMEN65 |
| G3889 | P26590 | 157 | 35S | Direct promoter-fusion | pMEN65 |
| G1646 | P964 | 158 | 35S | Direct promoter-fusion | pMEN65 |
| G3543 | P26598 | 159 | 35S | Direct promoter-fusion | pMEN65 |
| G1820 | P1284 | 160 | 35S | Direct promoter-fusion | pMEN65 |
| G1836 | P973 | 161 | 35S | Direct promoter-fusion | pMEN65 |
| G1819 | P1285 | 162 | 35S | Direct promoter-fusion | pMEN65 |
| G1818 | P1677 | 163 | 35S | Direct promoter-fusion | pMEN65 |
| G490 | P912 | 164 | 35S | Direct promoter-fusion | pMEN65 |
| G3074 | P2712 | 165 | 35S | Direct promoter-fusion | pMEN1963 |
| G1249 | P1184 | 166 | 35S | Direct promoter-fusion | pMEN65 |
| G3075 | P2797 | 167 | 35S | Direct promoter-fusion | pMEN1963 |
| G3883 | P26821 | 200 | 35S | Direct promoter-fusion | pMEN65 |
| G3894 | P26611 | 204 | 35S | Direct promoter-fusion | pMEN65 |
|  | P5326 | 191 | AP1 | AP1::LexA-GAL4TA driver construct in two-component system | pMEN48 |
| G1819 | P4039 | 192 |  | Transcription factor component of two-component system (opLexA::G1819) | pMEN53 |
|  | P5287 | 193 | LTP1 | LTP1::LexA-GAL4TA driver construct in two-component system | pMEN48 |
| G2344 | P6063 | 194 |  | Transcription factor component of two-component system (opLexA::G2344) | pMEN53 |
|  | P5324 | 205 | Cruciferin | CRU::LexA-GAL4TA driver construct in two-component system | pMEN48 |
| G926 | P5562 | 207 |  | Transcription factor component of two-component system (opLexA::G926) | pMEN53 |
|  | P5318 | 208 | STM | STM::LexA-GAL4TA driver construct in two-component system | pMEN48 |

TABLE 5-continued

Expression constructs, sequences of promoter fragments and the expressed transgene sequences

| Gene Identifier | Construct (PID) | SEQ ID NO: of PID | Promoter | Project type | Vector |
|---|---|---|---|---|---|
| G929 | P9107 | 206 | | Transcription factor component of two-component system (opLexA::G929) | pMEN53 |
| | P25800 | 168 | 35S | YFP fusion vector | |
| | pMEN1963 | 169 | 35S | 35S expression vector | |
| | pMEN20 | 170 | 35S | 35S expression vector | |
| | pMEN48 | 195 | 35S | Two component driver vector | |
| | pMEN53 | 196 | | LexA operator and polylinker sequence two component target vector | |
| | pMEN65 | 171 | 35S | 35S expression vector | |

Example II

Transformation of *Agrobacterium* with the Expression Vector

After the plasmid vector containing the gene was constructed, the vector was used to transform *Agrobacterium tumefaciens* cells expressing the gene products. The stock of *Agrobacterium tumefaciens* cells for transformation was made as described by Nagel et al. (1990) *FEMS MicroBiol. Letts*. 67: 325-328. *Agrobacterium* strain ABI was grown in 250 ml LB medium (Sigma) overnight at 28° C. with shaking until an absorbance ($A_{600}$) of 0.5-1.0 was reached. Cells were harvested by centrifugation at 4,000×g for 15 min at 4° C. Cells were then resuspended in 250 µl chilled buffer (1 mM HEPES, pH adjusted to 7.0 with KOH). Cells were centrifuged again as described above and resuspended in 125 µl chilled buffer. Cells were then centrifuged and resuspended two more times in the same HEPES buffer as described above at a volume of 100 µl and 750 µl, respectively. Resuspended cells were then distributed into 40 µl aliquots, quickly frozen in liquid nitrogen, and stored at −80° C.

*Agrobacterium* cells were transformed with plasmids prepared as described above following the protocol described by Nagel et al. For each DNA construct to be transformed, 50-100 ng DNA (generally resuspended in 10 mM Tris-HCl, 1 mM EDTA, pH 8.0) was mixed with 40 µl of *Agrobacterium* cells. The DNA/cell mixture was then transferred to a chilled cuvette with a 2 mm electrode gap and subject to a 2.5 kV charge dissipated at 25 µF and 200 µF using a Gene Pulser II apparatus (Bio-Rad). After electroporation, cells were immediately resuspended in 1.0 ml LB and allowed to recover without antibiotic selection for 2-4 hours at 28° C. in a shaking incubator. After recovery, cells were plated onto selective medium of LB broth containing 100 µg/ml spectinomycin (Sigma) and incubated for 24-48 hours at 28° C. Single colonies were then picked and inoculated in fresh medium. The presence of the plasmid construct was verified by PCR amplification and sequence analysis.

Example III

Transformation of *Arabidopsis* Plants

Transformation of *Arabidopsis* was performed by an *Agrobacterium*-mediated protocol based on the method of Bechtold and Pelletier (1998). Most of the experiments were performed with the *Arabidopsis thaliana* ecotype Columbia (col-0). Some of the results, as noted, were obtained with transformed tomato plants (*Lycopersicon esculentum*).

Plant preparation. Seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial culture preparation. *Agrobacterium* stocks were inoculated from single colony plates or from glycerol stocks and grown with the appropriate antibiotics and grown until saturation. On the morning of transformation, the saturated cultures were centrifuged and bacterial pellets were re-suspended in Infiltration Media (0.5×MS, 1×B5 Vitamins, 5% sucrose, 1 mg/ml benzylaminopurine riboside, 200 µl/L Silwet L77) until an A600 reading of 0.8 was reached.

Transformation and seed harvest. The *Agrobacterium* solution was poured into dipping containers. All flower buds and rosette leaves of the plants were immersed in this solution for 30 seconds. The plants were laid on their side and wrapped with plastic wrap to keep the humidity high. The plants were kept this way overnight at 4° C. and then the pots were turned upright, unwrapped, and moved to growth racks.

The plants were maintained on growth racks under 24-hour light until seeds were ready to be harvested. Seeds were harvested when 80% of the siliques of the transformed plants were ripe (approximately 5 weeks after the initial transformation). This seed was deemed T0 seed, since it was obtained from the T0 generation, and was later plated on selection plates (either kanamycin or sulfonamide). Resistant plants that were identified on such selection plates comprised the T1 generation.

Example IV

Morphology

Morphological analysis was performed to determine whether changes in polypeptide levels affect plant growth and development. This was primarily carried out on the T1 generation, when at least 10-20 independent lines were examined. However, in cases where a phenotype required confirmation or detailed characterization, plants from subsequent generations were also analyzed.

Primary transformants were selected on MS medium with 0.3% sucrose and 50 mg/l kanamycin. T2 and later generation plants were selected in the same manner, except that kanamycin was used at 35 mg/l. In cases where lines carry a sulfonamide marker (as in all lines generated by super-transformation), seeds were selected on MS medium with 0.3% sucrose and 1.5 mg/l sulfonamide. KO lines were usually germinated on plates without a selection. Seeds were cold-treated (stratified) on plates for three days in the dark (in order to increase germination efficiency) prior to transfer to growth cabinets. Initially, plates were incubated at 22° C. under a light intensity of approximately 100 microEinsteins for 7 days. At this stage, transformants were green, possessed two true leaves, and were easily distinguished from bleached kanamycin or sulfonamide-susceptible seedlings. Resistant seedlings were then transferred onto soil (Sunshine potting mix). Following transfer to soil, trays of seedlings were covered with plastic lids for 2-3 days to maintain humidity while they became established. Plants were grown on soil under fluorescent light at an intensity of 70-95 microEinsteins and a temperature of 18-23° C. Light conditions consisted of a 24-hour photoperiod unless otherwise stated. In instances where alterations in flowering time were apparent, flowering time was re-examined under both 12-hour and 24-hour light to assess whether the phenotype was photoperiod dependent. Under our 24-hour light growth conditions, the typical generation time (seed to seed) was approximately 14 weeks.

Because many aspects of *Arabidopsis* development are dependent on localized environmental conditions, in all cases plants were evaluated in comparison to controls in the same flat. For a given construct, ten transformed lines were typically examined in subsequent plate based physiology assays. Controls for transgenic lines were wild-type plants or transgenic plants harboring an empty transformation vector selected on kanamycin or sulfonamide. Careful examination was made at the following stages: young seedling (1 week), rosette (2-3 weeks), flowering (4-7 weeks), and late seed set (8-12 weeks). Seed was also inspected. Young seedling size and morphology was assessed on selection plates. At all other stages, plants were macroscopically evaluated while growing on soil. All significant differences (including alterations in growth rate, size, biomass, etc., were recorded as noted in Example V.

Example V

Assessment of Growth Rate and Size

In subsequent Examples, unless otherwise indicted, morphological traits are disclosed in comparison to control plants. That is, a transformed plant that is described as large and/or has a faster growth rate was large and had a faster growth rate with respect to a control plant, the latter including wild-type plants, parental lines and lines transformed with a vector that does not contain the transcription factor sequence of interest (e.g., an "empty" vector). When a plant is said to have a better performance than controls, it generally was larger, had greater yield, and/or showed fewer stress symptoms than control plants.

Germination assays. All germination assays were performed in tissue culture. Growing the plants under controlled temperature and humidity on sterile medium produced uniform plant material that has not been exposed to additional stresses (such as water stress) which could cause variability in the results obtained.

Prior to plating, seed for all experiments were surface sterilized in the following manner: (1) 5 minute incubation with mixing in 70% ethanol, (2) 20 minute incubation with mixing in 30% bleach, 0.01% triton-X 100, (3) 5× rinses with sterile water, (4) Seeds were re-suspended in 0.1% sterile agarose and stratified at 4° C. for 3-4 days.

All germination assays followed modifications of the same basic protocol. Sterile seeds were sown on the conditional media that has a basal composition of 80% MS+Vitamins. Plates were incubated at 22° C. under 24-hour light (120-130 $\mu E\ m^{-2}\ s^{-1}$) in a growth chamber. Evaluation of germination and seedling vigor was performed five days after planting.

Growth assays. Assays were usually conducted on *Arabidopsis thaliana* ecotype Columbia (col-0) non-selected segregating T2 populations (in order to avoid the extra stress of selection). Control plants for assays on lines containing direct promoter-fusion constructs were wild-type Col-0 plants and/or Col-0 plants transformed with an empty transformation vector (pMEN65, SEQ ID NO: 171).

Example VI

Morphological Observations with HAP2 and HAP5 Overexpressors in *Arabidopsis* and Tomato Overexpression of HAP2 and HAP5 transcription factors in *Arabidopsis* or tomato plants produced the experimental observations related to size or growth rate that are listed in Tables 6 and 7. Experiments indicating larger seedlings or plants than controls also demonstrated a faster growth rate as the observed larger sizes were achieved in the same time period of growth for both controls and experimental plants. This may be particularly important for seedlings of overexpressors that were larger than controls as these plants may be more tolerant to environmental stresses encountered early in their growth.

TABLE 6

Yield-related experimental results obtained with HAP2 overexpressors

| GID | SEQ ID NO: of polypeptide | SEQ ID NO: of conserved domain | % Identity of conserved domain in first column to conserved domain of G929 | % Identity of conserved domain in first column to conserved domain of G3926 | Experimental Observations |
|---|---|---|---|---|---|
| At/G929 | 2 | 85 | 100% | 73% | Two 35S::G929 lines produced seedlings that were larger than controls, and three lines had larger rosettes at the flowering stage A transgenic tomato plant |

TABLE 6-continued

Yield-related experimental results obtained with HAP2 overexpressors

| GID | SEQ ID NO: of polypeptide | SEQ ID NO: of conserved domain | % Identity of conserved domain in first column to conserved domain of G929 | % Identity of conserved domain in first column to conserved domain of G3926 | Experimental Observations |
|---|---|---|---|---|---|
| At/G2344 | 4 | 86 | 86% | 75% | overexpressing G929 under the regulatory control of the cruciferin promoter was considerably larger than control plants (FIG. 6). Three of ten 35S::G2344 lines examined produced seedlings that were larger than controls, and one line had larger rosettes at the flowering stage. The average fruit weights of LTP1::G2344 tomato plants were within the top 1% of all tomato lines tested (plants comprised the two component expression system of SEQ ID NOs: 193 and 194), and STM::G2344 tomato plants were within the top 8% of all tomato lines tested (plants comprised the two component expression system of SEQ ID NOs: 208 and 194); empty vector controls were in the 56$^{th}$ percentile. |
| At/G931 | 6 | 87 | 76% | 80% | Four 35S::G931 lines produced plants that were larger than controls at the rosette stage, and two of these lines maintained larger rosettes at the flowering stage. |
| Gm/G3920 | 8 | 88 | 76% | 73% | Four of ten 35S::G3920 lines produced seedlings that were larger than controls; one line produced plants with larger rosettes than controls at the flowering stage. |
| At/G928 | 10 | 88 | 75% | 78% | Two 35S::G928 lines produced seedlings that were larger than controls, and one of these lines was also larger at the rosette and flowering stages. |
| At/G1782 | 12 | 90 | 75% | 85% | Four 35S::G1782 lines produced plants that were larger than controls at the rosette stage, and two of these lines maintained larger rosettes at the flowering stage. |
| At/G1363 | 14 | 91 | 73% | 84% | One 35S::G1363 line produced plants that were larger at the flowering stage; seven G1363-YFP fusion lines had broader leaves at the rosette stage, and four G1363-YFP fusion lines were large at the flowering stage. |
| Os/G3924 | 16 | 92 | 73% | 75% | Two of ten 35S::G3924 lines examined produced seedlings that were larger than controls. |

TABLE 6-continued

Yield-related experimental results obtained with HAP2 overexpressors

| GID | SEQ ID NO: of polypeptide | SEQ ID NO: of conserved domain | % Identity of conserved domain in first column to conserved domain of G929 | % Identity of conserved domain in first column to conserved domain of G3926 | Experimental Observations |
|---|---|---|---|---|---|
| Os/G3926 | 18 | 93 | 71% | 100% | Three of ten 35S::G3926 lines tested produced seedlings that were larger than controls. |
| Os/G3925 | 20 | 94 | 71% | 85% | Two of ten 35S::G3925 lines examine produced seedlings that were larger than controls. |
| Os/G4264 | 26 | 97 | 71% | 91% | Two of ten 35S::G4264 lines produced seedlings that were larger than controls; four lines produced plants with larger rosettes than controls at the flowering stage. |
| At/G2632 | 28 | 98 | 73% | 72% | None examined thus far have been found that were larger or had a faster growth rate than controls, and some 35S::G2632 seedlings were smaller than controls; |
| At/G1334 | 30 | 99 | 70% | 65% | Four of ten 35S::G1334 lines tested produced seedlings that were larger than controls. |
| At/G926 | 32 | 100 | 66% | 67% | Seedlings overexpressing G926-YFP fusion proteins were similar in size and growth rate to controls. However, the average fruit weights of 35S::G926 tomato plants were within the top 4% of all tomato lines tested (plants comprised the one component expression system of SEQ ID NO: 140), and the average fruit weights of cruciferin::G926 tomato plants were within the top 10% of all tomato lines tested (plants comprised the two component expression system of SEQ ID NOs: 205 and 207); empty vector controls were in the 56$^{th}$ percentile. |
| At/G927 | 34 | 101 | 64% | 57% | 35S::G927 seedlings were similar in size and growth rate to controls. |

TABLE 7

Yield-related experimental results obtained with HAP5 overexpressors

| GID | SEQ ID NO: of polypeptide | SEQ ID NO: of CCAAT-binding domain | % Identity of conserved domain in first column to conserved domain of G3911 | % Identity of conserved domain in first column to conserved domain of G3543 | Experimental Observations |
|---|---|---|---|---|---|
| Zm/G3911 | 36 | 102 | 100% | 83% | Nine 35S::G3911 lines produced seedlings that were larger than controls, and two lines had larger rosettes at their late flowering stage. |
| Os/G3546 | 38 | 103 | 100% | 83% | All ten 35S::G3546 lines tested produced seedlings that were larger than controls. |
| Zm/G3909 | 40 | 104 | 96% | 80% | Seven 35S::G3909 lines produced seedlings that were larger than controls, and seven lines had larger rosettes at their early flowering stage. |
| Le/G3894 | 202 | 203 | 89% | 81%% | Seedlings from a single line of 35S::G3894 plants of ten lines tested were larger and more vigorous than controls seven days after planting. |
| Zm/G3552 | 42 | 105 | 86% | 84% | Eight 35S::G3552 lines produced seedlings that were larger than controls, and one line had slightly broader leaves than controls at its early flowering stage. |
| At/G483 | 44 | 106 | 86% | 83% | 35S::G483 overexpressors were wild-type in size and growth rate in experiments performed to date |
| Gm/G3547 | 46 | 107 | 87% | 83% | Three 35S::G3547 lines produced seedlings that were larger than controls. |
| At/G714 | 48 | 108 | 87% | 81% | Three 35S::G714 lines had larger rosettes at their late flowering stage. |
| Os/G3542 | 50 | 109 | 86% | 84% | Five of ten 35S::G3542 lines tested produced seedlings that were larger than controls. |
| At/G489 | 52 | 110 | 87% | 81% | Thirteen G489-YFP fusion lines had larger rosettes than controls at their late flowering stage. |
| Os/G3544 | 54 | 111 | 84% | 84% | Two of ten 35S::G3544 lines tested produced seedlings that were larger than controls. |
| Gr/G3883 | 198 | 199 | 84% | 90% | 35S::G3883 overexpressors were wild-type in size and growth rate in experiments performed to date. |
| Gm/G3550 | 56 | 112 | 86% | 84% | Five of ten 35S::G3550 lines tested produced seedlings that were larger than controls. |
| Gm/G3548 | 58 | 113 | 86% | 84% | Three of ten 35S::G3548 lines tested produced seedlings that were larger than controls. |
| At/G715 | 60 | 114 | 84% | 90% | One of ten 35S::G715 lines tested produced seedlings that were larger than controls, and another line was larger at the early flowering stage |
| Gm/G3886 | 62 | 115 | 84% | 90% | One of ten 35S::G3886 lines tested produced seedlings that were slightly larger than controls. |
| Zm/G3889 | 64 | 116 | 84% | 96% | Five of ten 35S::G3889 lines tested produced seedlings that were larger than controls. |

TABLE 7-continued

Yield-related experimental results obtained with HAP5 overexpressors

| GID | SEQ ID NO: of polypeptide | SEQ ID NO: of CCAAT-binding domain | % Identity of conserved domain in first column to conserved domain of G3911 | % Identity of conserved domain in first column to conserved domain of G3543 | Experimental Observations |
|---|---|---|---|---|---|
| At/G1646 | 66 | 117 | 84% | 90% | One of ten 35S::G1646 lines tested produced seedlings that were slightly larger than controls; three lines had larger rosettes at early and late flowering stages. |
| Os/G3543 | 68 | 118 | 83% | 100% | Five of ten 35S::G3543 lines tested produced seedlings that were larger than controls. |
| At/G1820 | 70 | 119 | 73% | 71% | 35S::G1820 overexpressors were wild-type in size and growth rate in experiments performed to date. |
| At/G1836 | 72 | 120 | 63% | 63% | One 35S::G1836 line produced larger seedlings in germination and growth assays, and five lines had very full, large rosettes with broad leaves at the late flowering stage. |
| At/G1819 | 74 | 121 | 52% | 61% | One 35S::G1819 Arabidopsis line was slightly larger than controls at the early flowering stage. The average fruit weights of AP1::G1819 overexpressing tomato plants were within the top 5% of all tomato lines tested (plants comprised the two component expression system of SEQ ID NOs: 191 and 192; empty vector controls were in the 56$^{th}$ percentile). |
| At/G1818 | 76 | 122 | 55% | 55% | At late flowering to late stage, many 35S::G1818 lines produced large, full rosettes. |
| At/G490 | 78 | 123 | 44% | 47% | Two 35S::G490 lines produced larger fuller rosettes than controls at the late flowering stage. |
| At/G3074 | 80 | 124 | 37% | 39% | Two 35S::G3074 lines produced larger seedlings in germination and growth assays and five lines had slightly larger rosettes than controls. |
| At/G1249 | 82 | 125 | 34% | 34% | Two 35S::G1249 lines of ten lines tested of overexpressors produced larger seedlings in germination assays. |
| At/G3075 | 84 | 126 | 22% | 23% | 35S::G3075 overexpressors were wild-type in size and growth rate in experiments performed to date. |

Utilities of HAP2 and HAP5 Transcription Factors in Plants

Based on the data obtained in the above-disclosed Examples, the increased size, height and/or biomass of plants that overexpress HAP2 or HAP5 transcription factors indicate that these sequences when overexpressed may be used to improve yield of commercially valuable plants or to help these plants become established more successfully or quickly.

Example VII

Transformation of Dicots to Produce Increased Yield

Crop species that overexpress polypeptides of the invention may produce plants with increased growth rate, size, biomass and/or yield in both stressed and non-stressed conditions. Thus, polynucleotide sequences listed in the Sequence Listing recombined into, for example, one of the expression vectors of the invention, or another suitable expression vector, may be transformed into a plant for the purpose of modifying plant traits for the purpose of improving yield and/or quality. The expression vector may contain a constitutive, tissue-specific or inducible promoter operably linked to the polynucleotide. The cloning vector may be introduced into a variety of plants by means well known in the art such as, for example, direct DNA transfer or *Agrobacterium tumefaciens*-mediated transformation. It is now routine to produce transgenic plants using most dicot plants (see Weissbach and Weissbach, 1989; Gelvin et al., 1990; Herrera-Estrella et al., 1983; Bevan, 1984; and Klee, 1985). Methods for analysis of traits are routine in the art and examples are disclosed above.

Numerous protocols for the transformation of tomato and soy plants have been previously described, and are well known in the art. Gruber et al. (1993) and Glick and Thompson (1993) describe several expression vectors and culture methods that may be used for cell or tissue transformation and subsequent regeneration. For soybean transformation, methods are described by Miki et al. (1993) and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al., 1987; Christou et al., 1992; Sanford, 1993; Klein et al., 1987; U.S. Pat. No. 5,015,580 (Christou et al), issued May 14, 1991; and U.S. Pat. No. 5,322,783 (Tomes et al., issued Jun. 21, 1994)).

Alternatively, sonication methods (see, for example, Zhang et al., 1991); direct uptake of DNA into protoplasts using $CaCl_2$ precipitation, polyvinyl alcohol or poly-L-ornithine (see, for example, Hain et al., 1985; Draper et al., 1982); liposome or spheroplast fusion (see, for example, Deshayes et al., 1985); Christou et al., 1987); and electroporation of protoplasts and whole cells and tissues (see, for example, Donn et al., 1990; D'Halluin et al., 1992; and Spencer et al., 1994) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct lines of plants using traditional backcrossing techniques well known in the art. Transformation of tomato plants may be conducted using the protocols of Koommeef et al (1986), and in U.S. Pat. No. 6,613,962, the latter method described in brief here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 µM α-naphthalene acetic acid and 4.4 µM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS salts with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on 1/10 strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed was treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example VIII

Transformation of Monocots to Produce Increased Yield

Members of the family Gramineae, including turfgrass or other grasses such as *Miscanthus, Panicum virgatum* or other *Panicum* species, or cereal plants such as barley, corn, rice, rye, sorghum, or wheat, may be transformed with the present polynucleotide sequences, including monocot or dicot-derived sequences such as those presented in the present Tables 1-7, cloned into a vector containing a kanamycin-resistance marker, and expressed constitutively under, for example, the CaMV 35S, STM, AP1, LPT1, cruciferin, or COR15 promoters, or with other tissue-specific or inducible promoters. The expression vectors may be one found in the Sequence Listing, or any other suitable expression vector may be similarly used. For example, pMEN020 may be modified to replace the NptII coding region with the Bar gene of *Streptomyces hygroscopi-*

*cus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3 \times 10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from 5Prime-3Prime Inc. (Boulder, Colo.).

It is also routine to use other methods to produce transgenic plants of most cereal crops (Vasil, 1994) such as corn, wheat, rice, sorghum (Cassas et al., 1993), and barley (Wan and Lemeaux, 1994). DNA transfer methods such as the microprojectile method can be used for corn (Fromm et al., 1990; Gordon-Kamm et al., 1990; Ishida, 1990), wheat (Vasil et al., 1992; Vasil et al., 1993; Weeks et al., 1993), and rice (Christou, 1991; Hiei et al., 1994; Aldemita and Hodges, 1996; and Hiei et al., 1997). For most cereal plants, embryogenic cells derived from immature scutellum tissues are the preferred cellular targets for transformation (Hiei et al., 1997; Vasil, 1994). For transforming corn embryogenic cells derived from immature scutellar tissue using microprojectile bombardment, the A188XB73 genotype is the preferred genotype (Fromm et al., 1990; Gordon-Kamm et al., 1990). After microprojectile bombardment, the tissues are selected on phosphinothricin to identify the transgenic embryogenic cells (Gordon-Kamm et al., 1990). Transgenic plants are regenerated by standard corn regeneration techniques (Fromm et al., 1990; Gordon-Kamm et al., 1990).

Example IX

Expression and Analysis of Increased Yield in Non-*Arabidopsis* Species

It is expected that structurally similar orthologs of the HAP2 or HAP5 polypeptide sequences, including those found in the Sequence Listing, can confer increased yield relative to control plants.

Northern blot analysis, RT-PCR or microarray analysis of the regenerated, transformed plants may be used to show expression of a polypeptide or the invention and related genes that are capable of inducing increased growth rate and/or larger size of the plants, including larger seed, plant products or plant parts, such as leaves, roots or stems.

After a dicot plant, monocot plant or plant cell has been transformed (and the latter regenerated into a plant) and shown to have greater size, improved planting density, that is, able to tolerate greater planting density with a coincident increase in yield in the presence or absence of stress conditions, the transformed monocot plant may be crossed with itself or a plant from the same line, a non-transformed or wild-type monocot plant, or another transformed monocot plant from a different transgenic line of plants.

The function of specific polypeptides of the invention, including closely-related orthologs, have been analyzed and may be further characterized and incorporated into crop plants. The ectopic overexpression of these sequences may be regulated using constitutive, inducible, or tissue specific regulatory elements. Genes that have been examined and have been shown to modify plant traits (including increasing growth rate and/or yield) encode polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into any of a considerable variety of plants of different species, and including dicots and monocots. The polynucleotide and polypeptide sequences derived from monocots (e.g., the rice sequences) may be used to transform both monocot and dicot plants, and those derived from dicots (e.g., the *Arabidopsis* and soy genes) may be used to transform either group, although it is expected that some of these sequences will function best if the gene is transformed into a plant from the same group as that from which the sequence is derived.

It is expected that the same methods may be applied to identify other useful and valuable sequences of the present polypeptide clades, and the sequences may be derived from a broad range of plant species.

REFERENCES CITED

Aldemita and Hodges (1996) *Planta* 199: 612-617
Altschul (1990) *J. Mol. Biol.* 215: 403-410
Altschul (1993) *Mol. Evol.* 36: 290-300
Anderson and Young (1985) "Quantitative Filter Hybridisation", In: Hames and Higgins, ed., *Nucleic Acid Hybridisation, A Practical Approach*. Oxford, IRL Press, 73-111
Ausubel et al. (1997) Short Protocols in Molecular Biology, John Wiley & Sons, New York, N.Y., unit 7.7
Bairoch et al. (1997) *Nucleic Acids Res.* 25: 217-221
Bechtold and Pelletier (1998) *Methods Mol. Biol.* 82: 259-266
Berger and Kimmel (1987), "Guide to Molecular Cloning Techniques", in Methods in Enzymology, vol. 152, Academic Press, Inc., San Diego, Calif.
Bevan (1984) *Nucleic Acids Res.* 12: 8711-8721
Bhattacharjee et al. (2001) *Proc. Natl. Acad. Sci. USA* 98: 13790-13795
Borevitz et al. (2000) *Plant Cell* 12: 2383-2393
Boss and Thomas (2002) *Nature*, 416: 847-850
Bruce et al. (2000) *Plant Cell* 12: 65-79
Bucher (1990) *J. Mol. Biol.* 212: 563-578
Bucher and Trifonov (1988) *J. Biomol. Struct. Dyn.* 5: 1231-1236
Cassas et al. (1993) *Proc. Natl. Acad. Sci. USA* 90: 11212-11216
Cheikh et al. (2003) U.S. Patent Application No. 20030101479
Christou et al. (1987) *Proc. Natl. Acad. Sci. USA* 84: 3962-3966
Christou (1991) *Bio/Technol.* 9:957-962
Christou et al. (1992) *Plant. J.* 2: 275-281
Coupland (1995) *Nature* 377: 482-483
Daly et al. (2001) *Plant Physiol.* 127: 1328-1333
Dang et al. (1996) *J. Bacteriol.* 178: 1842-1849
Deshayes et al. (1985) *EMBO J.*, 4: 2731-2737
D'Halluin et al. (1992) *Plant Cell* 4: 1495-1505
Donn et al. (1990) in *Abstracts of VIIth International Congress on Plant Cell and Tissue Culture IAPTC*, A2-38: 53

Doolittle, ed. (1996) *Methods in Enzymology*, vol. 266: "Computer Methods for Macromolecular Sequence Analysis" Academic Press, Inc., San Diego, Calif., USA
Draper et al. (1982) *Plant Cell Physiol.* 23: 451-458
Eddy (1996) *Curr. Opin. Sir. Biol.* 6: 361-365
Edwards et al. (1998) *Plant Physiol.* 117: 1015-1022
Eisen (1998) *Genome Res.* 8: 163-167
Feng and Doolittle (1987) *J. Mol. Evol.* 25: 351-360
Forsburg and Guarente (1988) *Genes Dev.* 3: 1166-1178
Forsburg and Guarente (1989) *Genes Dev.* 3: 1166-1178
Fowler and Thomashow (2002) *Plant Cell* 14: 1675-1690
Fromm et al. (1990) *Bio/Technol.* 8: 833-839
Fu et al. (2001) *Plant Cell* 13: 1791-1802
Gancedo (1998) *Microbiol. Mol. Biol. Rev.* 62: 334-361
Gelinas et al. (1985) *Prog. Clin. Biol. Res.* 191: 125-139
Gelvin et al. (1990) *Plant Molecular Biology Manual*, Kluwer Academic Publishers
Gilmour et al. (1998) *Plant J.* 16: 433-442
Glick and Thompson (1993) *Methods in Plant Molecular Biology and Biotechnology*. eds., CRC Press, Inc., Boca Raton
Gruber et al. (in Glick and Thompson (1993) *Methods in Plant Molecular Biology and Biotechnology*. eds., CRC Press, Inc., Boca Raton
Goodrich et al. (1993) Cell 75: 519-530
Gordon-Kamm et al. (1990) Plant Cell 2: 603-618
Hain et al. (1985) *Mol. Gen. Genet.* 199: 161-168
Haymes et al. (1985) *Nucleic Acid Hybridization: A Practical Approach*, IRL Press, Washington, D. C.
He et al. (2000) *Transgenic Res.* 9: 223-227
Hein (1990) *Methods Enzymol.* 183: 626-645
Henikoff and Henikoff (1989) *Proc. Natl. Acad. Sci. USA* 89:10915
Henikoff and Henikoff (1991) Nucleic Acids Res. 19: 6565-6572
Herrera-Estrella et al. (1983) *Nature* 303: 209
Hiei et al. (1994) *Plant J.* 6:271-282
Hiei et al. (1997) *Plant Mol. Biol.* 35:205-218
Higgins and Sharp (1988) Gene 73: 237-244
Higgins et al. (1996) *Methods Enzymol.* 266: 383-402
Ishida (1990) *Nature Biotechnol.* 14:745-750
Jaglo et al. (2001) *Plant Physiol.* 127: 910-917
Kashima et al. (1985) *Nature* 313: 402-404
Kim et al. (2001) *Plant J.* 25: 247-259
Kimmel (1987) *Methods Enzymol.* 152: 507-511
Klee (1985) *Bio/Technology* 3: 637-642
Klein et al. (1987) *Nature* 327: 70-73
Koornneef et al (1986) in *Tomato Biotechnology*: Alan R. Liss, Inc., 169-178
Ku et al. (2000) *Proc. Natl. Acad. Sci. USA* 97: 9121-9126
Kyozuka and Shimamoto (2002) *Plant Cell Physiol.* 43: 130-135
Li et al. (1992) *Nucleic Acids Res.* 20: 1087-1091
Lin et al. (1991) *Nature* 353: 569-571
Mandel (1992a) *Nature* 360: 273-277
Mandel et al. (1992b) *Cell* 71-133-143
Masiero et al. (2002) *J. Biol. Chem.* 277, 26429-26435
Mazon et al. (1982) *Eur. J. Biochem.* 127: 605-608
Meyers (1995) Molecular Biology and Biotechnology, Wiley VCH, New York, N.Y., p 856-853
Miki et al. (1993) in *Methods in Plant Molecular Biology and Biotechnology*, p. 67-88, Glick and Thompson, eds., CRC Press, Inc., Boca Raton
Mount (2001), in *Bioinformatics: Sequence and Genome Analysis*, Cold Spring Harbor Laboratory Press, Cold Spring Harbor, N.Y., p. 543
Müller et al. (2001) *Plant J.* 28: 169-179
Nandi et al. (2000) *Curr. Biol.* 10: 215-218
Peng et al. (1997) *Genes Development* 11: 3194-3205)
Peng et al. (1999) *Nature* 400: 256-261
Ratcliffe et al. (2001) *Plant Physiol.* 126: 122-132
Ratcliffe et al. (2003) *Plant Cell* 15: 1159-1169
Riechmann et al. (2000a) *Science* 290: 2105-2110
Riechmann and Ratcliffe (2000b) *Curr. Opin. Plant Biol.* 3, 423-434
Rieger et al. (1976) *Glossary of Genetics and Cytogenetics: Classical and Molecular*, 4th ed., Springer Verlag, Berlin
Robson et al. (2001) *Plant J.* 28: 619-631
Romier et al. (2003) *J. Biol. Chem.* 278: 1336-1345
Sadowski et al. (1988) *Nature* 335: 563-564
Sambrook et al. (1989) *Molecular Cloning: A Laboratory Manual*, 2nd Ed., Cold Spring Harbor Laboratory, Cold Spring Harbor, N.Y.
Sanford et al. (1987) *Part. Sci. Technol.* 5:27-37
Sanford (1993) *Methods Enzymol.* 217: 483-509
Shpaer (1997) Methods Mol. Biol. 70: 173-187
Smith et al. (1992) *Protein Engineering* 5: 35-51
Sonnhammer et al. (1997) *Proteins* 28: 405-420
Spencer et al. (1994) *Plant Mol. Biol.* 24: 51-61
Suzuki et al. (2001) *Plant J.* 28: 409-418
Tasanen et al. (1992) J. Biol. Chem. 267: 11513-11519
Thompson et al. (1994) *Nucleic Acids Res.* 22: 4673-4680
Tudge (2000) in *The Variety of Life*, Oxford University Press, New York, N.Y. pp. 547-606
Vasil et al. (1992) *Bio/Technol.* 10:667-674
Vasil et al. (1993) *Bio/Technol.* 11:1553-1558
Vasil (1994) *Plant Mol. Biol.* 25: 925-937
Wahl and Berger (1987) *Methods Enzymol.* 152: 399-407
Wan and Lemeaux (1994) *Plant Physiol.* 104: 37-48
Weeks et al. (1993) *Plant Physiol.* 102:1077-1084
Weigel and Nilsson (1995) *Nature* 377: 482-500
Weissbach and Weissbach (1989) *Methods for Plant Molecular Biology*, Academic Press
Xu et al. (2001) *Proc. Natl. Acad. Sci. USA* 98: 15089-15094
Zhang et al. (1991) *Bio/Technology* 9: 996-997

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the Claims. Modifications that become apparent from the foregoing description and accompanying figures fall within the scope of the following Claims.

The invention claimed is:

1. An expression vector comprising a recombinant polynucleotide encoding a polypeptide that comprises a conserved domain that has at least 87% identity to amino acids 83-148 of SEQ ID NO: 36;

wherein the recombinant polynucleotide is operably linked to a heterologous promoter;

wherein when the expression vector is introduced into a plant to produce a transgenic plant, the polypeptide is expressed in the transgenic plant;

the polypeptide regulates transcription in the transgenic plant; and due to the expression of the polypeptide in the transgenic plant, the transgenic plant is larger at the seedling stage, or has greater growth rate, greater biomass with respect to a control plant that does not contain the recombinant polynucleotide.

2. The expression vector of claim 1, wherein the conserved domain has at least 96% identity to amino acids 83-148 of SEQ ID NO: 36.

3. The expression vector of claim 1, wherein the conserved domain comprises amino acids 83-148 of SEQ ID NO: 36.

4. The expression vector of claim 1, wherein the recombinant polynucleotide comprises SEQ ID NO: 35.

5. An isolated recombinant host cell comprising the expression vector of claim 1.

6. The expression vector of claim 1, wherein the expression vector further comprises a constitutive, inducible, or tissue-specific promoter operably linked to the recombinant polynucleotide.

7. The expression vector of claim 6, wherein the tissue-specific promoter regulates transcription in a tissue selected from the group consisting of floral meristem, epidermis, vascular, shoot apical meristem, embryo, endosperm, and fruit.

8. A transgenic plant or plant part or plant tissue thereof, wherein the transgenic plant or plant part or plant tissue comprises a recombinant polynucleotide encoding a polypeptide that comprises a conserved domain that has at least 87% identity to amino acids 83-148 of SEQ ID NO: 36;
   wherein the polypeptide is expressed in the transgenic plant;
   wherein the polypeptide regulates transcription in the transgenic plant; and
   due to expression of the polypeptide in the transgenic plant, the transgenic plant is larger at the seedling stage, or has greater growth rate, greater biomass with respect to a control plant that does not contain the recombinant polynucleotide.

9. The transgenic plant, or plant part or plant tissue thereof of claim 8, wherein the expression of the polypeptide is regulated by a tissue-specific, inducible, or constitutive promoter.

10. A transgenic seed produced by the transgenic plant of claim 8, wherein the transgenic seed comprises the recombinant polynucleotide.

11. The transgenic plant, or plant part or plant tissue thereof of claim 8, wherein the conserved domain has at least 96% identity to amino acids 83-148 of SEQ ID NO: 36.

12. The transgenic plant, or plant part or plant tissue thereof of claim 8, wherein the conserved domain comprises amino acids 83-148 of SEQ ID NO: 36.

13. The transgenic plant, or plant part or plant tissue thereof of claim 8, wherein the polypeptide comprises SEQ ID NO: 36.

14. A method for producing and selecting a transgenic plant that is larger at the seedling stage, or has greater growth rate, greater biomass, or greater yield, with respect to a control plant, the method including:
   (a) transforming a target plant with a recombinant polynucleotide that encodes a polypeptide that comprises a conserved domain that has at least 87% identity to amino acids 83-148 of SEQ ID NO: 36;
   wherein, due to expression of the polypeptide in the transgenic plant, the transgenic plant is larger at the seedling stage, or has greater growth rate, or greater biomass with respect to the control plant; and
   (b) selecting a transgenic plant that expresses the polypeptide, and is larger at the seedling stage, or has greater growth rate, or greater biomass, with respect to the control plant, wherein the control plant does not contain the recombinant polynucleotide.

15. The method of claim 14, wherein the expression of the polypeptide is regulated by a tissue-specific, inducible, or constitutive promoter.

16. The method of claim 14, wherein the method further comprises selfing or crossing the transgenic plant with itself or another plant, respectively, to produce a transgenic seed that comprises the recombinant polynucleotide.

17. The method of claim 14, wherein the conserved domain has at least 96% identity to amino acids 83-148 of SEQ ID NO: 36.

18. The method of claim 14, wherein the conserved domain comprises amino acids 83-148 of SEQ ID NO: 36.

19. The method of claim 14, wherein the polypeptide comprises SEQ ID NO: 36.

20. The transgenic plant of claim 8, wherein the conserved domain has at least 96% identity to amino acids 83-148 of SEQ ID NO: 36.

* * * * *